(12) United States Patent
Barrio García et al.

(10) Patent No.: US 11,781,189 B2
(45) Date of Patent: Oct. 10, 2023

(54) METHOD FOR DETERMINING THE PRESENCE OR ABSENCE OF MINIMAL RESIDUAL DISEASE (MRD) IN A SUBJECT WHO HAS BEEN TREATED FOR A DISEASE

(71) Applicants: FUNDACIÓN PARA LA INVESTIGACIÓN BIOMÉDICA DEL HOSPITAL UNIVERSITARIO 12 DE OCTUBRE, Madrid (ES); FUNDACIÓN DEL SECTOR PÚBLICO ESTATAL CENTRO NACIONAL DE INVESTIGACIONES ONCOLOGICAS CARLOS III (F.S.P. CNIO), Madrid (ES)

(72) Inventors: Santiago Barrio García, Madrid (ES); Rosa María Ayala Díaz, Madrid (ES); María Inmaculada Rapado Martinez, Madrid (ES); Eva María Garrido Martín, Madrid (ES); Luis Paz-Ares Rodriguez, Madrid (ES); Maria Esther Onecha De La Fuente, Palencia (ES); Joaquín Martínez López, Madrid (ES)

(73) Assignees: Fundación para la Investigación Biomédica del Hospital Universitario 12 de Octubre; Fundación del Sector Público Estatal Centro Nacional de Investigaciones Oncológicas Carlos III (F.S.P. CNIO)

( * ) Notice: Subject to any disclaimer, the term of this patent is extended or adjusted under 35 U.S.C. 154(b) by 0 days.

(21) Appl. No.: 17/638,035

(22) PCT Filed: Aug. 27, 2020

(86) PCT No.: PCT/EP2020/073960
§ 371 (c)(1),
(2) Date: Feb. 24, 2022

(87) PCT Pub. No.: WO2021/037971
PCT Pub. Date: Mar. 4, 2021

(65) Prior Publication Data
US 2022/0380852 A1 Dec. 1, 2022

(30) Foreign Application Priority Data

Aug. 27, 2019 (EP) .................... 19382730

(51) Int. Cl.
*G16B 30/10* (2019.01)
*G16B 20/20* (2019.01)
(Continued)

(52) U.S. Cl.
CPC .......... *C12Q 1/6886* (2013.01); *G16B 20/20* (2019.02); *G16B 25/20* (2019.02); *G16B 30/10* (2019.02);
(Continued)

(58) Field of Classification Search
None
See application file for complete search history.

(56) References Cited

FOREIGN PATENT DOCUMENTS

EP 3018214 A1 11/2014

OTHER PUBLICATIONS

Beillard et al. Evaluation of candidate control genes for diagnosis and residual disease detection in leukemic patients using "real-time" quantitative reverse-transcriptase polymerase chain reaction (RQ-PCR)—Europe against cancer program. Leukemia, 2003, 17:2474-2486.

*Primary Examiner* — Joseph Woitach
(74) *Attorney, Agent, or Firm* — Tristan A. Fuierer; Casimir Jones, SC

(57) ABSTRACT

The present invention is focused on a method, kit and system for determining the presence or absence of minimal residual disease in a subject who has been treated for a proliferative disease wherein said method, kit and system comprise:
(A) amplifying and sequencing at least one nucleotide sequence comprised in genomic DNA from a biological sample obtained from said subject prior to treatment for said disease, to obtain a first list of characters reading from left to right;
(B) amplifying and sequencing at least one nucleotide sequence comprised in genomic DNA from a biological sample obtained from said subject after treatment for said disease, to obtain a second list of characters reading from left to right,
wherein when a nucleotide sequence is mutated it is a genetic marker for said proliferative disease;
(C) determining, for each second list of characters obtained in step (B), the degree of similarity, DS, with each first list of characters obtained in step (A);
(D) selecting, for each second list of characters obtained in step (B), the DS of highest value, $DS_{HV}$;
(E) adding up the number of second lists of characters which have a $DS_{HV}$ that is greater than a threshold value, T, to obtain $L_c$,
(F) adding up the total number of second lists of characters, $L_t$;
(G) calculating the level of minimal residual disease, MRD, according to any of the following formulae:

$MRD=(L_c \times k)/(L_t \times D)$ or $MRD=L_c/L_t$ or $MRD=g \times L_c \times (D/k)/L_t^2$;

(H) determining (i) the minimum variant read frequency, min VRF, of said genetic marker, (ii) the limit of
(Continued)

detection, D-limit, of said genetic marker (iii) the average mutation noise, avMut and (iv) the average position noise, avPos;

(I) determining the experimental sensitivity, ES, from the greater of the min VRF, D-limit, avMut and avPos or from the greater of min VRF and D-limit;

(J) determining the presence or absence of minimal residual disease in said subject by comparing the value of the level of minimal residual disease with the value of ES, the values of min VRF, D-limit, avMut and avPos, or the values of min VRF and D-limit;

wherein when said level of minimal residual disease is equal to or greater than said ES, min VRF, D-limit, avMut or avPos values, minimal residual disease is present in said subject.

20 Claims, 44 Drawing Sheets

Specification includes a Sequence Listing.

(51) Int. Cl.
- *G16B 25/20* (2019.01)
- *G16B 40/20* (2019.01)
- *C12Q 1/6886* (2018.01)
- C12Q 1/6858 (2018.01)
- C12Q 1/6869 (2018.01)

(52) U.S. Cl.
CPC ............ *G16B 40/20* (2019.02); *C12Q 1/6858* (2013.01); *C12Q 1/6869* (2013.01); *C12Q 2600/112* (2013.01); *C12Q 2600/156* (2013.01)

KRAS G12A

KRAS G12C

NRAS G12D

NRAS G12V

KIT D816V

NPM1 Ins

METHOD FOR DETERMINING THE PRESENCE OR ABSENCE OF MINIMAL RESIDUAL DISEASE (MRD) IN A SUBJECT WHO HAS BEEN TREATED FOR A DISEASE

CROSS-REFERENCE TO RELATED APPLICATIONS

This application is filed under the provisions of 35 U.S.C. § 371 and claims the priority of International Patent Application No. PCT/EP2020/073960, filed on 27 Aug. 2020 entitled "METHOD FOR DETERMINING THE PRESENCE OR ABSENCE OF MINIMAL RESIDUAL DISEASE (MRD) IN A SUBJECT WHO HAS BEEN TREATED FOR A DISEASE" in the name of Santiago BARRIO GARCIA, et al., which claims priority to European Patent Application No. 19382730.0 filed on 27 Aug. 2019, both of which are hereby incorporated by reference herein in their entirety.

FIELD OF THE INVENTION

The present invention may be included in the field of medicine in general, more particularly in the field of diagnosis of disease.

In particular, the present invention is focused on a method and kit and system for determining the presence or absence of minimal residual disease in a subject who has been treated for a proliferative disease by analysing mutations therein. In addition, the present invention is focused on a method of treatment that is personalised for said subject which comprises a step of administering therapy to said subject after using the aforementioned method or kit or system for determining the presence or absence of minimal residual disease (MRD) in said subject.

BACKGROUND TO THE INVENTION

Current methods for the detection and treatment of proliferative disease mean that it is possible to control many diseases at a clinical level, thereby obliterating all traces of the disease. Nevertheless, it may be that some diseases are not detected or that the subject's recovery is not complete after treatment. In the latter case, the disease may develop drug resistance under selective pressure of treatment by a process of clonal selection, thus allowing expansion and ultimately disease recidivism or relapse. It is therefore very important to monitor the number of diseased cells in a given tissue. In particular, it is especially beneficial to monitor the level of minimal residual disease (MRD) in subjects who have been treated for a disease. MRD is the name given to the disease or diseased cells (e.g. cancer cells) that remain in a subject or a particular tissue thereof during or after treatment of said disease. Typically, MRD refers to the proliferative disease that remains in a subject during or after treatment thereof by, for example, chemotherapy.

Currently monitoring through, for example, determination of MRD level may be performed by different techniques. The gold-standard, flow cytometry (FCM), can use up to 8 different markers to determine the disease phenotype. Another method used to this end is allele specific oligonucleotide PCR (ASO-PCR) of immunoglobulin (Ig) genes, which requires the design of specific primers for each patient or a specific molecular marker and is applicable only to 40% of cases.

EP3018214 A1 discloses calculation of MRD according to the following formula: $MRD = L_c \times (D/k)/L_t^2$. In contrast, *Blood Cancer J.* (2003) 17(12): 2474-2486 discloses calculation of MRD according to the following formulae: $MRD = 10^{((\Delta Ct_{FUP} - \Delta Ct_{DX})/-3.4)}$ and $MRD = (FG_{CN}/CG_{CN})_{FUP}/(FG_{CN}/CG_{CN})_{DX}$.

It is therefore the problem of the present invention to provide a method for determining the presence or absence of minimal residual disease (MRD) in a subject who has been treated for a disease, wherein said method exhibits improved sensitivity, greater analytical reproducibility and more accurate determination of said levels, wherein said method can be fully automated, and thus easily standardized, thereby minimizing lab-to-lab variation. It is a further problem of the present invention to provide a universal method which is capable of determining the presence or absence of minimal residual disease (MRD) in a subject who has been treated for a disease, irrespective of the characteristics of the marker(s) of said disease, and thus allows diagnosis of the presence of disease in said subject with the capacity to develop relapse and, hence, the need for further treatment. In addition, it is a problem of the present invention to provide a method which is subject-specific and does not require access to external databases comprising data obtained from populations of subjects.

In addition, it is a problem of the present invention to provide a method for treatment of a disease which is patient-specific and ensures that the disease is treated sufficiently as to eliminate as much minimal residual disease as possible, yet also avoid unnecessarily subjecting said patient to therapy beyond that which is required to treat the disease.

BRIEF DESCRIPTION OF THE INVENTION

The present invention is based on the recognition that comparison of the level of MRD against a threshold value indicative of experimental sensitivity in a subject who has been treated for a proliferative disease provides a statistically sensitive and specific means for determining the presence or absence of minimal residual disease in said subject. Unlike prior art methods which conventionally rely on immunoglobulin rearrangement data, the present method is also found to reliably determine the presence or absence of minimal residual disease based on data relating to point mutations (single nucleotide variants, SNVs) and insertion-deletion mutations (indels) in subjects.

The present invention relates to a method for determining the presence or absence of minimal residual disease (MRD) in a subject who has been treated for a disease, wherein said disease is a proliferative disease, wherein said method comprises the following steps:

(A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
sequencing each amplified nucleotide sequence, whereby a first list of characters reading from left to right is obtained from each nucleotide sequence thus sequenced;

(B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and sequencing each amplified nucleotide sequence, whereby a second list of characters reading from left to right is obtained from each nucleotide sequence thus sequenced;

wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;

(C) determining, for each second list of characters obtained in step (B), the degree of similarity with each first list of characters obtained in step (A), wherein a degree of similarity, DS, of a second list of characters obtained in step (B) with a first list of characters obtained in step (A) is determined by:
  (i) counting the total number of characters, $C_c$, in the second and first lists of characters which are the same as in the first and second lists of characters, respectively;
  (ii) counting the total number of characters, $C_t$, in the first and second lists of characters; and
  (iii) calculating DS according to the following formula:

$DS = C_c/C_t$ (D) selecting, for each second list of characters obtained in step (B), the DS of highest value, $DS_{HV}$;

(E) adding up the number of second lists of characters which have a $DS_{HV}$ that is greater than a threshold value, T, to obtain the total number of second lists of characters, $L_c$, which are the same as a first list of characters;

(F) adding up
  (i) $L_c$; and
  (ii) the number of second lists of characters which do not have a $DS_{HV}$ that is greater than T,
to obtain the total number of second lists of characters, $L_t$; and (G) calculating the level of minimal residual disease, MRD, according to any of the following formulae:

$MRD = (L_c \times k)/(L_t \times D)$ or $MRD = L_c/L_t$ or $MRD = g \times L_c \times (D/k)/L_t^2$ wherein g is the number of gene copies per cell, D is in units of ng and k is in units of ng/cell;

(H) determining:
  (i) the minimum variant read frequency, min VRF, of said genetic marker, wherein min VRF is calculated according to the following formula:

$\text{min VRF} = k/D$ wherein D and k are as defined above; and
  (ii) the limit of detection, D-limit, of said genetic marker, by:
    (a) obtaining a first composition by diluting one part of a solution of genomic DNA comprising said genetic marker with 10 parts of a solution of genomic DNA which does not comprise said genetic marker;
    (b) determining the level of MRD of said genetic marker in said first composition;
    (c) obtaining a second composition by diluting one part of said first composition with 10 parts of a solution of genomic DNA which does not comprise said genetic marker;
    (d) determining the level of MRD of said genetic marker in said second composition;
    (e) obtaining a third composition by diluting one part of said second composition with 10 parts of a solution of genomic DNA which does not comprise said genetic marker;
    (f) determining the level of MRD of said genetic marker in said third composition;
    (g) obtaining a fourth composition by diluting one part of said third composition with 10 parts of a solution of genomic DNA which does not comprise said genetic marker;
    (h) determining the level of MRD of said genetic marker in said fourth composition;
    (i) calculating:
      the average logarithm of the level of MRD, av log MRD1, of said genetic marker in the first, second and third compositions and the average logarithm of the concentration, av log C1, of said genetic marker in the first, second and third compositions; and
      the average logarithm of the level of MRD, av log MRD2, of said genetic marker in the second, third and fourth compositions and the average logarithm of the concentration, av log C2, of said genetic marker in the second, third and fourth compositions;
    (j) calculating:
      the difference, D1A, between the logarithm of the level of MRD of said genetic marker in the first composition and the av log MRD1;
      the difference, D1B, between the logarithm of the level of MRD of said genetic marker in the second composition and the av log MRD1;
      the difference, D1C, between the logarithm of the level of MRD of said genetic marker in the third composition and the av log MRD1;
      the difference, D1D, between the logarithm of the concentration of said genetic marker in the first composition and the av log C1;
      the difference, D1E, between the logarithm of the concentration of said genetic marker in the second composition and the av log C1;
      the difference, D1F, between the logarithm of the concentration of said genetic marker in the third composition and the av log C1;
      the difference, D2A, between the logarithm of the level of MRD of said genetic marker in the second composition and the av log MRD2;
      the difference, D2B, between the logarithm of the level of MRD of said genetic marker in the third composition and the av log MRD2;
      the difference, D2C, between the logarithm of the level of MRD of said genetic marker in the fourth composition and the av log MRD2;
      the difference, D2D, between the logarithm of the concentration of said genetic marker in the second composition and the av log C2;
      the difference, D2E, between the logarithm of the concentration of said genetic marker in the third composition and the av log C2; and the difference, D2F, between the logarithm of the concentration of said genetic marker in the fourth composition and the av log C2;
(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;
(l) calculating:
S1 using the following formula:

$$S1=(R1+R2+R3)/(R4+R5+R6)$$

S2 using the following formula:

$$S2=(R7+R8+R9)/(R10+R11+R12);$$

(m) comparing S1 and S2, whereby:
when S2 is at least 30% lower than S1, the concentration of the third composition is the D-limit; and
when S2 is equal to S1 or less than 30% lower than S1, steps (H)(ii)(a) to (H)(ii)(l) are repeated using said first composition in place of said solution of genomic DNA comprising said genetic marker; and
(iii) the average mutation noise, avMut, when said mutation is a single nucleotide variant mutation, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
(b) sequencing each amplified nucleotide sequence, whereby a third list of characters reading from left to right is obtained from each nucleotide sequence thus sequenced;
(c) repeating steps (H)(iii)(a) and (H)(iii)(b) in m subjects without said disease and without said genetic marker, wherein m is at least 9; and
(d) calculating the average fraction of third lists of characters which are identical to that obtained from sequencing said genetic marker, wherein said average fraction is avMut; and
(iv) the average position noise, avPos, when said mutation is a single nucleotide variant mutation, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;
(I) determining the experimental sensitivity, ES, wherein ES is:
(i) the greater of min VRF, D-limit, avMut and avPos, as calculated in step (H), when said mutation is a single nucleotide variant mutation; or
(ii) the greater of min VRF and D-limit, as calculated in step (H), when said mutation is an indel mutation or somatic gene rearrangement mutation; and
(J) determining the presence or absence of minimal residual disease in said subject by either:
(i) comparing the value of the level of minimal residual disease, MRD, calculated in step (G) with the value of the experimental sensitivity, ES, determined in step (I), wherein
(a) when said level of MRD value is equal to or greater than said ES value, minimal residual disease is present in said subject; and
(b) when said level of MRD value is less than said ES value, minimal residual disease is absent from said subject
or
(ii) when said mutation is a single nucleotide variant mutation, comparing the value of the level of minimal residual disease, MRD, calculated in step (G) with the value of min VRF calculated in step (H), wherein
(a) when said level of MRD value is equal to or greater than said min VRF value, minimal residual disease is present in said subject; and
comparing the value of the level of minimal residual disease, MRD, calculated in step (G) with the value of avMut calculated in step (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in step (G) with the value of avPos calculated in step (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in step (G) with the value of D-limit calculated in step (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;
or
(iii) when said mutation is an indel mutation or somatic gene rearrangement mutation, comparing the value of the level of minimal residual disease, MRD, calculated in step (G) with the value of min VRF calculated in step (I), wherein
(f) when said level of MRD value is equal to or greater than said min VRF value, minimal residual disease is present in said subject; and
comparing the value of the level of minimal residual disease, MRD, calculated in step (G) with the value of D-limit calculated in step (H) when said level of MRD value is less than said min VRF value, wherein
(g) when said level of MRD value is equal to or greater than said D-limit value, minimal residual disease is present in said subject; and
(h) when said level of MRD value is less than said min VRF and D-limit values, minimal residual disease is absent from said subject.

In addition, the present invention relates to a system for determining the presence or absence of minimal residual disease (MRD) in a subject who has been treated for a disease, wherein said disease is a proliferative disease, wherein said system comprises the following:

(A)—means for amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and means for sequencing each amplified nucleotide sequence, whereby a first list of characters reading from left to right is obtained from each nucleotide sequence thus sequenced;

(B)—means for amplifying by polymerase chain reaction using the same locus-specific forward primer and the same locus-specific reverse primer as in (A), at least one nucleotide sequence comprised in an amount, D, of genomic DNA from a biological sample obtained from said subject after treatment for said disease, wherein the genomic DNA has an average weight, k, per diploid cell of said biological sample; and means for sequencing each amplified nucleotide sequence, whereby a second list of characters reading from left to right is obtained from each nucleotide sequence thus sequenced;

wherein each nucleotide sequence amplified in (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;

(C) means for determining, for each second list of characters obtained in (B), the degree of similarity with each first list of characters obtained in (A), wherein a degree of similarity, DS, of a second list of characters obtained in (B) with a first list of characters obtained in (A) is determined by:

(i) counting the total number of characters, $C_c$, in the second and first lists of characters which are the same as in the first and second lists of characters, respectively;

(ii) counting the total number of characters, $C_t$, in the first and second lists of characters; and (iii) calculating DS according to the following formula:

$$DS = C_c/C_t$$

(D) means for selecting, for each second list of characters obtained in (B), the DS of highest value, $DS_{HV}$;

(E) means for adding up the number of second lists of characters which have a $DS_{HV}$ that is greater than a threshold value, T, to obtain the total number of second lists of characters, $L_c$, which are the same as a first list of characters;

(F) means for adding up
(i) $L_c$; and
(ii) the number of second lists of characters which do not have a $DS_{HV}$ that is greater than T,
to obtain the total number of second lists of characters, $L_t$; and (G) means for calculating the level of minimal residual disease, MRD, according to any of the following formulae:

$$MRD = (L_c \times k)/(L_t \times D)$$

or $$MRD = L_c/L_t$$

or $$MRD = g \times L_c \times (D/k)/L_t^2$$

wherein g is the number of gene copies per cell, D is in units of ng and k is in units of ng/cell;

(H) means for determining:

(i) the minimum variant read frequency, min VRF, of said genetic marker, wherein min VRF is calculated according to the following formula:

$$\min VRF = k/D$$

wherein D and k are as defined above; and (ii) the limit of detection, D-limit, of said genetic marker by:

(a) obtaining a first composition by diluting one part of a solution of genomic DNA comprising said genetic marker with 10 parts of a solution of genomic DNA which does not comprise said genetic marker;

(b) determining the level of MRD of said genetic marker in said first composition;

(c) obtaining a second composition by diluting one part of said first composition with 10 parts of a solution of genomic DNA which does not comprise said genetic marker;

(d) determining the level of MRD of said genetic marker in said second composition;

(e) obtaining a third composition by diluting one part of said second composition with 10 parts of a solution of genomic DNA which does not comprise said genetic marker;

(f) determining the level of MRD of said genetic marker in said third composition;

(g) obtaining a fourth composition by diluting one part of said third composition with 10 parts of a solution of genomic DNA which does not comprise said genetic marker;

(h) determining the level of MRD of said genetic marker in said fourth composition;

(i) calculating:
the average logarithm of the level of MRD, av log MRD1, of said genetic marker in the first, second and third compositions and the average logarithm of the concentration, av log C1, of said genetic marker in the first, second and third compositions; and the average logarithm of the level of MRD, av log MRD2, of said genetic marker in the second, third and fourth compositions and the average logarithm of the concentration, av log C2, of said genetic marker in the second, third and fourth compositions;

(j) calculating:
the difference, D1A, between the logarithm of the level of MRD of said genetic marker in the first composition and the av log MRD1;
the difference, D1B, between the logarithm of the level of MRD of said genetic marker in the second composition and the av log MRD1; and
the difference, D1C, between the logarithm of the level of MRD of said genetic marker in the third composition and the av log MRD1;

the difference, D1D, between the logarithm of the concentration of said genetic marker in the first composition and the av log C1;

the difference, D1E, between the logarithm of the concentration of said genetic marker in the second composition and the av log C1;

the difference, D1F, between the logarithm of the concentration of said genetic marker in the third composition and the av log C1;

the difference, D2A, between the logarithm of the level of MRD of said genetic marker in the second composition and the av log MRD2;

the difference, D2B, between the logarithm of the level of MRD of said genetic marker in the third composition and the av log MRD2;

the difference, D2C, between the logarithm of the level of MRD of said genetic marker in the fourth composition and the av log MRD2;

the difference, D2D, between the logarithm of the concentration of said genetic marker in the second composition and the av log C2;

the difference, D2E, between the logarithm of the concentration of said genetic marker in the third composition and the av log C2; and the difference, D2F, between the logarithm of the concentration of said genetic marker in the fourth composition and the av log C2;

(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;

(l) calculating:
S1 using the following formula:

$S1=(R1+R2+R3)/(R4+R5+R6)$

S2 using the following formula:

$S2=(R7+R8+R9)/(R10+R11+R12);$ (m) comparing S1 and S2, whereby:
when S2 is at least 30% lower than S1, the concentration of the third composition is the D-limit; and
when S2 is equal to S1 or less than 30% lower than S1, (H)(ii)(a) to (H)(ii)(l) are repeated using said first composition in place of said solution of genomic DNA comprising said genetic marker; and (iii) the average mutation noise, avMut, when said mutation is a single nucleotide variant mutation, using:
(a) means for amplifying by polymerase chain reaction using the same locus-specific forward primer and the same locus-specific reverse primer as in (A), at least one nucleotide sequence of genomic DNA from a biological sample obtained from a subject without said disease and without said genetic marker;

(b) means for sequencing each amplified nucleotide sequence, whereby a third list of characters reading from left to right is obtained from each nucleotide sequence thus sequenced;

(c) means for repeating (H)(iii)(a) and (H)(iii)(b) in m subjects without said disease and without said genetic marker, wherein m is at least 9; and (d) means for calculating the average fraction of third lists of characters which are identical to that obtained from sequencing said genetic marker, wherein said average fraction is avMut; and (iv) the average position noise, avPos, when said mutation is a single nucleotide variant mutation, using means for calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;

(I) means for determining the experimental sensitivity, ES, wherein ES is:
(i) the greater of min VRF, D-limit, avMut and avPos, as calculated in (H), when said mutation is a single nucleotide variant mutation; and
(ii) the greater of min VRF and D-limit, as calculated in (H), when said mutation is an indel mutation or somatic gene rearrangement mutation;

and (J) means for determining the presence or absence of minimal residual disease in said subject by either:
(i) comparing the value of the level of minimal residual disease, MRD, calculated in (G) with the value of the experimental sensitivity, ES, determined in (I), wherein
(a) when said level of MRD value is equal to or greater than said ES value, minimal residual disease is present in said subject; and
(b) when said level of MRD value is less than said ES value, minimal residual disease is absent from said subject or (ii) when said mutation is a single nucleotide variant mutation, comparing the value of the level of minimal residual disease, MRD, calculated in (G) with the value of min VRF calculated in (H), wherein
(a) when said level of MRD value is equal to or greater than said min VRF value, minimal residual disease is present in said subject; and
comparing the value of the level of minimal residual disease, MRD, calculated in (G) with the value of avMut calculated in (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in (G) with the value of avPos calculated in (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in (G) with the value of D-limit calculated in (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in (G) with the value of min VRF calculated in (I), wherein
(f) when said level of MRD value is equal to or greater than said min VRF value, minimal residual disease is present in said subject; and
comparing the value of the level of minimal residual disease, MRD, calculated in (G) with the value of D-limit calculated in (H) when said level of MRD value is less than said min VRF value, wherein
(g) when said level of MRD value is equal to or greater than said D-limit value, minimal residual disease is present in said subject; and
(h) when said level of MRD value is less than said min VRF and D-limit values, minimal residual disease is absent from said subject.

Furthermore, the present invention relates to a kit for determining the presence or absence of minimal residual disease (MRD) in a subject who has been treated for a disease, wherein said disease is a proliferative disease, wherein said system comprises the following:

(A)—means for amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
means for sequencing each amplified nucleotide sequence, whereby a first list of characters reading from left to right is obtained from each nucleotide sequence thus sequenced;

(B)—means for amplifying by polymerase chain reaction using the same locus-specific forward primer and the same locus-specific reverse primer as in (A), at least one nucleotide sequence comprised in an amount, D, of genomic DNA from a biological sample obtained from said subject after treatment for said disease, wherein the genomic DNA has an average weight, k, per diploid cell of said biological sample; and
means for sequencing each amplified nucleotide sequence, whereby a second list of characters reading from left to right is obtained from each nucleotide sequence thus sequenced;

wherein each nucleotide sequence amplified in (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;

(C) means for determining, for each second list of characters obtained in (B), the degree of similarity with each first list of characters obtained in (A), wherein a degree of similarity, DS, of a second list of characters obtained in (B) with a first list of characters obtained in (A) is determined by:
(i) counting the total number of characters, $C_c$, in the second and first lists of characters which are the same as in the first and second lists of characters, respectively;
(ii) counting the total number of characters, $C_t$, in the first and second lists of characters; and
(iii) calculating DS according to the following formula:

$$DS = C_c/C_t$$

(D) means for selecting, for each second list of characters obtained in (B), the DS of highest value, $DS_{HV}$;
(E) means for adding up the number of second lists of characters which have a $DS_{HV}$ that is greater than a threshold value, T, to obtain the total number of second lists of characters, $L_c$, which are the same as a first list of characters;
(F) means for adding up
(i) $L_c$; and
(ii) the number of second lists of characters which do not have a $DS_{HV}$ that is greater than T,
to obtain the total number of second lists of characters, $L_t$; and
(G) means for calculating the level of minimal residual disease, MRD, according to any of the following formulae:

$$MRD = (L_c \times k)/(L_t \times D)$$

or $$MRD = L_c/L_t$$

or $$MRD = g \times L_c \times (D/k)/L_t^2 D$$

wherein g is the number of gene copies per cell, D is in units of ng and k is in units of ng/cell;

(H) means for determining:
(i) the minimum variant read frequency, min VRF, of said genetic marker, wherein min VRF is calculated according to the following formula:

$$min\ VRF = k/D$$

wherein D and k are as defined above; and
(ii) the limit of detection, D-limit, of said genetic marker by:
(a) obtaining a first composition by diluting one part of a solution of genomic DNA comprising said genetic marker with 10 parts of a solution of genomic DNA which does not comprise said genetic marker;
(b) determining the level of MRD of said genetic marker in said first composition;
(c) obtaining a second composition by diluting one part of said first composition with 10 parts of a solution of genomic DNA which does not comprise said genetic marker;
(d) determining the level of MRD of said genetic marker in said second composition;
(e) obtaining a third composition by diluting one part of said second composition with 10 parts of a solution of genomic DNA which does not comprise said genetic marker;
(f) determining the level of MRD of said genetic marker in said third composition;

(g) obtaining a fourth composition by diluting one part of said third composition with 10 parts of a solution of genomic DNA which does not comprise said genetic marker;
(h) determining the level of MRD of said genetic marker in said fourth composition;
(i) calculating:
the average logarithm of the level of MRD, av log MRD1, of said genetic marker in the first, second and third compositions and the average logarithm of the concentration, av log C1, of said genetic marker in the first, second and third compositions; and
the average logarithm of the level of MRD, av log MRD2, of said genetic marker in the second, third and fourth compositions and the average logarithm of the concentration, av log C2, of said genetic marker in the second, third and fourth compositions;
(j) calculating:
the difference, D1A, between the logarithm of the level of MRD of said genetic marker in the first composition and the av log MRD1;
the difference, D1B, between the logarithm of the level of MRD of said genetic marker in the second composition and the av log MRD1; and
the difference, D1C, between the logarithm of the level of MRD of said genetic marker in the third composition and the av log MRD1;
the difference, D1D, between the logarithm of the concentration of said genetic marker in the first composition and the av log C1;
the difference, D1E, between the logarithm of the concentration of said genetic marker in the second composition and the av log C1;
the difference, D1F, between the logarithm of the concentration of said genetic marker in the third composition and the av log C1;
the difference, D2A, between the logarithm of the level of MRD of said genetic marker in the second composition and the av log MRD2;
the difference, D2B, between the logarithm of the level of MRD of said genetic marker in the third composition and the av log MRD2;
the difference, D2C, between the logarithm of the level of MRD of said genetic marker in the fourth composition and the av log MRD2;
the difference, D2D, between the logarithm of the concentration of said genetic marker in the second composition and the av log C2;
the difference, D2E, between the logarithm of the concentration of said genetic marker in the third composition and the av log C2; and
the difference, D2F, between the logarithm of the concentration of said genetic marker in the fourth composition and the av log C2;
(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;
(l) calculating:
S1 using the following formula:

$$S1=(R1+R2+R3)/(R4+R5+R6)$$

S2 using the following formula:

$$S2=(R7+R8+R9)/(R10+R11+R12);$$

(m) comparing S1 and S2, whereby:
when S2 is at least 30% lower than S1, the concentration of the third composition is D-limit; and
when S2 is equal to S1 or less than 30% lower than S1, (H)(ii)(a) to (H)(ii)(l) are repeated using said first composition in place of said solution of genomic DNA comprising said genetic marker; and
(iii) the average mutation noise, avMut, when said mutation is a single nucleotide variant mutation, using:
(a) means for amplifying by polymerase chain reaction using the same locus-specific forward primer and the same locus-specific reverse primer as in (A), at least one nucleotide sequence of genomic DNA from a biological sample obtained from a subject without said disease and without said genetic marker;
(b) means for sequencing each amplified nucleotide sequence, whereby a third list of characters reading from left to right is obtained from each nucleotide sequence thus sequenced;
(c) means for repeating (H)(iii)(a) and (H)(iii)(b) in m subjects without said disease and without said genetic marker, wherein m is at least 9; and
(d) means for calculating the average fraction of third lists of characters which are identical to that obtained from sequencing said genetic marker, wherein said average fraction is avMut; and
(iv) the average position noise, avPos, when said mutation is a single nucleotide variant mutation, using means for calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;
(I) means for determining the experimental sensitivity, ES, wherein ES is:
(i) the greater of min VRF, D-limit, avMut and avPos, as calculated in (H), when said mutation is a single nucleotide variant mutation; and
(ii) the greater of min VRF and D-limit, as calculated in (H), when said mutation is an indel mutation or somatic gene rearrangement mutation;
and
(J) means for determining the presence or absence of minimal residual disease in said subject by either:
(i) comparing the value of the level of minimal residual disease, MRD, calculated in (G) with the value of the experimental sensitivity, ES, determined in (I), wherein
(a) when said level of MRD value is equal to or greater than said ES value, minimal residual disease is present in said subject; and (b) when said level of MRD value is less than said ES value, minimal residual disease is absent from said subject or (ii) when said mutation is a single nucleotide variant mutation, comparing the value of the level of minimal residual disease, MRD, calculated in (G) with the value of min VRF calculated in (H), wherein
  (a) when said level of MRD value is equal to or greater than said min VRF value, minimal residual disease is present in said subject; and
  comparing the value of the level of minimal residual disease, MRD, calculated in (G) with the value of avMut calculated in (H) when said level of MRD value is less than said min VRF value, wherein
    (b) when said level of MRD value is equal to or greater than said avMut value, minimal residual disease is present in said subject; and
  comparing the value of the level of minimal residual disease, MRD, calculated in (G) with the value of avPos calculated in (H) when said level of MRD value is less than said avMut value, wherein
    (c) when said level of MRD value is equal to or greater than said avPos value, minimal residual disease is present in said subject; and
  comparing the value of the level of minimal residual disease, MRD, calculated in (G) with the value of D-limit calculated in (H) when said level of MRD value is less than said avPos value, wherein
    (d) when said level of MRD value is equal to or greater than said D-limit value, minimal residual disease is present in said subject; and
    (e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in (G) with the value of min VRF calculated in (I), wherein
  (f) when said level of MRD value is equal to or greater than said min VRF value, minimal residual disease is present in said subject; and
  comparing the value of the level of minimal residual disease, MRD, calculated in (G) with the value of D-limit calculated in (H) when said level of MRD value is less than said min VRF value, wherein
    (g) when said level of MRD value is equal to or greater than said D-limit value, minimal residual disease is present in said subject; and
    (h) when said level of MRD value is less than said min VRF and D-limit values, minimal residual disease is absent from said subject.

The present invention also relates to a method for treatment of disease in a subject who has been treated for said disease, wherein said disease is a proliferative disease, comprising the steps of:

(1) administering therapy to a subject, wherein said therapy is selected from chemotherapy, immunotherapy or radiotherapy, or combinations thereof; and
(2) determining the presence or absence of minimal residual disease (MRD) in a subject wherein said method comprises the following steps:
(A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
sequencing each amplified nucleotide sequence, whereby a first list of characters reading from left to right is obtained from each nucleotide sequence thus sequenced;
(B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and
sequencing each amplified nucleotide sequence, whereby a second list of characters reading from left to right is obtained from each nucleotide sequence thus sequenced;
wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;
(C) determining, for each second list of characters obtained in step (B), the degree of similarity with each first list of characters obtained in step (A), wherein a degree of similarity, DS, of a second list of characters obtained in step (B) with a first list of characters obtained in step (A) is determined by:
  (i) counting the total number of characters, $C_c$, in the second and first lists of characters which are the same as in the first and second lists of characters, respectively;
  (ii) counting the total number of characters, $C_t$, in the first and second lists of characters; and
  (iii) calculating DS according to the following formula:

$$DS=C_c/C_t$$

(D) selecting, for each second list of characters obtained in step (B), the DS of highest value, $DS_{HV}$;
(E) adding up the number of second lists of characters which have a $DS_{HV}$ that is greater than a threshold value, T, to obtain the total number of second lists of characters, $L_c$, which are the same as a first list of characters;
(F) adding up
  (i) $L_c$; and
  (ii) the number of second lists of characters which do not have a $DS_{HV}$ that is greater than T,
  to obtain the total number of second lists of characters, $L_t$; and
(G) calculating the level of minimal residual disease, MRD, according to any of the following formulae:

$$MRD=(L_c \times k)/(L_t \times D)$$

or $$MRD=L_c/L_t$$

or $$MRD=g \times L_c \times (D/k)/L_t^2$$

wherein g is the number of gene copies per cell, D is in units of ng and k is in units of ng/cell;

(H) determining:
(i) the minimum variant read frequency, min VRF, of said genetic marker, wherein min VRF is calculated according to the following formula:

$$\text{min VRF} = k/D$$

wherein D and k are as defined above; and (ii) the limit of detection, D-limit, of said genetic marker, by:
(a) obtaining a first composition by diluting one part of a solution of genomic DNA comprising said genetic marker with 10 parts of a solution of genomic DNA which does not comprise said genetic marker;
(b) determining the level of MRD of said genetic marker in said first composition;
(c) obtaining a second composition by diluting one part of said first composition with 10 parts of a solution of genomic DNA which does not comprise said genetic marker;
(d) determining the level of MRD of said genetic marker in said second composition;
(e) obtaining a third composition by diluting one part of said second composition with 10 parts of a solution of genomic DNA which does not comprise said genetic marker;
(f) determining the level of MRD of said genetic marker in said third composition;
(g) obtaining a fourth composition by diluting one part of said third composition with 10 parts of a solution of genomic DNA which does not comprise said genetic marker;
(h) determining the level of MRD of said genetic marker in said fourth composition;
(i) calculating:
the average logarithm of the level of MRD, av log MRD1, of said genetic marker in the first, second and third compositions and the average logarithm of the concentration, av log C1, of said genetic marker in the first, second and third compositions; and
the average logarithm of the level of MRD, av log MRD2, of said genetic marker in the second, third and fourth compositions and the average logarithm of the concentration, av log C2, of said genetic marker in the second, third and fourth compositions;
(j) calculating:
the difference, D1A, between the logarithm of the level of MRD of said genetic marker in the first composition and the av log MRD1;
the difference, D1B, between the logarithm of the level of MRD of said genetic marker in the second composition and the av log MRD1;
the difference, D1C, between the logarithm of the level of MRD of said genetic marker in the third composition and the av log MRD1;
the difference, D1D, between the logarithm of the concentration of said genetic marker in the first composition and the av log C1;
the difference, D1E, between the logarithm of the concentration of said genetic marker in the second composition and the av log C1;
the difference, D1F, between the logarithm of the concentration of said genetic marker in the third composition and the av log C1;
the difference, D2A, between the logarithm of the level of MRD of said genetic marker in the second composition and the av log MRD2;
the difference, D2B, between the logarithm of the level of MRD of said genetic marker in the third composition and the av log MRD2;
the difference, D2C, between the logarithm of the level of MRD of said genetic marker in the fourth composition and the av log MRD2;
the difference, D2D, between the logarithm of the concentration of said genetic marker in the second composition and the av log C2;
the difference, D2E, between the logarithm of the concentration of said genetic marker in the third composition and the av log C2; and
the difference, D2F, between the logarithm of the concentration of said genetic marker in the fourth composition and the av log C2;
(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;
(l) calculating:
S1 using the following formula:

$$S1 = (R1+R2+R3)/(R4+R5+R6)$$

S2 using the following formula:

$$S2 = (R7+R8+R9)/(R10+R11+R12);$$

(m) comparing S1 and S2, whereby:
when S2 is at least 30% lower than S1, the concentration of the third composition is the D-limit; and
when S2 is equal to S1 or less than 30% lower than S1, steps (H)(ii)(a) to (H)(ii)(l) are repeated using said first composition in place of said solution of genomic DNA comprising said genetic marker; and
(iii) the average mutation noise, avMut, when said mutation is a single nucleotide variant mutation, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
(b) sequencing each amplified nucleotide sequence, whereby a third list of characters reading from left to right is obtained from each nucleotide sequence thus sequenced;
(c) repeating steps (H)(iii)(a) and (H)(iii)(b) in m subjects without said disease and without said genetic marker, wherein m is at least 9; and (d) calculating the average fraction of third lists of characters which are identical to that obtained from sequencing said genetic marker, wherein said average fraction is avMut; and (iv) the average position noise, avPos, when said mutation is a single nucleotide variant mutation, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;

(I) determining the experimental sensitivity, ES, wherein ES is:
 (i) the greater of min VRF, D-limit, avMut and avPos, as calculated in step (H), when said mutation is a single nucleotide variant mutation; or
 (ii) the greater of min VRF and D-limit, as calculated in step (H), when said mutation is an indel mutation or somatic gene rearrangement mutation;
and (J) determining the presence or absence of minimal residual disease in said subject by either:
 (i) comparing the value of the level of minimal residual disease, MRD, calculated in step (G) with the value of the experimental sensitivity, ES, determined in step (I), wherein
  (a) when said level of MRD value is equal to or greater than said ES value, minimal residual disease is present in said subject; and
  (b) when said level of MRD value is less than said ES value, minimal residual disease is absent from said subject
or
 (ii) when said mutation is a single nucleotide variant mutation, comparing the value of the level of minimal residual disease, MRD, calculated in step (G) with the value of min VRF calculated in step (H), wherein
  (a) when said level of MRD value is equal to or greater than said min VRF value, minimal residual disease is present in said subject; and
 comparing the value of the level of minimal residual disease, MRD, calculated in step (G) with the value of avMut calculated in step (H) when said level of MRD value is less than said min VRF value, wherein
  (b) when said level of MRD value is equal to or greater than said avMut value, minimal residual disease is present in said subject; and
 comparing the value of the level of minimal residual disease, MRD, calculated in step (G) with the value of avPos calculated in step (H) when said level of MRD value is less than said avMut value, wherein
  (c) when said level of MRD value is equal to or greater than said avPos value, minimal residual disease is present in said subject; and
 comparing the value of the level of minimal residual disease, MRD, calculated in step (G) with the value of D-limit calculated in step (H) when said level of MRD value is less than said avPos value, wherein
  (d) when said level of MRD value is equal to or greater than said D-limit value, minimal residual disease is present in said subject; and
  (e) when said level of MRD value is less than said min VRF, avMut, avPos and D-limit values, minimal residual disease is absent from said subject;
or
 (iii) when said mutation is an indel mutation or somatic gene rearrangement mutation, comparing the value of the level of minimal residual disease, MRD, calculated in step (G) with the value of min VRF calculated in step (I), wherein
  (f) when said level of MRD value is equal to or greater than said min VRF value, minimal residual disease is present in said subject; and
 comparing the value of the level of minimal residual disease, MRD, calculated in step (G) with the value of D-limit calculated in step (H) when said level of MRD value is less than said min VRF value, wherein
  (g) when said level of MRD value is equal to or greater than said D-limit value, minimal residual disease is present in said subject; and
  (h) when said level of MRD value is less than said min VRF and D-limit values, minimal residual disease is absent from said subject,
wherein when minimal residual disease is determined to be present in said subject, steps (1) and (2) are repeated, wherein each repetition of step (1) comprises administering the same therapy as previously administered to said subject or therapy different to that previously administered to said subject.

DETAILED DESCRIPTION OF THE INVENTION

Figure 5A:
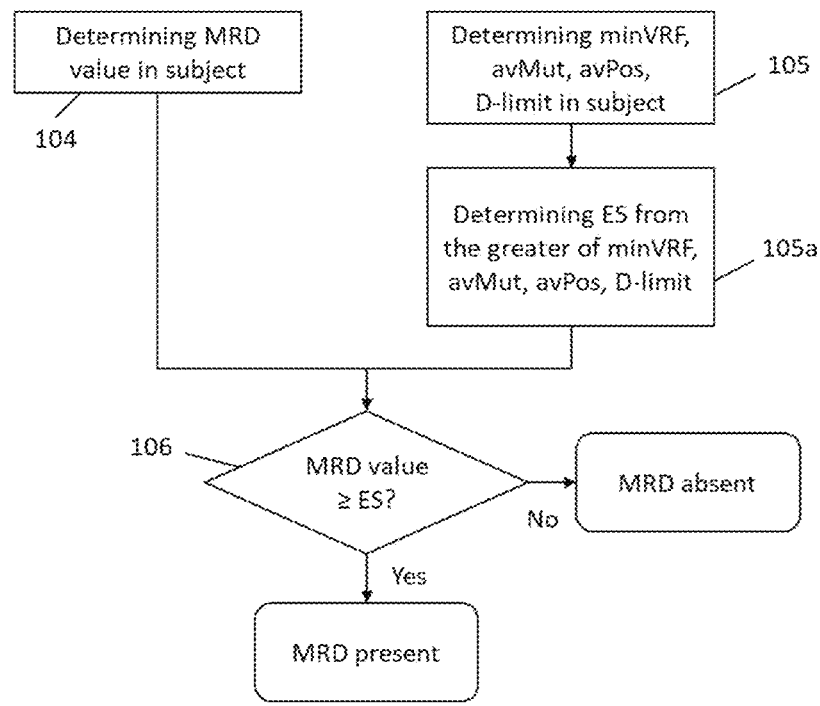
FIG. 5. A. Flowchart of an example of a generalised method for determining the presence or absence of minimal residual disease (MRD) in a subject who has been treated for a disease in accordance with an embodiment of the present invention. B. Flowchart of an example of a generalised method for determining the presence or absence of minimal residual disease (MRD) in a subject who has been treated for a disease in accordance with another embodiment of the present invention. Level of MRD, min VRF, avMut, avPos, D-limit and ES determined as per the present invention, wherein min VRF=minimum variant read frequency, avMut=average mutation noise, avPos=average position noise, D-limit=limit of detection, ES=experimental sensitivity, defined as the greater of min VRF, avMut, avPos and D-limit.
Figure 5B:
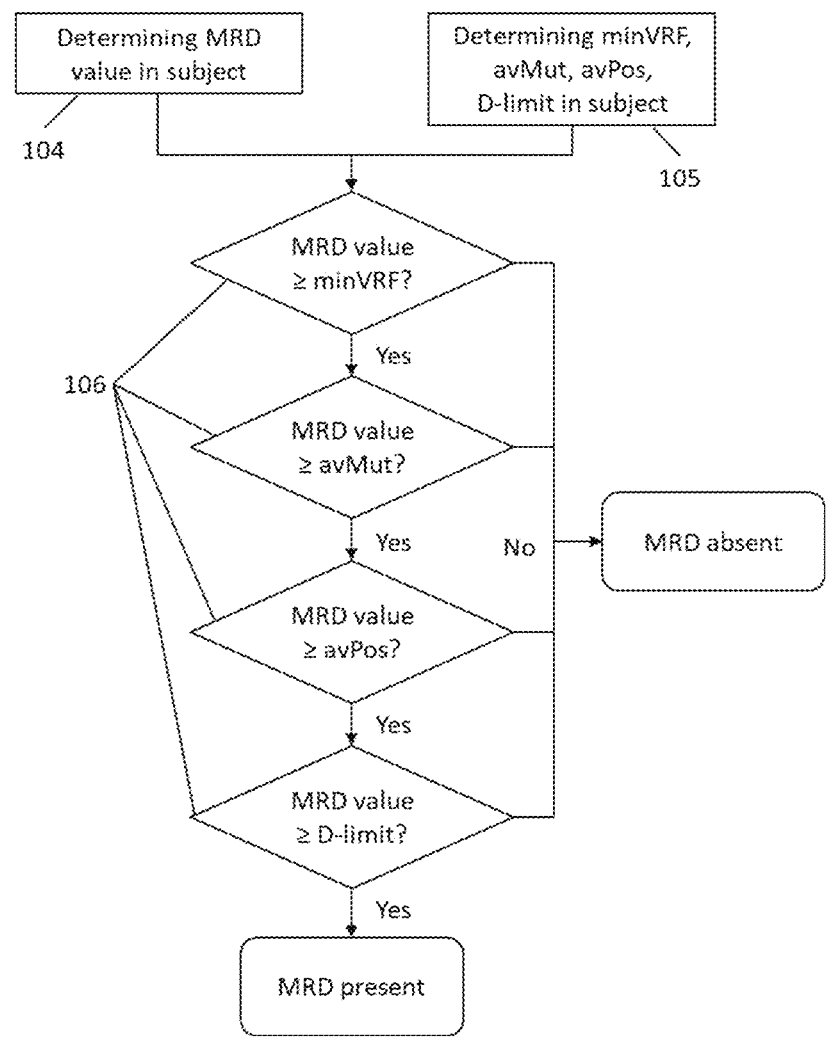

The present invention relates to a method, system and kit for determining the presence or absence of minimal residual disease (MRD) in a subject who has been treated for a disease. The present invention also relates to a method of treatment of disease in a subject who has been treated for said disease which comprises said method for determining the presence or absence of minimal residual disease. Preferably, the method, system, and kit (exemplified in FIGS. 5A and 5B) as well as the method of treatment (exemplified in FIGS. 11A and 11B) use biological techniques and a computer program product.

In particular, the present invention relates to a method, system and kit for determining the presence or absence of minimal residual disease (MRD) in a subject, as well as a method of treatment of disease in a subject who has been treated for said disease which comprises said method for determining the presence or absence of minimal residual disease, wherein said disease is a proliferative disease. Thus, said subject is an individual who has been treated for any such proliferative disease.

MRD is the name given to the disease that remains in a subject after treatment of a proliferative disease. Thus, determining the presence or absence of MRD means determining the presence or absence of diseased cells that remain proliferating in a subject or determining the presence or absence of genetic material that is associated with proliferative disease in a subject after treatment of said proliferative disease. Preferably, determining the presence or absence of MRD means determining the presence or absence of diseased cells that remain proliferating in a biological sample or tissue from a subject after treatment of said proliferative disease, or determining the presence or absence of MRD means determining the presence or absence of genetic material that is associated with proliferative disease in a biological sample or tissue from a subject, after treatment of said proliferative disease. The presence or absence of a proliferative disease may be identified based on the expression or lack of expression of a genetic marker on, in or outside diseased cells.

Figure 1A:
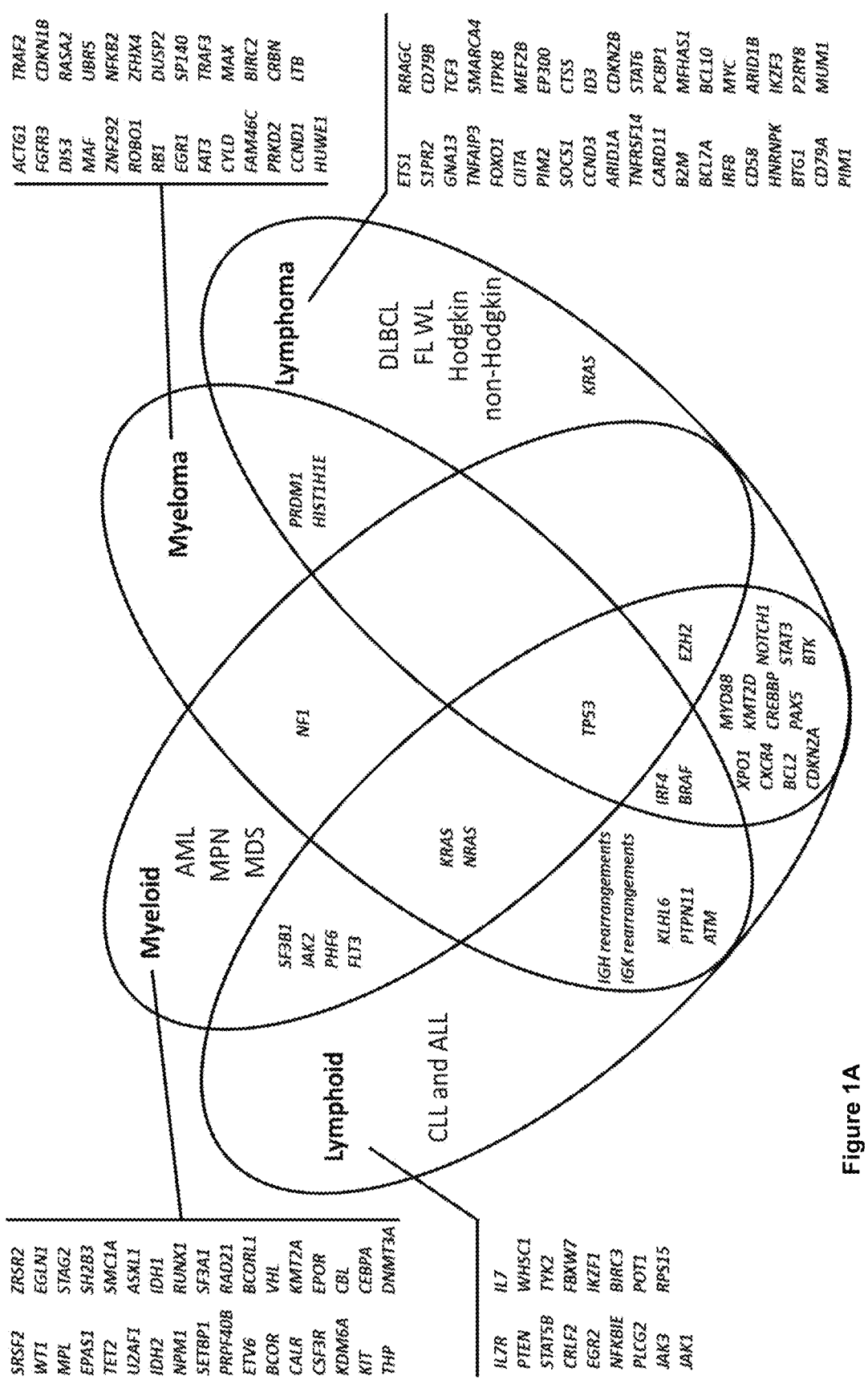
FIG. 1. A. Venn diagram defining genetic markers for onco-hematological diagnosis comprising four different panels collectively comprising ten heme-dyscrasias. Panels show overlapping nature of recurrent gene mutations in lymphoid leukaemia [chronic lymphocytic leukaemia (CLL) and acute lymphoblastic leukaemia (ALL)], myeloid cancer [acute myeloid leukaemia (AML), myelodysplastic syndrome (MDS) and myeloproliferative neoplasm (MNP)], multiple myeloma (MM), and lymphoma [diffuse large B-cell lymphoma (DLBCL), follicular lymphoma (FL), Waldenström's lymphoma (WL) and Hodgkin's lymphoma], resulting in 13 different groupings of genetic markers. The coding (exonic) regions of many genes (italics) are mutated in diseases disclosed in more than one panel. The lymphoid leukaemia panel covers all coding regions of 48 frequently mutated genes plus IgH and IgK rearrangements, the myeloid cancer panel covers coding regions of 43 frequently mutated genes, the multiple myeloma panel covers coding regions of 38 frequently mutated genes plus IgH and IgK rearrangements and the lymphoma panel covers coding regions of 56 frequently mutated genes. B. Venn diagram defining genetic markers for solid tumor diagnosis comprising four different panels each relating to a different solid tumor. Panels show overlapping nature of recurrent gene mutations in lung, breast, colorectal and pancreatic solid tumors), resulting in 12 different groupings of genetic markers. The coding (exonic) regions of many genes (italics) are mutated in diseases disclosed in more than one panel. The lung cancer panel covers all coding regions of 21 frequently mutated genes, the breast cancer panel covers all coding regions of 20 frequently mutated genes, the colorectal cancer panel covers all coding regions of 20 frequently mutated genes and the pancreas cancer panel covers all coding regions of 20 frequently mutated genes.
Figure 1B:
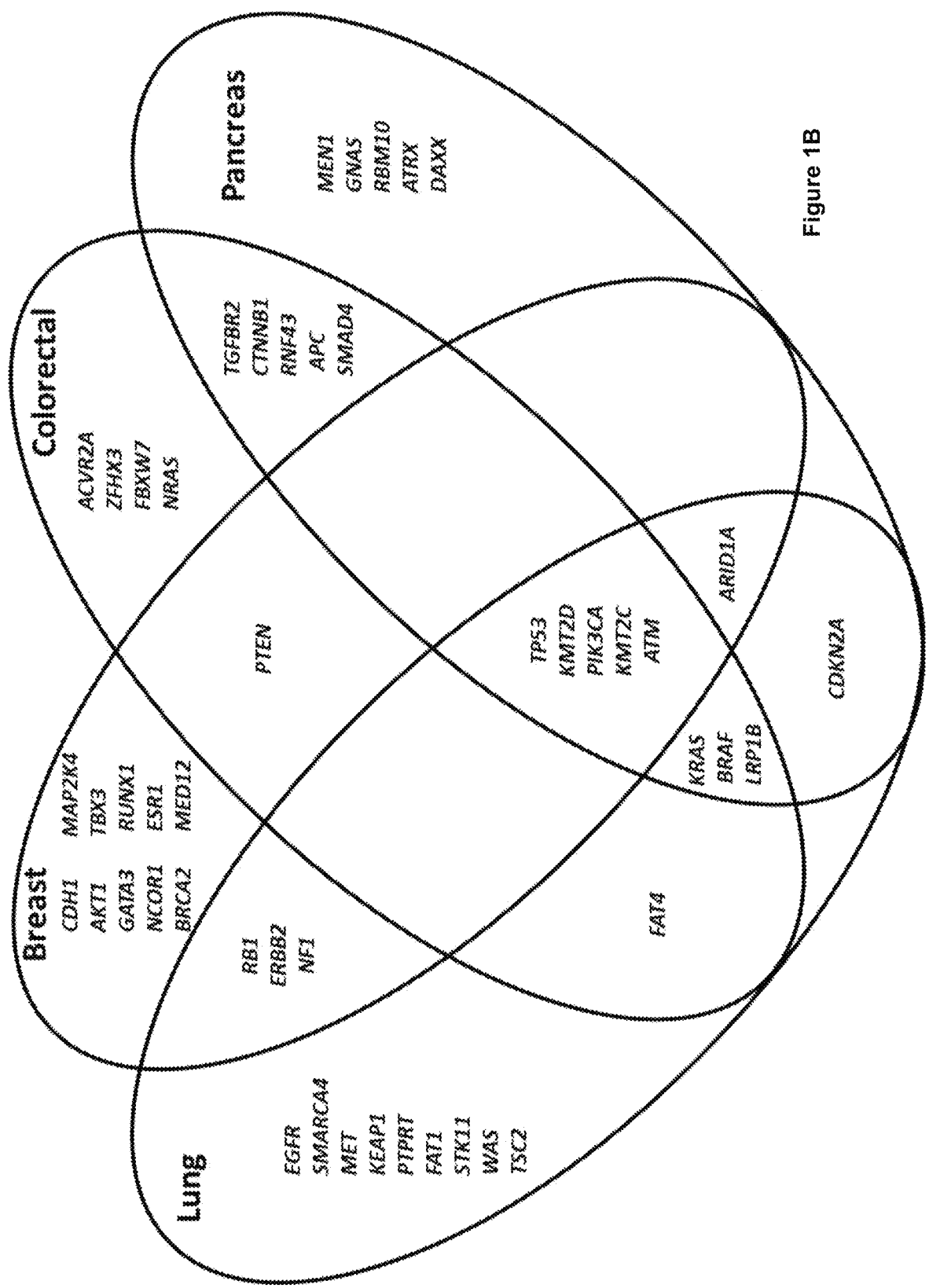

A proliferative disease is a disease characterised by excessive proliferation of cells. Preferably, said proliferative disease is a tumour of the haematopoietic or lymphoid tissues, more preferably selected from the group consisting of a lymphoproliferative disease, a leukaemia, a lymphoma, a myelodysplastic syndrome, myeloproliferative neoplasm or a solid tumour. Said leukemia is any blood cancer resulting in high numbers of abnormal blood cells, preferably selected from the group consisting of a myeloid cancer and a lymphoid leukaemia, wherein said myeloid cancer is selected from the group consisting of acute myeloid leukaemia (AML), myelodysplastic syndrome (MDS) and myeloproliferative neoplasm (MPN), while said lymphoid leukaemia is selected from the group consisting of chronic lymphocytic leukaemia (CLL) and acute lymphoblastic leukaemia (ALL). Said lymphoma is any blood cancer that develops from lymphocytes, preferably selected from the group consisting of a Hodgkin's lymphoma (HL), a non-Hodgkin lymphoma (NHL), and a lymphoproliferative disease, more preferably Hodgkin's lymphoma (HL) or a non-Hodgkin lymphoma (NHL) selected from the group consisting of follicular lymphoma (FL), Waldenström's lymphoma (Waldenström's macroglobulinemia, WL) and diffuse large B-cell lymphoma (DLBCL). Said solid tumour is any cancer that does not contain cysts and is preferably selected from the group consisting of a sarcoma, a carcinoma and a lymphoma, more preferably lung, breast, colorectal, pancreatic, liver, brain, kidney, stomach, uterine, cervical, prostate and testicular cancers, even more preferably selected from the group consisting of lung, breast, colorectal and pancreatic cancers. In a more preferred embodiment, said proliferative disease is selected from the group consisting of:
  a myeloid cancer selected from the group consisting of acute myeloid leukaemia (AML), myelodysplastic syndrome (MDS) and myeloproliferative neoplasm (MPN);
  multiple myeloma (MM);
  a lymphoid leukaemia selected from the group consisting of chronic lymphocytic leukaemia (CLL) and acute lymphoblastic leukaemia (ALL);
  a lymphoma selected from the group consisting of diffuse large B-cell lymphoma (DLBCL), follicular lymphoma (FL), Waldenström's lymphoma (WL) and Hodgkin's lymphoma; and a solid tumour (liquid biopsy) selected from the group consisting of lung, breast, colorectal and pancreatic cancers. In an even more preferred embodiment, said proliferative disease is selected from the group consisting of: acute myeloid leukaemia (AML), multiple myeloma (MM), chronic lymphocytic leukaemia (CLL), acute lymphoblastic leukaemia (ALL), diffuse large B-cell lymphoma (DLBCL), follicular lymphoma (FL), Waldenström's lymphoma (WL), Hodgkin's lymphoma (HL), myeloproliferative neoplasm (MNP) and myelodysplastic syndrome (MDS). In a particularly preferred embodiment of the present invention, said proliferative disease is selected from one of the following four groups (also shown in FIG. 1) (1) a lymphoid leukaemia selected from the group consisting of: chronic lymphocytic leukaemia (CLL) and acute lymphoblastic leukaemia (ALL), (2) a myeloid cancer selected from the group consisting of: acute myeloid leukaemia (AML), myeloproliferative neoplasm (MPN) and myelodysplastic syndrome (MDS), (3) multiple myeloma (MM), and (4) a lymphoma selected from the group consisting of: Hodgkin's lymphoma (HL), diffuse large B-cell lymphoma (DLBCL), follicular lymphoma (FL) and Waldenström's lymphoma (WL). In a more particularly preferred embodiment of the present invention, said proliferative disease is selected from the group consisting of acute myeloid leukaemia (AML), multiple myeloma (MM), myelodysplastic syndrome (MDS) and follicular lymphoma (FL), most preferably said proliferative disease is acute myeloid leukaemia (AML) and multiple myeloma (MM).

Figure 6:
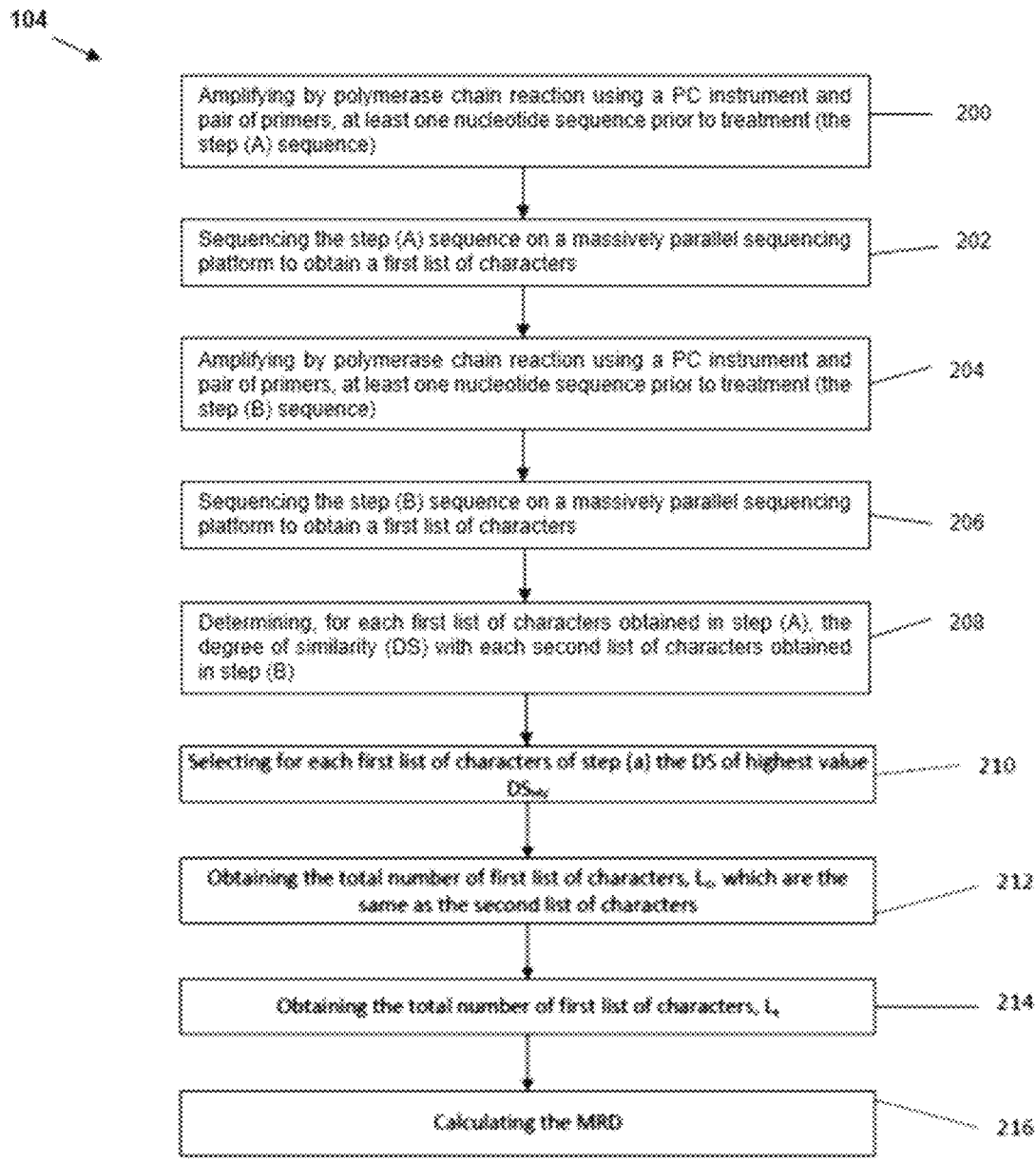
FIG. 6. Flowchart of an example of a method for calculating the level of minimum residual disease (MRD) in accordance with part of the method of the present invention.

Step (A) of the method, system or kit for determining the presence or absence of minimal residual disease (MRD) in a subject who has been treated for a disease, as well as step (A) of the method of treatment of disease in a subject who has been treated for said disease which comprises said method for determining the presence or absence of minimal residual disease, comprises the sequential steps (biological techniques) of:
  amplifying by polymerase chain reaction using a pair of primers comprising a locus-specific forward primer and a locus-specific reverse primer, at least one nucleotide sequence comprised in genomic DNA from a tissue sample obtained from said subject prior to treatment for said disease (block 200 of FIG. 6); and
  sequencing each amplified nucleotide sequence, whereby a first list of characters reading from left to right is obtained from each nucleotide sequence thus sequenced (block 202 of FIG. 6);

In an analogous manner, the step (B) of the method, system or kit for determining the presence or absence of minimal residual disease (MRD) in a subject who has been treated for a disease comprises the sequential steps (biological techniques) of:
  amplifying by polymerase chain reaction using the same locus-specific forward primer and the same locus-specific reverse primer as in step (A), at least one nucleotide sequence comprised in an amount, D, of genomic DNA from a tissue sample obtained from said subject after treatment for said disease, wherein the genomic DNA has an average weight, k, per diploid cell of said biological sample (block 204 of FIG. 6); and
  sequencing each amplified nucleotide sequence, whereby a second list of characters reading from left to right is obtained from each nucleotide sequence thus sequenced (block 206 of FIG. 6); Steps (A) and (B) may be performed at the same time or sequentially, either with step (A) before step (B) or vice versa. Each nucleotide sequence amplified in steps (A) and (B) is shorter than 400 nucleotides (and thus, shorter than 400 base pairs), preferably shorter than 350 nucleotides, more preferably shorter than 300 nucleotides. Said nucleotide sequence is either a mutated nucleotide sequence or a non-mutated nucleotide sequence of a gene, wherein when a nucleotide sequence is mutated it is a genetic marker.

In the present invention, said mutated nucleotide sequence comprises a mutation selected from the group of: a single nucleotide variant mutation, an indel mutation and somatic gene rearrangement mutation. Thus, in the present invention, the disease is characterised by the presence of at least one somatic mutation in a nucleotide sequence of a gene, wherein said mutation is a single nucleotide variant mutation (SNV) or an insertion-deletion (indel) mutation or a somatic gene rearrangement mutation. In one embodiment, said disease results from a single nucleotide variant mutation or an indel mutation or a somatic gene rearrangement mutation. Preferably, said somatic gene rearrangement mutation is an immunoglobulin gene rearrangement mutation. More preferably said disease is characterised by high allelic load and/or at least one tumor clonotypic nucleotide sequence at least one point mutation (SNV) or at least one indel.

In a preferred embodiment, said disease is acute myeloid leukaemia (AML), myeloproliferative neoplasm (MPN) or a myelodysplastic syndrome (MDS), and is characterised by a mutation in the nucleotide sequence of a gene selected from the group (panel 1) consisting of: ASXL1, BCOR, BCORL1, CALR, CBL, CEBPA, CSF3R, DNMT3A, EGLN1, EPAS1, EPOR, ETV6, EZH2, FLT3, IDH1, IDH2, JAK2, KDM6A, KIT, KMT2A, KRAS, MPL, NF1, NPM1, NRAS, PHF6, PRPF40B, RAD21, RUNX1, SETBP1, SF3A1, SF3B1, SH2B3, SMC1A, SRSF2, STAG2, TET2, THPO, TP53, U2AF1, VHL, WT1 and ZRSR2. More preferably, said disease is acute myeloid leukaemia (AML), myeloproliferative neoplasm (MPN) or a myelodysplastic syndrome (MDS), and is characterised by:
 an indel mutation in the nucleotide sequence of a gene selected from the group (panel 1.2) consisting of: ASXL1, BCOR, BCORL1, CALR, CBL, CEBPA, CSF3R, DNMT3A, EGLN1, EPAS1, EPOR, ETV6, EZH2, FLT3, IDH1, IDH2, JAK2, KDM6A, KIT, KMT2A, KRAS, MPL, NF1, NPM1, NRAS, PHF6, PRPF40B, RAD21, RUNX1, SETBP1, SF3A1, SF3B1, SH2B3, SMC1A, SRSF2, STAG2, TET2, THPO, TP53, U2AF1, VHL, WT1 and ZRSR2, or
 a single nucleotide variant mutation in the nucleotide sequence of a gene selected from the group (panel 1.3) consisting of: ASXL1, BCOR, BCORL1, CALR, CBL, CEBPA, CSF3R, DNMT3A, EGLN1, EPAS1, EPOR, ETV6, EZH2, FLT3, IDH1, IDH2, JAK2, KDM6A, KIT, KMT2A, KRAS, MPL, NF1, NPM1, NRAS, PHF6, PRPF40B, RAD21, RUNX1, SETBP1, SF3A1, SF3B1, SH2B3, SMC1A, SRSF2, STAG2, TET2, THPO, TP53, U2AF1, VHL, WT1 and ZRSR2.

Even more preferably, said disease is acute myeloid leukaemia (AML), myeloproliferative neoplasm (MPN) or a myelodysplastic syndrome (MDS), and is characterised by:
 an indel mutation or single nucleotide variant mutation in the nucleotide sequence of a gene selected from the group (panel 1.4) consisting of: IDH1, IDH2, JAK2, KIT, KRAS, NPM1 and NRAS, still more preferably in the group (panel 1.4.1) consisting of: IDH1 R132C, IDH1 R132H, IDH2 R140Q, IDH2 R172K, JAK2 V617F, KIT D816V, KRAS G12A, KRAS G12C, KRAS G12D, KRAS G12R, KRAS G12S, KRAS G12V, KRAS G13D, KRAS T58I, NPM1 W290fs (NPM1 ins), NRAS G13D, NRAS G12V, NRAS G12D and NRAS Q61R.

In another preferred embodiment, said disease is chronic lymphocytic leukaemia (CLL) or acute lymphoblastic leukaemia (ALL), and is characterised by a mutation in the nucleotide sequence of a gene selected from the group (panel 2) consisting of: IGH, IGK, EZH2, FLT3, JAK2, KRAS, NRAS, PHF6, SF3B1, TP53, IL7R, PTEN, STAT5B, CRLF2, EGR2, NFKBIE, PLCG2, JAK3, JAK1, IL7, WHSC1, TYK2, FBXW7, IKZF1, BIRC3, POT1, RPS15, KLHL6, PTPN11, ATM, IRF4, BRA, XPO1, CXCR4, BCL2, CDKN2A, MYD88, KMT2D, CREBBP, PAX5, NOTCH1, STAT3 and BTK. More preferably, said disease is chronic lymphocytic leukaemia (CLL) or acute lymphoblastic leukaemia (ALL), and is characterised by:
 a somatic gene rearrangement mutation in the nucleotide sequence of a gene selected from the group (panel 2.1) consisting of: IGH and IGK, or
 an indel mutation in the nucleotide sequence of a gene selected from the group (panel 2.2) consisting of: EZH2, FLT3, JAK2, KRAS, NRAS, PHF6, SF3B1, TP53, IL7R, PTEN, STAT5B, CRLF2, EGR2, NFKBIE, PLCG2, JAK3, JAK1, IL7, WHSC1, TYK2, FBXW7, IKZF1, BIRC3, POT1, RPS15, KLHL6, PTPN11, ATM, IRF4, BRA, XPO1, CXCR4, BCL2, CDKN2A, MYD88, KMT2D, CREBBP, PAX5, NOTCH1, STAT3 and BTK, or
 a single nucleotide variant mutation in the nucleotide sequence of a gene selected from the group (panel 2.3) consisting of: EZH2, FLT3, JAK2, KRAS, NRAS, PHF6, SF3B1, TP53, IL7R, PTEN, STAT5B, CRLF2, EGR2, NFKBIE, PLCG2, JAK3, JAK1, IL7, WHSC1, TYK2, FBXW7, IKZF1, BIRC3, POT1, RPS15, KLHL6, PTPN11, ATM, IRF4, BRA, XPO1, CXCR4, BCL2, CDKN2A, MYD88, KMT2D, CREBBP, PAX5, NOTCH1, STAT3 and BTK.

Even more preferably, said disease is chronic lymphocytic leukaemia (CLL) or acute lymphoblastic leukaemia (ALL), and is characterised by:
 a somatic gene rearrangement mutation in the nucleotide sequence of a gene selected from the group (panel 2.4) consisting of: IGH and IGK, or
 an indel mutation or single nucleotide variant mutation in the nucleotide sequence of a gene selected from the group (panel 2.5) consisting of: JAK2, KRAS and NRAS, still more preferably in the group (panel 2.5.1) consisting of: JAK2 V617F, KRAS G12A, KRAS G12C, KRAS G12D, KRAS G12R, KRAS G12S, KRAS G12V, KRAS G13D, NRAS G13D, NRAS G12V, NRAS G12D and NRAS Q61R.

In another preferred embodiment, said disease is diffuse large B-cell lymphoma (DLBCL), follicular lymphoma (FL), Waldenström's lymphoma (WL) or Hodgkin's lymphoma, and is characterised by a mutation in the nucleotide sequence of a gene selected from the group (panel 3) consisting of: ARID1A, ARID1B, B2M, BCL10, BCL2, BCL7A, BRAF, BTG1, BTK, CARD11, CCND3, CD58, CD79A, CD79B, CDKN2A, CDKN2B, CIITA, CREBBP, CTSS, CXCR4, EP300, ETS1, EZH2, FOXO1, GNA13, HIST1H1E, HNRNPK, ID3, IKZF3, IRF4, IRF8, ITPKB, KMT2D, KRAS, MEF2B, MFHAS1, MUM1, MYC, MYD88, NOTCH1, P2RY8, PAX5, PCBP1, PIM1, PIM2, PRDM1, RRAGC, S1PR2, SMARCA4, SOCS1, STAT3, STAT6, TCF3, TNFAIP3, TNFRSF14, TP53 and XPO1. More preferably, said disease is diffuse large B-cell lymphoma (DLBCL), follicular lymphoma (FL), Waldenström's lymphoma (WL) or Hodgkin's lymphoma, and is characterised by:
- an indel mutation in the nucleotide sequence of a gene selected from the group (panel 3.2) consisting of: ARID1A, ARID1B, B2M, BCL10, BCL2, BCL7A, BRAF, BTG1, BTK, CARD11, CCND3, CD58, CD79A, CD79B, CDKN2A, CDKN2B, CIITA, CREBBP, CTSS, CXCR4, EP300, ETS1, EZH2, FOXO1, GNA13, HIST1H1E, HNRNPK, ID3, IKZF3, IRF4, IRF8, ITPKB, KMT2D, KRAS, MEF2B, MFHAS1, MUM1, MYC, MYD88, NOTCH1, P2RY8, PAX5, PCBP1, PIM1, PIM2, PRDM1, RRAGC, S1PR2, SMARCA4, SOCS1, STAT3, STAT6, TCF3, TNFAIP3, TNFRSF14, TP53 and XPO1, or
- a single nucleotide variant mutation in the nucleotide sequence of a gene selected from the group (panel 3.3) consisting of: ARID1A, ARID1B, B2M, BCL10, BCL2, BCL7A, BRAF, BTG1, BTK, CARD11, CCND3, CD58, CD79A, CD79B, CDKN2A, CDKN2B, CIITA, CREBBP, CTSS, CXCR4, EP300, ETS1, EZH2, FOXO1, GNA13, HIST1H1E, HNRNPK, ID3, IKZF3, IRF4, IRF8, ITPKB, KMT2D, KRAS, MEF2B, MFHAS1, MUM1, MYC, MYD88, NOTCH1, P2RY8, PAX5, PCBP1, PIM1, PIM2, PRDM1, RRAGC, S1PR2, SMARCA4, SOCS1, STAT3, STAT6, TCF3, TNFAIP3, TNFRSF14, TP53 and XPO1.

Even more preferably, said disease is diffuse large B-cell lymphoma (DLBCL), follicular lymphoma (FL), Waldenström's lymphoma (WL) or Hodgkin's lymphoma, and is characterised by:
- an indel mutation or single nucleotide variant mutation in the nucleotide sequence of a gene selected from the group (panel 3.4) consisting of: EZH2, KMT2D and KRAS, still more preferably in the group (panel 3.4.1) consisting of: EZH2 Y646S, KMT2D Q2014fs (KMT2D p.Q2014fs) and KRAS G12A (KRAS p.G12A). Yet even more preferably, said disease is follicular lymphoma (FL) and is characterised by:
- a single nucleotide variant mutation in the nucleotide sequence of a gene selected from the group consisting of: EZH2, KMT2D and KRAS, still more preferably from the group consisting of: EZH2 Y646S, KMT2D Q2014fs and KRAS G12A.

In yet another preferred embodiment, said disease is multiple myeloma (MM), and is characterised by a mutation in the nucleotide sequence of a gene selected from the group (panel 4) consisting of: IGH, IGK, CRBN, IRF4, TP53, NFKB2, KRAS, NRAS, BRAF, FAM46C, FGFR3, DIS3, TRAF3, ATM, MAX, RB1, CYLD, CCND1, NF1, KLHL6, PTPN11, ACTG1, MAF, ZNF292, ROBO1, EGR1, FAT3, PRKD2, HUWE1, TRAF2, CDKN1B, RASA2, UBR5, ZFHX4, DUSP2, SP140, BIRC2, CRBN and LTB. More preferably, said disease is multiple myeloma (MM), and is characterised by:
- a somatic gene rearrangement mutation in the nucleotide sequence of a gene selected from the group (panel 4.1) consisting of: IGH and IGK, or
- an indel mutation in the nucleotide sequence of a gene selected from the group (panel 4.2) consisting of: CRBN, IRF4, TP53, NFKB2, KRAS, NRAS, BRAF, FAM46C, FGFR3, DIS3, TRAF3, ATM, MAX, RB1, CYLD, CCND1, NF1, KLHL6, PTPN11, ACTG1, MAF, ZNF292, ROBO1, EGR1, FAT3, PRKD2, HUWE1, TRAF2, CDKN1B, RASA2, UBR5, ZFHX4, DUSP2, SP140, BIRC2, CRBN and LTB, or
- a single nucleotide variant mutation in the nucleotide sequence of a gene selected from the group (panel 4.3) consisting of: CRBN, IRF4, TP53, NFKB2, KRAS, NRAS, BRAF, FAM46C, FGFR3, DIS3, TRAF3, ATM, MAX, RB1, CYLD, CCND1, NF1, KLHL6, PTPN11, ACTG1, MAF, ZNF292, ROBO1, EGR1, FAT3, PRKD2, HUWE1, TRAF2, CDKN1B, RASA2, UBR5, ZFHX4, DUSP2, SP140, BIRC2, CRBN and LTB.

Even more preferably, said disease is multiple myeloma (MM), and is characterised by:
- a somatic gene rearrangement mutation in the nucleotide sequence of a gene selected from the group (panel 4.4) consisting of: IGH and IGK, or
- an indel mutation or single nucleotide variant mutation in the nucleotide sequence of a gene selected from the group (panel 4.5) consisting of: KRAS and NRAS, still more preferably in the group (panel 4.5.1) consisting of: KRAS G12A, KRAS G12C, KRAS G12D, KRAS G12R, KRAS G12S, KRAS G12V, KRAS G13D, KRAS Q61R, NRAS G13D, NRAS G12V, NRAS G12D, NRAS Q61H and NRAS Q61R.

In another preferred embodiment, said disease is a solid lung tumor and is characterised by a mutation in the nucleotide sequence of a gene selected from the group (panel 5) consisting of: TSC2, WAS, EGFR, SMARCA4, MET, KEAP1, PTPRT, FAT1, STK11, RB1, ERBB2, NF1, FAT4, TP53, KMT2D, PIK3CA, KMT2C, ATM, KRAS, BRAF, LRP1B, ARID1A and CDKN2A. More preferably, said disease is lung cancer, and is characterised by:
- an indel mutation in the nucleotide sequence of a gene selected from the group (panel 5.1) consisting of: EGFR, SMARCA4, MET, KEAP1, PTPRT, FAT1, STK11, RB1, ERBB2, NF1, FAT4, TP53, KMT2D, PIK3CA, KMT2C, ATM, KRAS, BRAF, LRP1B, ARID1A and CDKN2A, or
- a single nucleotide variant mutation in the nucleotide sequence of a gene selected from the group (panel 5.2) consisting of: TSC2, WAS, EGFR, SMARCA4, MET, KEAP1, PTPRT, FAT1, STK11, RB1, ERBB2, NF1, FAT4, TP53, KMT2D, PIK3CA, KMT2C, ATM, KRAS, BRAF, LRP1B, ARID1A and CDKN2A. Even more preferably, said disease is a solid lung tumor and is characterised by a single nucleotide variant mutation in the nucleotide sequence of a gene selected from the group (panel 5) consisting of: TSC2 L248V (TSC2 p.L248V) and WAS T45M (WAS p.T45M).

In another preferred embodiment, said disease is a solid breast tumor and is characterised by a mutation in the nucleotide sequence of a gene selected from the group (panel 6) consisting of: CDH1, AKT1, GATA3, NCOR1, BRCA2, MAP2K4, TBX3, RUNX1, ESR1, MED12, RB1, ERBB2, NF1, PTEN, TP53, KMT2D, PIK3CA, KMT2C, ATM and ARID1A. More preferably, said disease is breast cancer, and is characterised by:
- an indel mutation in the nucleotide sequence of a gene selected from the group (panel 6.1) consisting of: CDH1, AKT1, GATA3, NCOR1, BRCA2, MAP2K4, TBX3, RUNX1, ESR1, MED12, RB1, ERBB2, NF1, PTEN, TP53, KMT2D, PIK3CA, KMT2C, ATM and ARID1A, or
- a single nucleotide variant mutation in the nucleotide sequence of a gene selected from the group (panel 6.2) consisting of: CDH1, AKT1, GATA3, NCOR1, BRCA2, MAP2K4, TBX3, RUNX1, ESR1, MED12, RB1, ERBB2, NF1, PTEN, TP53, KMT2D, PIK3CA, KMT2C, ATM and ARID1A.

In another preferred embodiment, said disease is a solid colorectal tumor and is characterised by a mutation in the nucleotide sequence of a gene selected from the group (panel 7) consisting of: TGFBR2, CTNNB1, RNF43, APC, SMAD4, FAT4, TP53, KMT2D, PIK3CA, KMT2C, ATM, KRAS, BRAF, LRP1B and PTEN. More preferably, said disease is colorectal cancer, and is characterised by:
- an indel mutation in the nucleotide sequence of a gene selected from the group (panel 7.1) consisting of: TGFBR2, CTNNB1, RNF43, APC, SMAD4, FAT4, TP53, KMT2D, PIK3CA, KMT2C, ATM, KRAS, BRAF, LRP1B and PTEN, or
- a single nucleotide variant mutation in the nucleotide sequence of a gene selected from the group (panel 7.2) consisting of: TGFBR2, CTNNB1, RNF43, APC, SMAD4, FAT4, TP53, KMT2D, PIK3CA, KMT2C, ATM, KRAS, BRAF, LRP1B and PTEN.

In another preferred embodiment, said disease is a solid pancreatic tumor and is characterised by a mutation in the nucleotide sequence of a gene selected from the group (panel 8) consisting of: TGFBR2, CTNNB1, RNF43, APC, SMAD4, MEN1, GNAS, RBM10, ATRX, DAXX, TP53, KMT2D, PIK3CA, KMT2C, ATM, KRAS, BRAF, LRP1B, ARID1A and CDKN2A. More preferably, said disease is pancreas cancer, and is characterised by:
- an indel mutation in the nucleotide sequence of a gene selected from the group (panel 8.1) consisting of: TGFBR2, CTNNB1, RNF43, APC, SMAD4, MEN1, GNAS, RBM10, ATRX, DAXX, TP53, KMT2D, PIK3CA, KMT2C, ATM, KRAS, BRAF, LRP1B, ARID1A and CDKN2A, or
- a single nucleotide variant mutation in the nucleotide sequence of a gene selected from the group (panel 8.2) consisting of: TGFBR2, CTNNB1, RNF43, APC, SMAD4, MEN1, GNAS, RBM10, ATRX, DAXX, TP53, KMT2D, PIK3CA, KMT2C, ATM, KRAS, BRAF, LRP1B, ARID1A and CDKN2A.

In a yet more preferred embodiment, said proliferative disease is selected from the group consisting of acute myeloid leukaemia (AML), multiple myeloma (MM), myelodysplastic syndrome (MDS), follicular lymphoma (FL) and lung cancer (adenocarcinoma), wherein:
- when said disease is acute myeloid leukaemia, it is characterised by a mutation in the nucleotide sequence of a gene selected from the group consisting of: KRAS, NRAS, NPM1 and IDH2, more preferably KRAS G12D, NRAS Q61R, NPM1 W290fs (NPM1 ins) and IDH2 R172K;
- when said disease is multiple myeloma, it is characterised by a mutation in the nucleotide sequence of a gene selected from the group consisting of: KRAS, NRAS, IGK and IGH, more preferably KRAS G12D, KRAS G12A, KRAS Q61R, NRAS Q61H, IGK and IGH;
- when said disease is myelodysplastic syndrome, it is characterised by a mutation in the nucleotide sequence of a gene selected from the group consisting of: KRAS, more preferably KRAS T58I;
- when said disease is follicular lymphoma, it is characterised by a mutation in the nucleotide sequence of a gene selected from the group consisting of: EZH2, KMT2D and KRAS, more preferably EZH2 Y646S, KMT2D Q2014fs and KRAS G12A; and
- when said disease is lung cancer, it is characterised by a mutation in the nucleotide sequence of a gene selected from the group consisting of: TSC2 and WAS, more preferably TSC2 L248V and WAS T45M.

In an even more preferred embodiment, said proliferative disease is selected from the group consisting of acute myeloid leukaemia (AML), multiple myeloma (MM), myelodysplastic syndrome (MDS) and follicular lymphoma (FL), wherein:
- when said disease is acute myeloid leukaemia it is characterised by a mutation in the nucleotide sequence of a gene selected from the group consisting of: KRAS, NRAS, NPM1 and IDH2, more preferably KRAS G12D, NRAS Q61R, NPM1 W290fs (NPM1 ins) and IDH2 R172K;
- when said disease is multiple myeloma it is characterised by a mutation in the nucleotide sequence of a gene selected from the group consisting of: KRAS, NRAS, IGK and IGH, more preferably KRAS G12D, KRAS G12A, KRAS Q61R, NRAS Q61H, IGK and IGH;
- when said disease is myelodysplastic syndrome it is characterised by a mutation in the nucleotide sequence of a gene selected from the group consisting of: KRAS, more preferably KRAS T58I;
- when said disease is follicular lymphoma it is characterised by a mutation in the nucleotide sequence of a gene selected from the group consisting of: EZH2, more preferably EZH2 Y646S.

In a particularly more preferred embodiment, said proliferative disease is acute myeloid leukaemia (AML) or multiple myeloma (MM):
- when said disease is acute myeloid leukaemia it is characterised by a mutation in the nucleotide sequence of a gene selected from the group consisting of: KRAS, NRAS and NPM1, more preferably KRAS G12D, NRAS Q61R and NPM1 W290fs (NPM1 ins);
- when said disease is multiple myeloma it is characterised by a mutation in the nucleotide sequence of a gene selected from the group consisting of: NRAS, IGK and IGH, more preferably NRAS Q61H, IGK and IGH.

The biological sample in steps (A), (B) and (H)(iii)(a) comprises a sample of biological matter taken from a subject. Said tissue sample comprises at least one nucleotide sequence in a region of gene comprised in at least one cell. Preferably said biological sample comprises at least one nucleotide sequence in the genomic DNA of at least one cell in a tissue, blood, urine, faeces, saliva, mucus, sperm, bone, hair and/or nails. The biological sample in step (A) is a diagnosis (or calibration or control) sample obtained from the subject in whom the presence or absence of minimal residual disease (MRD) is being determined and is diagnostic for the disease prior to a treatment. The biological sample in step (B) is a test (or follow-up) sample also obtained from said subject diagnostic for minimal residual disease. The biological sample in step (H)(iii)(a) is a control sample obtained from a subject without:
- the disease that the subject in whom the presence or absence of minimal residual disease (MRD) is being determined has been treated for, and
- the genetic marker (and thus mutation) by which the disease is characterised. The biological sample in step (A) which was taken before treatment of the disease from the same subject as the biological sample in step (B) and preferably is a sample with high allelic or clonal load. The nucleotide sequence amplified in step (B) is comprised in an amount, D, of genomic DNA obtained from a biological sample. The biological sample in step (B) has an average weight, k, of genomic DNA per diploid cell.

Said genomic DNA in each biological sample is preferably circulating free DNA (cfDNA), even more preferably circulating tumor DNA (ctDNA).

Each nucleotide sequence in the genomic DNA is amplified by PCR using a pair of primers, whereby said pair of primers comprises a locus-specific forward primer and a locus-specific reverse primer which bind to different complementary sequences on the Watson and Crick strands adjacent to said nucleotide sequence, thereby identifying the 5' and 3' limits of said nucleotide sequence. In particular, the 3' end of the nucleotide sequence of the Watson strand begins with the nucleotide which is adjacent to the nucleotide at the 5' end of the sequence that is annealed with the forward primer. Conversely, the 5' end of the nucleotide sequence of the Watson strand begins with the nucleotide complementary to the nucleotide which is adjacent to the nucleotide at the 5' end of the sequence that is annealed with the reverse primer. Likewise, the 3' end of the nucleotide sequence of the Crick strand begins with the nucleotide which is adjacent to the nucleotide at the 5' end of the sequence that is annealed with the reverse primer. Conversely, the 5' end of the nucleotide sequence of the Crick strand begins with the nucleotide complementary to the nucleotide which is adjacent to the nucleotide at the 5' end of the sequence that is annealed with the forward primer. Accordingly, a DNA polymerase attaches to the 5' end of the aforementioned primers and replicates the nucleotide sequence multiple times.

The primers are locus-specific primers chosen so as to identify a specific mutation or variant of a nucleotide sequence (i.e. a genetic marker) that may be present in the biological sample in step (A), wherein said mutation is indicative of the disease for which said subject has been treated. Thus, the method of the present invention applies to any genetic marker of a proliferative disease that is detectable using an amplicon sequencing approach.

The mutation or variant of a nucleotide sequence present in the biological sample obtained from the subject prior to treatment for the disease is the genetic marker which is indicative of said disease and is preferably that identified in said biological sample in greatest proportion (i.e. greatest variant read frequency, VRF). Variant read frequency is the relative frequency of a genetic marker, as defined herein, expressed as a fraction (or as a percentage by multiplying said fraction by 100). In other words, it is the relative frequency of the mutation in the at least one nucleotide sequence comprised in genomic DNA that is amplified by the locus-specific forward primer and a locus-specific reverse primer and is calculated by determining the fraction of the lists of characters obtained from nucleotide sequences comprising said genetic marker out of the total of all lists of characters obtained from nucleotide sequences.

Preferably, said pair of primers is selected from any of the pairs of sequences of SEQ ID NO:1 to SEQ ID NO:130 disclosed in Tables 1, 2 and 3. More preferably, when the mutation is a somatic gene rearrangement mutation the primers used to amplify a nucleotide sequence of the IgH gene are any of SEQ ID NO:1 to SEQ ID NO:28 shown in Table (wherein SEQ ID NO:28 may be combined with any of SEQ ID NO:1 to 27), while the primers used to amplify a nucleotide sequence of the IgK gene are any of SEQ ID NO:29 to SEQ ID NO:38 shown in Table 2 (wherein SEQ ID NO:29 to 34 may be combined with any of SEQ ID NO:35 or 36 to form a primer pair and SEQ ID NO: 37 and 38 are a pair).

TABLE 1

Primers for amplification of nucleotide sequences of IgH

| Family primers | Tube | Sequence identifier | Primer name | Sequence | Sense |
|---|---|---|---|---|---|
| $V_H$ | Tube A (CDR1) | SEQ ID NO: 1 | $V_H$1-FR1 | GGCCTCAGTGAAGGTCTCCTGCAAG | Forward |
| | | SEQ ID NO: 2 | $V_H$2-FR1 | GTCTGGTCCTACGCTGGTGAAACCC | |
| | | SEQ ID NO: 3 | $V_H$3-FR1 | CTGGGGGGTCCCTGAGACTCTCCTG | |
| | | SEQ ID NO: 4 | $V_H$4-FR1 | CTTCGGAGACCCTGTCCCTCACCTG | |
| | | SEQ ID NO: 5 | $V_H$5-FR1 | CGGGGAGTCTCTGAAGATCTCCTGT | |
| | | SEQ ID NO: 6 | $V_H$6-FR1 | TCGCAGACCCTCTCACTCACCTGTG | |
| | Tube B (CDR2) | SEQ ID NO: 7 | $V_H$1-FR2 | CTGGGTGCGACAGGCCCCTGGACAA | |
| | | SEQ ID NO: 8 | $V_H$2-FR2 | TGGATCCGTCAGCCCCCAGGGAAGG | |
| | | SEQ ID NO: 9 | $V_H$3-FR2 | GGTCCGCCAGGCTCCAGGGAA | |
| | | SEQ ID NO: 10 | $V_H$4-FR2 | TGGATCCGCCAGCCCCCAGGGAAGG | |
| | | SEQ ID NO: 11 | $V_H$5-FR2 | GGGTGCGCCAGATGCCCGGGAAAGG | |
| | | SEQ ID NO: 12 | $V_H$6-FR2 | TGGATCAGGCAGTCCCCATCGAGAG | |
| | | SEQ ID NO: 13 | $V_H$7-FR2 | TTGGGTGCGACAGGCCCCTGGACAA | |
| | Tube C (CDR3) | SEQ ID NO: 14 | $V_H$1-FR3 | TGGAGCTGAGCAGCCTGAGATCTGA | |
| | | SEQ ID NO: 15 | $V_H$2-FR3 | CAATGACCAACATGGACCCTGTGGA | |
| | | SEQ ID NO: 16 | $V_H$3-FR3 | TCTGCAAATGAACAGCCTGAGAGCC | |
| | | SEQ ID NO: 17 | $V_H$4-FR3 | GAGCTCTGTGACCGCCGCGGACACG | |
| | | SEQ ID NO: 18 | $V_H$5-FR3 | CAGCACCGCCTACCTGCAGTGGAGC | |

TABLE 1-continued

Primers for amplification of nucleotide sequences of IgH

| Family primers | Tube | Sequence identifier | Primer name | Sequence | Sense |
|---|---|---|---|---|---|
| | | SEQ ID NO: 19 | $V_H6$-FR3 | GTTCTCCCTGCAGCTGAACTCTGTG | |
| | | SEQ ID NO: 20 | $V_H7$-FR3 | CAGCACGGCATATCTGCAGATCAG | |
| $D_H$ | Tube D | SEQ ID NO: 21 | $D_H1$ | GGCGGAATGTGTGCAGGC | |
| | | SEQ ID NO: 22 | $D_H2$ | GCACTGGGCTCAGAGTCCTCT | |
| | | SEQ ID NO: 23 | $D_H3$ | GTGGCCCTGGGAATATAAAA | |
| | | SEQ ID NO: 24 | $D_H4$ | AGATCCCCAGGACGCAGCA | |
| | | SEQ ID NO: 25 | $D_H5$ | CAGGGGGACACTGTGCATGT | |
| | | SEQ ID NO: 26 | $D_H6$ | TGACCCCAGCAAGGGAAGG | |
| | Tube E | SEQ ID NO: 27 | $D_H7$ | CACAGGCCCCCTACCAGC | |
| $J_H$ | Tubes A-E | SEQ ID NO: 28 | JH57 | CTTACCTGAGGAGACGGTGACC | Reverse |

TABLE 2

Primers for amplification of nucleotide sequences of IgK

| Family primers | Tube | Sequence identifier | Primer name | Sequence | Sense |
|---|---|---|---|---|---|
| $V_K$ | Tube F, G | SEQ ID NO: 29 | $V_K1$ f/6 | TCAAGGTTCAGCGGCAGTGGATCTG | Forward |
| | | SEQ ID NO: 30 | $V_K2f$ | GGCCTCCATCTCCTGCAGGTCTAGTC | |
| | | SEQ ID NO: 31 | $V_K3f$ | CCCAGGCTCCTCATCTATGATGCATCC | |
| | | SEQ ID NO: 32 | $V_K4$ | CAACTGCAAGTCCAGCCAGAGTGTTTT | |
| | | SEQ ID NO: 33 | $V_K5$ | CCTGCAAAGCCAGCCAAGACATTGAT | |
| | | SEQ ID NO: 34 | $V_K6$ | GACCGATTTCACCCTCACAATTAATCC | |

TABLE 2-continued

Primers for amplification of nucleotide sequences of IgK

| Family primers | Tube | Sequence identifier | Primer name | Sequence | Sense |
|---|---|---|---|---|---|
| $J_K$ | Tube F | SEQ ID NO: 35 | $J_K1$-4 | CTTACGTTTGATCTCCACCTTGGTCCC | Reverse |
| | | SEQ ID NO: 36 | $J_K5$ | CTTACGTTTAATCTCCAGTCGTGTCCC | |
| KDEL | Tube G, H | SEQ ID NO: 37 | KDEL | CCTCAGAGGTCAGAGCAGGTTGTCCTA | |
| $J_K$-$C_K$ Intron | Tube H | SEQ ID NO: 38 | INTR | CGTGGCACCGCGAGCTGTAGAC | Forward |

Even more preferably, when the mutation is a single nucleotide variant mutation or an indel mutation the primer pair used to amplify a nucleotide sequence of the genes listed in Table 3 are any of the 46 pairs represented by the primers having SEQ ID NO:39 to SEQ ID NO:130 shown therein.

TABLE 3

Primers for amplification of nucleotide sequences of some genes that comprise single nucleotide variant mutations or indel mutations and the diseases characterised by mutations in said nucleotide sequences.

| Exemplary disease | Gene | Primer sequence 5'-3' | Sequence identifier | Sense |
|---|---|---|---|---|
| All diseases | TP53 | AAGGTGATAAAAGTGAATCTGAGGCAT | SEQ ID NO: 39 | Forward |
| | | AATGGGACAGGTAGGACCTGAT | SEQ ID NO: 40 | Reverse |
| | TP53 | CTGCTCACCATCGCTATCTGAG | SEQ ID NO: 41 | Forward |
| | | CTTTCAACTCTGTCTCCTTCCTCTTC | SEQ ID NO: 42 | Reverse |
| | TP53 | TGTGATGAGAGGTGGATGGGTA | SEQ ID NO: 43 | Forward |
| | | CCTCATCTTGGGCCTGTGTTAT | SEQ ID NO: 44 | Reverse |
| | TP53 | TCATAGGGCACCACCACACTAT | SEQ ID NO: 45 | Forward |
| | | TACAAGCAGTCACAGCACACGA | SEQ ID NO: 46 | Reverse |

TABLE 3-continued

Primers for amplification of nucleotide sequences of some genes that comprise single nucleotide variant mutations or indel mutations and the diseases characterised by mutations in said nucleotide sequences.

| Exemplary disease | Gene | Primer sequence 5'-3' | Sequence identifier | Sense |
|---|---|---|---|---|
| | TP53 | CTTGCTTACCTCGCTTAGTGCT | SEQ ID NO: 47 | Forward |
| | | GCTTCTCTTTTCCTATCCTGAGTAGTG | SEQ ID NO: 48 | Reverse |
| | TP53 | GGCTCCTGACCTGGAGTCTT | SEQ ID NO: 49 | Forward |
| | | AAGGCGCACTGGCCTCATC | SEQ ID NO: 50 | Reverse |
| | TP53 | GGCCAGACCTAAGAGCAATCAG | SEQ ID NO: 51 | Forward |
| | | CATGGCCATCTACAAGCAGTCA | SEQ ID NO: 52 | Reverse |
| | TP53 | ACAACCTCCGTCATGTGCT | SEQ ID NO: 53 | Forward |
| | | GTCTCCTTCCTCTTCCTACAGTACTC | SEQ ID NO: 54 | Reverse |
| AML, MPN, MDS, MM, CLL, ALL, cotrectal | NRAS | GCTCCTAGTACCTGTAGAGGTTAATATCC | SEQ ID NO: 55 | Forward |
| | | GTTATAGATGGTGAAACCTGTTTGTTGG | SEQ ID NO: 56 | Reverse |
| | NRAS | CGACAAGTGAGAGACAGGATCA | SEQ ID NO: 57 | Forward |
| | | TCTTGCTGGTGTGAAATGACTGAG | SEQ ID NO: 58 | Reverse |
| | KRAS | CAAAGAATGGTCCTGCACCAGTA | SEQ ID NO: 59 | Forward |
| | | AAGGCCTGCTGAAAATGACTGAATATA | SEQ ID NO: 60 | Reverse |
| | KRAS | GCTGTATCGTCAAGGCACTCTTG | SEQ ID NO: 61 | Forward |
| | | AGGTACTGGTGGAGTATTTGATAGTGTATT | SEQ ID NO: 62 | Reverse |
| | KRAS | TGTCAGCTTATTATATTCAATTTAAACCCACCT | SEQ ID NO: 63 | Forward |
| | | TCTTGGATATTCTCGACACAGCAG | SEQ ID NO: 64 | Reverse |
| MM, CLL, DLBCL, FL, WL, lung, colorectal pancreas | BRAF | CCTTCAATGACTTTCTAGTAACTCAGCA | SEQ ID NO: 65 | Forward |
| ALL, HL, AML, MPN, MDS, CLL, ALL | | CTTACCTAAACTCTTCATAATGCTTGCTCT | SEQ ID NO: 66 | Reverse |
| | FLT3 | CCCTGACAACATAGTTGGAATCACT | SEQ ID NO: 67 | Forward |
| | | CACTCCAGGATAATACACATCACAGTAAAT | SEQ ID NO: 68 | Reverse |
| | SF3B1 | CAAGATGGCACAGCCCATAAGAATA | SEQ ID NO: 69 | Forward |
| | | AGCTTTTGCTGTTGTAGCCTCT | SEQ ID NO: 70 | Reverse |
| | SF3B1 | CAAGATGGCACAGCCCATAAGA | SEQ ID NO: 71 | Forward |
| | | ACTCATGACTGTCCTTTCTTTGTTTACAT | SEQ ID NO: 72 | Reverse |
| | SF3B1 | AGGTAATTGGTGGATTTACCTTTCCT | SEQ ID NO: 73 | Forward |
| | | GGCATAGTTAAAACCTGTGTTTGGTTT | SEQ ID NO: 74 | Reverse |
| | SF3B1 | TCATTTCCTCATCAGGAGACTGGAA | SEQ ID NO: 75 | Forward |
| | | TGTGTTAAAGCCTTTATGGAAGGGTATC | SEQ ID NO: 76 | Reverse |
| | SF3B1 | GTTGGCGGATACCCTTCCATAA | SEQ ID NO: 77 | Forward |
| | | GGCATAGTTAAAACCTGTGTTTGGTTTT | SEQ ID NO: 78 | Reverse |

TABLE 3-continued

Primers for amplification of nucleotide sequences of some genes that comprise single nucleotide variant mutations or indel mutations and the diseases characterised by mutations in said nucleotide sequences.

| Exemplary disease | Gene | Primer sequence 5'-3' | Sequence identifier | Sense |
|---|---|---|---|---|
| AML, MPN, MDS, CLL, ALL, DLBCL FL, WL, HL | EZH2 | AGTTCCAATTCTCACGTCAAAGGT | SEQ ID NO: 79 | Forward |
| | | AATTATTCACTGGGCTGTGCTTACT | SEQ ID NO: 80 | Reverse |
| | EZH2 | AGTGCCTTACCTCTCCACAGTA | SEQ ID NO: 81 | Forward |
| | | CCAGTCCATTTTCACCCTCCTTTTT | SEQ ID NO: 82 | Reverse |
| CLL, ALL, DLBCL, FL, WL, HL | CREBBP | TCGCCAGAGACAAGCACTG | SEQ ID NO: 83 | Forward |
| | | GTGCAGCTCCACCAGCAT | SEQ ID NO: 84 | Reverse |
| | BCL2 | GCACCTGACGCCCTTCAC | SEQ ID NO: 85 | Forward |
| | | AAGAAGGCCACAATCCTCCC | SEQ ID NO: 86 | Reverse |
| | MYD88 | TTGGCTTGCAGGTGCCC | SEQ ID NO: 87 | Forward |
| | | GGTTGGTGTAGTCGCAGACA | SEQ ID NO: 88 | Reverse |
| | BTK | TCTTTCCCATGAGAAGCTGG | SEQ ID NO: 89 | Forward |
| | | CATCCTTGCACATCTCTAGC | SEQ ID NO: 90 | Reverse |
| | NOTCH1 | GAACTGAGGCCTGAGAGCTT | SEQ ID NO: 91 | Forward |
| | | CAGACCTGTGAGGTCGACAT | SEQ ID NO: 92 | Reverse |
| | NOTCH1 | GTCCCGCAGACATCCTGA | SEQ ID NO: 93 | Forward |
| | | GGTGGCCGATTTGGGAGATC | SEQ ID NO: 94 | Reverse |
| | NOTCH1 | CCGAAGGCTTGGGAAAGGA | SEQ ID NO: 95 | Forward |
| | | CCTCGCCTGTGGACAACAC | SEQ ID NO: 96 | Reverse |
| | XPO1 | CTCCAACCTGAACCTGAACGAA | SEQ ID NO: 97 | Forward |
| | | CTCACTGGAAATTTCTGAAGACTGTAGTT | SEQ ID NO: 98 | Reverse |
| CLL, ALL | BIRC3 | CTTTAGTAGAAGCCTGGTAAAACAGACA | SEQ ID NO: 99 | Forward |
| | | AAAAACCTGACTGGATTGAGTATATTTTCA | SEQ ID NO: 100 | Reverse |
| | BIRC3 | TTCTTAGTTTTTCACTGAAGAAGCAAACTG | SEQ ID NO: 101 | Forward |
| | | TGGTTCTTCTTCATGAAAGAAATGTACGA | SEQ ID NO: 102 | Reverse |
| | EGR2 | TCTGTCTCAGGTGGATCTTGGT | SEQ ID NO: 103 | Forward |
| | | TGACCACCTCACCACCCATAT | SEQ ID NO: 104 | Reverse |
| | FBXW7 | TTTTTGGACTGTACTGGATCAGCA | SEQ ID NO: 105 | Forward |
| | | CATGTTTTGATGGGTCATGTTGCA | SEQ ID NO: 106 | Reverse |
| | FBXW7 | TAGAGGAAGAAGTCCCAACCATGA | SEQ ID NO: 107 | Forward |
| | | TCACTTTTCCTTTCTACCCAAAAGTAATCA | SEQ ID NO: 108 | Reverse |
| | FBXW7 | CAACTGTCCTTGCTGGGAATCA | SEQ ID NO: 109 | Forward |
| | | CAAGAAGTAGCAAGCTGGCTTT | SEQ ID NO: 110 | Reverse |
| | NFKBIE | GGGACTTGAAGGATCTTCACG | SEQ ID NO: 111 | Forward |
| | | GGCTGATTCCACCTATGGCTC | SEQ ID NO: 112 | Reverse |
| AML, MPN, MDS | IDH1 | AAGAATAAAACACATACAAGTTGGAAATTTCT | SEQ ID NO: 113 | Forward |

TABLE 3-continued

Primers for amplification of nucleotide sequences of some genes that comprise single nucleotide variant mutations or indel mutations and the diseases characterised by mutations in said nucleotide sequences.

| Exemplary disease | Gene | Primer sequence 5'-3' | Sequence identifier | Sense |
|---|---|---|---|---|
| | | GAGAAGCCAT TATCTGCAAA AATATCCC | SEQ ID NO: 114 | Reverse |
| | IDH2 | GGACTAGGCG TGGGATGTTT | SEQ ID NO: 115 | Forward |
| | | GGGTTCAAAT TCTGGTTGAA AGATGG | SEQ ID NO: 116 | Reverse |
| | U2AF1 | ATTAACTGTC TTTGAAAAGA ACATGAAGTT T | SEQ ID NO: 117 | Forward |
| | | TTTCCCTTAC AGAGTCAACT GTTCATTT | SEQ ID NO: 118 | Reverse |
| | RUNX1 | AATCTGAGAC ATGGTCCCTG AGTA | SEQ ID NO: 119 | Forward |
| | | CCATCACTGT CTTCACAAAC CCA | SEQ ID NO: 120 | Reverse |
| | RUNX1 | AGACCGAGTT TCTAGGGATT CCA | SEQ ID NO: 121 | Forward |
| | | CTACCGCAGC CATGAAGAAC CAG | SEQ ID NO: 122 | Reverse |
| | KIT | AATGAAAGTT AATATGGAGA AGTTAATTGC TGC | SEQ ID NO: 123 | Forward |
| | | GTGATGCCAG CTATTATATT TCTCCTGTA | SEQ ID NO: 124 | Reverse |
| | KIT | TGAATTTAAA TGGTTTTCTT TTCTCCTCCA AC | SEQ ID NO: 125 | Forward |
| | | CACGTTTCCT TTAACCACAT AATTAGAATC ATT | SEQ ID NO: 126 | Reverse |
| | KIT | ATTTTGGTCT AGCCAGAGAC ATCAAG | SEQ ID NO: 127 | Forward |
| | | TGTGTGATAT CCCTAGACAG GATTTACATT | SEQ ID NO: 128 | Reverse |
| | KIT | TGGATGGCAC CTGAAAGCAT TT | SEQ ID NO: 129 | Forward |
| | | GAAACTTCAA GAAGATGCTC TGAGTCTAA | SEQ ID NO: 130 | Reverse |

AML = acute myeloid leukaemia
MDS = myelodysplastic syndrome
MPN = myeloproliferative neoplasm
DLBCL = diffuse large B-cell lymphoma
CLL = chronic lymphocytic leukaemia
FL = follicular lymphoma
WL = Waldenstrom's lymphoma (Waldenstrom's macroglobulinemia)
MM = multiple myeloma
HL = Hodgkin's lymphoma.

As a consequence of the fact that at least one specific variant of a nucleotide sequence is thus identified in steps (A) and (B), the steps (A) and (B) involve identifying, amplifying and sequencing at least one nucleotide sequence (i.e. one or more nucleotide sequences) in a biological sample, thus affording at least one list of characters (i.e. one or more lists of characters) corresponding thereto.

Thus, amplification of at least one nucleotide sequence present in each biological sample is performed with specific primers identifying at least one region of interest (i.e. at least one specific mutation indicative of the disease for which a subject has been treated), before processing each on a massively parallel sequencing platform. Accordingly, the test sample on this at least one region of interest was amplified and sequenced with higher, or equal to, expected sensitivity coverage. For amplification of the test sample, an amount, D, of genomic DNA (gDNA) from said test (follow-up) sample is used in PCR, and amplification is preferably repeated until a quantity sufficient for sequencing with a desired sensitivity is obtained. Preferably, an amount, D, of gDNA from said test sample is used in PCR to ensure that a sensitivity equivalent to that obtainable from sampling a given number of cells is obtained. The sensitivity is determined in every instance for application to the study of disease and residual circulating tumor cells.

The amount, D (ng), of the genomic DNA from the test (follow-up) sample which is used in PCR for sequencing with a desired sensitivity (S) is established first by measuring the concentration of DNA ([DNA], ng/µL) in the biological sample obtained from a subject after treatment for said disease (test sample) and multiplying it by the volume of said sample (µL). This value is then used to determine the number of equivalent cells (N) of the test sample used in PCR according to the following formula:

$$N=D/k$$

wherein N and D are as defined above, and k is the average weight of the genomic DNA per diploid cell of the test sample, whereby k preferably assumes a value of $6.49 \times 10^{-3}$ nanograms per cell. The number of equivalent cells used in PCR (N) of the test sample subsequently allows calculation of the volume of sample (V, µL) which it is necessary to use in the PCR in order to reach a desired sensitivity (S) according to the following formula:

$$V=1/(N \times S)$$

A sensitivity of $10^{-5}$ equates with that achievable from use of genomic DNA from at least 100,000 equivalent cells. The volume of test sample (V) determines the number of PCR experiments necessary to obtain a sufficient amount (D, ng) of genomic DNA for sequencing and, in addition, is used to calculate the amount (D) of the genomic DNA from the test sample which is used in PCR according to the following formula:

$$D=[DNA] \times V$$

Amplification may be performed by any one of the following PCR techniques selected from multiplex-PCR, and single PCR using a pair of primers. Preferably amplification is performed by multiplex-PCR.

Optionally, steps (A) and (B) may comprise a further step of isolating said at least one amplified nucleotide sequence prior to the step of sequencing using routine methods in the art. Thus, the first step of steps (A) and (B) comprises amplification of at least one nucleotide sequence obtained from at least one longer nucleotide sequence by selective amplification of said at least one nucleotide sequence over said at least one longer nucleotide sequence, wherein each longer nucleotide sequence comprises a polynucleotide, wherein said polynucleotide is preferably selected from double- or single-stranded DNA or RNA, more preferably double-stranded DNA, furthermore preferably double stranded genomic DNA. When said polynucleotide is single-stranded DNA, a complementary sequence is synthesised therefrom prior to carrying out steps (A) or (B) to afford double-stranded DNA. When said polynucleotide is RNA, a complementary double-stranded DNA is synthesised (retrotranscribed) therefrom prior to carrying out steps (A) or (B).

The at least one nucleotide sequence of each of steps (A) and (B), thus amplified and optionally isolated, is subsequently sequenced. Sequencing of a nucleotide sequence of step (A) affords a first list of characters reading from left to right corresponding thereto, wherein each first list of characters has a total number of characters, $C_t$. Moreover, the total number of first lists of characters ($L_t$) corresponds to the total number of different nucleotide sequences in step (A). Sequencing of a nucleotide sequence of step (B) likewise affords a second list of characters reading from left to right, corresponding thereto.

The sequencing is a multiplex and/or high-throughput nucleotide sequencing technique. Preferably, the sequencing is performed by a next-generation technique, more preferably massively parallel sequencing [e.g. massively parallel signature sequencing (MPSS)]. In one embodiment of the present invention, when multiple primers are used in sequencing, the sequencing steps in steps (A) and (B) are performed using barcodes to identify between the different primers used. In one especially preferred embodiment of the present invention, the sequencing is performed by massively parallel sequencing using emulsion-PCR.

Each of the separate steps of amplifying and sequencing said at least one nucleotide sequence in steps (A) and (B) may be performed by separate means (i.e. by separate instruments). Alternatively, two or all of these separate steps may be performed by the same instrument.

Sequencing of a nucleotide sequence in steps (A) and (B) affords a corresponding list of characters, whereby each character in each list of characters comprises a letter. In one embodiment of the present invention, sequencing of a nucleotide sequence in steps (A) and (B) affords a corresponding list of characters, whereby each character in each list of characters comprises a letter associated with a number (or symbol). More preferably, each letter represents the nucleotide that is identified at the corresponding position in the nucleotide sequence which has the highest quality (Q) within the limits of the sequencing method, and the number or symbol associated therewith is the quality (Q), wherein Q is an integer mapping of the probability that the letter which represents a nucleotide that is identified at the corresponding position in the nucleotide sequence is incorrect. Thus, each of the lists of characters obtained in steps (A) and (B) of the present invention is preferably comprised in a sequence format file, more preferably a .fastq file.

Alternatively, each character more preferably represents the nucleotide that is identified at the corresponding position in the nucleotide sequence in greatest proportion. In one furthermore preferred embodiment of this alternative, the letter associated with said character represents the nucleotide that is identified at the corresponding position in the nucleotide sequence in highest proportion and the number or symbol associated therewith is the proportion (e.g. as a percentage, fraction or ratio) of said nucleotide that is identified therein.

A continuous sequence of characters is a list which is unbroken by another character or absence of a character, wherein said continuous sequence of characters represents an unbroken continuous sequence of nucleotides. Analogous with that described above, each character in the continuous sequence of characters comprises one or more letter, preferably one or more letter associated with a number or symbol, more preferably wherein each letter represents the nucleotide that is identified at the corresponding position in the nucleotide sequence which has the highest quality (Q) within the limits of the sequencing method, and the number or symbol associated therewith is the quality (Q), wherein Q is an integer mapping of the probability that the letter which represents a nucleotide that is identified at the corresponding position in the nucleotide sequence is incorrect. As such, in this more preferred embodiment of the invention, said continuous sequence of characters comprises a continuous sequence of letters representing a continuous sequence of nucleotides, when each character in the continuous sequence of characters represents the nucleotide that is identified at the corresponding position which has the highest quality (Q) within the limits of the sequencing method.

Alternatively, each character in the continuous sequence of characters preferably comprises a letter associated with a number or symbol, more preferably wherein each letter represents the nucleotide that is identified at the corresponding position in the nucleotide sequence in greatest proportion. In one embodiment of this more preferred alternative, the letter associated with said character in the continuous sequence of characters represents the nucleotide that is identified at the corresponding position in the nucleotide sequence in highest proportion and the number or symbol associated therewith is the proportion (e.g. as a percentage, fraction or ratio) of said nucleotide that is identified therein. As such, in this more preferred alternative embodiment, said continuous sequence of characters comprises a continuous sequence of letters representing a continuous sequence of nucleotides, when each character in the continuous sequence of characters represents the nucleotide that is identified at the corresponding position in the continuous sequence of nucleotides in greatest proportion.

Each character in each list of characters corresponds to one nucleotide in said nucleotide sequence and the order of characters in said list corresponds to the order of nucleotides in said nucleotide sequence. Thus, the character at the left-hand end of said list corresponds to the nucleotide or proportion of nucleotides at the 3' end of the Watson strand of said nucleotide sequence and the character at the right-hand end of said list corresponds to the nucleotide or proportion of nucleotides at the 5' end of the Watson strand of said nucleotide sequence. Analogously, a complementary (or partly complementary) list of characters is obtained representing each Crick strand of said nucleotide sequence, whereby the character at the left-hand end of said list corresponds to the nucleotide or proportion of nucleotides at the 3' end of the Crick strand of said nucleotide sequence and the character at the right-hand end of said list corresponds to the nucleotide or proportion of nucleotides at the 5' end of the Crick strand of said nucleotide sequence.

Subsequently, comparison of each first list of characters obtained in step (A) is made with each second list of characters obtained in step (B). Said comparison is made so as to ultimately determine the total number of first lists of characters, $L_c$, which are the same as a second list of characters. In other words, the comparison is made so as to determine the $L_c$ which are identical with (i.e. match) a second list of characters. In order to determine $L_c$, it is necessary to determine the degree of similarity of each first list of characters obtained in step (A) with each second list of characters obtained in step (B), wherein a degree of similarity, DS, is determined for a second list of characters obtained in step (B) with a first list of characters obtained in step (A). Although methods adapted to bioinformatics are known which access external data (e.g. genetic databases derived from populations) in order to carry out the comparison step and somehow implement "biological knowledge" the method of the present invention works without the need to access external data [i.e. without the need to access data other than that obtained in steps (A) or (B)]. To this end, the first feature that is considered essential to implement is a fuzzy logic. The rate of failure of sequencers using a classical binary logic—in which sequences can only be equal or different—is so high that it is not useful. A high proportion (nearly all) of nucleotide sequences that evaluate as different, are equal but appear as different because of an error in the sequencer. Therefore, a comparison process to evaluate the degree of similarity between any two lists of characters is implemented.

In one embodiment of the invention, each character in a list of characters comprises a letter, such that a character in the first list of characters is determined as the same as a character in the second list of characters, when the letter is the same in the first and second lists of characters (i.e. a character in one list of characters is determined as the same as a character in another list of characters when the letters are the same in each list). In one preferred embodiment of the invention, each character in a list of characters comprises a letter associated with a number or symbol, more preferably wherein each letter represents the nucleotide that is identified at the corresponding position in the nucleotide sequence in the highest quality (Q) within the limits of the sequencing method and wherein each number or symbol represents the quality (Q). Thus, in said more preferred embodiment of the method of the invention, wherein each character in a first list of characters and each character in a second list of characters comprises a letter associated with a number or symbol, wherein said number or symbol represents quality (Q) and wherein said letter represents the nucleotide that is identified at the corresponding position in the nucleotide sequence having the highest quality (Q), a character in the first list of characters is determined as the same as a character in the second list of characters, when the letter having the highest quality is the same in the first and second lists of characters (i.e. a character in one list of characters is determined as the same as a character in another list of characters when the letters are the same in each list). Further to this, not only the letters but also the numbers or symbols associated therewith may be compared between lists, preferably by comparing the letter and the number or symbol representing the quality (Q) associated therewith for each character in each list. Thus, in a yet more preferred embodiment of the method of the invention, a character in one list of characters which comprises a letter associated with a quality (Q) is determined as the same as a character in another list of characters which comprises a letter associated with a quality (Q), when the letter having the highest quality is the same in each list, and the quality (Q) of letters is the same in each list within a cut-off limit or an error, more preferably a cut-off limit. For example, a character at a given position which is assigned as T with a quality of 1.00 (i.e. 100%) may be considered the same as a character at a given position which is assigned as T with a quality of 0.99 (i.e. 99%), when the cut-off limit is set at 0.99 (i.e. the error is set at 1%).

Thus, in the following step (c), each step of selecting the character or longest continuous sequence of characters which are the same, within a cut-off limit, in the first and second lists of characters or parts thereof, comprises firstly making the aforementioned comparison between the first list of characters and the second list of characters or parts thereof, and secondly choosing the character or longest continuous sequence of characters based on the criteria given in the following, when one or more characters or one or more continuous sequences of characters are identified as longest from said comparison. In this method, the cut-off limit is preferably set at a quality (Q) of 0.99, more preferably at 0.999, furthermore preferably at 0.9999, most preferably 0.99999, and/or the error is set at a maximum of 1%, more preferably 0.1%, furthermore preferably 0.01%, most preferably 0.001%. In one yet more preferred embodiment of the method of the invention, a character in a first list of characters is determined as the same as a character in a second list of characters, when the letter having the highest quality (Q) is the same in the first and second lists of characters, and the quality of the letter in the first list of characters is within 0.01 (1%) of the quality of the letter in the second list of characters, furthermore preferably within 0.001 (0.1%), still more preferably within 0.0001 (0.01%), most preferably within 0.00001 (0.001%).

Alternatively, comparison is performed by comparing the letter comprising each character which is present in greatest quality (Q) or in greatest proportion in each list of characters. Thus, in the method of the invention, a character in one list of characters is determined as the same as a character in another list of characters preferably when the letters are the same.

Alternatively, comparison is performed by comparing the proportion of each one or more letter comprising each character. Thus, comparison is performed by comparing the proportion of each one or more nucleotide that is identified at each position in the nucleotide sequence. In this method, a character in one list of characters is determined as the same as a character in another list of characters when the proportion of letters is the same within error. For example, a character for which the proportion of A at a given position is 0.11 and the proportion of T at said given position is 0.89 (i.e. the ratio of A:T is 0.11:0.89) may be considered the same as a character for which the proportion of A at a given position is 0.1 and the proportion of T at said given position is 0.9 (i.e. the ratio of A:T is 0.1:0.9), when the error is set at 5% error. Thus, in the following step (C), each step of selecting the character or longest continuous sequence of characters which are the same in the first list of characters and second list of characters or parts thereof comprises firstly making the aforementioned comparison between the first list of characters and second list of characters or parts thereof, and secondly choosing the character or longest continuous sequence of characters based on the criteria given in the following, when one or more characters or one or more continuous sequences of characters are identified as longest from said comparison. In this method, the error is set at a maximum of 1%, more preferably 0.1%, furthermore preferably 0.01%, most preferably 0.001%.

Thus, for each second list of characters obtained in step (B), the degree of similarity with each first list of characters obtained in step (A) is subsequently determined in step (C), wherein a degree of similarity, DS, of a second list of characters obtained in step (B) with a first list of characters obtained in step (A) is determined by:
 (i) counting the total number of characters, $C_c$, in the second and first lists of characters which are the same as in the first and second lists of characters, respectively;
 (ii) counting the total number of characters, $C_t$, in the first and second lists of characters; and
 (iii) calculating DS according to the following formula:

$$DS=C_c/C_t$$

Figure 2:
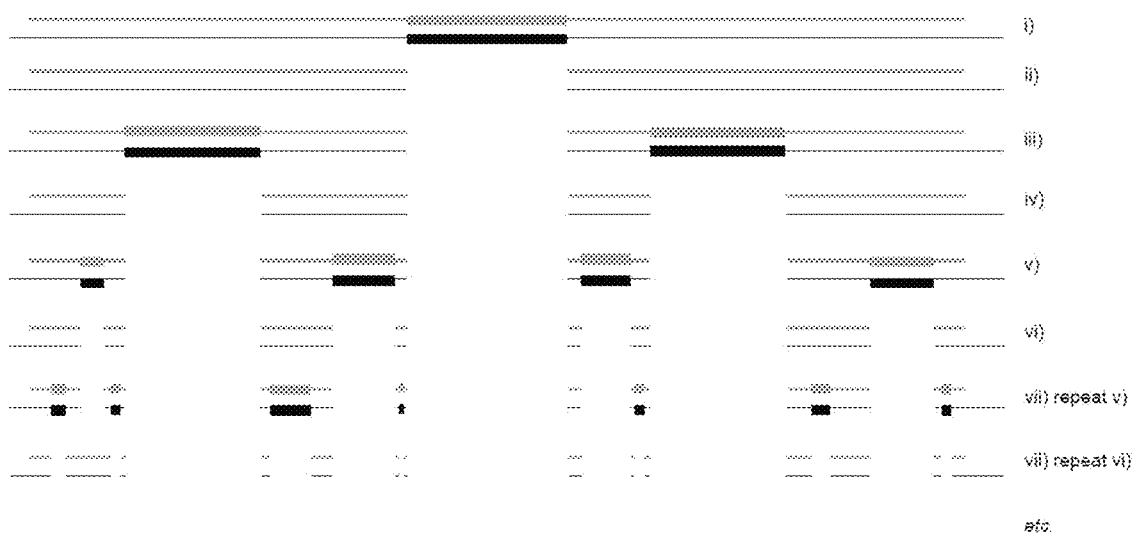
FIG. 2. Schematic diagram representing sub-steps (i) to (vii) of step (c) according to the invention, wherein the narrow grey line ( ---------- ) represents a first character list and the narrow black line ( ———— ) represents a second character list. Selection of a character or longest continuous sequence of characters which are the same in the first list of characters and the second list of characters is represented by broader lines ( ▨▨▨▨ ) and ( ▬▬▬ ), respectively, that are subsequently excluded from the aforementioned character lists.
Figure 3:
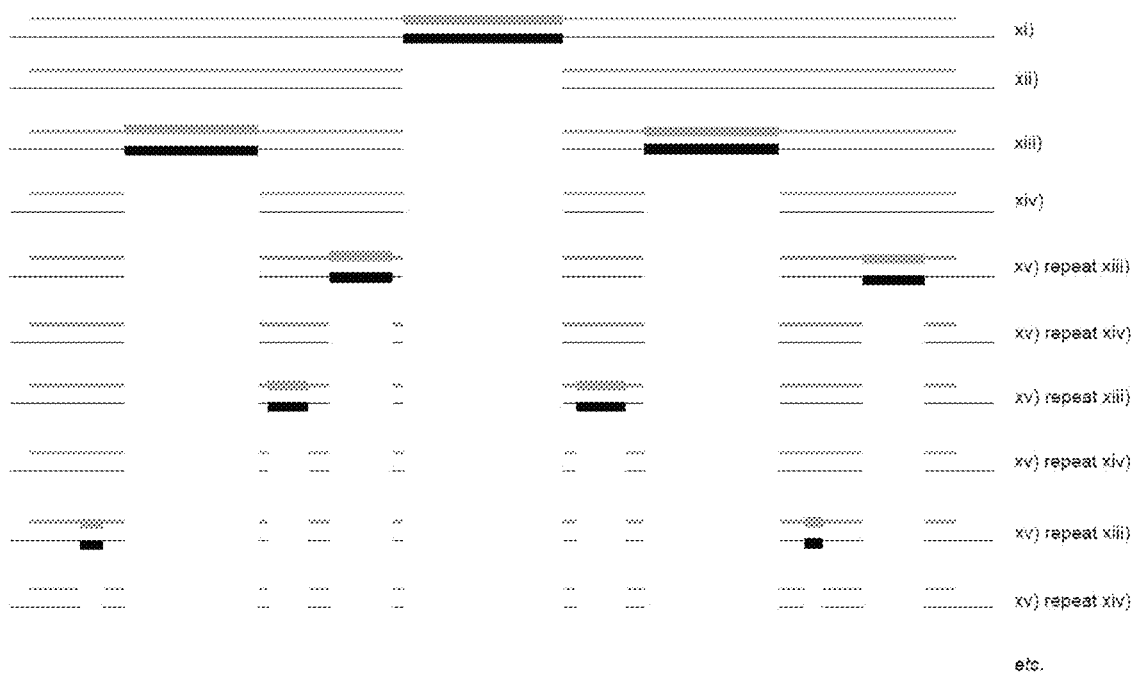
FIG. 3. Schematic diagram representing sub-steps (xi) to (xv) of step (c) according to the invention, wherein the narrow grey line ( ┄┄┄ ) represents a first character list and the narrow black line ( ─── ) represents a second character list. Selection of a character or longest continuous sequence of characters which are the same in the first list of characters and the second list of characters is represented by broader lines ( ▨▨▨▨ ) and ( ▬▬▬ ), respectively, that are subsequently excluded from the aforementioned character lists.
Figure 7A:
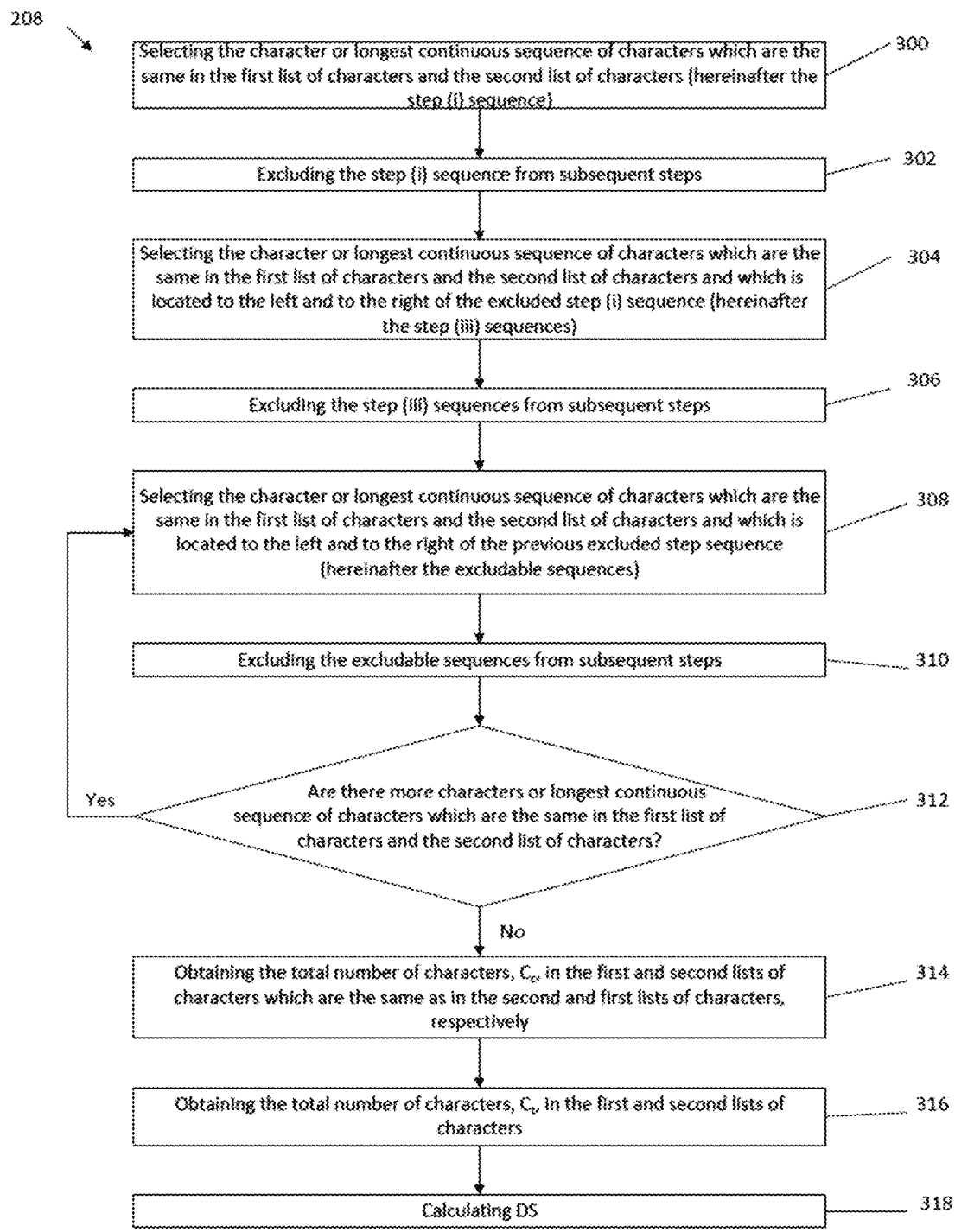
FIG. 7. A. Flowchart of an example of a step for determining the degree of similarity (DS) in accordance with an embodiment of the present invention wherein the mutation is an immunoglobulin rearrangement. B. Flowchart of an example of a step for determining the degree of similarity (DS) in accordance with another embodiment of the present invention wherein the mutation is an immunoglobulin rearrangement.
Figure 7B:
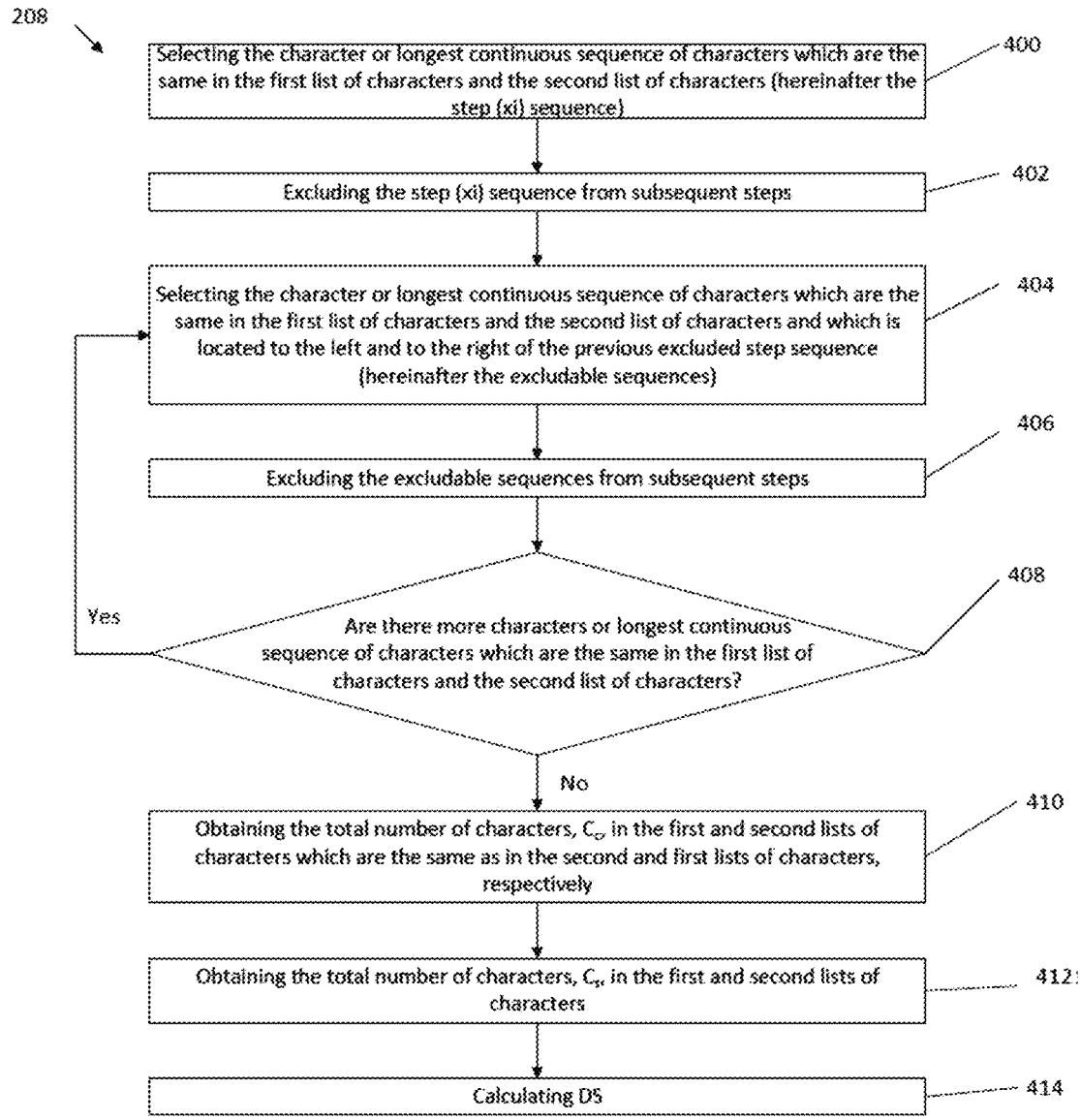

In a particularly preferred embodiment when the mutation is an immunoglobulin rearrangement, a degree of similarity, DS, of a first list of characters obtained in step (A) with a second list of characters obtained in step (B) is determined either by sub-steps (i) to (x) [sub-steps (i) to (vii) of which are represented schematically in FIG. 2] or (xi) to (xviii) [sub-steps (xi) to (xv) of which are represented schematically in FIG. 3]. FIGS. 7A and 7B disclose flowcharts of examples of a step (method) 208 for determining the degree of similarity (DS) in accordance with such a particularly preferred embodiment. In said particularly preferred embodiment, step (C) comprises determining a degree of similarity, DS, of a second list of characters obtained in step (B) with a first list of characters obtained in step (A) either by:
 (i) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 300 of FIG. 7A);
 (ii) excluding the character or longest continuous sequence of characters selected in step (i) from subsequent steps of selecting a character or longest continuous sequence of characters which is the same in the first list of characters and the second list of characters (block 302 of FIG. 7A);
 (iii)—selecting the character or longest continuous sequence of characters which is located to the left of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the right in the lists of characters is selected; and
 selecting the character or longest continuous sequence of characters which is located to the right of the character or longest continuous sequence of characters excluded in step (ii) which are the same in the first list of characters and the second list of characters, wherein when two or more characters or two or more longest continuous sequences of the same length are selected, only the character or longest continuous sequence of characters which is most to the left in the lists of characters is selected (block 304 of FIG. 7A);
 (iv) excluding each character and/or each longest continuous sequence of characters selected in step (iii) from subsequent steps of selecting a character or longest continuous sequence of characters which is the same in the first list of characters and the second list of characters (block 306 of FIG. 7A);
 (v)—selecting the character or longest continuous sequence of characters which is located in the continuous sequence of characters to the immediate left of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the right in the lists of characters is selected; and
 selecting the character or longest continuous sequence of characters which is located in the continuous sequence of characters to the immediate right of each character or each longest continuous sequence of characters excluded in the previous step which are the same in the first list of characters and the second list of characters, wherein when two or more characters or two or more longest continuous sequences of the same length are selected, only the character or longest continuous sequence of characters which is most to the left in the lists of characters is selected (block 308 of FIG. 7A);
 (vi) excluding each character and/or each longest continuous sequences of characters selected in step (v) from subsequent steps of selecting a character or longest continuous sequence of characters which is the same in the first list of characters and the second list of characters (block 310 of FIG. 7A);
 (vii) repeating steps (v) and (vi) until no character or longest continuous sequence of characters which is the same in the first list of characters and the second list of characters is selected (decided in block 312 of FIG. 7A);
 (viii) adding up
   the number of characters in the first list of characters which were excluded in any of the steps (i) to (vii); and
   the number of characters in the second list of characters which were excluded in any of the steps (i) to (vii) to obtain the total number of characters, $C_c$, in the first and second lists of characters which are the same as in the second and first lists of characters, respectively (block 314 of FIG. 7A);
 (ix) adding up
   $C_c$; and
   the number of characters in the first list of characters which are located between the characters and/or longest continuous sequences of characters that were excluded from the first list of characters, and which were not excluded in any of the steps (i) to (vii) of step (c); and the number of characters in the second list of characters which are located between the characters and/or longest continuous sequences of characters that were excluded from the second list of characters, and which were not excluded in any of the steps (i) to (vii) of step (c), to obtain the total number of characters, $C_t$, in the first and second lists of characters (block 316 of FIG. 7A); and (x) calculating DS according to the following formula:

$$DS=C_c/C_t$$

(block 318 of FIG. 7A)

or by:

(xi) selecting the character or longest continuous sequence of characters which are the same in the first list of characters and the second list of characters, wherein when two or more characters or two or more longest continuous sequences of the same length are selected, only the character or longest continuous sequence of characters which is most to the right in the lists of characters is selected (block 400 of FIG. 7B);

(xii) excluding the character or longest continuous sequence of characters selected in step (xi) from subsequent steps of selecting a character or longest continuous sequence of characters which is the same in the first list of characters and the second list of characters (block 402 of FIG. 7B);

(xiii)—selecting the character or longest continuous sequence of characters which is located to the left of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the right in the lists of characters is selected; and selecting the character or longest continuous sequence of characters which is located to the right of the character or longest continuous sequence of characters excluded in step (xii) which are the same in the first list of characters and the second list of characters, wherein when two or more characters or two or more longest continuous sequences of the same length are selected, only the character or longest continuous sequence of characters which is most to the left in the lists of characters is selected (block 404 of FIG. 7B);

(xiv) excluding each character and/or each longest continuous sequence of characters selected in step (xiii) from subsequent steps of selecting a character or longest continuous sequence of characters which is the same in the first list of characters and the second list of characters (block 406 of FIG. 7B);

(xv) repeating steps (xiii) and (xiv) until no character or longest continuous sequence of characters which is the same in the first list of characters and the second list of characters is selected (decided in block 408 of FIG. 7B);

(xvi) adding up the number of characters in the first list of characters which were excluded in any of the steps (xi) to (xv); and the number of characters in the second list of characters which were excluded in any of the steps (xi) to (xv)

to obtain the total number of characters, $C_e$, in the first and second lists of characters which are the same as in the second and first lists of characters, respectively (block 410 of FIG. 7B);

(xvii) adding up $C_c$; and the number of characters in the first list of characters which are located between the characters and/or longest continuous sequences of characters that were excluded from the first list of characters, and which were not excluded in any of the steps (xi) to (xv) of step (c); and the number of characters in the second list of characters which are located between the characters and/or longest continuous sequences of characters that were excluded from the second list of characters, and which were not excluded in any of the steps (xi) to (xv) of step (c), to obtain the total number of characters, $C_t$, in the first and second lists of characters (block 412 of FIG. 7B); and (xviii) calculating DS according to the following formula:

$$DS=C_c/C_t$$

(block 414 of FIG. 7B).

In step (C) of said particularly preferred embodiment, the sub-steps (i) and (xi) of selecting the character which is the same in the first and second lists of characters involve comparing individual characters in the first and second lists of characters according to the foregoing criteria for comparison. Moreover, said sub-steps (i) and (xi) of selecting the longest continuous sequence of characters which is the same in the first and second lists of characters involve comparing consecutive individual characters in the first and second lists of characters according to the foregoing criteria for comparison. It should be noted that sub-steps (i) to (iv) and (xi) to (xiv) of step (C) of said particularly preferred embodiment are identical.

In step (C) of said particularly preferred embodiment, after each step of selecting the character or longest continuous sequence of characters which are the same in the first and second lists of characters or parts thereof, a step of excluding said character or longest continuous sequence of characters, thus selected, takes place, wherein each step of excluding comprises removing the character or longest continuous sequence of characters, thus selected, from consideration in subsequent steps of selecting the character or longest continuous sequence of characters which is the same in the first and second lists of characters. It should be noted that each step of excluding results in a non-continuous sequence of characters which is broken at the point between each character which flanks the character or longest continuous sequence of characters, thus excluded. As such, any subsequent step of selecting the character or longest continuous sequence of characters which are the same in the first and second lists of characters or parts thereof in sub-steps (v) to (vii) of step (C) of said particularly preferred embodiment does not consider a sequence which extends beyond a previously excluded character or longest continuous sequence of characters, but instead considers the continuous sequence of characters located adjacent to each character or each longest continuous sequence of characters excluded in the previous step. Moreover, any subsequent step of selecting the character or longest continuous sequence of characters which are the same in the first and second lists of characters or parts thereof in sub-steps (xiii) to (xv) of step (C) of said particularly preferred embodiment will not consider a sequence which bridges the characters on either side of the excluded character or longest continuous sequence of characters.

Each cycle of selecting and excluding a character or longest continuous sequence of characters which is the same in the first and second lists of characters is repeated in step (C) of said particularly preferred embodiment until no character or longest continuous sequence of characters which is the same in the first and second lists of characters is selected. In sub-steps (iii) and (xiii) of step (C) of said particularly preferred embodiment, selection is preferably repeated simultaneously for the continuous sequence of characters which is located to the left of the character or longest continuous sequence of characters excluded in sub-steps (ii) and (xii) of step (C) of said particularly preferred embodiment, respectively, and for the continuous sequence of characters which is located to the right of the character or longest continuous sequence of characters excluded in sub-steps (ii) and (xii) of step (C) of said particularly preferred embodiment, respectively. Alternatively, this may be repeated first for the continuous sequence of characters which is located to the left of the character or longest continuous sequence of characters excluded in sub-steps (ii) and (xii) of step (C) of said particularly preferred embodiment, respectively, and then for the continuous sequence of characters which is located to the right of the character or longest continuous sequence of characters excluded in sub-steps (ii) and (xii) of step (C) of said particularly preferred embodiment, respectively. Alternatively, this may be repeated first for the continuous sequence of characters which is located to the right of the character or longest continuous sequence of characters excluded in sub-steps (ii) and (xii) of step (C) of said particularly preferred embodiment, respectively, and then for the continuous sequence of characters which is located to the left of the character or longest continuous sequence of characters excluded in sub-steps (ii) and (xii) of step (C) of said particularly preferred embodiment, respectively.

Analogously, in sub-step (v) of step (C) of said particularly preferred embodiment, selection is preferably repeated simultaneously for the continuous sequence of characters to the immediate left of each character or each longest continuous sequence of characters excluded in the previous step, and for the continuous sequence of characters to the immediate right of each character or each longest continuous sequence of characters excluded in the previous step. Alternatively, this may be repeated first for the continuous sequence of characters to the immediate left of each character or each longest continuous sequence of characters excluded in the previous step, and then for the continuous sequence of characters to the immediate right of each character or each longest continuous sequence of characters excluded in the previous step. Alternatively, this may be repeated first for the continuous sequence of characters to the immediate right of each character or each longest continuous sequence of characters excluded in the previous step, and then for the continuous sequence of characters to the immediate left of each character or each longest continuous sequence of characters excluded in the previous step.

Moreover, in a more preferred embodiment of step (C) of said particularly preferred embodiment (i.e. wherein the mutation is an immunoglobulin rearrangement), each step of selecting the character or longest continuous sequence of characters is a step of selecting the longest continuous sequence of characters, wherein said longest continuous sequence of characters comprises a minimum of two characters. As such, each cycle of selecting and excluding a character or longest continuous sequence of characters which is the same in the first and second lists of characters is repeated in step (C) of said even more particularly preferred embodiment until no longest continuous sequence of characters having a minimum of two characters which is the same in the first and second lists of characters is selected. More preferably, said longest continuous sequence of characters comprises a minimum of 3 characters, furthermore preferably a minimum of 4 characters.

Once it is not possible to select a character or longest continuous sequence of characters which is the same in the first list of characters and second list of characters (because all characters or longest continuous sequences of characters which are the same in the first list of characters and second list of characters have been excluded), the total number of characters, $C_c$, which were excluded in the first list of characters and excluded in the second list of characters is obtained by sub-steps (viii) and/or (xvi) of step (C) of said particularly preferred embodiment, wherein the number of characters in the first list of characters which were respectively excluded in any of the sub-steps (i) to (vii) and (xi) to (xv) of step (C) of said particularly preferred embodiment and the number of characters in the second list of characters which were respectively excluded in any of the sub-steps (i) to (vii) and (xi) to (xv) of step (C) of said particularly preferred embodiment is added up. The total number of characters, $C_c$, which were excluded in the first and second lists of characters may also be thought of as 2×(the number of characters which were excluded in the first list of characters), or as 2×(the number of characters which were excluded in the second list of characters). Analogously, the total number of characters, $C_t$, in the first list of characters is obtained by sub-steps (ix) and/or (xvii) of step (C) of said particularly preferred embodiment, wherein $C_c$, plus the number of characters in the first list of characters which are located between the characters and/or longest continuous sequences of characters that were excluded from the first list of characters which were not excluded in any of the sub-steps (i) to (vii) and (xi) to (xv) of step (C) of said particularly preferred embodiment, plus the number of characters in the second list of characters which are located between the characters and/or longest continuous sequences of characters that were excluded from the second list of characters which were not excluded in any of the sub-steps (i) to (vii) and (xi) to (xv) of step (C) of said particularly preferred embodiment, is added up.

Thus, the method, system or kit of the present invention, as well as the method for determining the presence or absence of minimal residual disease which is comprised in the method of treatment of disease in a subject who has been treated for said disease, is intended to detect a list of characters representing a specific nucleotide sequence, which is supplied as an argument to the method, within a data file that contains a mix of lists of characters each representing a nucleotide sequence fragmented in places that, from an informatics point of view are considered random. Therefore, the at least one lists of characters in the mix have random lengths and it is not known in advance where a list of characters representing a specific nucleotide sequence [in step (A)] can be found in each at least one list of characters. Thus, the method of the present invention comprises a combination of alignment and comparison. Since it comprises a mix of alignment and comparison, it is considered that in the invention, comparison is made only from the first character or longest continuous sequence of characters which is the same in the first list of characters and the second list of characters and the last character or longest continuous sequence of characters which is the same in the first and second lists of characters (i.e. including and between the matching characters or longest continuous sequences of characters closest to the extremes of the first and second lists of characters), whereby $C_c$ and $C_t$ are determined over that portion of the first and second lists of characters which is from the first character or longest continuous sequence of characters which is the same in the first and second lists of characters and the last character or longest continuous sequence of characters which is the same in the first and second lists of characters. Accordingly, in a preferred embodiment, each of the characters or longest continuous sequences of characters which are eliminated in either of sub-steps (i) to (vii) or (xi) to (xv) of step (C) of said particularly preferred embodiment are placed in a .dna file and sub-steps (viii) and (xvi) of step (C) of said particularly preferred embodiment may use the data in a .dna file to calculate $C_c$ using a -trim option, such that comparison is made only between the first and the last character or longest continuous sequence of characters in the first list which are the same as in the second list.

Subsequent to step (C), a step (D) is carried out, in which for each second list of characters obtained in step (B), the DS of highest value, $DS_{HV}$, is selected (block 210 of FIG. 6). However, by virtue of the fact that each nucleotide sequence in steps (A) and (B) (arbitrarily herein defined as the Watson strand) has a complementary nucleotide sequence (in particular the reverse complementary sequence, arbitrarily herein defined as the Crick strand), such that first list of characters obtained in step (A) and a second list of characters obtained in step (B) also have a corresponding reverse complementary first list of characters and a corresponding reverse complementary second list of characters, respectively, in a preferred embodiment not only the aforementioned nucleotide sequence in steps (A) and (B) but also the complementary nucleotide sequence may be subjected to steps (A) and (B) of the method of the invention, in conjunction with step (C).

Figure 9:
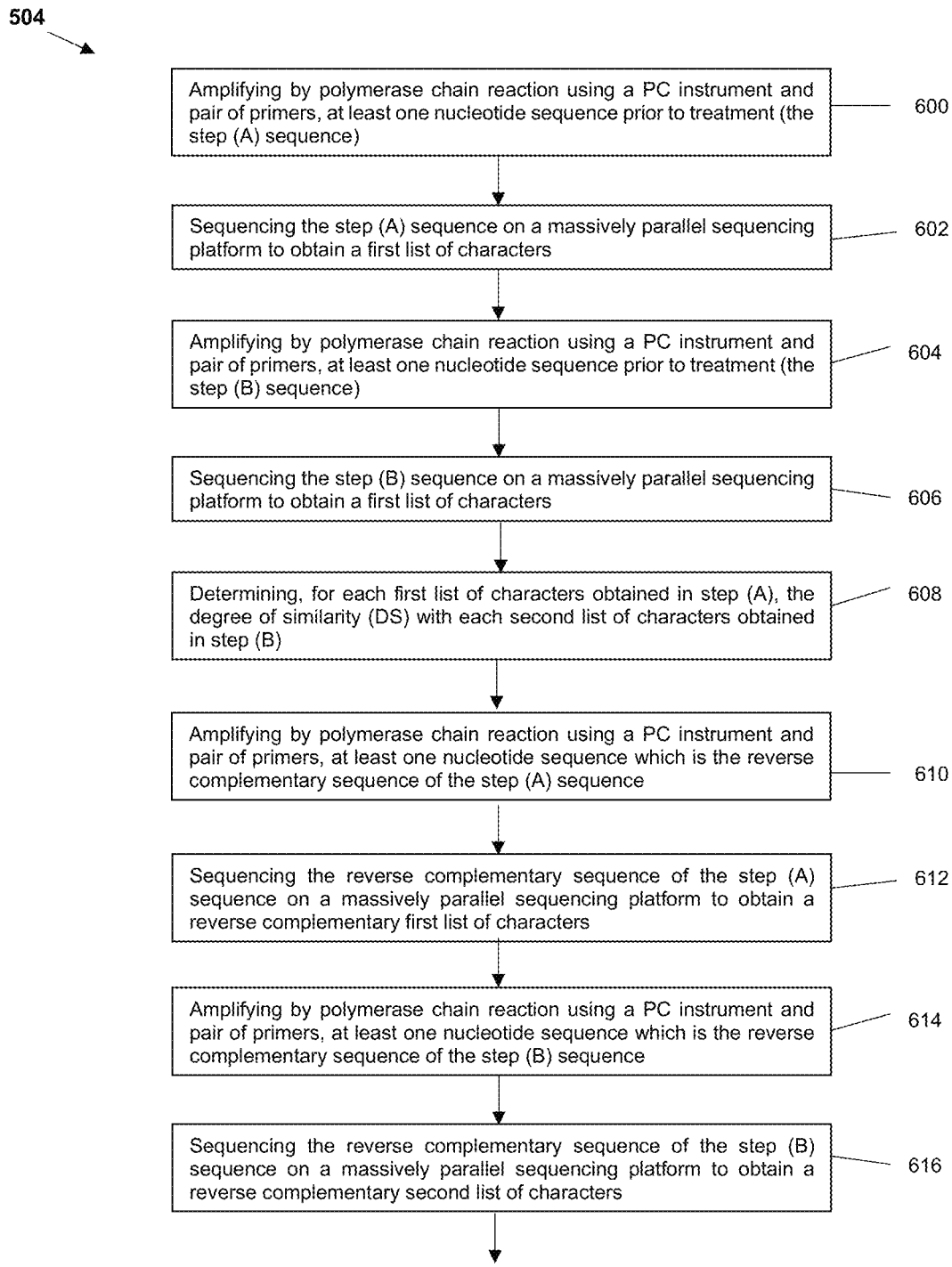
FIG. 9. Flowchart of an example of a method for quantifying the minimum residual disease (MRD) in accordance with an embodiment of the present invention.
Figure 9:
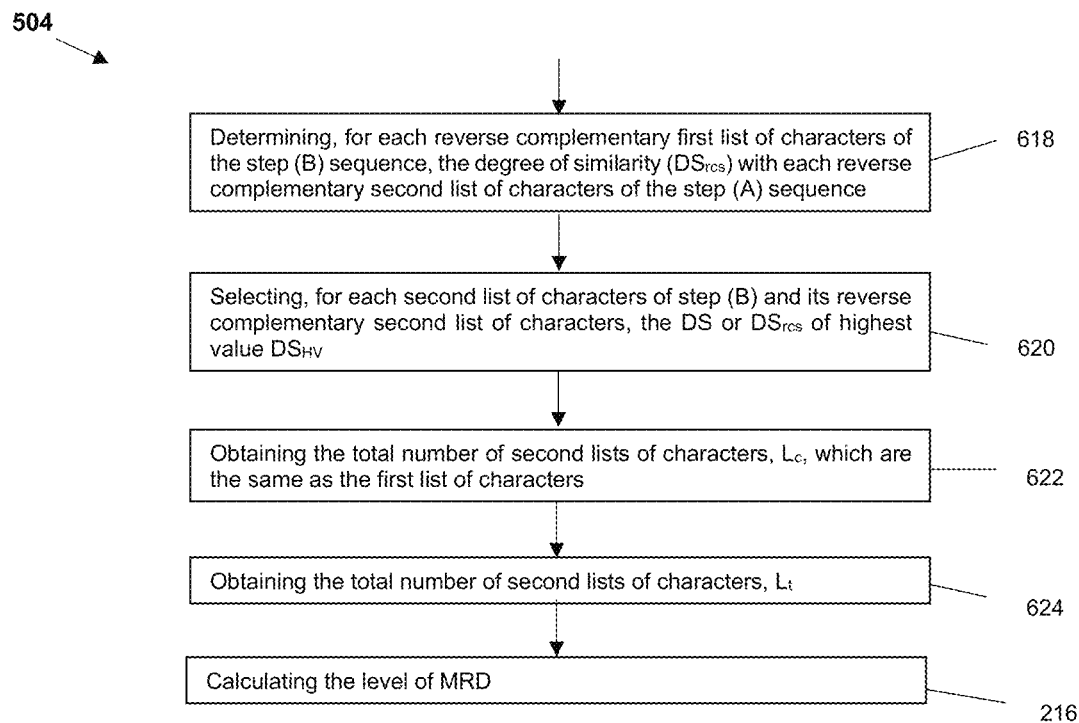

FIG. 9 discloses a flowchart of a method 504 of quantifying the level of minimal residual disease in a subject, exemplifying the following preferred embodiment of the present invention. In said preferred embodiment, the present invention relates to a method for quantifying the level of minimal residual disease (MRD) in a subject, wherein said subject has been treated for said disease, wherein steps (A), (B), (C), (E), (F) and (G) are as disclosed in the present method, system and kit of the present invention (blocks 600 to 608, 622, 624 and 216 of FIG. 9), but wherein the following steps are also comprised:

(A')—amplifying by polymerase chain reaction using a PCR instrument and a pair of primers, each at least one nucleotide sequence which is the reverse complementary sequence complementary to the at least one nucleotide sequence in step (A), and sequencing on a massively parallel sequencing platform said at least one reverse complementary nucleotide sequence to obtain at least one reverse complementary first list of characters reading from left to right, wherein said pair of primers comprises a locus-specific forward primer and a locus-specific reverse primer (blocks 610 and 612 of FIG. 9); and (B')—amplifying by polymerase chain reaction using a PCR instrument and the same locus-specific forward primer and the same locus-specific reverse primer as in the previous step, each at least one nucleotide sequence which is the reverse complementary sequence complementary to the at least one nucleotide sequence in step (B), and sequencing on a massively parallel sequencing platform said at least one reverse complementary nucleotide sequence to obtain at least one reverse complementary second list of characters reading from left to right (blocks 614 and 616 of FIG. 9); and (C')—determining, for each reverse complementary second list of characters obtained in step (B'), the degree of similarity with each reverse complementary first list of characters obtained in step (A') (block 618 of FIG. 9), wherein a degree of similarity, $DS_{rcs}$, of a reverse complementary second list of characters obtained in step (B') with a reverse complementary first list of characters obtained in step (A') is determined using at least one computer program product, by:

(i) counting the total number of characters, $C_{crcs}$, in the reverse complementary second and first lists of characters which are the same as in the reverse complementary first and second lists of characters, respectively;

(ii) counting the total number of characters, $C_{trcs}$, in the first and second lists of characters; and (iii) calculating $DS_{rcs}$ according to the following formula:

$$DS_{rcs}=C_{crcs}/C_{trcs},$$

and wherein step (D) is replaced by:

step (D') of selecting, using at least one computer program product, for each second list of characters obtained in step (A) and its corresponding reverse complementary second list of characters, the DS or $DS_{rcs}$ of highest value, $DS_{HV}$ (block 620 of FIG. 9).

Figure 10A:
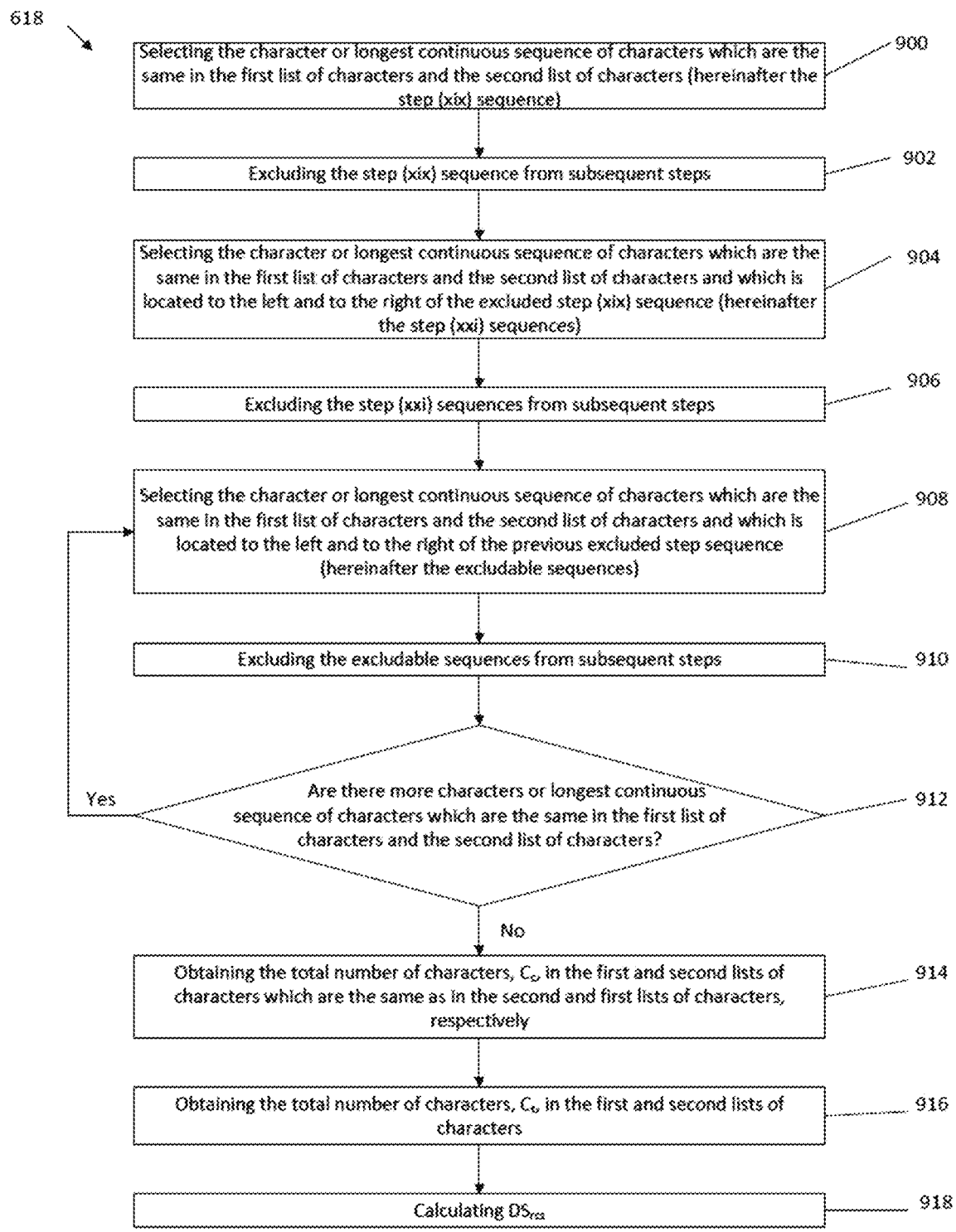
FIG. 10. A. Flowchart of an example of a step for determining the reverse complementary degree of similarity ($DS_{rcs}$) in accordance with an embodiment of the present invention wherein the mutation is an immunoglobulin rearrangement. B. Flowchart of an example of a step for determining the reverse complementary degree of similarity ($DS_{rcs}$) in accordance with another embodiment of the present invention wherein the mutation is an immunoglobulin rearrangement.
Figure 10B:
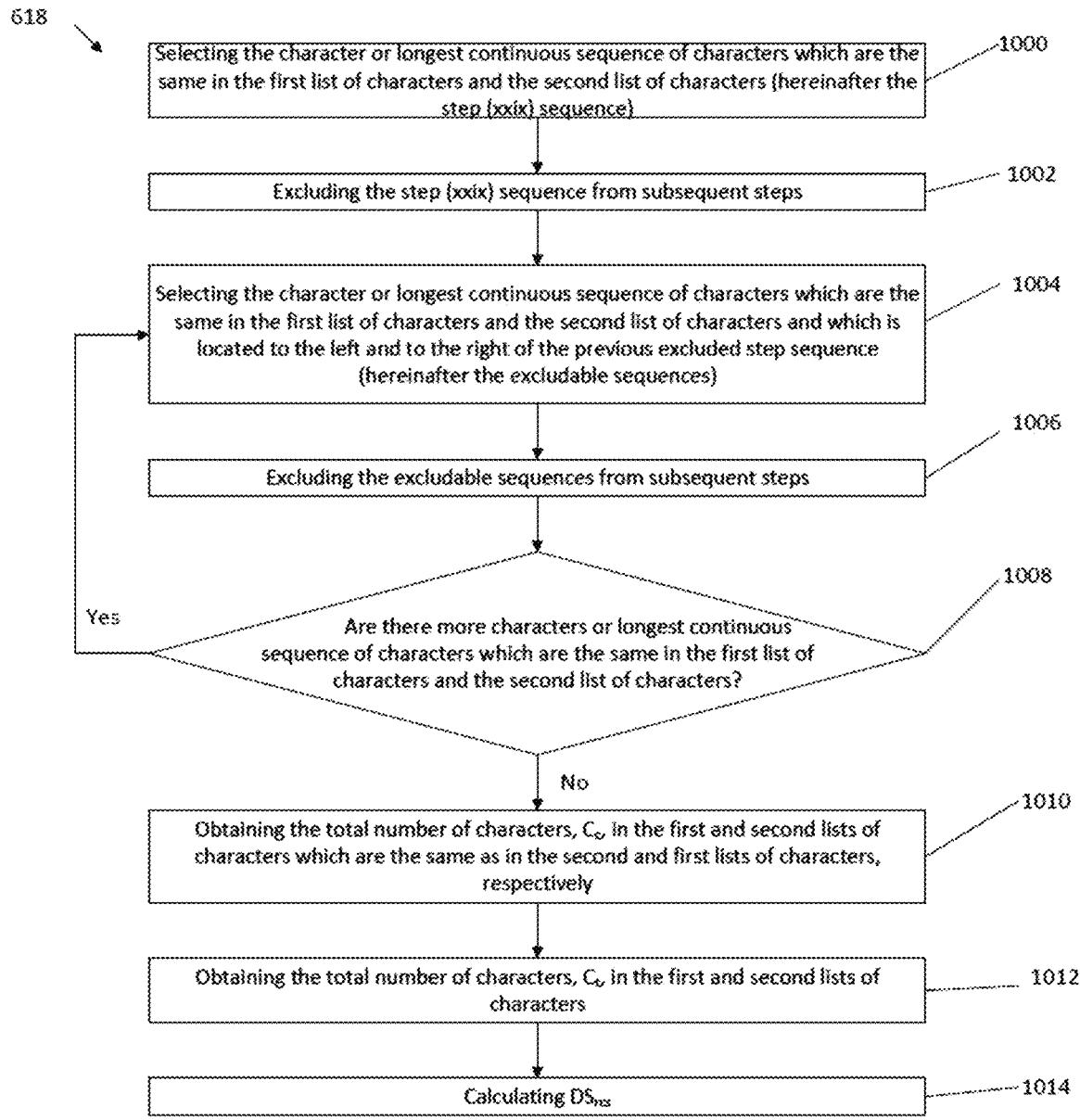

FIGS. 10A and 10B disclose flowcharts of a step 618 of determining the reverse complementary degree of similarity ($DS_{rcs}$) according to a preferred embodiment of said particularly preferred embodiment wherein said mutation is an immunoglobulin rearrangement, thereby exemplifying the alternatives of said step of determining the reverse complementary degree of similarity. Thus, in said preferred embodiment of said particularly preferred embodiment, the step (D) comprises:

amplifying by polymerase chain reaction using primers, each at least one nucleotide sequence which is the reverse complementary sequence complementary to the at least one nucleotide sequence in step (A), and sequencing said at least one reverse complementary nucleotide sequence to obtain at least one reverse complementary first list of characters reading from left to right; and amplifying by polymerase chain reaction using the same primers as in the previous step, each at least one nucleotide sequence which is the reverse complementary sequence complementary to the at least one nucleotide sequence in step (B), and sequencing said at least one reverse complementary nucleotide sequence to obtain at least one reverse complementary second list of characters reading from left to right; and determining, for each reverse complementary second list of characters obtained in step (B), the degree of similarity with each reverse complementary first list of characters obtained in step (A), wherein a degree of similarity, $DS_{rcs}$, of a reverse complementary second list of characters obtained in step (B) with a reverse complementary first list of characters obtained in step (A) is determined either by:

(xix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected (block 900 of FIG. 10A);

(xx) excluding the character or longest continuous sequence of characters selected in step (xix) from subsequent steps of selecting a character or longest continuous sequence of characters which is the same in the reverse complementary first list of characters and the reverse complementary second list of characters (block 902 of FIG. 10A);

(xxi)—selecting the character or longest continuous sequence of characters which is located to the left of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 904 of FIG. 10A);

(xxii) excluding each character and/or each longest continuous sequence of characters selected in step (xxi) from subsequent steps of selecting a character or longest continuous sequence of characters which is the same in the reverse complementary first list of characters and the reverse complementary second list of characters (block 906 of FIG. 10A);

(xxiii)—selecting the character or longest continuous sequence of characters which is located in the continuous sequence of characters to the immediate left of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located in the continuous sequence of characters to the immediate right of each character or each longest continuous sequence of characters excluded in the previous step which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 908 of FIG. 10A);

(xxiv) excluding each character and/or each longest continuous sequences of characters selected in step (xxiii) from subsequent steps of selecting a character or longest continuous sequence of characters which is the same in the reverse complementary first list of characters and the reverse complementary second list of characters (block 910 of FIG. 10A);

(xxv) repeating steps (xxiii) and (xxiv) until no character or longest continuous sequence of characters which is the same in the reverse complementary first list of characters and the reverse complementary second list of characters is selected (decided in block 912 of FIG. 10A);

(xxvi) adding up the number of characters in the reverse complementary first list of characters which were excluded in any of the steps (xix) to (xxv); and the number of characters in the reverse complementary second list of characters which were excluded in any of the steps (xix) to (xxv)

to obtain the total number of characters, $C_{crcs}$, in the reverse complementary first and second lists of characters which are the same as in the reverse complementary second and first lists of characters, respectively (block 914 of FIG. 10A, wherein $C_c$ refers to $C_{crcs}$);

(xxvii) adding up $C_{crcs}$; and the number of characters in the reverse complementary first list of characters which are located between the characters and/or longest continuous sequences of characters that were excluded from the reverse complementary first list of characters, and which were not excluded in any of the steps (xix) to (xxv) of step (C); and the number of characters in the reverse complementary second list of characters which are located between the characters and/or longest continuous sequences of characters that were excluded from the reverse complementary second list of characters, and which were not excluded in any of the steps (xix) to (xxv) of step (C), to obtain the total number of characters, $C_{trcs}$, in the reverse complementary first and second lists of characters (block 916 of FIG. 10A, wherein $C_t$ refers to $C_{trcs}$); and (xxviii) calculating DS according to the following formula:

$$DS_{rcs} = C_{crcs}/C_{trcs}$$

(block 918 of FIG. 10A)

or by:

(xxix) selecting the character or longest continuous sequence of characters which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected (block 1000 of FIG. 10B);

(xxx) excluding the character or longest continuous sequence of characters selected in step (xxix) from subsequent steps of selecting a character or longest continuous sequence of characters which is the same in the reverse complementary first list of characters and the reverse complementary second list of characters (block 1002 of FIG. 10B);

(xxxi)—selecting the character or longest continuous sequence of characters which is located to the left of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the right in the reverse complementary lists of characters is selected; and selecting the character or longest continuous sequence of characters which is located to the right of the character or longest continuous sequence of characters excluded in step (xxx) which are the same in the reverse complementary first list of characters and the reverse complementary second list of characters, wherein when two or more characters or two or more longest continuous sequences of the same length are selected, only the character or longest continuous sequence of characters which is most to the left in the reverse complementary lists of characters is selected (block 1004 of FIG. 10B);

(xxxii) excluding each character and/or each longest continuous sequence of characters selected in step (xxxi) from subsequent steps of selecting a character or longest continuous sequence of characters which is the same in the reverse complementary first list of characters and the reverse complementary second list of characters (block 1006 of FIG. 10B);

(xxxiii) repeating steps (xxxi) and (xxxii) until no character or longest continuous sequence of characters which is the same in the reverse complementary first list of characters and the reverse complementary second list of characters is selected (decided in block 1008 of FIG. 10B);

(xxvi) adding up the number of characters in the reverse complementary first list of characters which were excluded in any of the steps (xix) to (xxv); and the number of characters in the reverse complementary second list of characters which were excluded in any of the steps (xix) to (xxv)

to obtain the total number of characters, $C_{crcs}$, in the reverse complementary first and second lists of characters which are the same as in the reverse complementary second and first lists of characters, respectively (block 1010 of FIG. 10B, wherein $C_c$ refers to $C_{crcs}$);

(xxvii) adding up $C_{crcs}$; and the number of characters in the reverse complementary first list of characters which are located between the characters and/or longest continuous sequences of characters that were excluded from the reverse complementary first list of characters, and which were not excluded in any of the steps (xix) to (xxv) of step (C); and the number of characters in the reverse complementary second list of characters which are located between the characters and/or longest continuous sequences of characters that were excluded from the reverse complementary second list of characters, and which were not excluded in any of the steps (xix) to (xxv) of step (C), to obtain the total number of characters, $C_{trcs}$, in the reverse complementary first and second lists of characters (block 1012 of FIG. 10B, wherein $C_t$ refers to $C_{trcs}$); and (xxviii) calculating $DS_{rcs}$ according to the following formula:

$$DS_{rcs} = C_{crcs}/C_{trcs}$$

(block 1014 of FIG. 10B)

wherein when DS is determined for each second list of characters obtained in step (B) using sub-steps (i) to (x), $DS_{rcs}$ is determined for each corresponding reverse complementary first list of characters using sub-steps (xix) to (xxviii), and when DS is determined for each second list of characters obtained in step (B) using sub-steps (xi) to (xviii), $DS_{rcs}$ is determined for each corresponding reverse complementary first list of characters using sub-steps (xxix) to (xxxvi); and selecting, for each second list of characters obtained in step (B) and its corresponding reverse complementary second list of characters, the DS or $DS_{rcs}$ of highest value, $DS_{HV}$ (following on from block 1014 of FIG. 10B but not shown therein).

Thus, a DS or $DS_{rcs}$ of 0.0 means that no characters in a first list of characters are the same as in a second list of characters, whereas a DS or $DS_{rcs}$ of 1.0 means that all characters in a first list of characters are the same as in a second list of characters (i.e. a nucleotide sequence from a biological sample from a subject after treatment for said disease is strictly equal with a nucleotide sequence from a biological sample obtained from a subject prior to treatment for said disease). Therefore, the method of the present invention provides information on how many nucleotide sequences in the biological sample from a subject contain the argument sequence (the nucleotide sequence from a biological sample obtained from a subject with said disease), either in its original (Watson) form or in its reverse complement (Crick) version.

Having determined $DS_{HV}$ for each of the at least one second list of characters obtained in step (B), the number of second lists of characters obtained in step (B) which have a $DS_{HV}$ that is greater than a threshold value, T, is subsequently added up in a step (E) to obtain the total number of second lists of characters, $L_c$, which are the same as a first list of characters (block 212 of FIG. 6). Similarly, in a step (F), $L_c$ and the number of second lists of characters which do not have a $DS_{HV}$ that is greater than T are added up to obtain $L_t$ (block 214 of FIG. 6). $L_t$ corresponds to the total number of second lists of characters. Preferably said threshold value, T, for the DS and $DS_{rcs}$ is set at 0.99, more preferably at 0.999, furthermore preferably at 0.9999, most preferably at 0.99999. Steps (E) and (F) may be performed simultaneously or step (E) may be performed before or after step (F), preferably step (F) is performed after step (E).

Subsequently, a step (G) is performed to calculate the level of MRD (block 216 of FIG. 6). Calculating the level of MRD is performed according to any of the following formulae:

$$MRD = (L_c \times k)/(L_t \times D)$$

or $$MRD = L_c/L_t$$

or $$MRD = g \times L_c \times (D/k)/L_t^2$$

wherein $L_c$, D, k and $L_t$ are as previously defined, and as defined below:
$L_c$ = total number of first lists of characters which are the same as a second list of characters;
D = amount, D (ng), of genomic DNA from a biological sample obtained from a subject after treatment for a disease (from which said at least one first list of characters is obtained by sequencing);
k = average weight, k, of genomic DNA per diploid cell (ng/cell) from a biological sample obtained from a subject after treatment for a disease;
$L_t$ = total number of first lists of characters; and
g = number of gene copies per cell (g=2 in diploid cells).
Step (H) comprises determining:
(i) the minimum variant read frequency, min VRF, of the genetic marker (min VRF represents initial cell equivalents), said genetic marker being the mutated form of the nucleotide sequence which is amplified in steps (A) and (B) by the same locus-specific forward primer and the same locus-specific reverse primer as in step (A),
(ii) the limit of detection, D-limit, of said genetic marker,
(iii) the average mutation noise, avMut, and
(iv) the average position noise, avPos.

These values may be each determined simultaneously or stepwise, in addition to which step (G) may be performed before or after step (H), preferably step (H) is performed after step (G).

In particular, step (H) comprises determining:
(i) the minimum variant read frequency, min VRF, of said genetic marker, wherein min VRF is calculated according to the following formula:

$$\min VRF = k/D$$

wherein D is in units of ng/µL and k is in units of ng; and
(ii) the limit of detection, D-limit, of said genetic marker, by the difference in slope method comprising:
(a) obtaining a first composition by diluting one part of a solution of genomic DNA comprising said genetic marker with 10 parts of a solution of genomic DNA which does not comprise said genetic marker;
(b) determining the level of MRD of said genetic marker in said first composition;
(c) obtaining a second composition by diluting one part of said first composition with 10 parts of a solution of genomic DNA which does not comprise said genetic marker;
(d) determining the level of MRD of said genetic marker in said second composition;
(e) obtaining a third composition by diluting one part of said second composition with 10 parts of a solution of genomic DNA which does not comprise said genetic marker;
(f) determining the level of MRD of said genetic marker in said third composition;
(g) obtaining a fourth composition by diluting one part of said third composition with 10 parts of a solution of genomic DNA which does not comprise said genetic marker;
(h) determining the level of MRD of said genetic marker in said fourth composition;
(i) calculating:
the average logarithm of the level of MRD, av log MRD1, of said genetic marker in the first, second and third compositions and the average logarithm of the concentration, av log C1, of said genetic marker in the first, second and third compositions; and
the average logarithm of the level of MRD, av log MRD2, of said genetic marker in the second, third and fourth compositions and the average logarithm of the concentration, av log C2, of said genetic marker in the second, third and fourth compositions;
(j) calculating:
the difference, D1A, between the logarithm of the level of MRD of said genetic marker in the first composition and the av log MRD1;
the difference, D1B, between the logarithm of the level of MRD of said genetic marker in the second composition and the av log MRD1;
the difference, D1C, between the logarithm of the level of MRD of said genetic marker in the third composition and the av log MRD1;
the difference, D1D, between the logarithm of the concentration of said genetic marker in the first composition and the av log C1;
the difference, D1E, between the logarithm of the concentration of said genetic marker in the second composition and the av log C1;
the difference, D1F, between the logarithm of the concentration of said genetic marker in the third composition and the av log C1;
the difference, D2A, between the logarithm of the level of MRD of said genetic marker in the second composition and the av log MRD2;
the difference, D2B, between the logarithm of the level of MRD of said genetic marker in the third composition and the av log MRD2;
the difference, D2C, between the logarithm of the level of MRD of said genetic marker in the fourth composition and the av log MRD2;
the difference, D2D, between the logarithm of the concentration of said genetic marker in the second composition and the av log C2;
the difference, D2E, between the logarithm of the concentration of said genetic marker in the third composition and the av log C2; and
the difference, D2F, between the logarithm of the concentration of said genetic marker in the fourth composition and the av log C2;
(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;

R11 by multiplying D2B by D2B;
R12 by multiplying D2C by D2C;
(l) calculating:
S1 using the following formula:

$$S1=(R1+R2+R3)/(R4+R5+R6)$$

S2 using the following formula:

$$S2=(R7+R8+R9)/(R10+R11+R12);$$

(m) comparing S1 and S2, whereby:
when S2 is at least 30% lower than S1 (i.e. the difference between S2 and S1 is 30% or more of the value of S1), the concentration of the third composition is D-limit; and
when S2 is equal to S1 or less than 30% lower than S1 (i.e. the difference between S2 and S1 is from 0 to less than 30% of the value of S1), steps (H)(ii)(a) to (H)(ii)(l) are repeated using said first composition in place of said solution of genomic DNA comprising said genetic marker; and (iii) the average mutation noise, avMut (representing the average error rate of the amplification and sequencing steps), when said mutation is a single nucleotide variant mutation, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
(b) sequencing each amplified nucleotide sequence, whereby a third list of characters reading from left to right is obtained from each nucleotide sequence thus sequenced;
(c) repeating steps (H)(iii)(a) and (H)(iii)(b) in m subjects without said disease and without said genetic marker, wherein m is at least 9, more preferably m is at least 99; and
(d) calculating the average fraction of third lists of characters which are identical to that obtained from sequencing said genetic marker, wherein said average fraction is avMut; and (iv) the average position noise, avPos, when said mutation is a single nucleotide variant mutation, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos. In steps (H)(i) to (H)(iv), the genetic marker is the mutated form of the nucleotide sequence which is amplified in steps (A) and (B) by the same locus-specific forward primer and the same locus-specific reverse primer as in step (A). It follows that the level of MRD determined in steps (H)(ii)(b), (d), (f) and (h) may be determined by (A1)—amplifying by polymerase chain reaction using the same locus-specific forward primer and the same locus-specific reverse primer as in step (A), at least one nucleotide sequence comprised in said solution of genomic DNA comprising said genetic marker; and
sequencing each amplified nucleotide sequence, whereby a list of characters reading from left to right is obtained from each nucleotide sequence thus sequenced; and (B1)—amplifying by polymerase chain reaction using the same locus-specific forward primer and the same locus-specific reverse primer as in step (A1), at least one nucleotide sequence comprised in an amount, D1, of DNA comprised in the first, second, third and fourth compositions, respectively; and
sequencing each amplified nucleotide sequence, whereby a list of characters reading from left to right is obtained from each nucleotide sequence thus sequenced; and (C1) determining the level of MRD in each of the first, second, third and fourth compositions by carrying out steps (C) to (G) for each composition, wherein each list of characters obtained in step (B1) replaces each second list of characters obtained in step (B) and each list of characters obtained in step (A1) for a given composition replaces each first list of characters obtained in step (A), D1 replaces D, k is a constant ($6.49 \times 10^{-3}$ ng) and the formula used in step (G) is the same as used in calculation of the level of MRD using the list of characters obtained in steps (A) and (B). Note that the concentration of said genetic marker in the first, second, third and fourth compositions is measured in terms of volume of a solution of genomic DNA comprising said genetic marker per unit volume of a solution of genomic DNA which does not comprise said genetic marker and thus equates with dilution, such that, for example, the average logarithm of the concentration, av log C1, of said genetic marker in the first, second and third compositions is the same as the average logarithm of the dilution of said genetic marker in the first, second and third compositions.

Following determination of the min VRF of the genetic marker, the D-limit of said genetic marker, the avMut and the avPos in step (H), experimental sensitivity, ES, is determined in step (I). The experimental sensitivity, ES, is:
(i) the greater of min VRF, D-limit, avMut and avPos, as calculated in step (H), when said mutation is a single nucleotide variant mutation; or
(ii) the greater of min VRF and D-limit, as calculated in step (H), when said mutation is an indel mutation or somatic gene rearrangement mutation.

Finally, step (J) is that in which the presence or absence of minimal residual disease is determined, having determined the level of MRD in step (G), the min VRF of the genetic marker, the D-limit of said genetic marker, the avMut and the avPos in step (H), and the ES in step (I). Step (J) comprises determining the presence or absence of minimal residual disease in said subject by either of the following three steps (J)(i), (J)(ii) or (J)(iii), as follows:
(i) comparing the value of the level of minimal residual disease, MRD, calculated in step (G) with the value of the experimental sensitivity, ES, determined in step (I), wherein
(a) when said level of MRD value is equal to or greater than said ES value, minimal residual disease is present in said subject; and
(b) when said level of MRD value is less than said ES value, minimal residual disease is absent from said subject
or
(ii) when said mutation is a single nucleotide variant mutation,
comparing the value of the level of minimal residual disease, MRD, calculated in step (G) with the value of min VRF calculated in step (H), wherein (a) when said level of MRD value is equal to or greater than said min VRF value, minimal residual disease is present in said subject; and comparing the value of the level of minimal residual disease, MRD, calculated in step (G) with the value of avMut calculated in step (H) when said level of MRD value is less than said min VRF value, wherein (b) when said level of MRD value is equal to or greater than said avMut value, minimal residual disease is present in said subject; and comparing the value of the level of minimal residual disease, MRD, calculated in step (G) with the value of avPos calculated in step (H) when said level of MRD value is less than said avMut value, wherein (c) when said level of MRD value is equal to or greater than said avPos value, minimal residual disease is present in said subject; and comparing the value of the level of minimal residual disease, MRD, calculated in step (G) with the value of D-limit calculated in step (H) when said level of MRD value is less than said avPos value, wherein (d) when said level of MRD value is equal to or greater than said D-limit value, minimal residual disease is present in said subject; and (e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in step (G) with the value of min VRF calculated in step (I), wherein (f) when said level of MRD value is equal to or greater than said min VRF value, minimal residual disease is present in said subject; and comparing the value of the level of minimal residual disease, MRD, calculated in step (G) with the value of D-limit calculated in step (H) when said level of MRD value is less than said min VRF value, wherein (g) when said level of MRD value is equal to or greater than said D-limit value, minimal residual disease is present in said subject; and (h) when said level of MRD value is less than said min VRF and D-limit values, minimal residual disease is absent from said subject.

However, in the method of treatment of the present invention, step (J) additionally comprises repeating steps (1) and (2) when minimal residual disease is determined to be present in said subject, wherein each repetition of step (1) comprises administering the same therapy as previously administered to said subject or therapy different to that previously administered to said subject.

In one embodiment of the foregoing method, system, kit and method of treatment, the variant read frequency, VRF, of said genetic marker in said genomic DNA from a tissue sample obtained from said subject prior to treatment for said disease is:

(i) at least 5% when said mutation is a single nucleotide variant mutation; or (ii) at least 2% when said mutation is an indel mutation or a somatic gene rearrangement mutation.

In another embodiment of the present invention, the genetic marker indicative of said disease in said subject in who the presence or absence of minimal residual disease (MRD) is being determined, is selected by the following steps:

(P) identifying at least one mutation comprised in a nucleotide sequence of a gene in said subject having said disease and determining the variant read frequency, VRF, of each mutation thus identified, (Q) selecting a mutation identified in step (P) having a VRF of greater than 10%, by identifying the mutation having a VRF of greater than 10% which:

(a) is the somatic gene rearrangement mutation having the highest VRF; or (b) is the indel mutation having the highest VRF, if no somatic gene rearrangement mutation identified in step (P) has a VRF of greater than 10%; or (c) is the single nucleotide variant mutation having the highest VRF, if no somatic gene rearrangement mutation or an indel mutation identified in step (P) has a VRF of greater than 10%; and (R) identifying a locus-specific forward primer and a locus-specific reverse primer which amplify by polymerase chain reaction the nucleotide sequence of the gene in said subject which comprises said mutation selected in step (Q), wherein said nucleotide sequence which comprises said mutation selected in step (Q) is said genetic marker. More preferably, the genetic marker indicative of said disease is a mutation identified in a nucleotide sequence present in one of the genes of the aforementioned panels of genes, by which said disease is characterised.

Preferably, a genetic marker having a variant read frequency, VRF, of greater than 10% is able to be identified in said genomic DNA from a tissue sample obtained from said subject prior to treatment for said disease. However, in the event that this is not the case, multiple genetic markers need to be used in the method, system and kit of the present invention if a genetic marker having a variant read frequency, VRF, of greater than 10% is not identified in said genomic DNA from a tissue sample obtained from said subject prior to treatment for said disease. Thus, in a preferred embodiment of the present invention, if no mutation identified in step (P) of the aforementioned embodiment of the present invention has a VRF of greater than 10%, the genetic marker is selected, together with a further n−1 genetic markers, by the following steps, wherein:

step (Q) is replaced by a step (Q') which comprises selecting:

(i) n mutations identified in step (P) having a VRF of between 2% and 10%, by identifying those mutations having a VRF of between 2% and 10% which:

(a) are the somatic gene rearrangement mutations having the highest VRF; or (b) are the indel mutations having the highest VRF, if less than n somatic gene rearrangement mutations identified in step (P) have a VRF of between 2% and 10% were not;

or if less than n somatic gene rearrangement mutations identified in step (P) have a VRF of between 2% and 10% and if less than n indel mutations identified in step (P) have a VRF of between 2% and 10%, step (Q') comprises selecting:

(ii) n mutations identified in step (P) having a VRF of between 5% and 10%, by identifying those mutations having a VRF of between 5% and 10% which are single nucleotide variant mutations; and step (R) is replaced by a step (R') which comprises:

(i) choosing one of the n mutations selected in step (Q') and identifying a locus-specific forward primer and a locus-specific reverse primer which amplify by polymerase chain reaction the nucleotide sequence of the gene in said subject which comprises said chosen mutation, wherein said nucleotide sequence which comprises said chosen mutation is the genetic marker; and (ii) repeating step (R')(i) n−1 times, each time for one of the remaining n−1 mutations selected in step (Q') not previously chosen in step (R')(i);

wherein said method additionally comprises repeating steps (A) to (I) a further n−1 times, each time using a different pair of primers identified in step (R'), and replacing step (J) with a step (J') of:

(i) comparing the average value of the level of minimal residual disease, avMRD, and the average value of the experimental sensitivity, avES, wherein (a) when said avMRD value is equal to or greater than said avES value, minimal residual disease is present in said subject; and (b) when said avMRD value is less than said avES value, minimal residual disease is absent from said subject or (ii) when said mutation is a single nucleotide variant mutation, comparing the average value of the level of minimal residual disease, avMRD, with the average value of min VRF, av min VRF, wherein (a) when said avMRD value is equal to or greater than said av min VRF value, minimal residual disease is present in said subject; and comparing the average value of the level of minimal residual disease, avMRD, with the average value of avMut, avavMut, when said avMRD value is less than said av min VRF value, wherein (b) when said avMRD value is equal to or greater than said avavMut value, minimal residual disease is present in said subject; and comparing the average value of the level of minimal residual disease, avMRD, with the average value of avPos, avavPos, when said avMRD value is less than said avavMut value, wherein (c) when said avMRD value is equal to or greater than said avavPos value, minimal residual disease is present in said subject; and comparing the average value of the level of minimal residual disease, avMRD, with the average value of D-limit, avD-limit, when said avMRD value is less than said avavPos value, wherein (d) when said avMRD value is equal to or greater than said avD-limit value, minimal residual disease is present in said subject; and (e) when said avMRD value is less than said av min VRF, avavMut, avavPos and avD-limit values, minimal residual disease is absent from said subject;

or (iii) when said mutation is an indel mutation or somatic gene rearrangement mutation, comparing the average value of the level of minimal residual disease, avMRD, with the average value of min VRF, av min VRF, wherein (f) when said avMRD value is equal to or greater than said av min VRF value, minimal residual disease is present in said subject; and comparing the average value of the level of minimal residual disease, avMRD, with the average value of D-limit, avD-limit, when said avMRD value is less than said av min VRF value, wherein (g) when said avMRD value is equal to or greater than said avD-limit value, minimal residual disease is present in said subject; and (h) when said avMRD value is less than said av min VRF and avD-limit values, minimal residual disease is absent from said subject wherein n is a natural number selected from 2 to 5 and more preferably n is a natural number selected from 2 or 3. Comparison of VRF values allows the effectiveness of any given mutation as a marker to be assessed independently of whether said marker is a single nucleotide variant mutation, indel mutation or immunoglobulin rearrangement mutation. Thus, the present invention also comprises a method for determining the presence or absence of genetic markers suitable for the assessment of minimal residual disease in a subject who has been treated for a disease. In particular, steps (P), (Q), (Q'), (R) and (R') of the present invention in themselves comprise a method for selecting said genetic markers, preferably for use in the method, kit, system and method of treatment described herein.

As previously described, the present invention also relates to a method for treating a subject who has already been treated for a disease, which comprises a step of administering therapy to said subject after using the aforementioned method, system or kit for determining the presence or absence of minimal residual disease (MRD) in said subject.

Figure 11A:
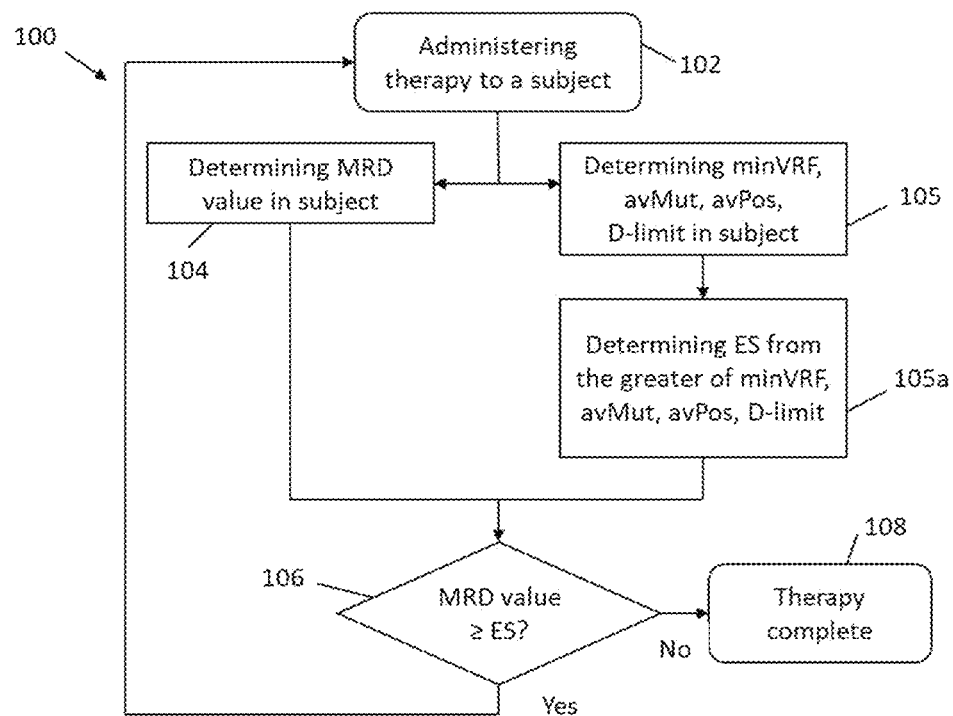
FIG. 11. A. Flowchart of an example of a generalised method for treatment of disease in a subject in accordance with an embodiment of the present invention. B. Flowchart of an example of a generalised method for treatment of disease in a subject in accordance with another embodiment of the present invention.
Figure 11B:
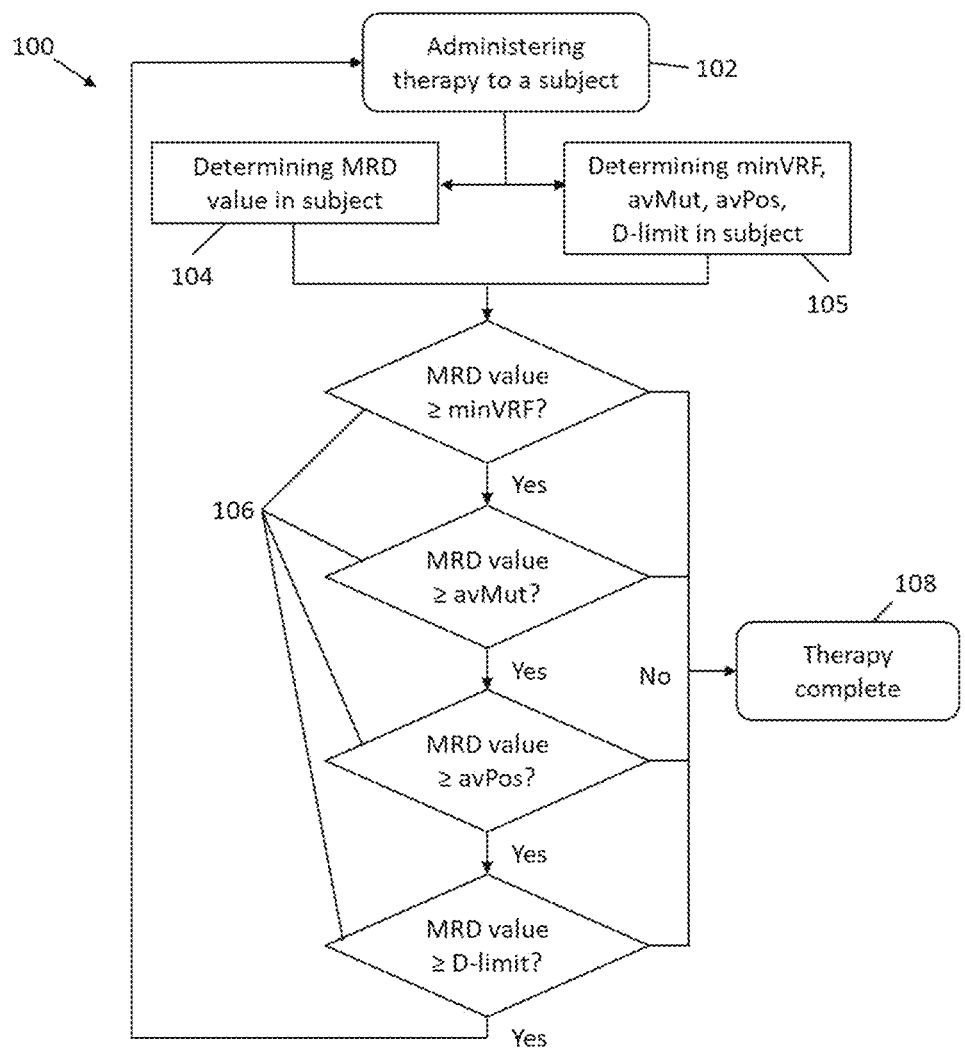
Figure 12:
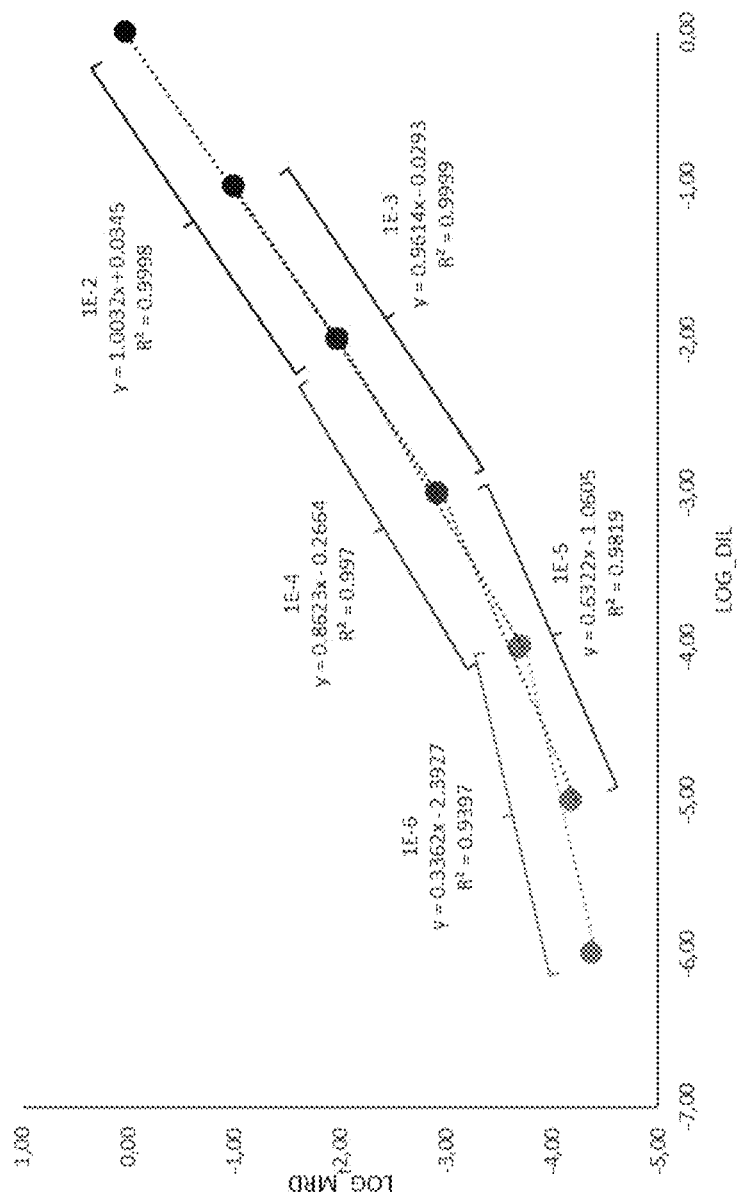
FIG. 12. Dilution curve exemplifying a generalised method (herein, "difference in slope" method) of determining the limit of detection (D-limit) of a genetic marker using least-squares regression between successive sets of three data points, wherein a given set is represented by a first, a second and a third composition of successively 10-fold decreased concentration of genetic marker, and a successive set of three data points by said second, said third and a fourth composition of successively 10-fold decreased concentration of genetic marker, each data point (dilution point) comprising the logarithm of the level of MRD (LOG_MRD) of said genetic marker in a given composition and the logarithm of the dilution (concentration, volume/volume) thereof (LOG_DIL), whereby when the slope of the regressed line of a set is at least 30% lower than that of the set which it is successive to, the concentration of the third composition is established as the D-limit [herein, the slope S2 of the final set of three data points is 0.3362 which is less than 30% of slope S1 (0.6322) of the set to which it is successive so the D-limit is the exponent of LOG_DIL=−5].
Figure 13A:
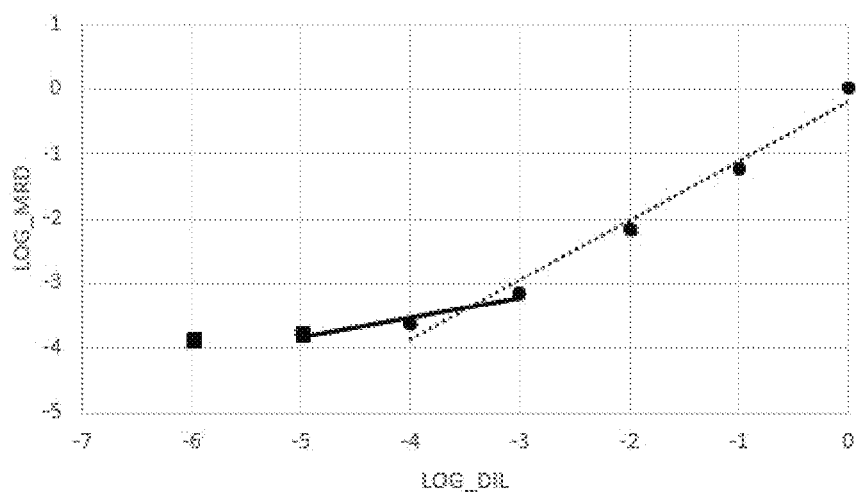
FIG. 13. Dilution curves for: A. IDH1 R132H; B. IDH1 R132C; C. IDH2 R172K; D. IDH2 R140Q; E. JAK2 V617F; F. KRAS G12V; G. KRAS G12A; H. KRAS G12C; I. KRAS G12D; J. KRAS G12S; K. KRAS G12R; L. KRAS G13D; M. NRAS G12D; N. NRAS G12V; O. NRAS G13D; P. NRAS Q61R; Q. KIT D816V; R. NPM1 Ins; S. IgK rearrangement and T. IgK rearrangement mutations, wherein the limit of dilution (D-limit) is represented by the concentration of the composition of genetic marker giving rise to the last (third, i.e. most diluted) dilution point of a given set of three dilution points obtained from a first, a second and a third composition having 10-fold successively increased dilution (decreased concentration, volume/volume) of genetic marker, wherein the slope of the regressed line of said set deviates by less than 30% from the slope of the regressed line of the three dilution points that are obtained from said second composition, said first composition, and a composition 10-fold less dilute than said first composition (black dots), wherein each dilution point represents the logarithm of the level of MRD (LOG_MRD) of said genetic marker in a given composition and the logarithm of the concentration thereof (LOG_DIL). The slope for each dilution point is defined by it and the two previous (i.e. less diluted) dilution points. Black squares represent dilution points out of range and solid line represents the dilution curve (line) calculated including the first point out of range.
Figure 13B:
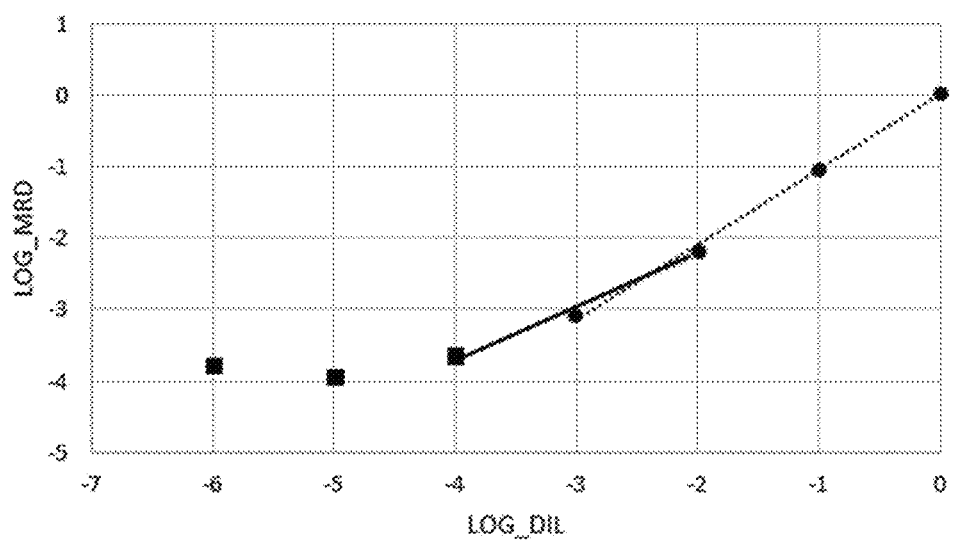
Figure 13C:
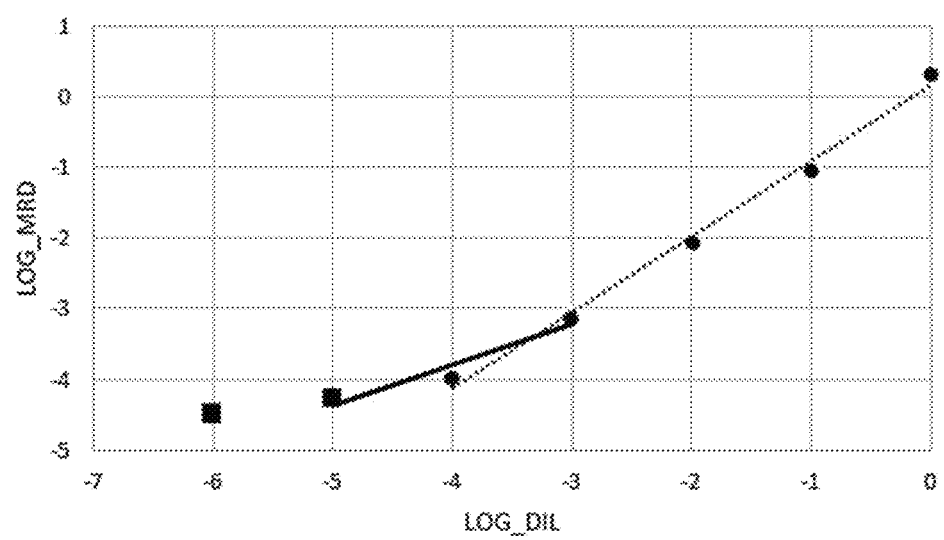
Figure 13D:
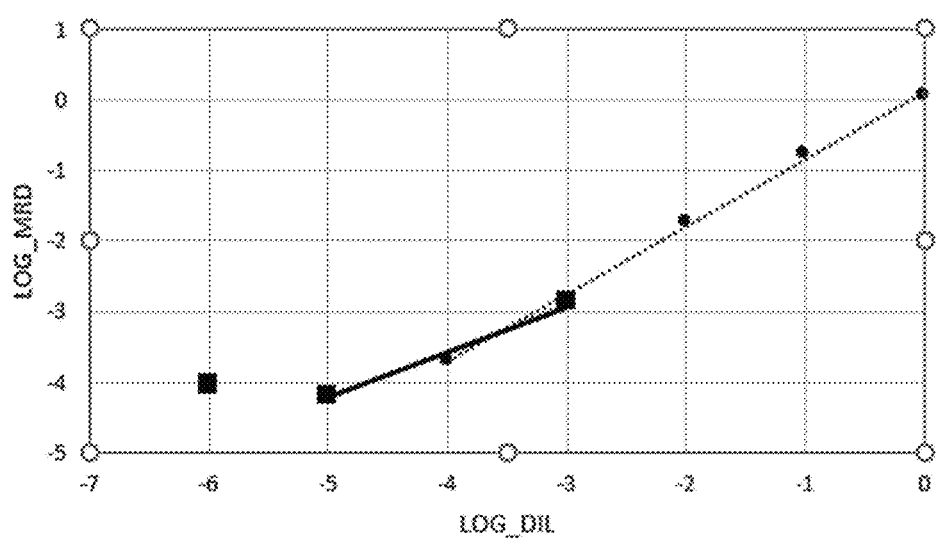
Figure 13E:
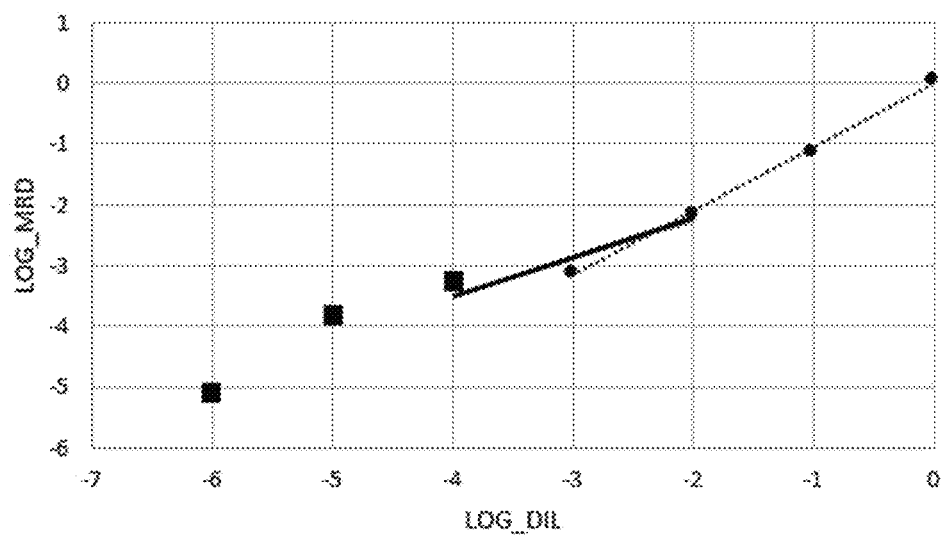
Figure 13F:
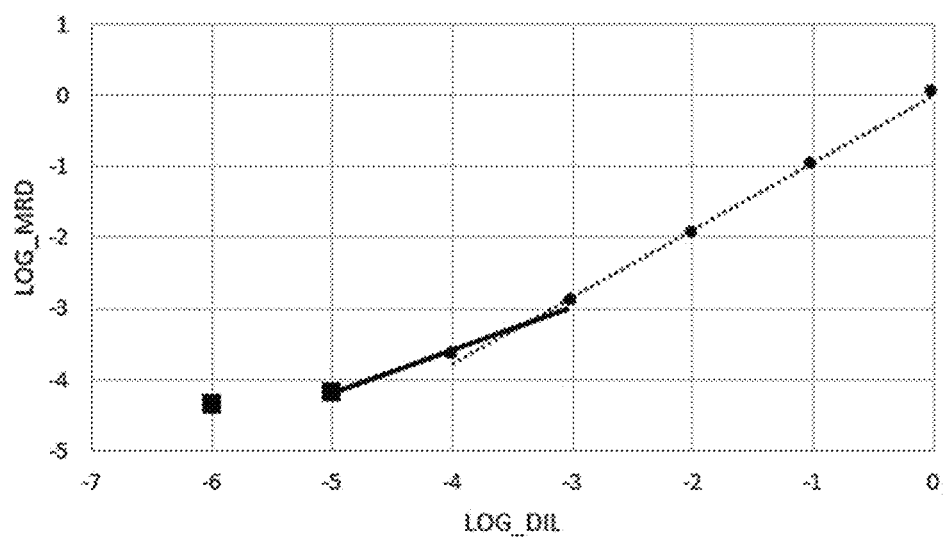
Figure 13G:
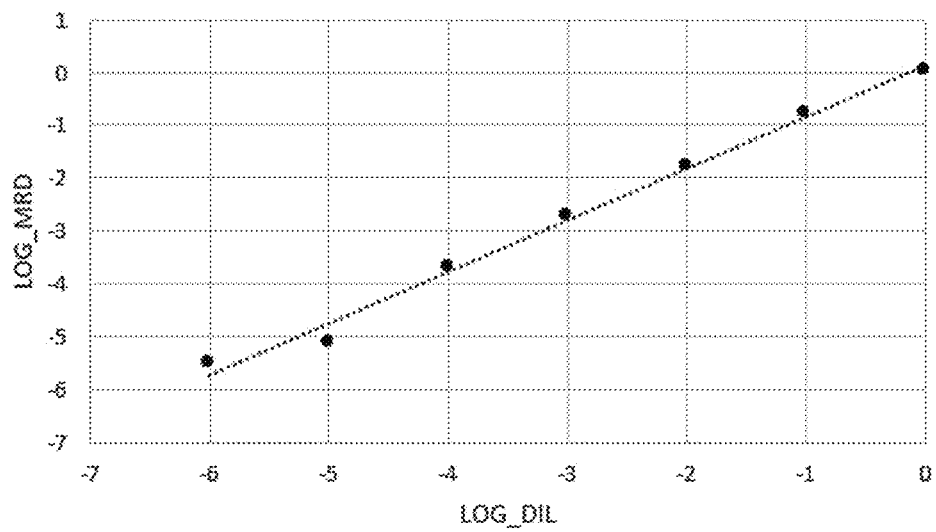
Figure 13H:
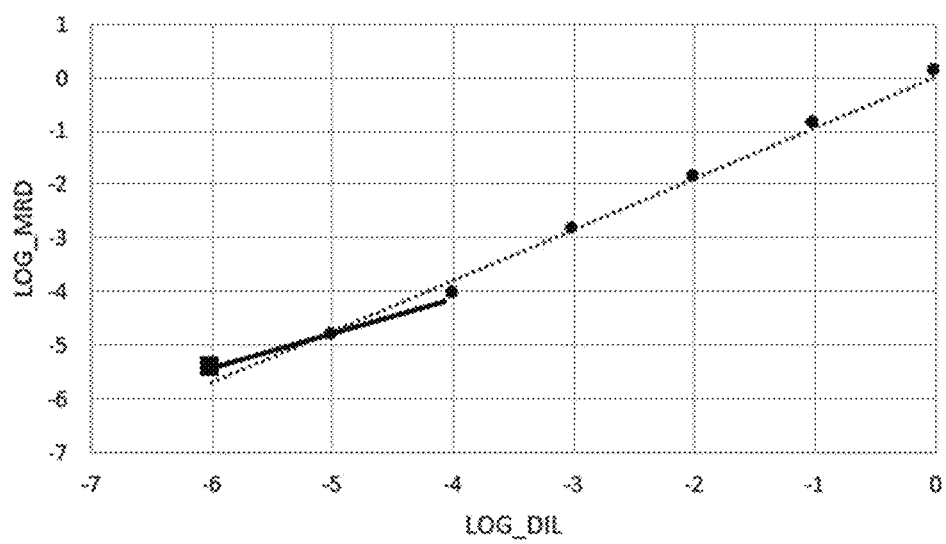
Figure 13I:
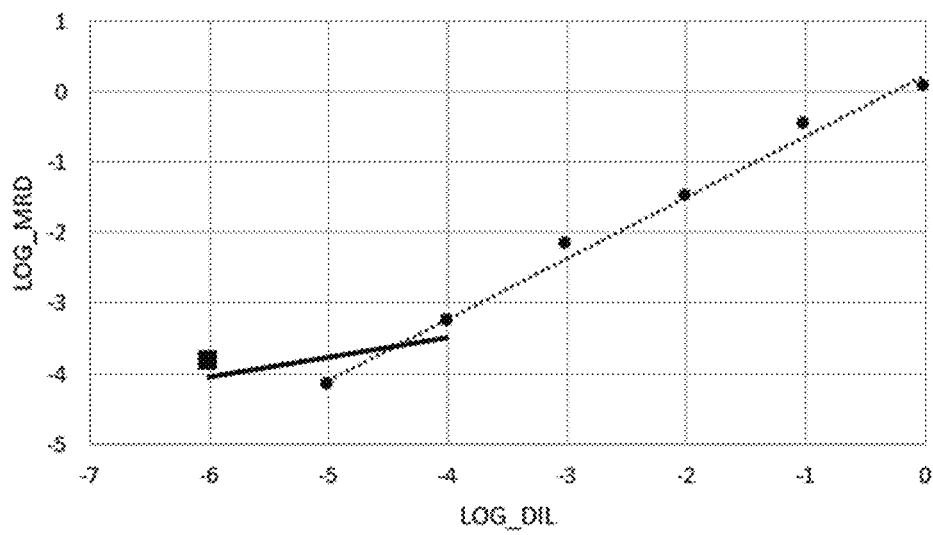
Figure 13J:
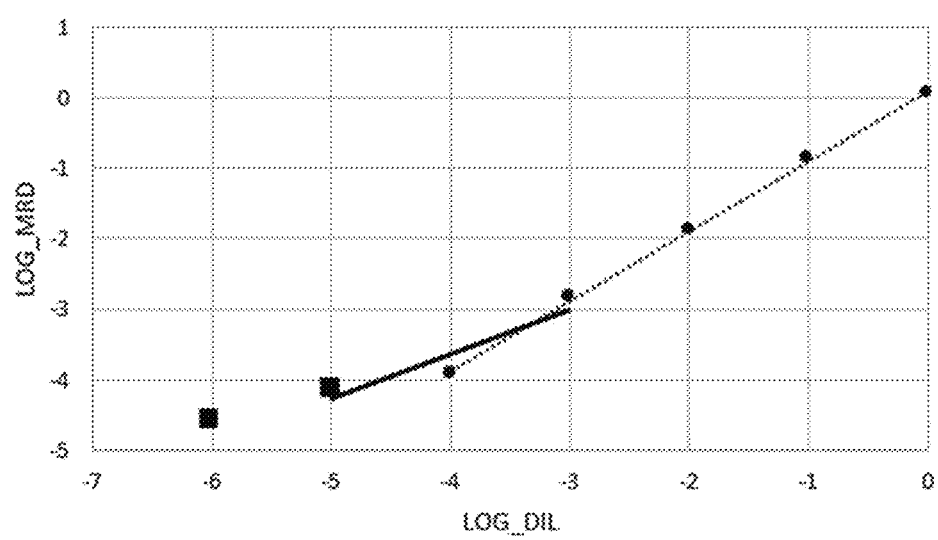
Figure 13K:
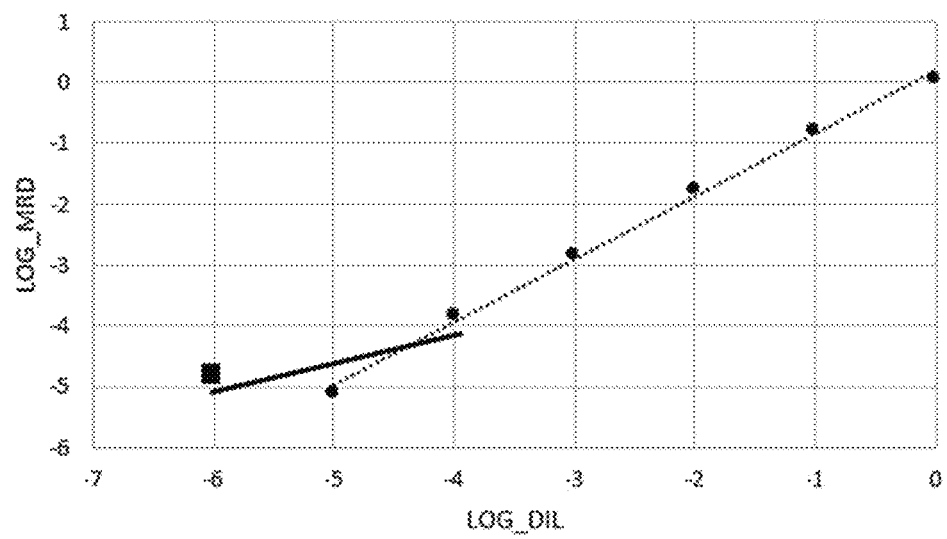
Figure 13L:
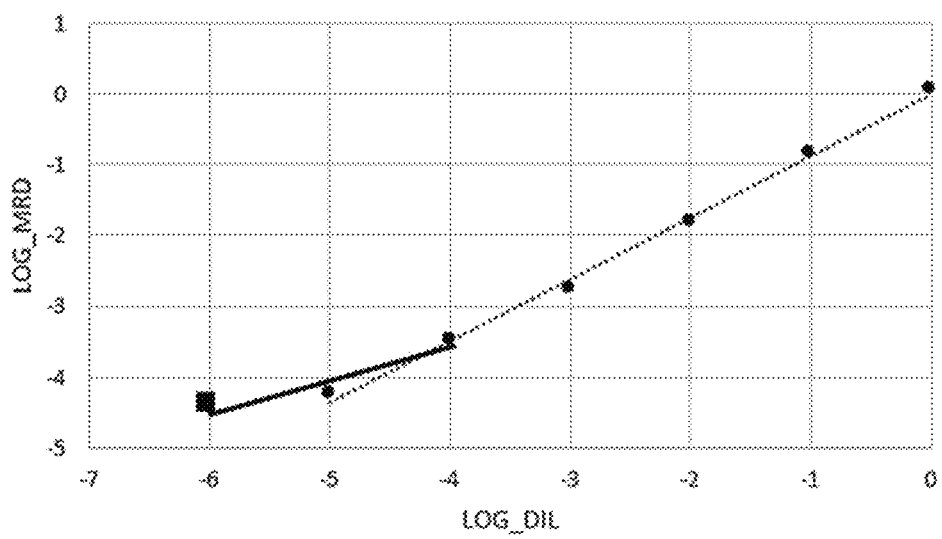
Figure 13M:
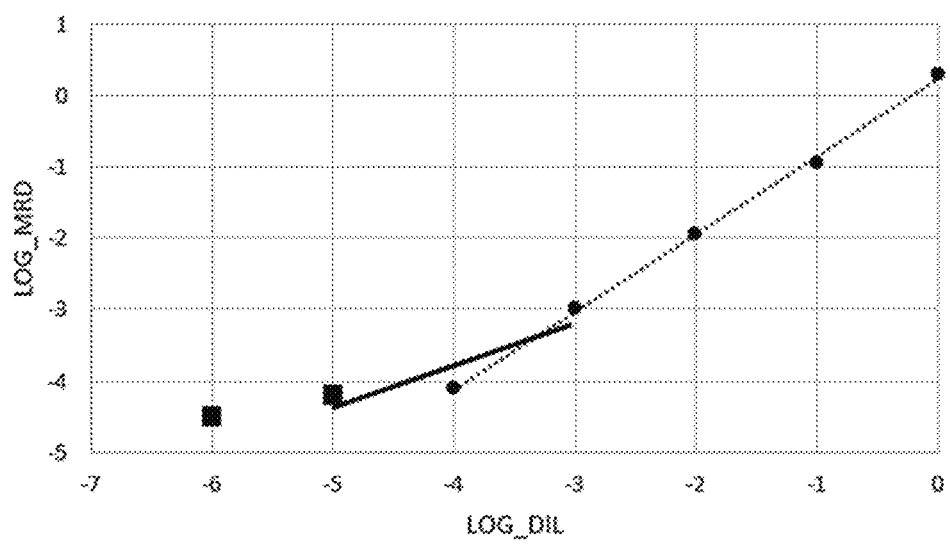
Figure 13N:
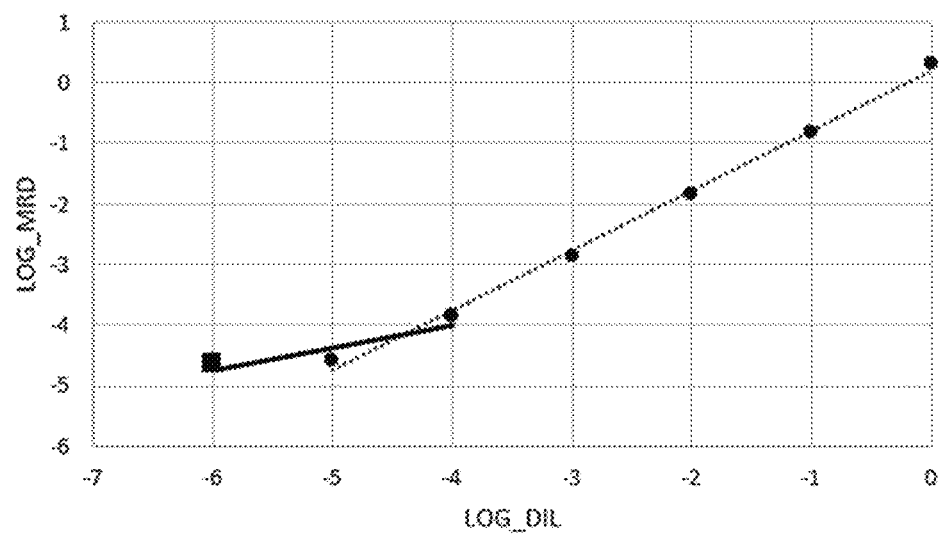
Figure 13O:
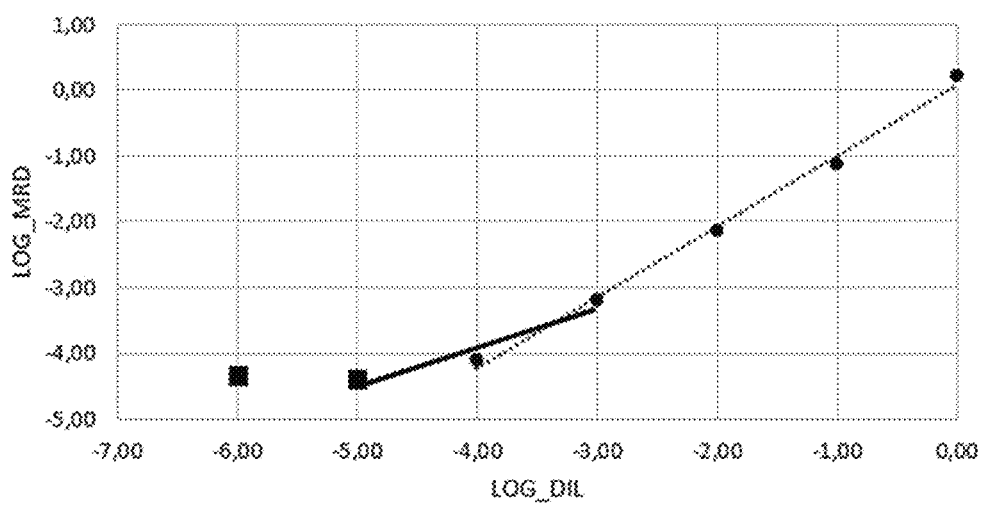
Figure 13P:
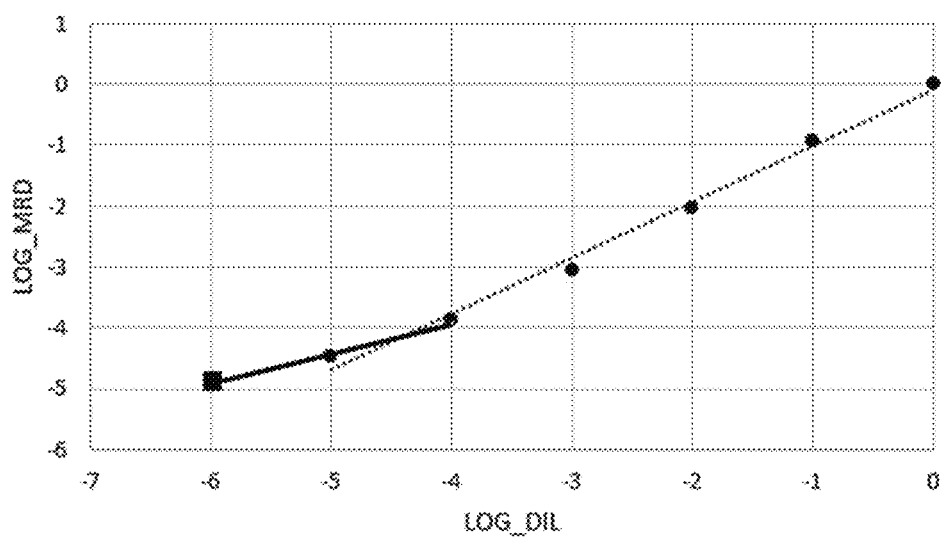
Figure 13Q:
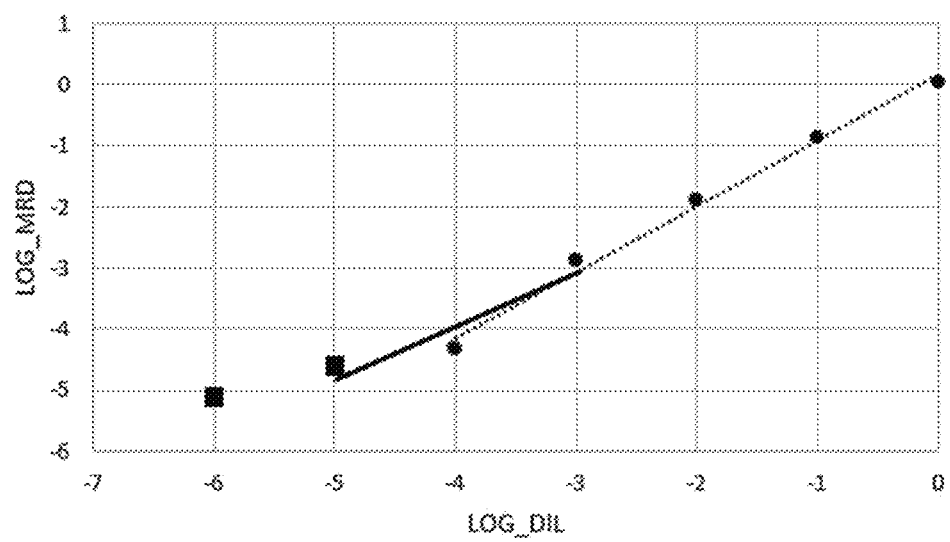
Figure 13R:
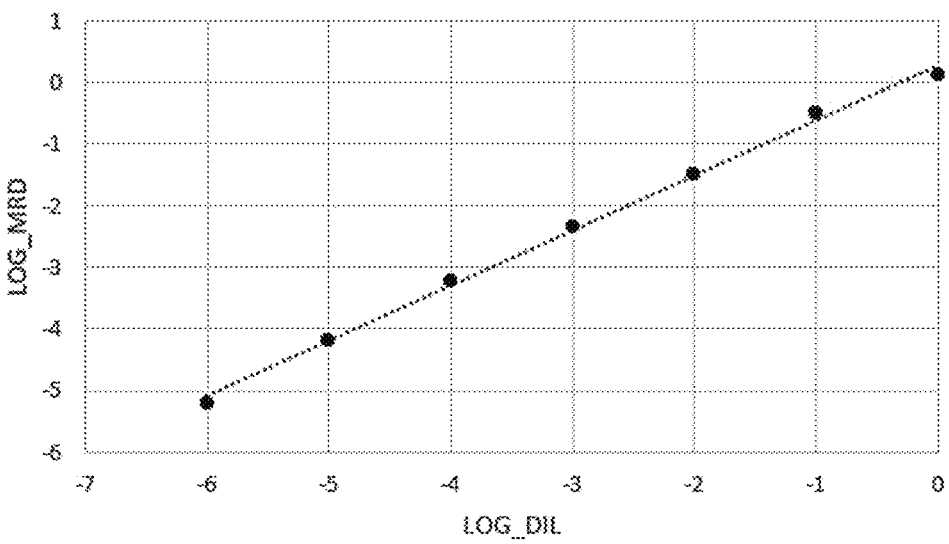
Figure 13S:
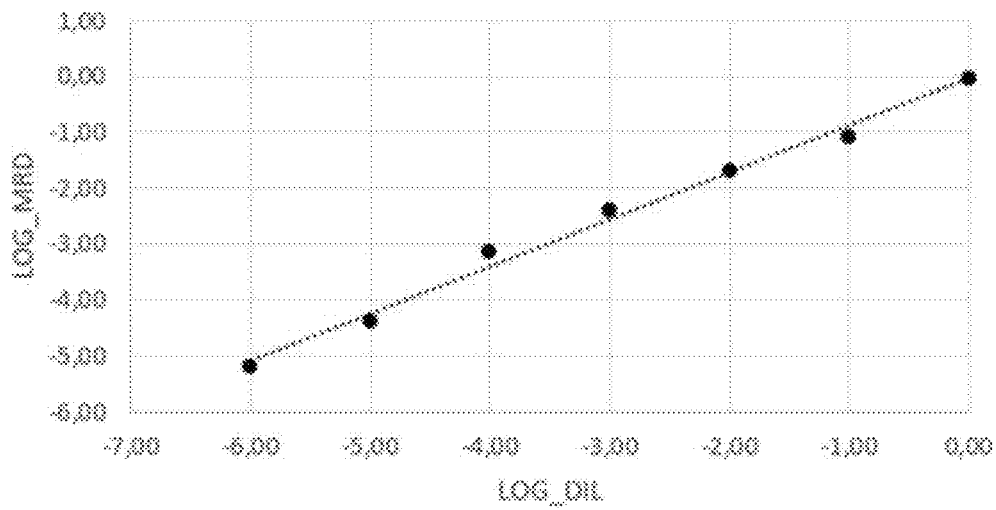
Figure 13T:
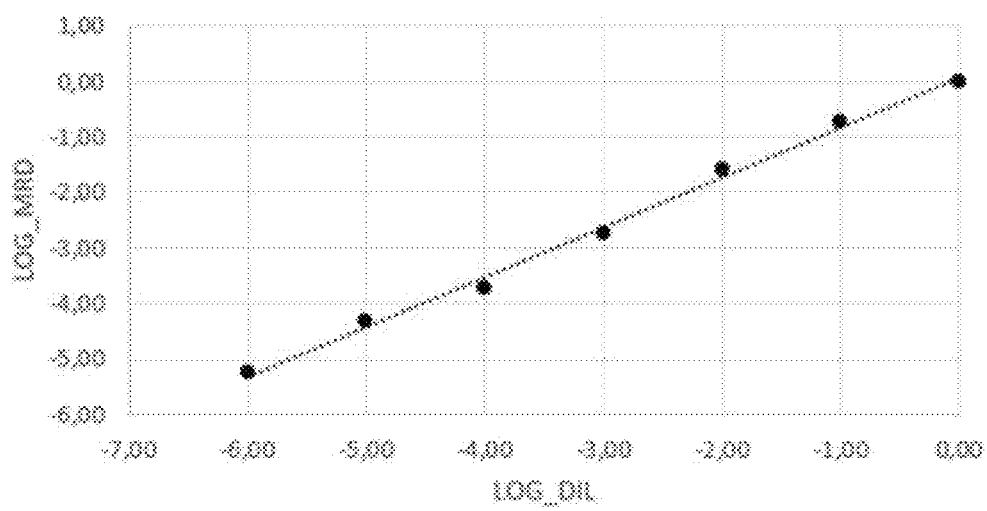

In particular, in the method of treatment of the present description, when the presence of MRD is determined in said subject (decided in block 106 of FIGS. 11A and 11B) a step of administering therapy to said subject is repeated, followed by determining the presence or absence of MRD in said subject until MRD is determined to be absent in said subject (block 108 of FIGS. 11A and 11B).

In other words, the method of treatment of the present description involves a step of treating the subject for the disease and a step of determining the presence or absence of MRD in said subject following said treatment and, if said disease persists in said subject following said treatment, the step of treating the subject for the disease and the subsequent step of determining the presence or absence of MRD in said subject following said treatment, are repeated until the disease no longer persists in said subject. In the method of treatment of the present description, each repetition of the step of treating the subject for the disease comprises administering the same therapy as previously administered to said subject or administering therapy different to that previously administered to said subject. Preferably, therapy different to that which is previously administered to said subject is administered in all subsequent repetitions of the step of treating the subject for the disease.

In the method of treatment of the present description, the step of treating the subject for the disease and the subsequent step of determining the presence or absence of MRD in said subject following said treatment are repeated until MRD is determined to be absent in said subject. However, the step of treating the subject for the disease and the subsequent step of determining the presence or absence of MRD in said subject following said treatment are preferably repeated for a maximum of 4 cycles of treatment, more preferably for 3 cycles of treatment, even more preferably for a maximum of two cycles of treatment, provided that MRD is determined to be absent in said subject at the end of each cycle of treatment.

Said method of treatment comprises administering therapy to said subject, wherein said therapy is preferably chemotherapy. More preferably, said chemotherapy comprises administration of:
- a proteasome inhibitor and an immunomodulator; or
- cytarabine and an anthracycline antibiotic or an anthracenedione, optionally followed by administration of cytarabine.

Even more preferably, said chemotherapy comprises administration of:
- bortezomib and prednisone (VMP); or
- administration of cytarabine and an anthracycline antibiotic or an anthracenedione, optionally followed by administration of cytarabine.

In an even more preferred embodiment, in the case of multiple myeloma or a lymphoma said chemotherapy consists of:
- between 9 and 18 cycles of treatment, each cycle comprising administration of bortezomib and prednisone (VMP); or
- in the case of a myeloid cancer, preferably acute myeloid leukaemia, said chemotherapy consists of:
  - 1 or 2 cycles of treatment, each cycle comprising administration of cytarabine over 7 days and subsequent administration of an anthracycline antibiotic or an anthracenedione over 3 days (post-induction treatment), or
  - 1 or 2 cycles of treatment, each cycle comprising administration of cytarabine over 7 days and subsequent administration of an anthracycline antibiotic or an anthracenedione over 3 days (post induction treatment), optionally followed by 1 or 2 cycles of treatment each comprising administration of cytarabine (post-consolidation treatment).

In a furthermore preferred embodiment of the present invention, said chemotherapy consists of between 9 and 18 cycles of treatment, each cycle comprising administration of bortezomib and prednisone (VMP), when said disease is multiple myeloma. In another furthermore preferred embodiment of the present invention, said chemotherapy consists of 1 or 2 cycles of treatment (with between 30 and 35 days between cycles), each cycle comprising administration of cytarabine over 7 days and subsequent administration of an anthracycline antibiotic or an anthracenedione over 3 days (post-induction treatment), when said disease is acute myeloid leukemia or any myeloid neoplasia. In yet another furthermore preferred embodiment of the present invention, said chemotherapy consists of 1 or 2 cycles of treatment (with between 30 and 35 days between cycles), each cycle comprising administration of cytarabine over 7 days and subsequent administration of an anthracycline antibiotic or an anthracenedione over 3 days, followed by 1 or 2 cycles of treatment each comprising administration of cytarabine (post-consolidation treatment), when said disease is acute myeloid leukemia or any myeloid neoplasia. In one embodiment of the method of treatment of the present invention the anthracycline antibiotic or anthracenedione is idarubicin.

In the present invention, the level of MRD is quantified in a subject who has been treated for said disease by a method comprising seven steps, (A) to (G) (collectively exemplified in block 104 of FIGS. 5A and 5B), and further exemplified for a method 104 comprising step (A) in blocks 200 and 202, step (B) in blocks 204 and 206, step (C) in block 208, step (D) in block 210, step (E) in block 212, step (F) in block 214 and step (G) in block 216 of FIG. 6]. These seven steps are preferably performed without the need to access an external database comprising data obtained from a population of subjects. Said steps are performed using biological techniques and at least one computer program product.

Figure 8A:
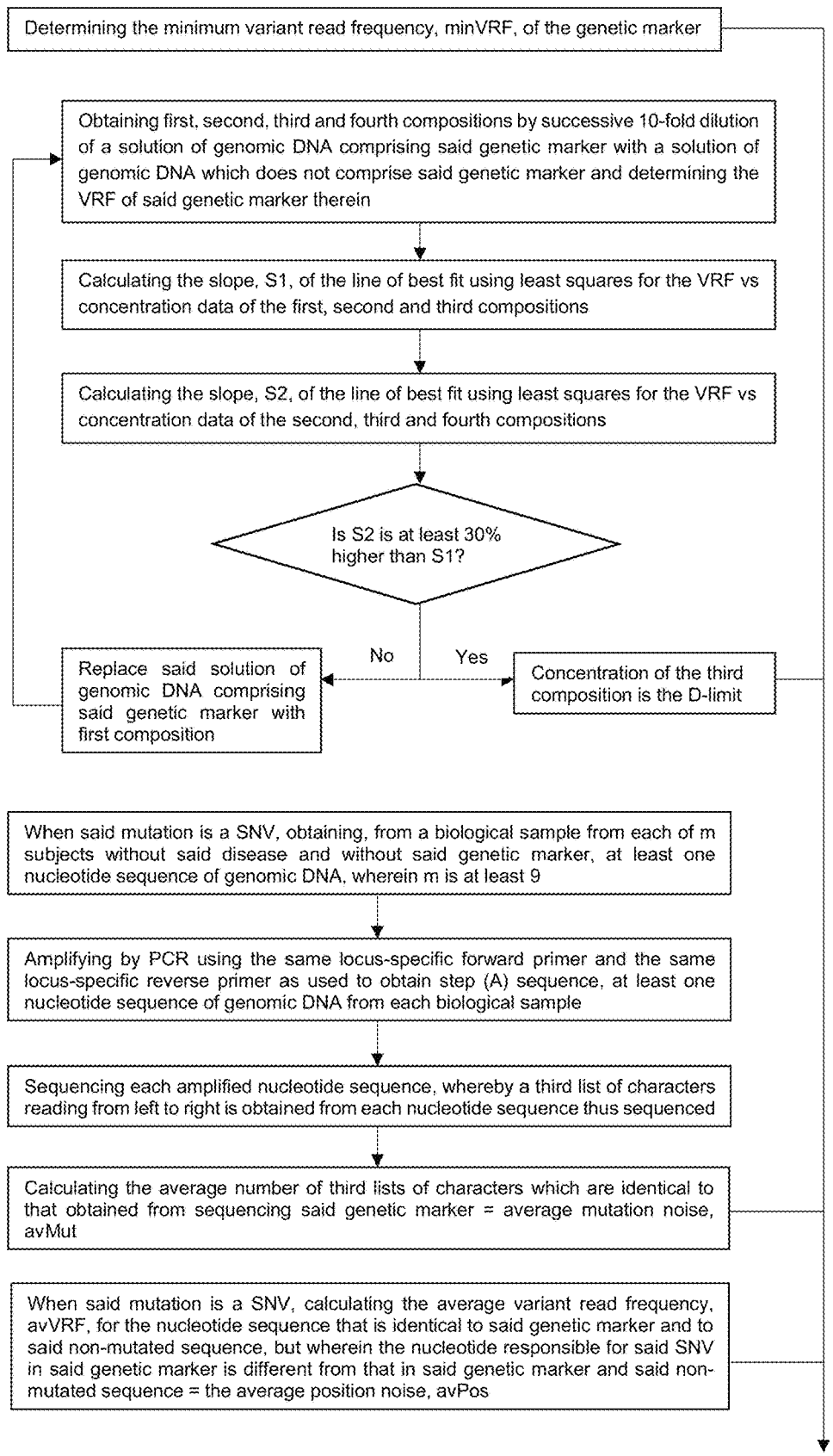
FIG. 8. A. Flowchart of an example of a step for determining the min VRF of the genetic marker, the D-limit of said genetic marker, the avMut and the avPos in accordance with an embodiment of the present invention. B. Flowchart of an example of a step for determining the ES in accordance with another embodiment of the present invention.
Figure 8B:
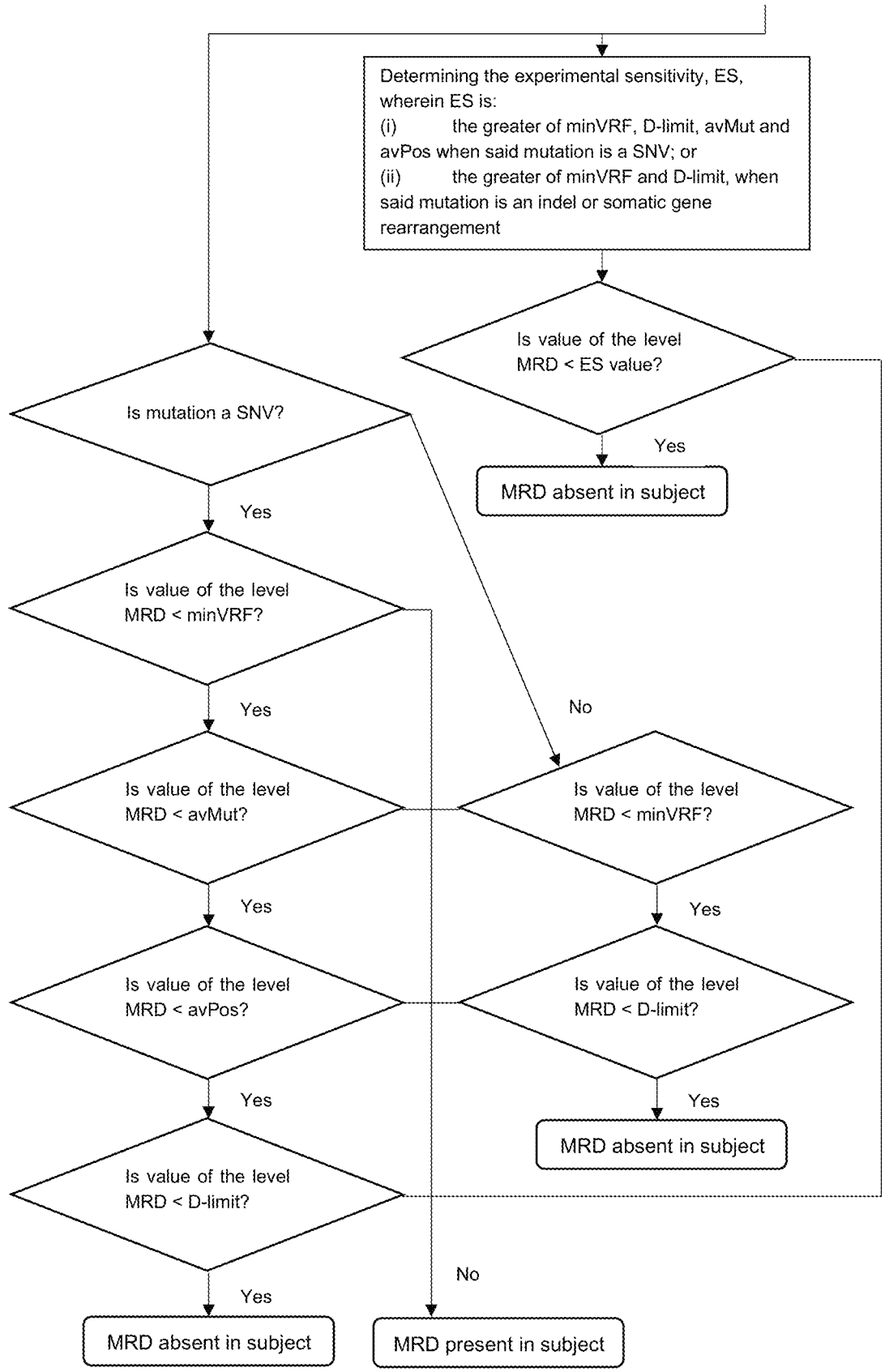

Moreover, the min VRF of the genetic marker, the D-limit of said genetic marker, the avMut and the avPos are determined in an additional step, (H), (collectively exemplified in block 105 of FIGS. 5A and 5B), and further exemplified for a method 304 comprising step (H)(i) in blocks 300 and 302, step (H)(ii) in blocks 304 and 306, step (H)(iii) in block 308 and step (H)(iv) in block 316 of FIG. 8A]. On the other hand, the ES is determined in another step (I) (collectively exemplified in block 105 of FIG. 5B), and further exemplified for a method 404 in block 416 of FIG. 8B].

An especially preferred embodiment of the present invention relates to a method for determining the presence or absence of minimal residual disease (MRD) in a subject who has been treated for a disease, wherein said disease is a proliferative disease selected from acute myeloid leukaemia (AML) or multiple myeloma (MM), wherein said method comprises the following steps:

(A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
sequencing each amplified nucleotide sequence, whereby a first list of characters reading from left to right is obtained from each nucleotide sequence thus sequenced;

(B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and
sequencing each amplified nucleotide sequence, whereby a second list of characters reading from left to right is obtained from each nucleotide sequence thus sequenced;

wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;

(C) determining, for each second list of characters obtained in step (B), the degree of similarity with each first list of characters obtained in step (A), wherein a degree of similarity, DS, of a second list of characters obtained in step (B) with a first list of characters obtained in step (A) is determined by:
  (i) counting the total number of characters, $C_c$, in the second and first lists of characters which are the same as in the first and second lists of characters, respectively;
  (ii) counting the total number of characters, $C_t$, in the first and second lists of characters; and
  (iii) calculating DS according to the following formula:

$$DS = C_c/C_t$$

(D) selecting, for each second list of characters obtained in step (B), the DS of highest value, $DS_{HV}$;

(E) adding up the number of second lists of characters which have a $DS_{HV}$ that is greater than a threshold value, T, to obtain the total number of second lists of characters, $L_c$, which are the same as a first list of characters;
(F) adding up
  (i) $L_c$; and
  (ii) the number of second lists of characters which do not have a $DS_{HV}$ that is greater than T,
    to obtain the total number of second lists of characters, $L_t$; and
(G) calculating the level of minimal residual disease, MRD, according to any of the following formulae:

$$MRD=(L_c \times k)/(L_t \times D)$$

or $$MRD=L_c/L_t$$

or $$MRD=g \times L_c \times (D/k)/L_t^2$$

wherein g is the number of gene copies per cell, D is in units of ng and k is in units of ng/cell;
(H) determining:
  (i) the minimum variant read frequency, min VRF, of said genetic marker, wherein min VRF is calculated according to the following formula:

$$\min VRF = k/D$$

wherein D and k are as defined above; and
  (ii) the limit of detection, D-limit, of said genetic marker, by:
    (a) obtaining a first composition by diluting one part of a solution of genomic DNA comprising said genetic marker with 10 parts of a solution of genomic DNA which does not comprise said genetic marker;
    (b) determining the level of MRD of said genetic marker in said first composition;
    (c) obtaining a second composition by diluting one part of said first composition with 10 parts of a solution of genomic DNA which does not comprise said genetic marker;
    (d) determining the level of MRD of said genetic marker in said second composition;
    (e) obtaining a third composition by diluting one part of said second composition with 10 parts of a solution of genomic DNA which does not comprise said genetic marker;
    (f) determining the level of MRD of said genetic marker in said third composition;
    (g) obtaining a fourth composition by diluting one part of said third composition with 10 parts of a solution of genomic DNA which does not comprise said genetic marker;
    (h) determining the level of MRD of said genetic marker in said fourth composition;
    (i) calculating:
      the average logarithm of the level of MRD, av log MRD1, of said genetic marker in the first, second and third compositions and the average logarithm of the concentration, av log C1, of said genetic marker in the first, second and third compositions; and
      the average logarithm of the level of MRD, av log MRD2, of said genetic marker in the second, third and fourth compositions and the average logarithm of the concentration, av log C2, of said genetic marker in the second, third and fourth compositions;
    (j) calculating:
      the difference, D1A, between the logarithm of the level of MRD of said genetic marker in the first composition and the av log MRD1;
      the difference, D1B, between the logarithm of the level of MRD of said genetic marker in the second composition and the av log MRD1;
      the difference, D1C, between the logarithm of the level of MRD of said genetic marker in the third composition and the av log MRD1;
      the difference, D1D, between the logarithm of the concentration of said genetic marker in the first composition and the av log C1;
      the difference, D1E, between the logarithm of the concentration of said genetic marker in the second composition and the av log C1;
      the difference, D1F, between the logarithm of the concentration of said genetic marker in the third composition and the av log C1;
      the difference, D2A, between the logarithm of the level of MRD of said genetic marker in the second composition and the av log MRD2;
      the difference, D2B, between the logarithm of the level of MRD of said genetic marker in the third composition and the av log MRD2;
      the difference, D2C, between the logarithm of the level of MRD of said genetic marker in the fourth composition and the av log MRD2;
      the difference, D2D, between the logarithm of the concentration of said genetic marker in the second composition and the av log C2;
      the difference, D2E, between the logarithm of the concentration of said genetic marker in the third composition and the av log C2; and
      the difference, D2F, between the logarithm of the concentration of said genetic marker in the fourth composition and the av log C2;
    (k) calculating:
      R1 by multiplying D1A and D1D;
      R2 by multiplying D1B and D1E;
      R3 by multiplying D1C and D1F;
      R4 by multiplying D1A by D1A;
      R5 by multiplying D1B by D1B;
      R6 by multiplying D1C by D1C;
      R7 by multiplying D2A and D2D;
      R8 by multiplying D2B and D2E;
      R9 by multiplying D2C and D2F;
      R10 by multiplying D2A by D2A;
      R11 by multiplying D2B by D2B;
      R12 by multiplying D2C by D2C;
    (l) calculating:
      S1 using the following formula:

$$S1=(R1+R2+R3)/(R4+R5+R6)$$

S2 using the following formula:

$$S2=(R7+R8+R9)/(R10+R11+R12);$$

(m) comparing S1 and S2, whereby:
      when S2 is at least 30% lower than S1, the concentration of the third composition is the D-limit; and
      when S2 is equal to S1 or less than 30% lower than S1, steps (H)(ii)(a) to (H)(ii)(l) are repeated using said first composition in place of said solution of genomic DNA comprising said genetic marker; and (iii) the average mutation noise, avMut, when said mutation is a single nucleotide variant mutation, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
(b) sequencing each amplified nucleotide sequence, whereby a third list of characters reading from left to right is obtained from each nucleotide sequence thus sequenced;
(c) repeating steps (H)(iii)(a) and (H)(iii)(b) in m subjects without said disease and without said genetic marker, wherein m is at least 9; and
(d) calculating the average fraction of third lists of characters which are identical to that obtained from sequencing said genetic marker, wherein said average fraction is avMut; and
(iv) the average position noise, avPos, when said mutation is a single nucleotide variant mutation, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;

(I) determining the experimental sensitivity, ES, wherein ES is:
(i) the greater of min VRF, D-limit, avMut and avPos, as calculated in step (H), when said mutation is a single nucleotide variant mutation; or
(ii) the greater of min VRF and D-limit, as calculated in step (H), when said mutation is an indel mutation or somatic gene rearrangement mutation; and (J) determining the presence or absence of minimal residual disease in said subject by either:
(i) comparing the value of the level of minimal residual disease, MRD, calculated in step (G) with the value of the experimental sensitivity, ES, determined in step (I), wherein
(a) when said level of MRD value is equal to or greater than said ES value, minimal residual disease is present in said subject; and
(b) when said level of MRD value is less than said ES value, minimal residual disease is absent from said subject or
(ii) when said mutation is a single nucleotide variant mutation, comparing the value of the level of minimal residual disease, MRD, calculated in step (G) with the value of min VRF calculated in step (H), wherein
(a) when said level of MRD value is equal to or greater than said min VRF value, minimal residual disease is present in said subject; and
comparing the value of the level of minimal residual disease, MRD, calculated in step (G) with the value of avMut calculated in step (H) when said level of MRD value is less than said min VRF value, wherein (b) when said level of MRD value is equal to or greater than said avMut value, minimal residual disease is present in said subject; and
comparing the value of the level of minimal residual disease, MRD, calculated in step (G) with the value of avPos calculated in step (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in step (G) with the value of D-limit calculated in step (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;

or
(iii) when said mutation is an indel mutation or somatic gene rearrangement mutation, comparing the value of the level of minimal residual disease, MRD, calculated in step (G) with the value of min VRF calculated in step (I), wherein
(f) when said level of MRD value is equal to or greater than said min VRF value, minimal residual disease is present in said subject; and
comparing the value of the level of minimal residual disease, MRD, calculated in step (G) with the value of D-limit calculated in step (H) when said level of MRD value is less than said min VRF value, wherein
(g) when said level of MRD value is equal to or greater than said D-limit value, minimal residual disease is present in said subject; and
(h) when said level of MRD value is less than said min VRF and D-limit values, minimal residual disease is absent from said subject, wherein when said proliferative disease is:
(i) acute myeloid leukaemia (AML), it is characterised by an indel mutation or single nucleotide variant mutation in the nucleotide sequence of a gene selected from the group consisting of: KRAS, NPM1 and NRAS, still more preferably the group consisting of: KRAS G12D, NPM1 W290fs (NPM1 ins) and NRAS Q61R; or
(ii) multiple myeloma (MM), it is characterised by:
a somatic gene rearrangement mutation in the nucleotide sequence of a gene selected from the group consisting of: IGH and IGK, or
an indel mutation or single nucleotide variant mutation in the nucleotide sequence of a gene selected from the group consisting of: NRAS, still more preferably NRAS Q61H.

Another especially preferred embodiment of the present invention relates to a method for determining the presence or absence of minimal residual disease (MRD) in a subject who has been treated for a disease, wherein said disease is a proliferative disease selected from follicular lymphoma (FL) or lung cancer (adenocarcinoma), wherein said method comprises the following steps:
(A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and sequencing each amplified nucleotide sequence, whereby a first list of characters reading from left to right is obtained from each nucleotide sequence thus sequenced;

(B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and sequencing each amplified nucleotide sequence, whereby a second list of characters reading from left to right is obtained from each nucleotide sequence thus sequenced;

wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a single nucleotide variant mutation;

(C) determining, for each second list of characters obtained in step (B), the degree of similarity with each first list of characters obtained in step (A), wherein a degree of similarity, DS, of a second list of characters obtained in step (B) with a first list of characters obtained in step (A) is determined by:
  (i) counting the total number of characters, $C_c$, in the second and first lists of characters which are the same as in the first and second lists of characters, respectively;
  (ii) counting the total number of characters, $C_t$, in the first and second lists of characters; and
  (iii) calculating DS according to the following formula:

$DS = C_c/C_t$ (D) selecting, for each second list of characters obtained in step (B), the DS of highest value, $DS_{HV}$;

(E) adding up the number of second lists of characters which have a $DS_{HV}$ that is greater than a threshold value, T, to obtain the total number of second lists of characters, $L_c$, which are the same as a first list of characters;

(F) adding up
  (i) $L_c$; and
  (ii) the number of second lists of characters which do not have a $DS_{HV}$ that is greater than T,
  to obtain the total number of second lists of characters, $L_t$; and (G) calculating the level of minimal residual disease, MRD, according to any of the following formulae:

$MRD = (L_c \times k)/(L_t \times D)$ or $MRD = L_c/L_t$ or $MRD = g \times L_c \times (D/k)/L_t^2$ wherein g is the number of gene copies per cell, D is in units of ng and k is in units of ng/cell;

(H) determining:
  (i) the minimum variant read frequency, min VRF, of said genetic marker, wherein min VRF is calculated according to the following formula:

$\min VRF = k/D$ wherein D and k are as defined above; and (ii) the limit of detection, D-limit, of said genetic marker, by:
  (a) obtaining a first composition by diluting one part of a solution of genomic DNA comprising said genetic marker with 10 parts of a solution of genomic DNA which does not comprise said genetic marker;
  (b) determining the level of MRD of said genetic marker in said first composition;
  (c) obtaining a second composition by diluting one part of said first composition with 10 parts of a solution of genomic DNA which does not comprise said genetic marker;
  (d) determining the level of MRD of said genetic marker in said second composition;
  (e) obtaining a third composition by diluting one part of said second composition with 10 parts of a solution of genomic DNA which does not comprise said genetic marker;
  (f) determining the level of MRD of said genetic marker in said third composition;
  (g) obtaining a fourth composition by diluting one part of said third composition with 10 parts of a solution of genomic DNA which does not comprise said genetic marker;
  (h) determining the level of MRD of said genetic marker in said fourth composition;
  (i) calculating:
    the average logarithm of the level of MRD, av log MRD1, of said genetic marker in the first, second and third compositions and the average logarithm of the concentration, av log C1, of said genetic marker in the first, second and third compositions; and
    the average logarithm of the level of MRD, av log MRD2, of said genetic marker in the second, third and fourth compositions and the average logarithm of the concentration, av log C2, of said genetic marker in the second, third and fourth compositions;
  (j) calculating:
    the difference, D1A, between the logarithm of the level of MRD of said genetic marker in the first composition and the av log MRD1;
    the difference, D1B, between the logarithm of the level of MRD of said genetic marker in the second composition and the av log MRD1;
    the difference, D1C, between the logarithm of the level of MRD of said genetic marker in the third composition and the av log MRD1;
    the difference, D1D, between the logarithm of the concentration of said genetic marker in the first composition and the av log C1;
    the difference, D1E, between the logarithm of the concentration of said genetic marker in the second composition and the av log C1;
    the difference, D1F, between the logarithm of the concentration of said genetic marker in the third composition and the av log C1;
    the difference, D2A, between the logarithm of the level of MRD of said genetic marker in the second composition and the av log MRD2;

the difference, D2B, between the logarithm of the level of MRD of said genetic marker in the third composition and the av log MRD2;

the difference, D2C, between the logarithm of the level of MRD of said genetic marker in the fourth composition and the av log MRD2;

the difference, D2D, between the logarithm of the concentration of said genetic marker in the second composition and the av log C2;

the difference, D2E, between the logarithm of the concentration of said genetic marker in the third composition and the av log C2; and the difference, D2F, between the logarithm of the concentration of said genetic marker in the fourth composition and the av log C2;

(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;

(l) calculating:
S1 using the following formula:

$$S1=(R1+R2+R3)/(R4+R5+R6)$$

S2 using the following formula:

$$S2=(R7+R8+R9)/(R10+R11+R12);$$

(m) comparing S1 and S2, whereby:
when S2 is at least 30% lower than S1, the concentration of the third composition is the D-limit; and
when S2 is equal to S1 or less than 30% lower than S1, steps (H)(ii)(a) to (H)(ii)(l) are repeated using said first composition in place of said solution of genomic DNA comprising said genetic marker; and (iii) the average mutation noise, avMut, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
(b) sequencing each amplified nucleotide sequence, whereby a third list of characters reading from left to right is obtained from each nucleotide sequence thus sequenced;
(c) repeating steps (H)(iii)(a) and (H)(iii)(b) in m subjects without said disease and without said genetic marker, wherein m is at least 9; and
(d) calculating the average fraction of third lists of characters which are identical to that obtained from sequencing said genetic marker, wherein said average fraction is avMut; and (iv) the average position noise, avPos, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;

(I) determining the experimental sensitivity, ES, wherein ES is the greater of min VRF, D-limit, avMut and avPos, as calculated in step (H);

and (J) determining the presence or absence of minimal residual disease in said subject by either:
(i) comparing the value of the level of minimal residual disease, MRD, calculated in step (G) with the value of the experimental sensitivity, ES, determined in step (I), wherein
(a) when said level of MRD value is equal to or greater than said ES value, minimal residual disease is present in said subject; and
(b) when said level of MRD value is less than said ES value, minimal residual disease is absent from said subject or (ii) comparing the value of the level of minimal residual disease, MRD, calculated in step (G) with the value of min VRF calculated in step (H), wherein
(a) when said level of MRD value is equal to or greater than said min VRF value, minimal residual disease is present in said subject; and
comparing the value of the level of minimal residual disease, MRD, calculated in step (G) with the value of avMut calculated in step (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in step (G) with the value of avPos calculated in step (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in step (G) with the value of D-limit calculated in step (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;

wherein when said proliferative disease is:
(i) follicular lymphoma (FL), it is characterised by a single nucleotide variant mutation in the nucleotide sequence of a gene selected from the group consisting of: EZH2, KMT2D and KRAS, still more preferably the group consisting of: EZH2 Y646S, KMT2D Q2014fs and KRAS G12A; or
(ii) lung cancer (adenocarcinoma), it is characterised by a single nucleotide variant mutation in the nucleotide sequence of a gene selected from the group consisting of: TSC2 and WAS, still more preferably the group consisting of: TSC2 L248V and WAS T45M.

Another especially preferred embodiment of the present invention relates to a method for treatment of disease in a subject who has been treated for said disease, wherein said disease is a proliferative disease selected from acute myeloid leukaemia (AML) or multiple myeloma (MM), comprising the steps of:

(1) administering therapy to a subject, wherein said therapy is selected from chemotherapy, immunotherapy or radiotherapy, or combinations thereof; and (2) determining the presence or absence of minimal residual disease (MRD) in a subject wherein said method comprises the following steps:

(A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and sequencing each amplified nucleotide sequence, whereby a first list of characters reading from left to right is obtained from each nucleotide sequence thus sequenced;

(B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and sequencing each amplified nucleotide sequence, whereby a second list of characters reading from left to right is obtained from each nucleotide sequence thus sequenced;

wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;

(C) determining, for each second list of characters obtained in step (B), the degree of similarity with each first list of characters obtained in step (A), wherein a degree of similarity, DS, of a second list of characters obtained in step (B) with a first list of characters obtained in step (A) is determined by:

(i) counting the total number of characters, $C_c$, in the second and first lists of characters which are the same as in the first and second lists of characters, respectively;

(ii) counting the total number of characters, $C_t$, in the first and second lists of characters; and (iii) calculating DS according to the following formula:

$$DS = C_c/C_t$$

(D) selecting, for each second list of characters obtained in step (B), the DS of highest value, $DS_{HV}$;

(E) adding up the number of second lists of characters which have a $DS_{HV}$ that is greater than a threshold value, T, to obtain the total number of second lists of characters, $L_c$, which are the same as a first list of characters;

(F) adding up
(i) $L_c$; and
(ii) the number of second lists of characters which do not have a $DS_{HV}$ that is greater than T,
to obtain the total number of second lists of characters, $L_t$; and (G) calculating the level of minimal residual disease, MRD, according to any of the following formulae:

$$MRD = (L_c \times k)/(L_t \times D)$$

or $$MRD = L_c/L_t$$

or $$MRD = g \times L_c \times (D/k)/L_t^2$$

wherein g is the number of gene copies per cell, D is in units of ng and k is in units of ng/cell;

(H) determining:

(i) the minimum variant read frequency, min VRF, of said genetic marker, wherein min VRF is calculated according to the following formula:

$$\min VRF = k/D$$

wherein D and k are as defined above; and (ii) the limit of detection, D-limit, of said genetic marker, by:

(a) obtaining a first composition by diluting one part of a solution of genomic DNA comprising said genetic marker with 10 parts of a solution of genomic DNA which does not comprise said genetic marker;

(b) determining the level of MRD of said genetic marker in said first composition;

(c) obtaining a second composition by diluting one part of said first composition with 10 parts of a solution of genomic DNA which does not comprise said genetic marker;

(d) determining the level of MRD of said genetic marker in said second composition;

(e) obtaining a third composition by diluting one part of said second composition with 10 parts of a solution of genomic DNA which does not comprise said genetic marker;

(f) determining the level of MRD of said genetic marker in said third composition;

(g) obtaining a fourth composition by diluting one part of said third composition with 10 parts of a solution of genomic DNA which does not comprise said genetic marker;

(h) determining the level of MRD of said genetic marker in said fourth composition;

(i) calculating:

the average logarithm of the level of MRD, av log MRD1, of said genetic marker in the first, second and third compositions and the average logarithm of the concentration, av log C1, of said genetic marker in the first, second and third compositions; and the average logarithm of the level of MRD, av log MRD2, of said genetic marker in the second, third and fourth compositions and the average logarithm of the concentration, av log C2, of said genetic marker in the second, third and fourth compositions;

(j) calculating:

the difference, D1A, between the logarithm of the level of MRD of said genetic marker in the first composition and the av log MRD1;

the difference, D1B, between the logarithm of the level of MRD of said genetic marker in the second composition and the av log MRD1;

the difference, D1C, between the logarithm of the level of MRD of said genetic marker in the third composition and the av log MRD1;

the difference, D1D, between the logarithm of the concentration of said genetic marker in the first composition and the av log C1;

the difference, D1E, between the logarithm of the concentration of said genetic marker in the second composition and the av log C1;

the difference, D1F, between the logarithm of the concentration of said genetic marker in the third composition and the av log C1;

the difference, D2A, between the logarithm of the level of MRD of said genetic marker in the second composition and the av log MRD2;

the difference, D2B, between the logarithm of the level of MRD of said genetic marker in the third composition and the av log MRD2;

the difference, D2C, between the logarithm of the level of MRD of said genetic marker in the fourth composition and the av log MRD2;

the difference, D2D, between the logarithm of the concentration of said genetic marker in the second composition and the av log C2;

the difference, D2E, between the logarithm of the concentration of said genetic marker in the third composition and the av log C2; and the difference, D2F, between the logarithm of the concentration of said genetic marker in the fourth composition and the av log C2;

(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;

(l) calculating:
S1 using the following formula:

$S1=(R1+R2+R3)/(R4+R5+R6)$

S2 using the following formula:

$S2=(R7+R8+R9)/(R10+R11+R12);$ (m) comparing S1 and S2, whereby:
when S2 is at least 30% lower than S1, the concentration of the third composition is the D-limit; and
when S2 is equal to S1 or less than 30% lower than S1, steps (H)(ii)(a) to (H)(ii)(l) are repeated using said first composition in place of said solution of genomic DNA comprising said genetic marker; and (iii) the average mutation noise, avMut, when said mutation is a single nucleotide variant mutation, by
(a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;

(b) sequencing each amplified nucleotide sequence, whereby a third list of characters reading from left to right is obtained from each nucleotide sequence thus sequenced;

(c) repeating steps (H)(iii)(a) and (H)(iii)(b) in m subjects without said disease and without said genetic marker, wherein m is at least 9; and (d) calculating the average fraction of third lists of characters which are identical to that obtained from sequencing said genetic marker, wherein said average fraction is avMut; and (iv) the average position noise, avPos, when said mutation is a single nucleotide variant mutation, by calculating the variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;

(I) determining the experimental sensitivity, ES, wherein ES is:
(i) the greater of min VRF, D-limit, avMut and avPos, as calculated in step (H), when said mutation is a single nucleotide variant mutation; or
(ii) the greater of min VRF and D-limit, as calculated in step (H), when said mutation is an indel mutation or somatic gene rearrangement mutation;

and (J) determining the presence or absence of minimal residual disease in said subject by either:
(i) comparing the value of the level of minimal residual disease, MRD, calculated in step (G) with the value of the experimental sensitivity, ES, determined in step (I), wherein
(a) when said level of MRD value is equal to or greater than said ES value, minimal residual disease is present in said subject; and
(b) when said level of MRD value is less than said ES value, minimal residual disease is absent from said subject or (ii) when said mutation is a single nucleotide variant mutation, comparing the value of the level of minimal residual disease, MRD, calculated in step (G) with the value of min VRF calculated in step (H), wherein
(a) when said level of MRD value is equal to or greater than said min VRF value, minimal residual disease is present in said subject; and
comparing the value of the level of minimal residual disease, MRD, calculated in step (G) with the value of avMut calculated in step (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in step (G) with the value of avPos calculated in step (H) when said level of MRD value is less than said avMut value, wherein (c) when said level of MRD value is equal to or greater than said avPos value, minimal residual disease is present in said subject; and comparing the value of the level of minimal residual disease, MRD, calculated in step (G) with the value of D-limit calculated in step (H) when said level of MRD value is less than said avPos value, wherein (d) when said level of MRD value is equal to or greater than said D-limit value, minimal residual disease is present in said subject; and (e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in step (G) with the value of min VRF calculated in step (I), wherein (f) when said level of MRD value is equal to or greater than said min VRF value, minimal residual disease is present in said subject; and comparing the value of the level of minimal residual disease, MRD, calculated in step (G) with the value of D-limit calculated in step (H) when said level of MRD value is less than said min VRF value, wherein (g) when said level of MRD value is equal to or greater than said D-limit value, minimal residual disease is present in said subject; and (h) when said level of MRD value is less than said min VRF and D-limit values, minimal residual disease is absent from said subject, wherein when minimal residual disease is determined to be present in said subject, steps (1) and (2) are repeated, wherein each repetition of step (1) comprises administering the same therapy as previously administered to said subject or therapy different to that previously administered to said subject, wherein when said proliferative disease is:

(i) acute myeloid leukaemia (AML), it is characterised by an indel mutation or single nucleotide variant mutation in the nucleotide sequence of a gene selected from the group consisting of: KRAS, NPM1 and NRAS, still more preferably the group consisting of: KRAS G12D, NPM1 W290fs (NPM1 ins) and NRAS Q61R, and said therapy is chemotherapy comprising at least one cycle of administration of cytarabine over 7 days and subsequent administration of idarubicin over 3 days, followed by administration of cytarabine if a second round of treatment is required; or (ii) multiple myeloma (MM), it is characterised by:

a somatic gene rearrangement mutation in the nucleotide sequence of a gene selected from the group consisting of: IGH and IGK, or an indel mutation or single nucleotide variant mutation in the nucleotide sequence of a gene selected from the group consisting of: NRAS, still more preferably NRAS Q61H, and said therapy is chemotherapy comprising at least one cycle of administration of a proteasome inhibitor and an immunomodulator, preferably bortezomib and prednisone, respectively.

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may include, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and kits according to embodiments and/or steps of the invention. It will be understood that each square or diamond-shaped block of the flowchart illustrations and/or block diagrams, and combinations of blocks in the flowchart illustrations and/or block diagrams, can be implemented by biological techniques or computer readable program instructions, or combinations thereof.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and kits according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to embodiments of the invention in the form disclosed. Many modifications and variations will be apparent to those of ordinary skill in the art without departing from the scope and spirit of embodiments of the invention. The embodiment was chosen and described in order to best explain the principles of embodiments of the invention and the practical application, and to enable others of ordinary skill in the art to understand embodiments of the invention for various embodiments with various modifications as are suited to the particular use contemplated.

EXAMPLES

The following examples illustrate the invention and should not be considered as limiting, but rather illustrative of the invention.

Example 1: Determination of MRD Level in a Follow-Up Sample from a Patient Prior to Selection for Autologous Stem-Cell Transplant (FIG. 14)

i) Subject and Samples.

Figure 14A:
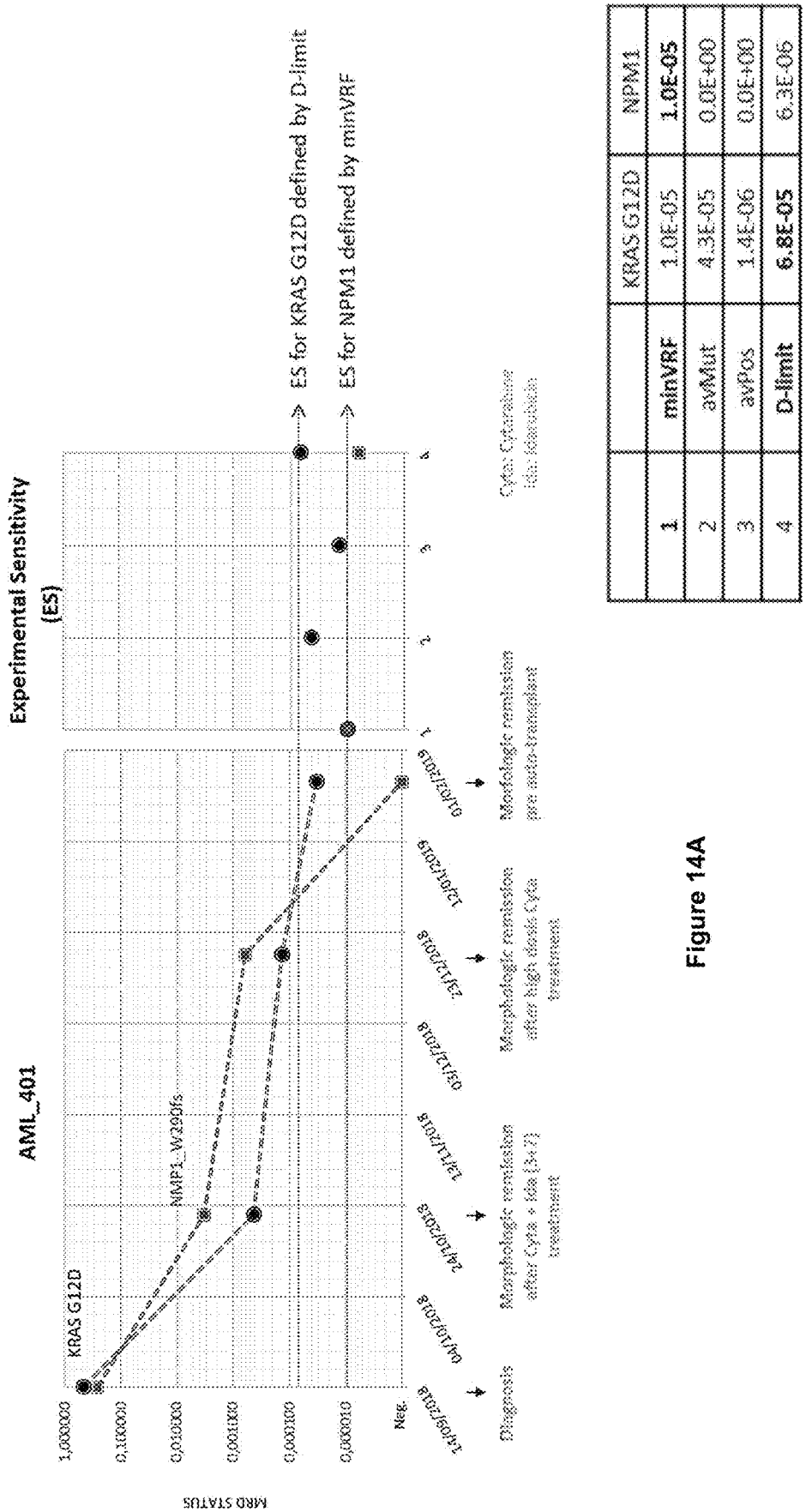
FIG. 14. A. Quantitative MRD status (i.e. level of MRD) vs. time and experimental sensitivity (ES) for last follow-up (Jan. 25, 2019) of a subject (AML_401) diagnosed with acute myeloid leukaemia (AML) in September 2018. At diagnosis the subject presented 2 different somatic mutations suitable for use as MRD markers: one clonal SNV in KRAS G12D (variant read frequency defined at diagnosis after applying $L_c/L_t$, VRFdiag=0.47), and one subclonal insertion in NPM1 (NPM1_W290fs) (VRFdiag=0.27). The subject was treated with Cytarabine+Idarubicin (3+7) [Cyta+Ida (3+7)] and subsequently with high dosis Cytarabine. In the last follow-up before autologous stem-cell transplant (auto-transplant), the ES in KRAS G12D is defined by the D-limit curve ($6.8 \times 10^{-5}$) and NPM1 is defined by min VRF ($1.0 \times 10^{-5}$). B. Values of min VRF, avMut, D-limit and avPos for the KRAS G12D mutation in AML_401, wherein min VAF is defined by the initial amount of DNA (650 ng), avMut is defined by the average of 10 negative controls, D-limit is defined by the concentration of genetic marker in the third composition of a set of four compositions comprising successively 10-fold decreased concentrations (volume/volume) of genetic marker, when the slope of the regressed line between the second set of three successive data points (comprising the composition of lowest concentration of genetic marker) on the log(level of MRD) vs logarithm of the dilution (concentration, volume/volume) curve is at least 30% lower than that of the first set of three successive data points (comprising the composition of highest concentration of genetic marker) on said curve, and avPos is defined by the error rate for the alternative reads, each as further defined herein. C. Values of min VRF, avMut, D-limit and avPos for the NPM1 ins mutation in AML_401, wherein min VRF is defined by the initial amount of DNA (650 ng), D-limit is defined by difference in slope method and both avMut and avPos=0, each as further defined herein.

Subject AML_401 was diagnosed with AML on 14 Sep. 2018 (diagnosis sample at timepoint TP1, as shown in FIG. 14A). Two different sequential samples were collected and analysed to define the level of response to standard-of-care treatment in AML: Cytarabine+Idarubicin (3+7) induction (timepoint TP2, Oct. 22, 2018) followed by high-dose Cytarabine (timepoint TP3, Dec. 18, 2018). The analysis of an extra timepoint (TP4, Jan. 2, 2019) collected prior to autologous stem cell transplant (auto-transplant), within the analysis of the diagnosis sample, as necessary to determine the genetic markers, is described in the present example.

ii) DNA Extraction and Quantification from Samples.

DNA extraction was performed in a Maxwell®16MDx instrument (Promega Biotech Iberica, SL) and quantified on a Qubit®2.0 Fluorometer (Invitrogen™, Thermo Fisher Scientific, Inc., WA, USA). The diagnosis sample presented 20 ng/µL in 30 µL elution volume. TP4 presented 46 ng/µL in 30 µL elution volume (total amount of DNA obtained in TP4=1380 ng).

iii) Determination of Genetic Markers at Diagnosis.

Aiming to define genetic markers for further tracking of the presence of MRD, a mutational profile screening was performed at diagnosis with a custom next-generation sequencing (NGS) using a myeloid panel of multiple genes that are frequently mutated in subjects with acute myeloid leukaemia (AML), myelodysplastic syndrome (MDS) and myeloproliferative neoplasm (MPN), as well as other myeloid cancers [see Table 4, showing genes included in said myeloid panel for NGS sequencing, including the chromosome where it is located, the number of amplicons that the panel includes for each gene, the region of the gene that encompasses all the amplicons expressed as a percentage, and the number of exons]. Library preparation and NGS sequencing of diagnosis sample TP1 was performed using said myeloid panel according to the standard protocols defined by Thermo Fisher Scientific Inc.

TABLE 4

Genes included in the NGS myeloid cancer panel

| Gene | Chr. | No. of Amp. | Coverage (%) | No. of Exons |
| --- | --- | --- | --- | --- |
| NRAS | chr1 | 5 | 100 | 4 |
| MPL | chr1 | 16 | 99.3 | 12 |
| CSF3R | chr1 | 26 | 100 | 18 |
| EGLN1 | chr1 | 10 | 89.3 | 5 |
| KMT2A | chr11 | 80 | 97.7 | 37 |
| CBL | chr11 | 23 | 96.9 | 16 |
| WT1 | chr11 | 15 | 91.5 | 12 |
| KRAS | chr12 | 7 | 100 | 5 |
| ETV6 | chr12 | 12 | 100 | 8 |
| SH2B3 | chr12 | 13 | 88.6 | 8 |
| PRPF40B | chr12 | 31 | 99.2 | 28 |
| FLT3 | chr13 | 28 | 98.4 | 24 |
| IDH2 | chr15 | 16 | 85 | 13 |
| TP53 | chr17 | 14 | 94.5 | 15 |

TABLE 4-continued

Genes included in the NGS myeloid cancer panel

| Gene | Chr. | No. of Amp. | Coverage (%) | No. of Exons |
|---|---|---|---|---|
| SRSF2 | chr17 | 5 | 100 | 2 |
| NF1 | chr17 | 94 | 99.7 | 59 |
| SETBP1 | chr18 | 30 | 100 | 6 |
| EPOR | chr19 | 14 | 94 | 8 |
| CALR | chr19 | 13 | 100 | 9 |
| CEBPA | chr19 | 8 | 97.6 | 4 |
| DNMT3A | chr2 | 32 | 96.8 | 25 |
| IDH1 | chr2 | 12 | 100 | 8 |
| SF3B1 | chr2 | 44 | 98.9 | 27 |
| EPAS1 | chr2 | 22 | 95.4 | 16 |
| ASXL1 | chr20 | 33 | 98.6 | 13 |
| RUNX1 | chr21 | 17 | 98.4 | 10 |
| U2AF1 | chr21 | 10 | 98.9 | 10 |
| SF3A1 | chr22 | 23 | 100 | 16 |
| VHL | chr3 | 5 | 96.6 | 3 |
| THPO | chr3 | 13 | 100 | 11 |
| TET2 | chr4 | 37 | 100 | 10 |
| KIT | chr4 | 27 | 100 | 22 |
| NPM1 | chr5 | 12 | 95.3 | 12 |
| EZH2 | chr7 | 23 | 100 | 21 |
| RAD21 | chr8 | 20 | 100 | 13 |
| JAK2 | chr9 | 38 | 100 | 23 |
| ZRSR2 | chrX | 14 | 100 | 11 |
| KDM6A | chrX | 45 | 99 | 31 |
| PHF6 | chrX | 13 | 89.4 | 11 |
| STAG2 | chrX | 50 | 100 | 33 |
| BCOR | chrX | 39 | 100 | 15 |
| BCORL1 | chrX | 40 | 97 | 13 |
| SMC1A | chrX | 33 | 98.3 | 26 |

Chr. = chromosome
Amp. = amplicons iv) Quantification of the Level of MRD and Determination of Experimental Sensitivity (ES)

After mutational screening to select the genetic marker, two cancer-specific (somatic) mutations were detected, one single nucleotide variation affecting KRAS G12D with a VRF of 26.7%, and one frameshift insertion (indel) on NPM1 (NPM1 W290fs, NPM1 ins) with a VRF of 47.2%, affecting amino acid W290. These specific mutations detected at diagnosis were subsequently studied in follow-up diagnoses.

Figure 4:
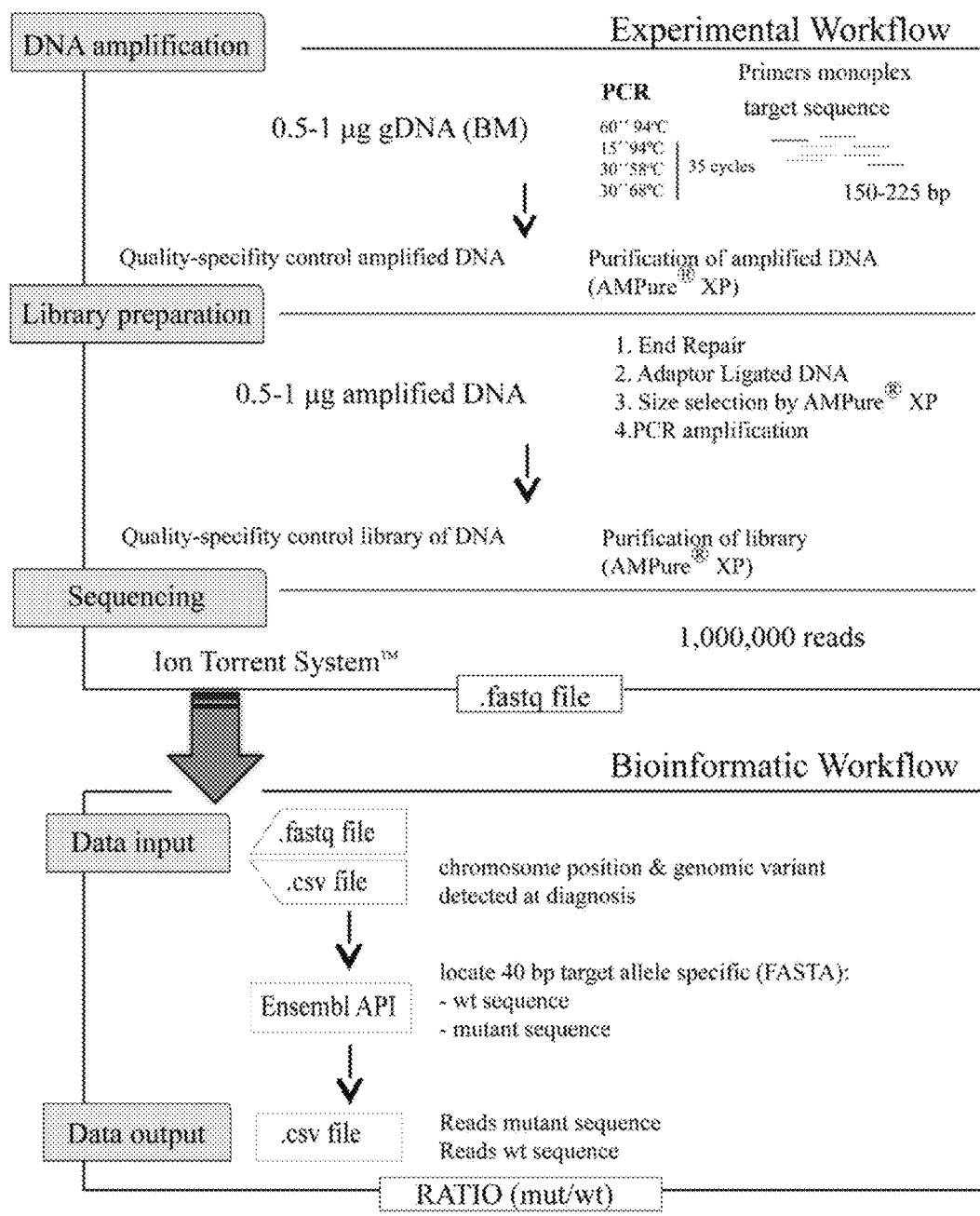
FIG. 4. DNA amplification, library preparation and sequencing experimental workflow of next-generation sequencing (NGS) method of the present invention. In particular, gDNA is amplified by qPCR using specific primers. The product is purified, and the quality and specificity are measured. Library preparation is carried out in four steps: end repair, adaptor ligation, size selection, and PCR amplification. The products are then purified, and the quality and specificity are measured. The library is then sequenced by NGS. A custom bioinformatic pipeline analyses the obtained sequences, focusing the search on the precise position and delimiting the chromosome region through Ensemble perl API annotation. This approach discriminates wild-type sequences from mutated sequences at specific positions and specific alternative fixed variants. The results are expressed as a ratio of sequences mutated among wild-type sequences.

Previously, a protocol (FIG. 4) that included DNA amplification, library preparation and sequencing as experimental steps was established, as follows:

(a) Specific primer pairs that cover these two mutations were selected from Table 3 and used to amplify 650 ng of gDNA from patient sample at timepoint TP4, collected prior to autologous transplant. The amount of gDNA used in PCR amplification allowed the first parameter of the error corrected algorithm, min VRF, to be determined as follows:

$$\min VRF = [6.49 \times 10^{-3} \text{ ng DNA per diploid cell}] / \text{ (FIGS. 14B and 14C)}$$

[amount of gDNA used in PCR amplification $$(ng) = 6.49 \times 10^{-3} / 650 \text{ ng gDNA} = 1.0 \times 10^{-5}.$$

(b) The gDNA was amplified by the first PCR using the selected primers and Platinum™ Taq DNA Polymerase High Fidelity (Invitrogen™, Thermo Fisher Scientific, Inc.) under the following conditions: 60 seconds at 94° C. for initial denaturation, followed by 35 cycles of 15 seconds at 94° C. for denaturation, 30 seconds at 58° C. for annealing and 30 seconds at 68° C. for extension. The final volume was 100 μL (79.6 μL DNA-H$_2$O, 10 μL 10× High Fidelity PCR Buffer, 4 μL 50 nM MgSO$_4$, 2 μL 10 mM dNTP Mix (NZYTech, Lda, Lisbon, Portugal), 0-4 μL DNA polymerase (5 U/μL), 2 μL of 10 μM forward primer and 2 μL of 10 μM reverse primer.

(c) Libraries were constructed using NEBNext® Fast DNA Library Prep Set for Ion Torrent™ (New England Biolabs, Inc., Ipswich, MA, USA). Specificity and quantification of the final product, both for amplified DNA and amplified libraries, was analysed with the Agilent Bioanalyser 2100 (Agilent Technologies, Palo Alto, CA, USA).

(d) Finally, the libraries were sequenced on the Ion Proton System platform (Life Technologies, Thermo Fisher Scientific Inc.) with an estimated depth of 1 million reads, generating .fastq files. These files were analysed with the method of quantifying the level of MRD employed in the present invention that specifically detects target mutated sequences and wild-type sequences in absolute values. Using Ensembl perl API, the mutated sequence and the wt sequence are located in FASTA format bounded at 40 bp. Finally, a .csv file that contains the name identifier, run and barcode identifier, chromosomal position, the variant, the specific sequence in FASTA researched [mutated forward, mutated reverse, wt (wild-type) forward and wt reverse], the counts of each of them and the ratio (mutated/wt) in absolute values was obtained.

Figure 14B:
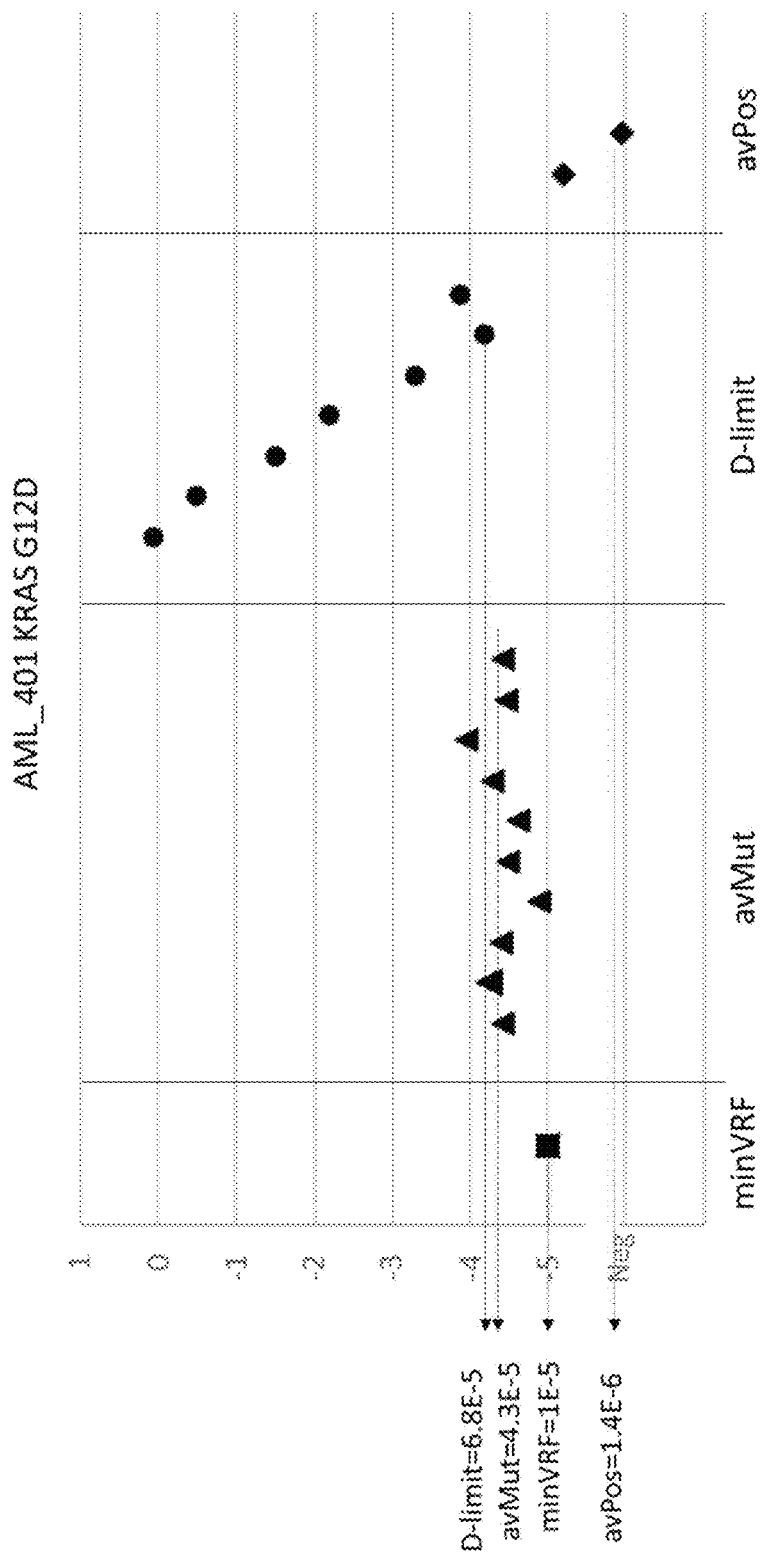
Figure 14C:
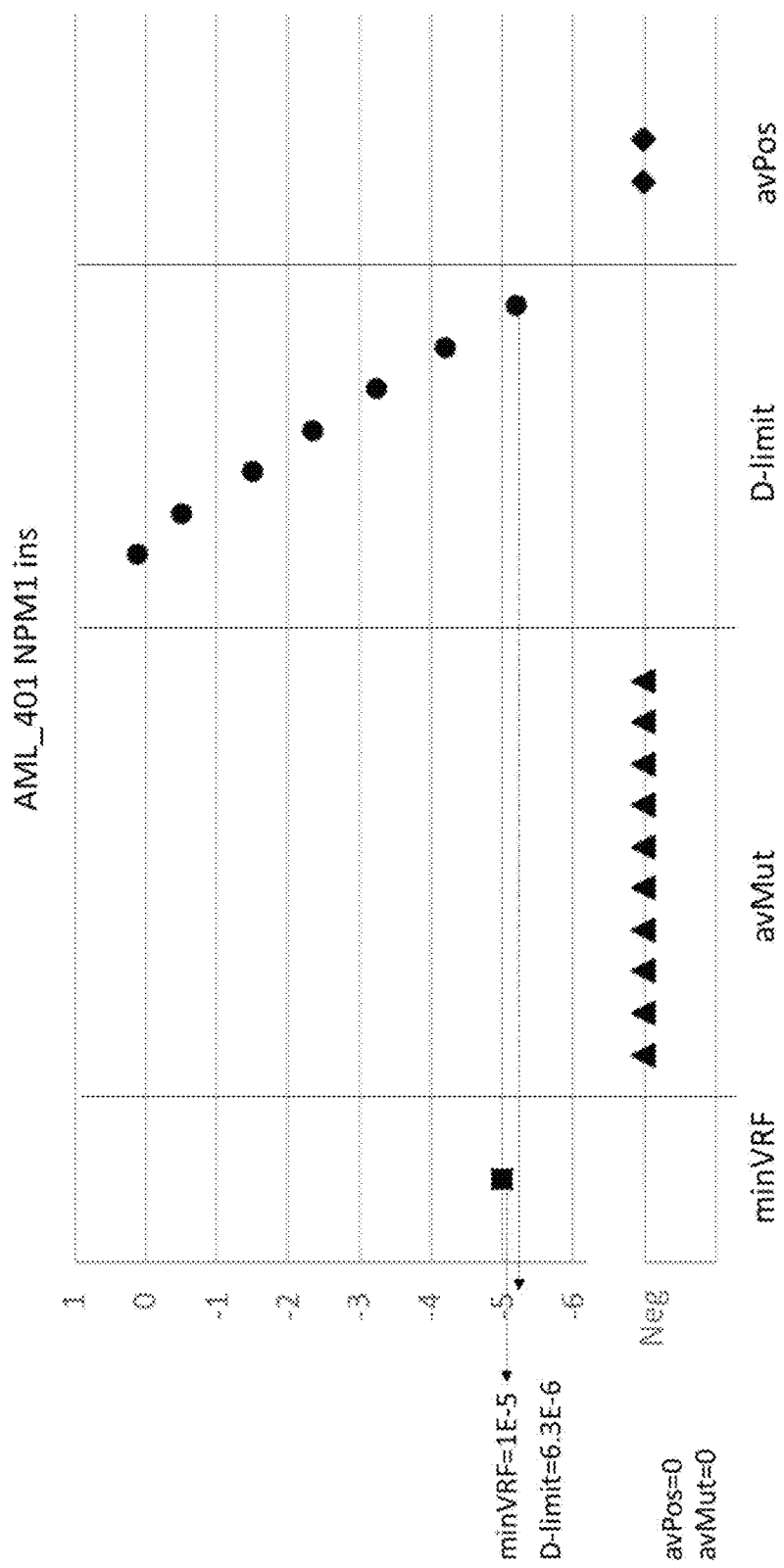

(e) The method also quantifies the avPos for point mutations like KRAS G12D, whereby avPos is the average variant read frequency, avVRF, for the nucleotide sequences (i.e. each alternative) that is identical to said genetic marker and to said non-mutated sequence, but wherein the nucleotide responsible for said single nucleotide variant mutation in said genetic marker is different from that in said genetic marker and said non-mutated sequence. In other words, the alternatives refer to two different non-native sequences that differ from the native sequence and the mutated sequence in that they have a different nucleotide (e.g. C or T) from that present in the mutated sequence (e.g. A) and that present in the native sequence (e.g. G) at the position of the SNV (the non-native alternative sequences, like the native sequence do not cause the disease, but the non-native (mutated) sequence may cause the disease). In particular, the median (or average) of the two alternatives is calculated, thereby establishing the avPos parameter of the error corrected algorithm. Applying this method, the number of alternative reads for single nucleotide variants (SNVs) in KRAS G12D for the position chr1:115258747 were obtained, with the number of mutated sequences for G>A real mutation being 11 of 683118 reads and with the number of non-native alternatives being 2 of 683118 reads for G>T and 0 of 683118 reads for G>C (FIG. 14B). The avPos parameter for indels like that in NPM1 which was detected in this subject or for immunoglobulin rearrangements need not be calculated or considered in this method, as the probability of having exactly the alternative sequence of mutations in the same position and in the same order is approximately 0 (FIG. 14C).

(f) The same approach as described in steps (a) to (e) was repeated in 10 samples from healthy donors without mutations affecting the KRAS gene in order to determine the avMut parameter of the error corrected algorithm as $4.3 \times 10^{-5}$ (FIG. 14B). The avMut parameter for indels like that in NPM1 which was detected in this subject or for immunoglobulin rearrangements need not be calculated or considered in this method, as the probability of having exactly the alternative sequence of mutations in the same position and in the same order is approximately 0 (FIG. 14C).

(g) The same approach as described in steps (a) to (e) was repeated in 10-fold dilution curves performed from an initial commercial DNA with the mutations under study (KRAS G12D and NPM1 ins) presenting in 50% of the molecules. Thus, dilution libraries of up to 7 successive 10-fold dilutions were prepared and sequenced as described above in order to calculate D-limit parameter by the method described herein (FIGS. 14B and 14C).

v) Interpretation of NGS Results

A summary of the MRD values and ES data obtained in subject AML_401 are shown in FIG. 14A, whereby the ES for the KRAS G12D marker at timepoint TP4 is defined by the higher of the four parameters calculated as described above, namely D-limit, such that $ES_{(KRAS\ G12D)}=6.8\times10^{-5}$. The MRD level calculated for this same marker at this same timepoint for this subject was $MRD_{(KRAS\ G12D)}=3.4\times10^{-5}$. Since ES>MRD for this marker, the MRD status at this timepoint in this subject is therefore MRD-negative.

Moreover, the ES for NPM1 ins is defined by the higher of the four parameters calculated as described above, namely min VRF, such that $ES_{(MPN1\ ins)}=1.0\times10^{-5}$. The MRD level calculated for this same marker at this same timepoint for this subject was 0. Since ES>MRD for this marker, the MRD status at this timepoint in this patient is therefore also determined as MRD-negative.

Thus, with either of said markers it can be concluded that minimal residual acute myeloid leukemia is absent from said subject.

Example 2: Determination of MRD Status in a Follow Up Sample from a Myeloma Patient Involved in Clinical Trial. (FIG. 15)

The following presents a method for quantification of tumor clonotypic sequences within the polyclonal background rearrangements of genes of immunoglobulins (Ig) via massively parallel sequencing (MPS). The detection of clonal rearrangement in B and T cell neoplasms allows the evolution of these pathologies to be monitored. To quantify these rearrangements in B cells, primers disclosed in Tables 1 and 2 for IgH, IgK and KDEL were used, because these fragments cover more than 90% of cases. The selection of these particular rearrangements is due to the design of primers which only amplify short (less than 200 bp) sequences; allowing to sequence these fragments in the ION platform S5 platform, with 540 chips. Patients negative for VDJ, IgH, GDR3, KVJ, KDEL diagnoses may be sequenced with the rest of the BIOMED primers like IgH, VDJ, CDRI and IgL DJ. As the size of these fragments is between 300 and 400 base pairs (bp), it is necessary to use other platforms like the PGM platform with a reactive kit for 400 bp or ION S5 platform with 530 chips, that allow to this fragment size to be covered.

Materials and Methods i) Subject Samples

The subject (MM_577) was diagnosed with multiple myeloma (MM) on the 28 Oct. 2013 (TP1). After a first cycle with conventional therapy the patient achieved complete response on 14 Jan. 2014 (TP2). In April 2015 the patient was enrolled in a clinical trial and maintained the complete response after induction with bortezomib and thalidomide containing therapy at 2 Jun. 2015 (TP3). The patient was selected for transplant and on 8 Oct. 2015 (TP4) presented complete remission after this was performed. The clinical study was ended in 2016 with the patient still in complete remission on 16 Jan. 2016 (TP5).

ii) DNA Extraction and Quantification from Sample

DNA extraction was performed in a Maxwell®16MDx instrument (Promega Biotech Iberica, SL) and quantified on a Qubit®2.0 Fluorometer (Invitrogen™, Thermo Fisher Scientific, Inc., WA, USA). The Diagnosis sample presented 214 ng/μL in 30 μL elution volume. TP5 presented 148 ng/μL in 30 μL elution volume (total amount of DNA obtained at TP5=6420 ng).

iii) PCR of the Samples

PCR was performed using Platinum® Taq DNA Polymerase High Fidelity (Life Technologies) and the primers used were those described in BIOMED-2 protocol for IgH and IgK. The primers used to amplify said fragments of the IgH gene are shown in Table 1, while the primers used to amplify said fragments of the IgK gene are shown in Table 2.

Amplification of the test sample was performed using the number of PCR experiments (i.e. PCR tubes) which were calculated as necessary based on the volume of the test sample (V, μL), the number of equivalent cells per microliter (min VRF) of said sample, the sensitivity (S) which it was desired to reach and the final PCR tube volume. Accordingly, the amounts of each component (per PCR tube) for each PCR reaction mix for the test sample were as follows:

a) PCR IgH
84 μL Platinum HIFI master mix
4 μL Primers CDR1/CDR2/CDR3 mix (Tubes A, B, C)
4 μL Primer JH57
8 μL gDNA b) PCR IgK
80 μL Platinum HIFI master mix
4 μL Primers KVmix (Tube F)
4 μL Primer JK5
4 μL Primer JK1-4
8 μL gDNA c) PCR DH
84 μL Platinum HIFI master mix
4 μL Primers DH1-6 (Tube D) or DH7 (Tube E)
4 μL JH57
8 μL gDNA d) PCR KDEL
80 μL Platinum HIFI master mix
4 μL Primers KVmix (Tube G)
4 μL INTR (Tube H)
4 μL KDEL
8 μL gDNA The diagnostic sample was amplified with the same reactions but using 1 μL of DNA (1 μL of DNA=approximately 20 ng gDNA, i.e. [DNA]=20 μg/mL) because it is not necessary to reach a given sensitivity in the diagnostic sample.

iv) Preparation of Amplicon Libraries without Fragmentation

The amplified products of both samples (diagnosis and follow-up) were used to prepare respective amplicon libraries without fragmentation using Ion Plus Fragment Library kit and Agencourt Ampure XP (Thermo-Fisher). It was found possible to use half of the volumes of all reactants using the Ion Plus Fragment Library kit. The final library concentration was determined using qPCR in the GeneRead Library Quant kit (Qiagen). The libraries were generated using specific barcodes for each sample.

v) Massive Parallel Sequencing

The main clone or clones were identified in the diagnostic sample via massive parallel sequencing of the product of the amplification of IGH and IGK genes using the primers described in Table 1 and Table 2. Clonal samples with fragments greater than 250 bp were sequenced on the PGM platform (Ion Torrent Personal Genome Machine™ platform) using OneTouch™ Ion v2 Kit Template 400 DL, 400 Ion PGM™ Sequencing Kit v2 and Ion Chip 318™ Kit according to the manufacturer's instructions (Thermo-Fisher). Fragments less than 250 bp (mainly from samples with the rearrangements KVJ and KDEL) were sequenced using the PROTON platform: Ion Proton™ I emulsion OT2 Template Kit and sequencing Ion Proton™ I Sequencing Kit (Thermo-Fisher). All reagents were purchased from Lifetech using their protocols with slight modifications: PGM platform technology sequences fragments up to 250 bp, but it is possible to sequence fragments up to 400 bp with another commercial kit of Lifetech using different chemistry.

vi) Bioinformatic Analysis

After sequencing, .fastq files of the two samples were obtained from the Torrent Browser according to the corresponding Barcode. Each .fastq file comprises a list of characters reading from left to right which represents the nucleotide sequence of the DNA comprised in said sample, and additionally comprises the quality score corresponding to each character of said list of characters.

The quantification of each clonotypic sequence or sequences in the diagnostic sample was determined using mathematical and computer methods (IT tools), namely using the FrequencyRank.sh Bourne shell script (frequency_rank.sh) to sort sequences in descending frequency order. Once the clonal sequences which are the same in the diagnostic sample as in the follow-up sample were determined, a .dna file was generated comprising each of said clonal sequences as a list of characters reading from left to right and having a total number of characters.

The number of clonal sequences (first lists of characters) identified in the diagnostic sample which were considered the same as the argument sequence (second lists of characters was counted using the SeqSearchFastq.java program with the -trim option and a match ratio (degree of similarity) of 0.99, to give a value, $L_c$. $L_t$ was determined from the total number of first lists of characters.

As the method of the invention involves a mixture of alignment and comparison, comparison was made only between the first and the last matching position and the -trim option instructs the process to act in this way, limiting the comparison from the first and last matching positions instead of first and last positions (regardless of matching) in the sample sequence. The output, $L_c$, from the SeqSearchFastq.java program is subsequently used, together with the values for $L_t$, k and D, to calculate the MRD.

viii) MRD Quantification

The previous method identified a clonal Ig rearrangement in the IgK gene, that represents 39.57% of the sequenced reads.

The sequencing of the Ig rearrangements in the follow-up cells revealed no reads associated with the clonal IgK rearrangement defined at diagnosis, meaning that the level of MRD=0 ix) Experimental Sensitivity Definition

The min VRF was defined as previously described, whereby:

$$\text{min}VRF = \left[6.49 \times 10^{-3} \text{ ng DNA per diploid cell}\right] / \text{ (FIGS. 15B and 15C)}$$

[amount of gDNA used in PCR amplification $(ng) = 6.49 \times 10^{-3} / 650 \text{ ng gDNA} = 1.0 \times 10^{-5}$.

Figure 15A:
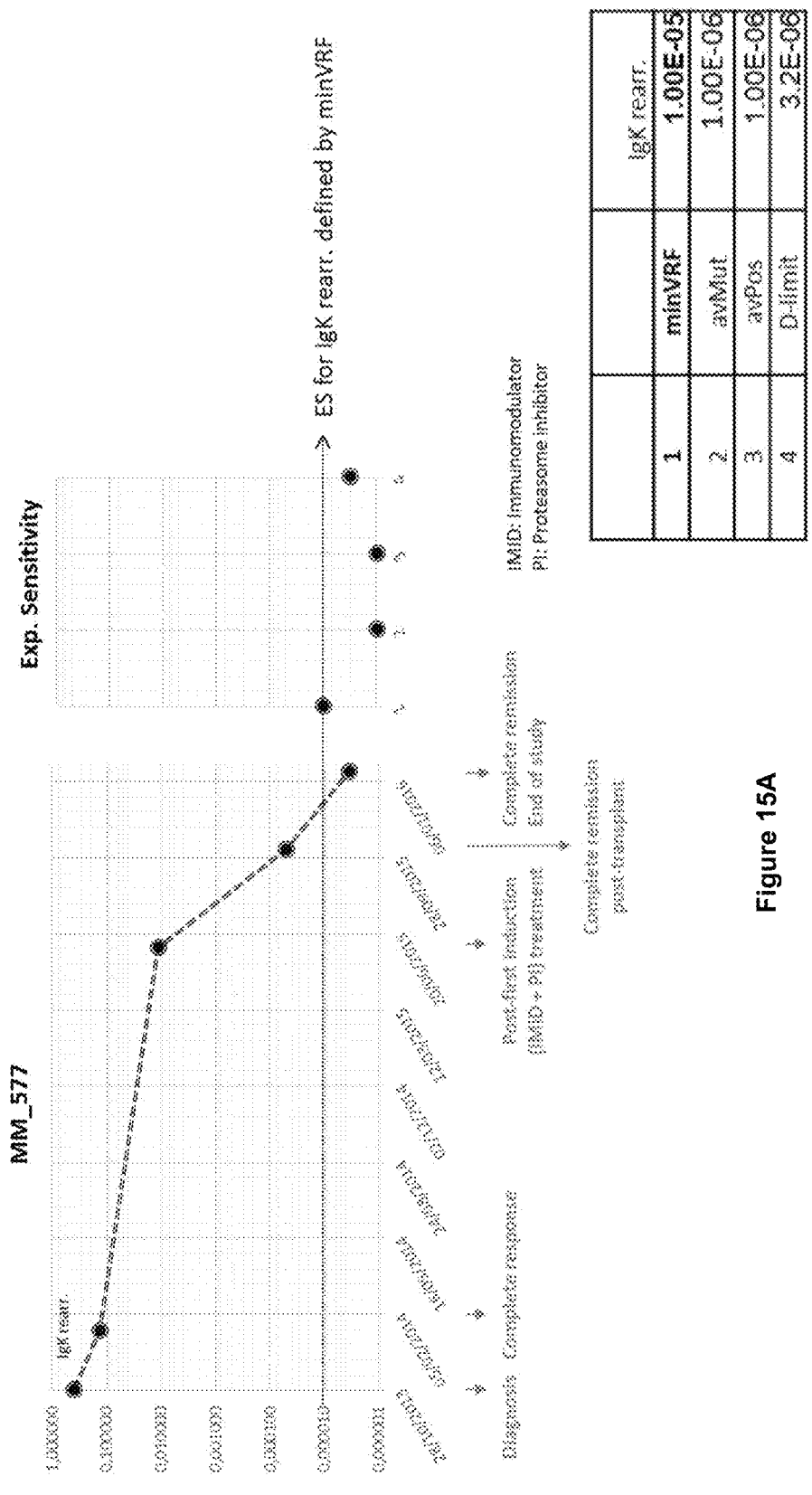
FIG. 15. A. Quantitative MRD status vs. time and experimental sensitivity (Exp. Sensitivity, ES) for last follow-up (Jan. 6, 2016) of a subject (MM_577) diagnosed with multiple myeloma (MM) in February 2014. At diagnosis the subject presented a mutation suitable for use as a MRD marker: a rearrangement in IgK (IgK rearr.). The subject was treated with immunomodulator+proteasome inhibitor (IMID+PI) and given an autologous stem-cell transplant. In the last follow-up, post-transplant, the ES in IgK rear. is defined by the min VRF ($1.00 \times 10^{-5}$). B. Values of min VRF, avMut, D-limit and avPos for the IgK rear. mutation in MM_577, wherein min VRF is defined by the initial amount of DNA (650 ng), avMut is defined by the average of 10 negative controls, D-limit is defined by difference in slope method and avPos is defined by the error rate for the alternative reads, each as further defined herein.
Figure 15B:
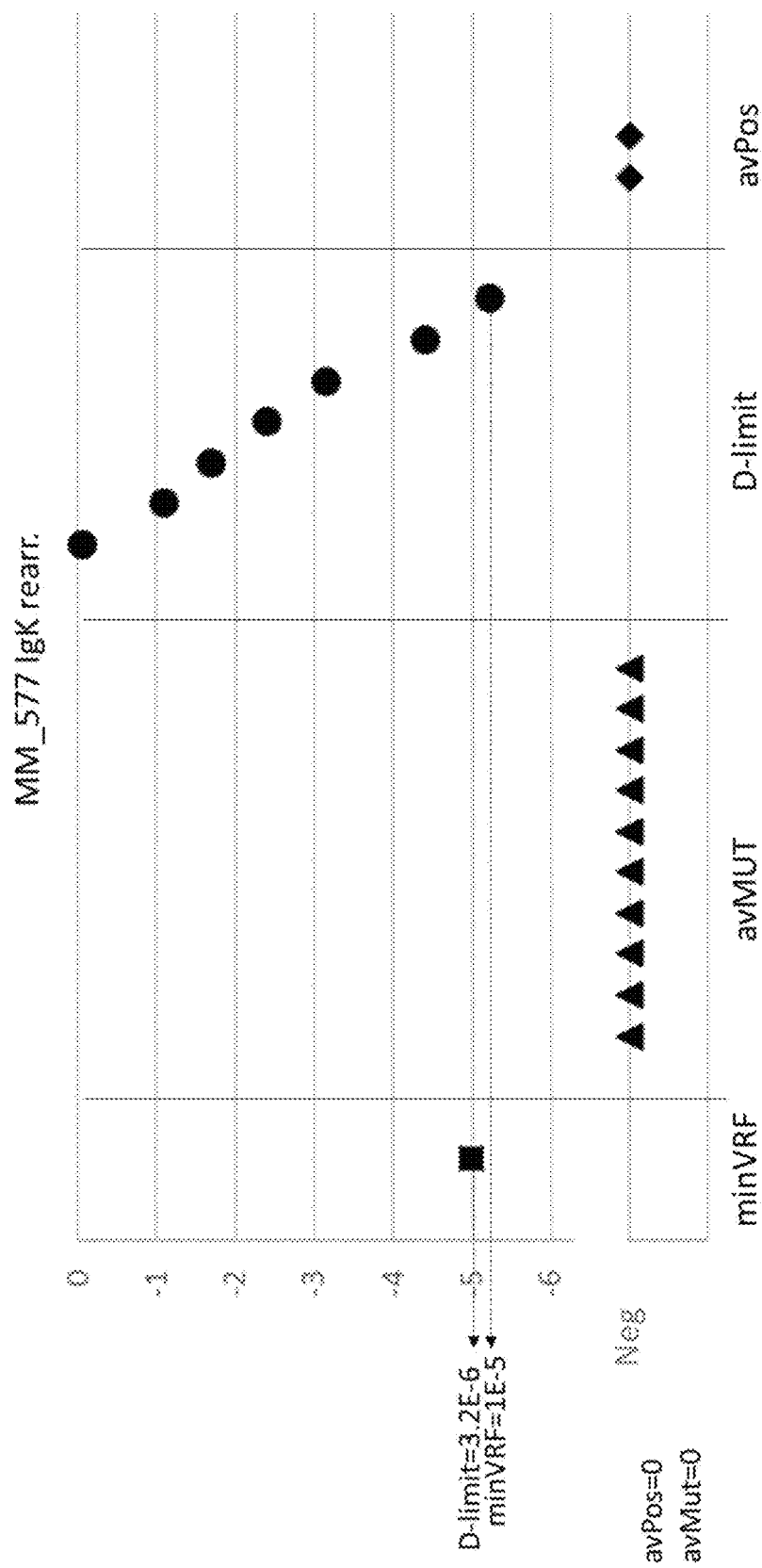
Figure 16:
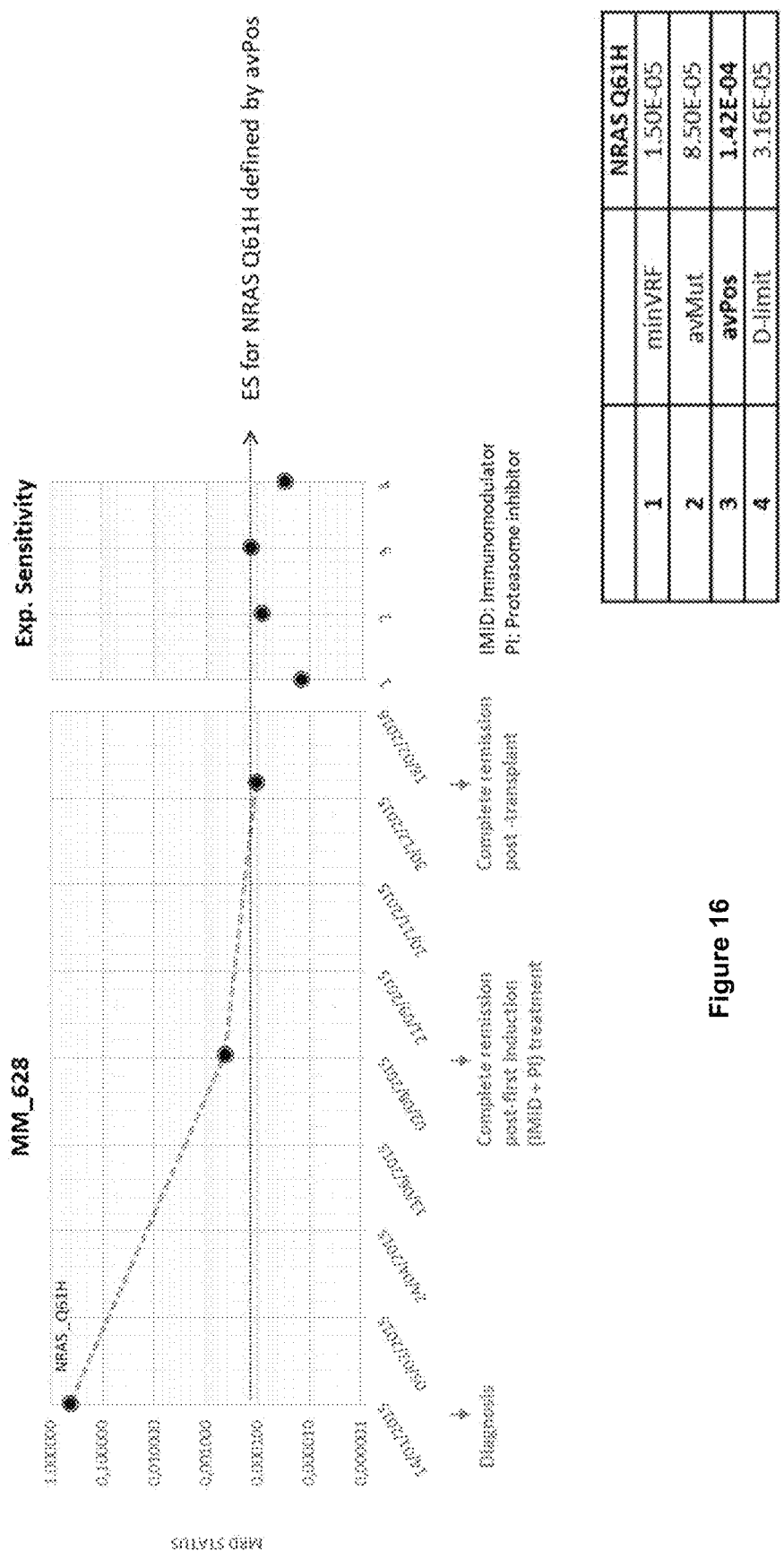
FIG. 16. Quantitative MRD status vs. time and experimental sensitivity (Exp. Sensitivity, ES) for last follow-up (Jan. 8, 2016) of a subject (MM_628) diagnosed with multiple myeloma (MM) in January 2015. At diagnosis the subject presented a somatic mutation suitable for use as a MRD marker: a clonal SNV in NRAS Q61H. The subject was treated with immunomodulator+proteasome inhibitor (IMID+PI) and given an autologous stem-cell transplant. In the last follow-up, post-transplant, the ES in NRAS Q61H is defined by the avPos ($1.4 \times 10^{-4}$).

The values for avPos and avMut for immunoglobulin rearrangements need not be calculated or considered in this method, as the probability of having exactly the alternative sequence of mutations in the same position and in the same order is approximately 0 (FIG. 15B).

The D-limit for IgK rearrangements was calculated to be $3.2 \times 10^{-6}$ (FIGS. 15A and 15B).

x) Interpretation

A summary of the MRD values and ES data obtained in subject MM_577 are shown in FIG. 15A, whereby the ES for the IgK rearrangement marker at timepoint TP5 is defined by the higher of the four parameters calculated as described above, namely min VRF, such that $ES_{(IgK)}=1.0 \times 10^{-5}$. The MRD level calculated for this same marker at this same timepoint for this subject was $MRD_{(IgK)}=0$. Since ES>MRD for this marker, the MRD status at this timepoint in this subject is therefore MRD-negative.

Figure 17:
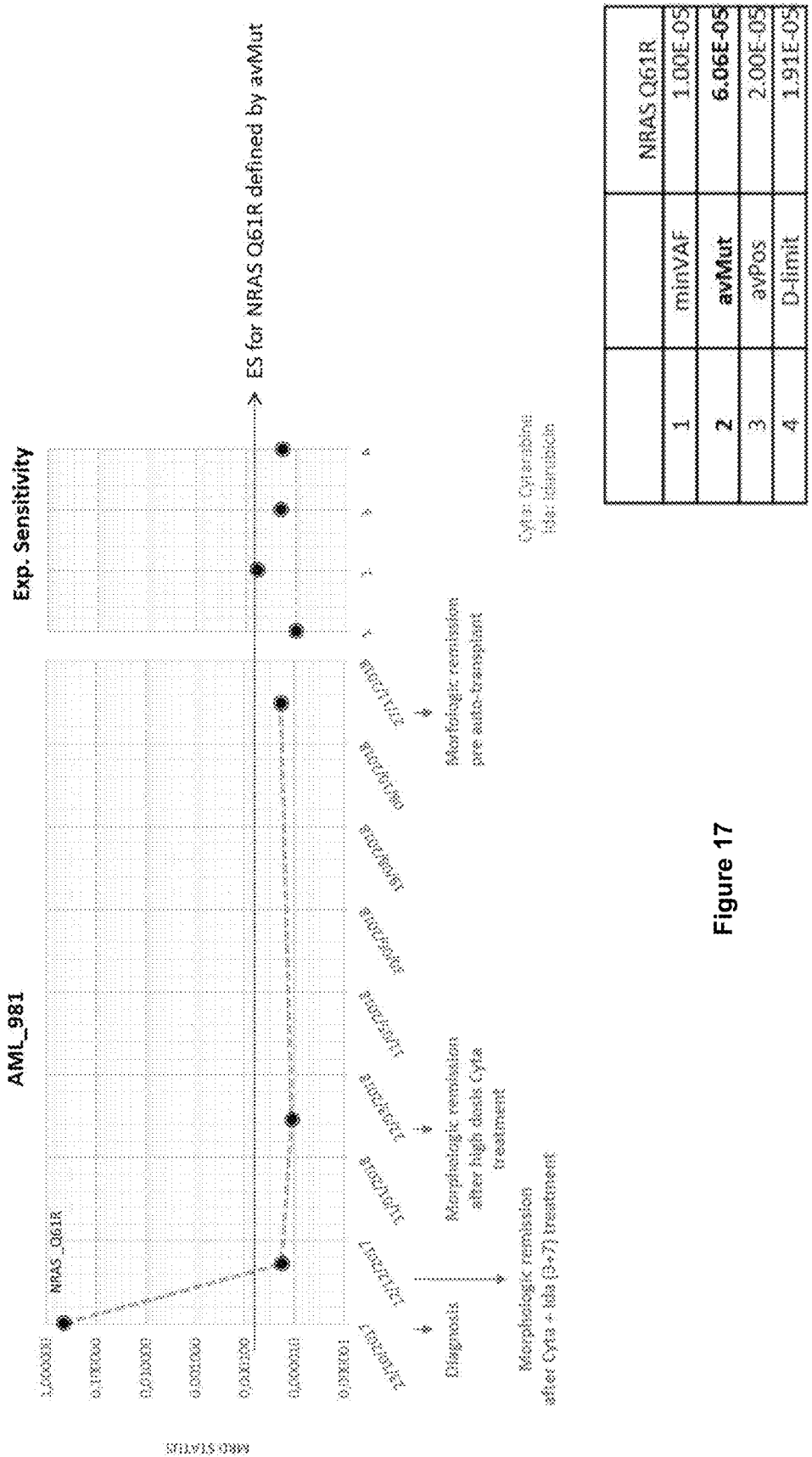
FIG. 17. Quantitative MRD status vs. time and experimental sensitivity (Exp. Sensitivity, ES) for last follow-up (Nov. 1, 2018) of a subject (AML_981) diagnosed with acute myeloid leukaemia (AML) in October 2017. At diagnosis the subject presented a somatic mutation suitable for use as a MRD marker: a clonal SNV in NRAS Q61R. The subject was treated with Cytarabine+Idarubicin (3+7) [Cyta+Ida (3+7)] and subsequently with high dosis Cytarabine. In the last follow-up before autologous stem-cell transplant (auto-transplant), the ES in NRAS Q61R is defined by the avMut ($6.06 \times 10^{-5}$).

Example 3: Determination of MRD Status in a Follow Up Sample from an AML Patient Involved in Clinical Trial (FIG. 17)

Materials and Methods i) Subject and Samples.

Subject AML_981 was diagnosed with AML on 23 Sep. 2017. Three different sequential samples were collected and analysed to define the level of response to standard-of-care treatment in AML after induction with Cytarabine+Idarubicin (3+7) (timepoint TP2, Nov. 28, 2017) followed by high-dose Cytarabine (timepoint TP3, Feb. 23, 2018). The analysis of an extra timepoint (TP4, Nov. 1, 2018) collected prior to autologous stem cell transplant (auto-transplant), within the analysis of the diagnosis sample, as necessary to determine the genetic markers, is described in the present example.

ii) DNA Extraction and Quantification from Samples, and Determination of Genetic Markers at Diagnosis.

Conducted as respectively described in items ii) and iii) of Example 1.

iii) Quantification of the Level of MRD and Determination of Experimental Sensitivity (ES)

After mutational screening to select the genetic marker, one cancer-specific (somatic) mutation was detected, inducing one single nucleotide variation affecting NRAS Q61R with a VRF of 46.0%, This specific mutation detected at diagnosis was subsequently studied in follow-up diagnoses.

Similar to Example 1, the amount of gDNA used in PCR amplification allowed the first parameter of the error corrected algorithm, min VRF, to be determined as follows:

$$\text{min}VRF = \left[6.49 \times 10^{-3} \text{ ng DNA per diploid cell}\right] /$$

[amount of gDNA used in PCR amplification $(ng) =$ $6.49 \times 10^{-3} / 650 \text{ ng gDNA} = 1.0 \times 10^{-5}$ Subsequently, the same protocol as defined in Example 1 was conducted.

The number of alternative reads for single nucleotide variants (SNVs) in NRAS Q61R for the position chr1: 115256528 were obtained, with the number of mutated sequences for A>G real mutation being 14 of 1618941 reads and with the number of non-native alternatives being 0 of 1618941 reads for A>T and 4 of 1618941 reads for A>C.

The same approach as described in steps (a) to (e) of item iv) of Example 1 was repeated in 10 samples from healthy donors without mutations affecting the NRAS gene in order to determine the avMut parameter of the error corrected algorithm as $6.06 \times 10^{-5}$.

The same approach as described in steps (a) to (e) of item iv) of Example 1 was repeated in 10-fold dilution curves performed from an initial commercial DNA with the mutations under study (NRAS Q61R presenting in 50% of the molecules. Thus, dilution libraries of up to 7 successive 10-fold dilutions were prepared and sequenced as described above in order to calculate D-limit parameter by the method described herein as $1.91 \times 10^{-5}$.

iv) Interpretation of NGS Results

The experimental sensitivity (ES) for the NRAS Q61R marker at timepoint TP4 is defined by the higher of the four parameters calculated as described above, namely avMut such that $ES_{(NRAS\ Q61R)} = 6.06 \times 10^{-5}$. The MRD level calculated for this same marker at this same timepoint for this subject was $MRD_{(NRAS\ Q61R)} = 1.91 \times 10^{-5}$. Since ES>MRD for this marker, the MRD status at this timepoint in this subject was therefore MRD-negative.

Thus, with said marker it can be concluded that minimal residual acute myeloid leukemia is absent from said subject.

Example 4: Determination of MRD Status in a Follow Up Sample from a Myeloma Patient Involved in Clinical Trial. (FIG. 18)

Materials and Methods i) Subject Samples

The subject (MM_606) was diagnosed with multiple myeloma (MM) on 2 Dec. 2014 (TP1). After a first cycle with conventional therapy the patient achieved complete response. On 9 Jul. 2014 (TP2), the patient continued in complete response under post-induction therapy. In November 2014 (TP3) the patient was in complete remission after autologous transplant. The clinical study was ended in 2016 with the patient still in complete remission in February 2016 (TP4). One year later, on 23 Feb. 2017 the patient experienced a relapse (TP5 and TP6).

ii) DNA Extraction and Quantification from Sample, PCR of the Samples, Preparation of Amplicon Libraries without Fragmentation, Massive Parallel Sequencing and Bioinformatic Analysis Conducted as respectively described in items ii) to vii) of Example 2.

iii) MRD Quantification

The previous method identified a clonal Ig rearrangement in the IgH gene that represents 55.6% of the sequenced reads.

The sequencing of the Ig rearrangements in the last follow-up sample (TP6) revealed reads associated with the clonal IgH rearrangement defined at diagnosis, indicating a level of MRD=0.045 iv) Experimental Sensitivity Definition

The min VRF was defined as previously described, whereby:

$$\min VRF = [6.49 \times 10^{-3} \text{ ng DNA per diploid cell}] / \text{ (FIGS. 18B and 18C)}$$
[amount of gDNA used in PCR amplification
$(ng) = 6.49 \times 10^{-3} / 650$ ng gDNA $= 1.0 \times 10^{-5}$.

Figure 18A:
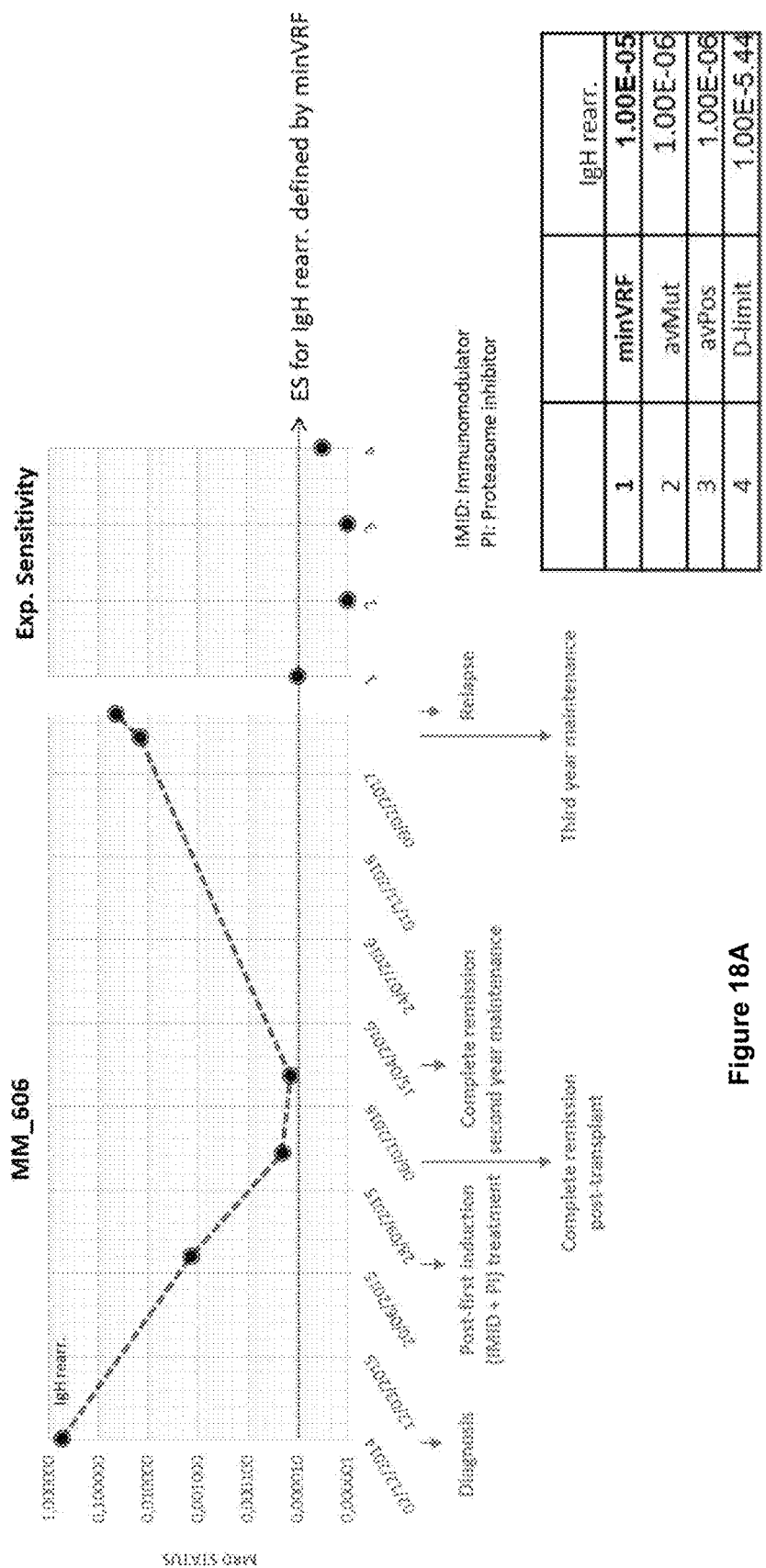
FIG. 18. A. Quantitative MRD status vs. time and experimental sensitivity (Exp. Sensitivity, ES) for last follow-up (post-February 2017) of a subject (MM_606) diagnosed with multiple myeloma (MM) in December 2014. At diagnosis the subject presented a mutation suitable for use as a MRD marker: a rearrangement in IgH (IgH rearr.). The subject was treated with immunomodulator+proteasome inhibitor (IMID+PI) and given an autologous stem-cell transplant before second and third years of maintenance. In the last follow-up, post-transplant, the ES in IgH rear. is defined by the min VRF ($1.00 \times 10^{-5}$). B. Values of min VRF, avMut, D-limit and avPos for the IgH rear. mutation in MM_606, wherein min VRF is defined by the initial amount of DNA (650 ng), avMut is defined by the average of 10 negative controls, D-limit is defined by difference in slope method and avPos is defined by the error rate for the alternative reads, each as further defined herein.
Figure 18B:
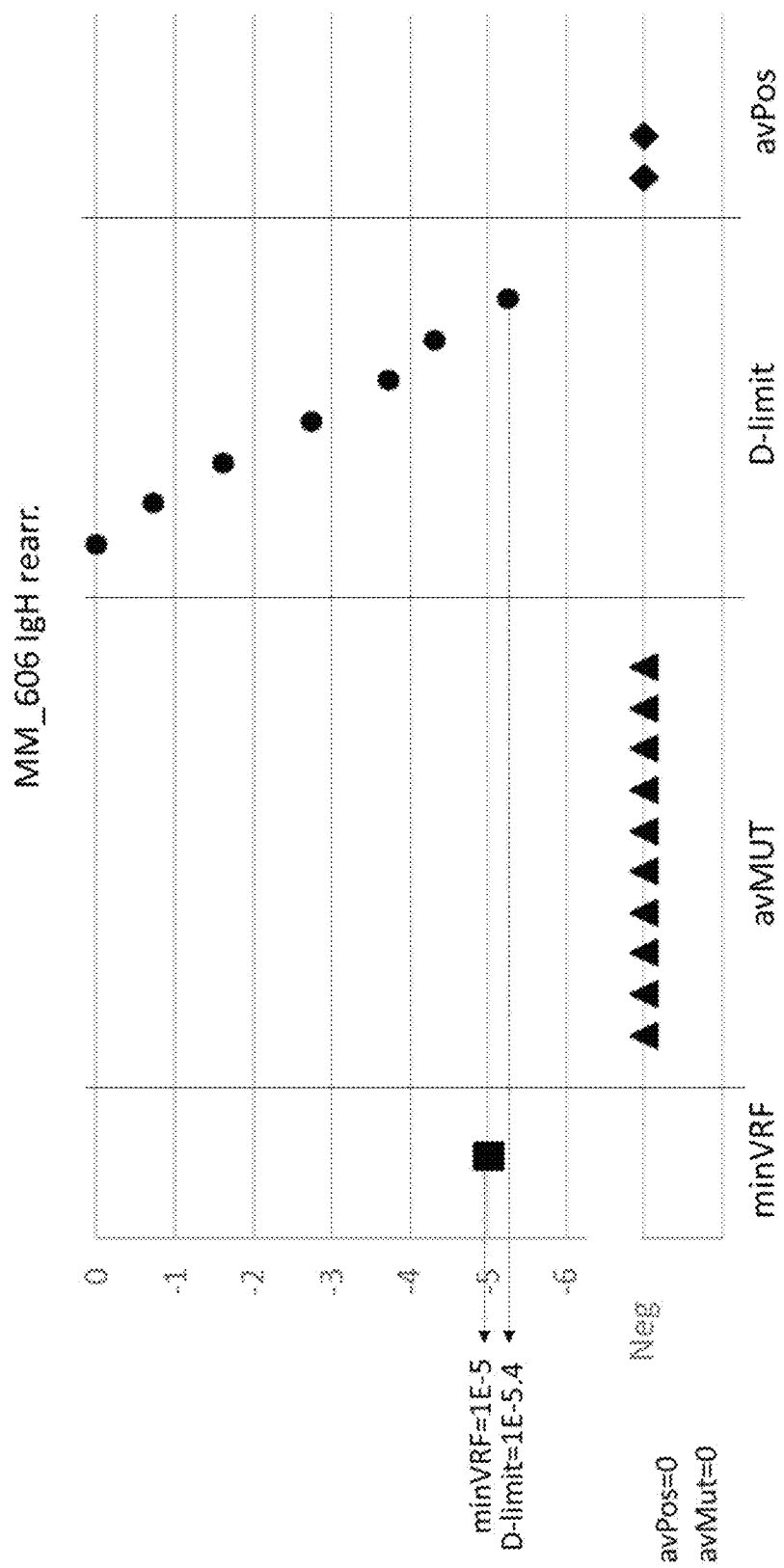
Figure 19A:
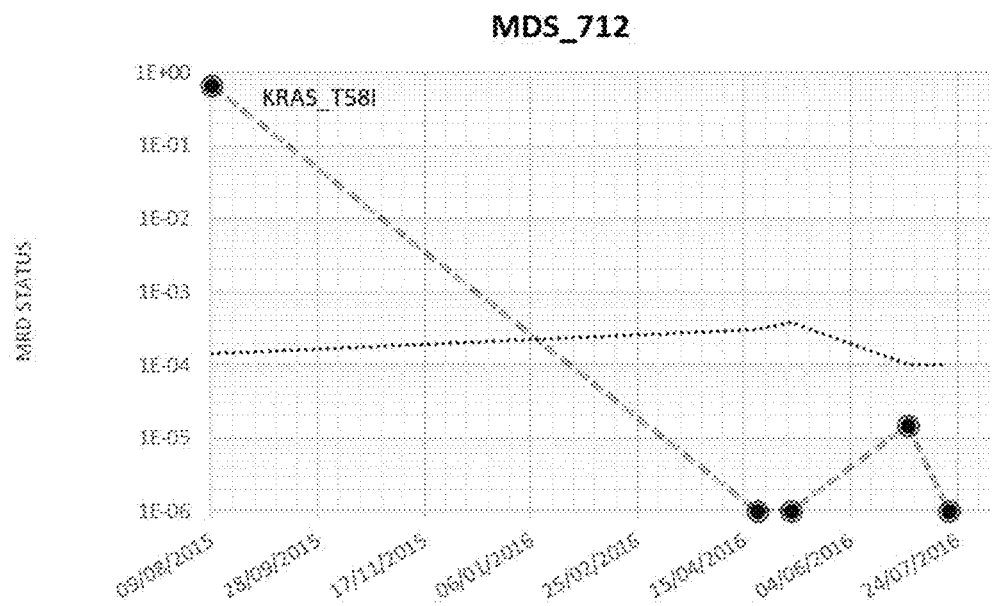
FIG. 19. Examples of determination of quantitative MRD status vs. time in subjects with different pathologies. A. myelodysplastic syndrome (MDS), in particular in subject MDS_712 using KRAS T58I mutation; B. multiple myeloma (MM), in particular in subject MM_581 using KRAS G12D mutation; C. follicular lymphoma (FL), in particular in subject FL_739 using EZH2 Y646S mutation; and D. acute myeloid leukaemia (AML), in particular in subject AML_101 using IDH2 R172K mutation.
Figure 19B:
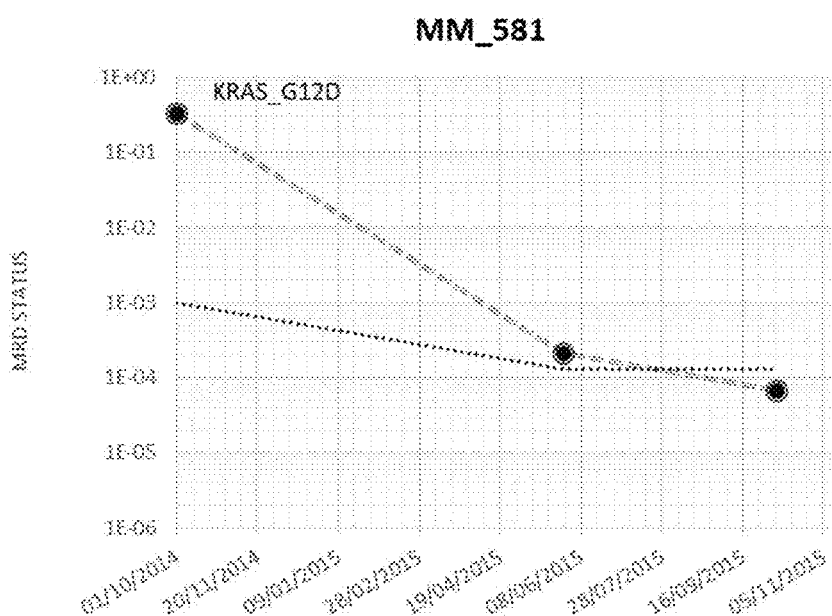
Figure 19C:
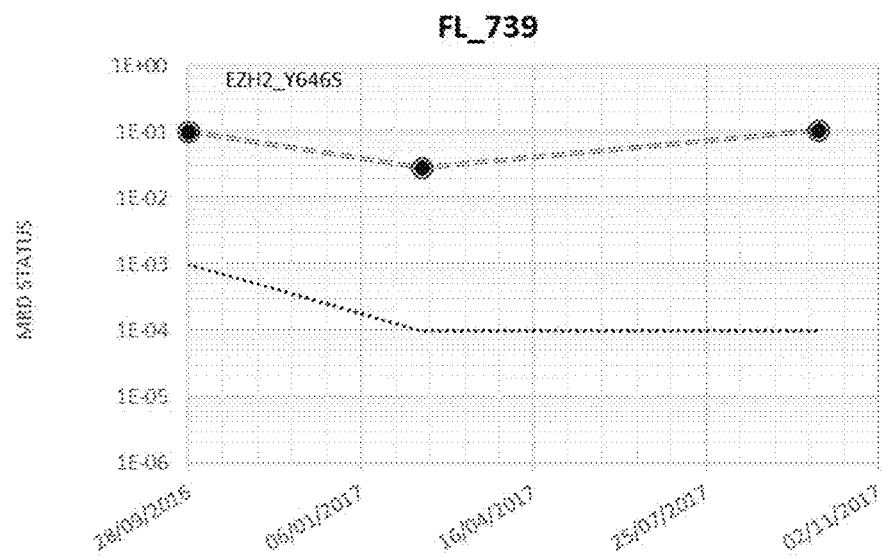
Figure 19D:
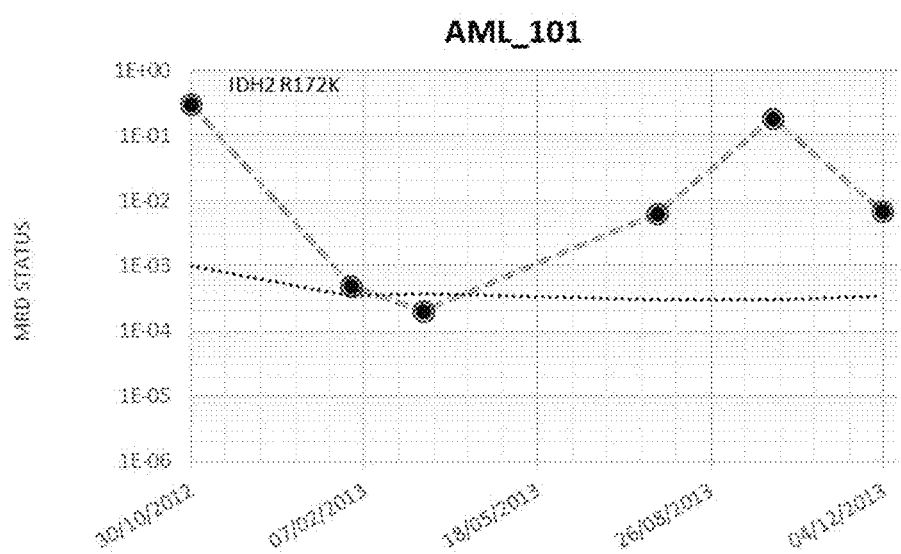
Figure 20A:
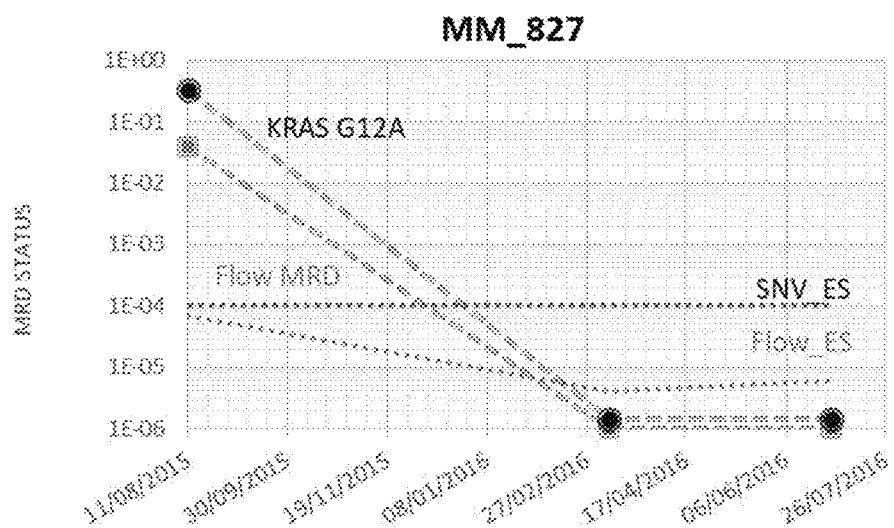
FIG. 20. Examples of determination of quantitative MRD status vs. time in four subjects with multiple myeloma, compared to the gold standard flow cytometry (Flow MRD). A. determined in subject MM_827 using KRAS G12A mutation; B. in subject MM_561 using KRAS G12D mutation; C. in subject MM_700 using KRAS Q61R mutation; and D. in subject MM_623 using KRAS G12A mutation. In each example, experimental sensitivity (ES) is determined using both the clonal SNV mutation (SNV_ES) and using flow cytometry (Flow_ES).
Figure 20B:
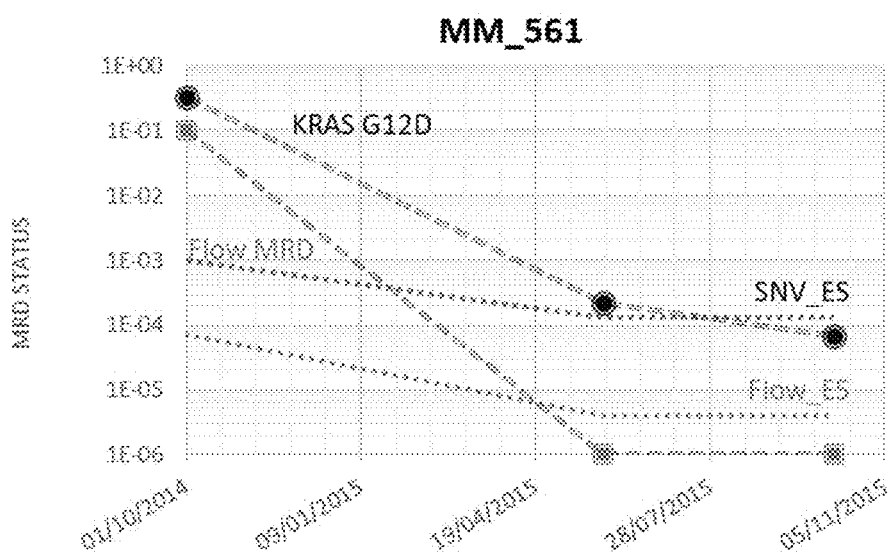
Figure 20C:
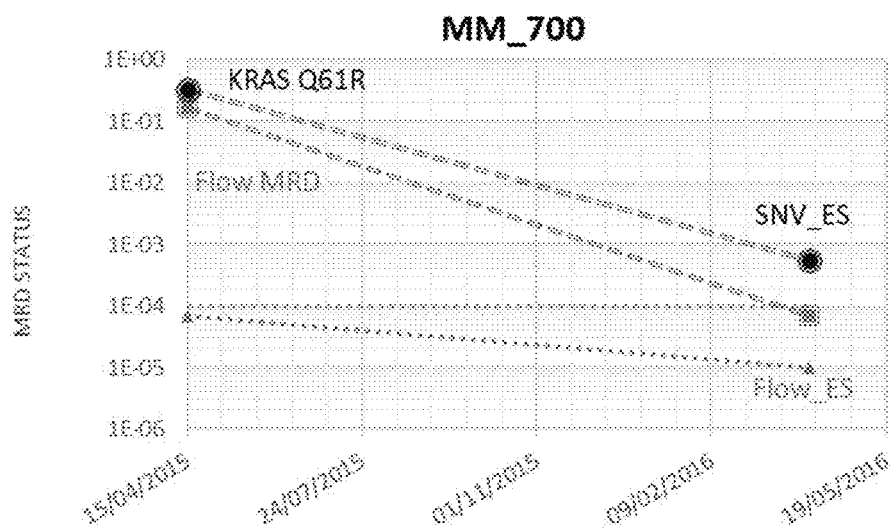
Figure 20D:
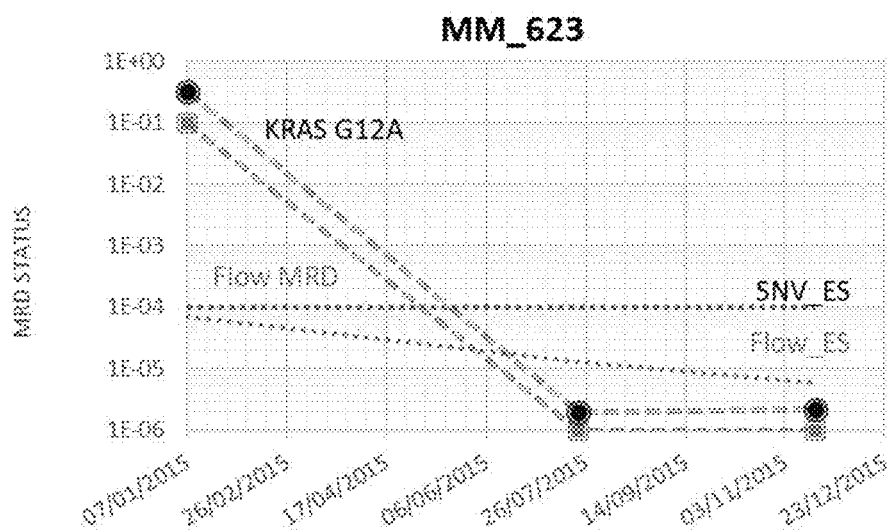

The values for avPos and avMut for immunoglobulin rearrangements need not be calculated or considered in this method, as the probability of having exactly the alternative sequence of mutations in the same position and in the same order is approximately 0 (FIG. 18B).

The D-limit for IgH rearrangements was calculated to be $1 \times 10^{-5.4}$ (FIGS. 18A and 18B).

v) Interpretation

A summary of the MRD values and ES data obtained in subject MM_606 are shown in FIG. 18A, whereby the ES for the IgH rearrangement marker at timepoint TP6 is defined by the higher of the four parameters calculated as described above, namely min VRF, such that $ES_{(IgH)} = 1.0 \times 10^{-5}$ The MRD level calculated for this same marker at this same timepoint for this subject was $MRD_{(IgK)} = 0.045$. Since ES<MRD for this marker, the MRD status at this timepoint in this subject is therefore MRD-positive.

Example 5: Determination of MRD Status in a Follow Up Sample from a Lung Adenocarcinoma in a Clinical Trial after Lobectomy and Chemotherapeutic Treatment (FIG. 21B)

Materials and Methods i) Subject and Samples.

Figure 21A:
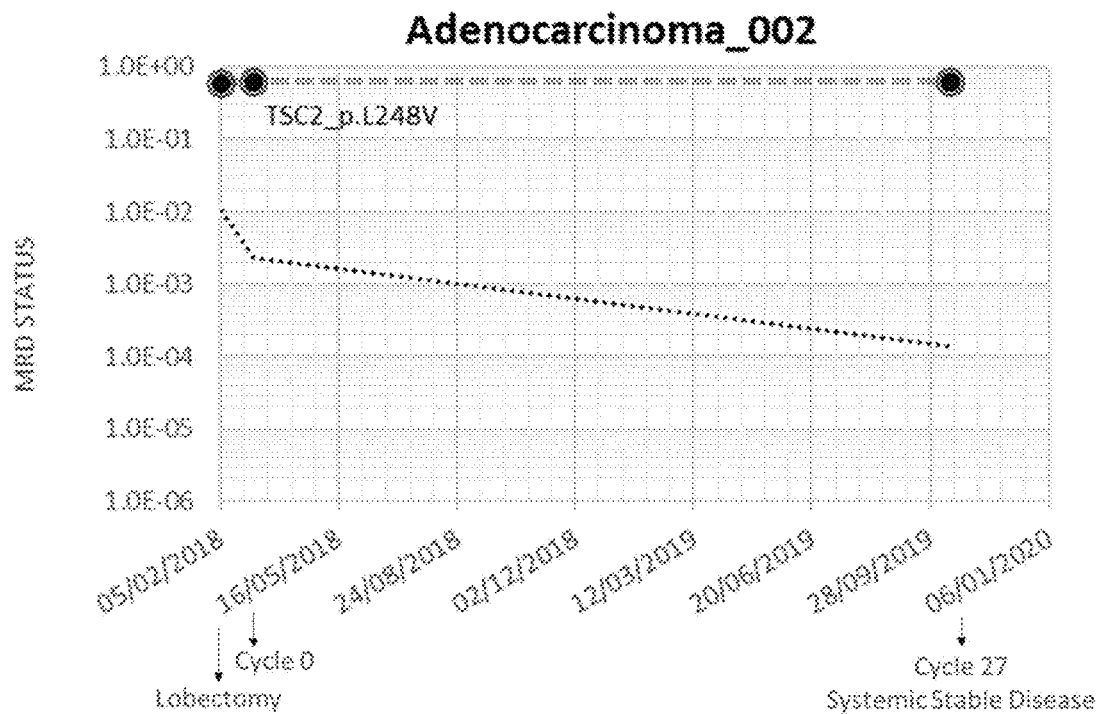
FIG. 21. Examples of determination of quantitative MRD status (dashed line) vs. time either in subjects with lung cancer (adenocarcinoma) determined in A. subject Adenocarcinoma_002 using TSC2 p.L248V mutation; and B. subject Adenocarcinoma_002 using WAS p.T45M mutation; or in subjects with follicular lymphoma determined in C. subject Folicular Lymphoma_547 using KMT2D p.Q2014* mutation; and D. subject Folicular Lymphoma_061 using KRAS p.G12A mutation. In each example, circulating free DNA is used as the source of genetic material and experimental sensitivity (dotted line) is determined using flow cytometry.
Figure 21B:
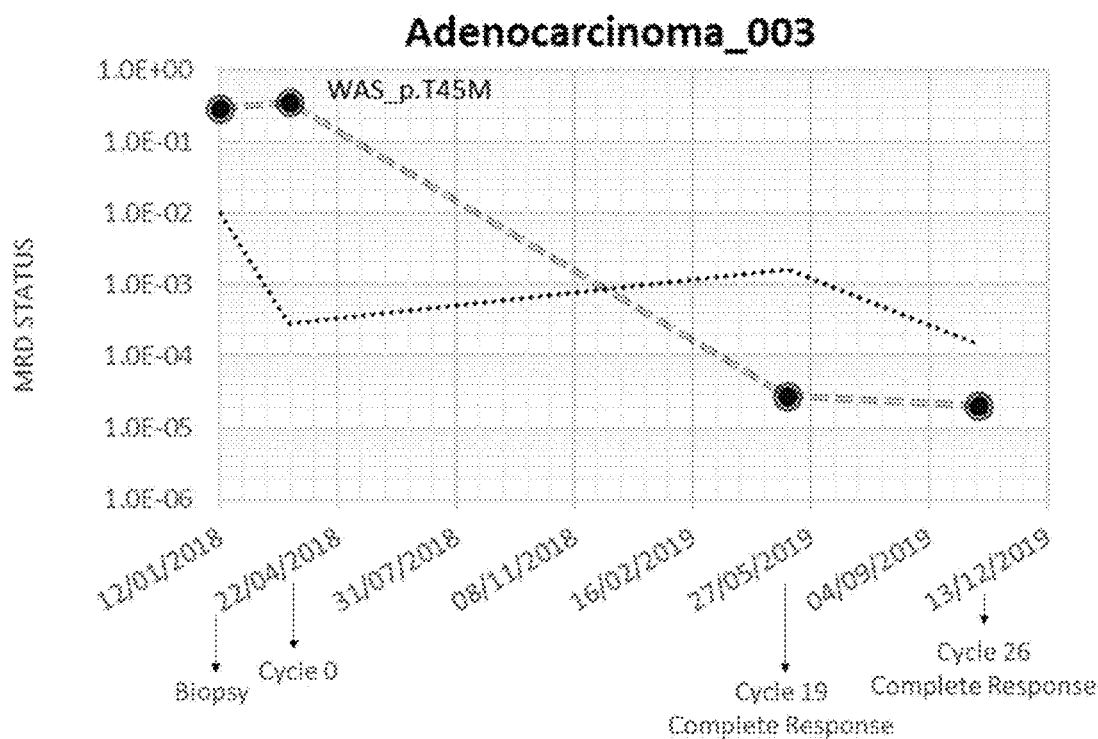
Figure 21C:
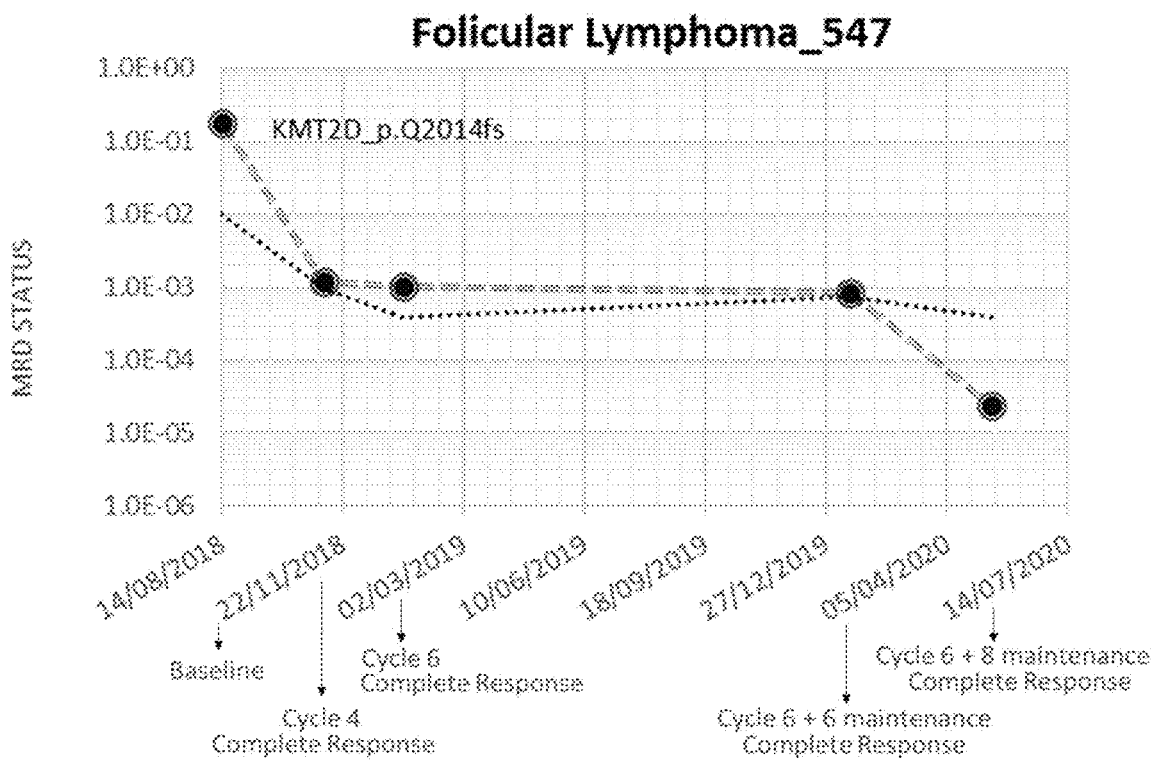

Subject AC_003 was diagnosed with stage IV Lung Adenocarcinoma in (AC) on 12 Jan. 2018 (diagnosis sample at timepoint TP1, as shown in FIG. 21B). Three different sequential samples were collected and analysed to define the level of response. Peripheral blood circulating free DNA (cfDNA) was collected was collected prior lobectomy (TP2, Mar. 12, 2018). cfDNA was collected from two more time-points (TP3, May 7, 2018 and TP4, Oct. 15, 2019) in complete response status, after 19 and 28 cycles of pembrolizumab. The MRD status for the last timepoint (TP4, cycle 29) within the analysis of the diagnosis sample, as necessary to determine the genetic markers, is described in the present example.

ii) DNA Extraction and Quantification from Samples.

cfDNA extraction was performed in a Maxwell®16MDx instrument (Promega Biotech Iberica, SL) and quantified on a Qubit®2.0 Fluorometer (Invitrogen™, Thermo Fisher Scientific, Inc., WA, USA). The diagnosis sample presented 23.08 ng/μL in 30 μL elution volume. TP4 presented 29.3 ng/μL in 30 μL elution volume (total amount of DNA obtained in TP4=88 ng).

iii) Determination of Genetic Markers at Diagnosis.

Aiming to define genetic markers for further tracking of the presence of MRD, a mutational profile screening was performed at diagnosis with a commercial targeted sequencing panel that cover all coding regions of 409 genes using 16000 amplicons (ion AmpliSeq™ Comprehensive Cancer Panel (Thermo-Fisher, Ref 4477685). Library preparation and NGS sequencing of diagnosis sample TP1 was performed using said commercial panel according to the standard protocols defined by Thermo Fisher Scientific Inc.

iv) Quantification of the Level of MRD and Determination of Experimental Sensitivity (ES)

After mutational screening to define the genetic markers, one cancer-specific (somatic) mutation was selected, namely one single nucleotide variation affecting WAS T45M with a VRF of 27.7%. This specific mutation detected at diagnosis was subsequently studied in follow-up diagnoses.

Previously, a protocol (FIG. 4) that included cfDNA amplification, library preparation and sequencing as experimental steps was established, as follows:

(a) Specific primer pairs that cover this mutation were designed and used to amplify 65 ng of cfDNA from patient sample at timepoint TP4, collected after 29 therapy cycles. The amount of cfDNA used in PCR amplification allowed the first parameter of the error corrected algorithm, min VRF, to be determined as follows:

min VRF=[6.49×10$^{-3}$ng DNA per diploid cell]/
[amount of gDNA used in PCR amplification (ng)=6.49×10$^{-3}$/65ng gDNA=1.0×10$^{-4}$.

(b) The cfDNA was amplified by the first PCR using the selected primers and Platinum™ Taq DNA Polymerase High Fidelity (Invitrogen™, Thermo Fisher Scientific, Inc.) under the following conditions: 60 seconds at 94° C. for initial denaturation, followed by 35 cycles of 15 seconds at 94° C. for denaturation, 30 seconds at 58° C. for annealing and 30 seconds at 68° C. for extension. The final volume was 100 µL (79.6 µL DNA-H$_2$O, 10 µL 10× High Fidelity PCR Buffer, 4 µL 50 nM MgSO$_4$, 2 µL 10 mM dNTP Mix (NZYTech, Lda, Lisbon, Portugal), 0-4 µL DNA polymerase (5 U/µL), 2 µL of 10 µM forward primer and 2 µL of 10 µM reverse primer.

(c) Libraries were constructed using NEBNext® Fast DNA Library Prep Set for Ion Torrent™ (New England Biolabs, Inc., Ipswich, MA, USA). Specificity and quantification of the final product, both for amplified DNA and amplified libraries, was analysed with the Agilent Bioanalyser 2100 (Agilent Technologies, Palo Alto, CA, USA).

(d) Finally, the libraries were sequenced on the Ion Proton System platform (Life Technologies, Thermo Fisher Scientific Inc.) with an estimated depth of 1 million reads, generating fastq files. These files were analysed with the method of quantifying the level of MRD employed in the present invention that specifically detects target mutated sequences and wild-type sequences in absolute values. Using Ensembl perl API, the mutated sequence and the wt sequence are located in FASTA format bounded at 40 bp. Finally, a .csv file that contains the name identifier, run and barcode identifier, chromosomal position, the variant, the specific sequence in FASTA researched [mutated forward, mutated reverse, wt (wild-type) forward and wt reverse], the counts of each of them and the ratio (mutated/wt) in absolute values was obtained.

(e) The method also quantified the avPos for point mutations like WAS T45M whereby avPos is the average variant read frequency, avVRF, for the nucleotide sequences (i.e. each alternative) that is identical to said genetic marker and to said non-mutated sequence, but wherein the nucleotide responsible for said single nucleotide variant mutation in said genetic marker is different from that in said genetic marker and said non-mutated sequence. In other words, the alternatives refer to two different non-native sequences that differ from the native sequence and the mutated sequence in that they have a different nucleotide (eg. C or T) from that present in the mutated sequence (eg. A) and that present in the native sequence (eg. G) at the position of the SNV (the non-native alternative sequences, like the native sequence do not cause the disease, but the non-native (mutated) sequence may cause the disease). In particular, the median (or average) of the two alternatives is calculated, thereby establishing the avPos parameter of the error corrected algorithm. Applying this method, the number of alternative reads for single nucleotide variants (SNVs) in WAS T45M for the position chrX:48542673 were obtained, with the number of mutated sequences for C>T real mutation being 6 of 269295 reads and with the number of non-native alternatives being 2 of 269295 reads for C>A and 0 of 269295 reads for C>T. The avPos parameter for indels like that in NPM1 which was detected in this subject or for immunoglobulin rearrangements need not be calculated or considered in this method, as the probability of having exactly the alternative sequence of mutations in the same position and in the same order is approximately 0.

(f) The same approach as described in steps (a) to (e) was repeated in 10 samples from healthy donors without mutations affecting the WAS gene in order to determine the avMut parameter of the error-corrected algorithm as $2.7 \times 10^{-5}$.

(g) The same approach as described in steps (a) to (e) was repeated in 10-fold dilution curves performed from an initial commercial DNA with the mutation understudy (WAS T45M) presenting in 50% of the molecules. Thus, dilution libraries of up to seven successive 10-fold dilutions were prepared and sequenced as described above in order to calculate D-limit parameter by the method described herein as $2.2 \times 10^{-5}$.

v) Interpretation of NGS Results

The ES for the WAS T45M marker at timepoint TP4 was defined by the higher of the four parameters calculated as described above, namely min VRF, such that $ES_{(WAS\ T45M)} = 1 \times 10^{-4}$. The MRD level calculated for this same marker at this same timepoint for this subject was $MRD_{(WAS\ T45M)} = 2.2 \times 10^{-5}$. Since ES>MRD for this marker, the MRD status at this timepoint in this subject was therefore MRD-negative.

Example 6: Determination of MRD Level in a Follow-Up Sample from a Follicular Lymphoma (FL) Patient Under Conventional Therapy (FIG. 21D)

Materials and Methods
i) Subject and Samples.

Figure 21D:
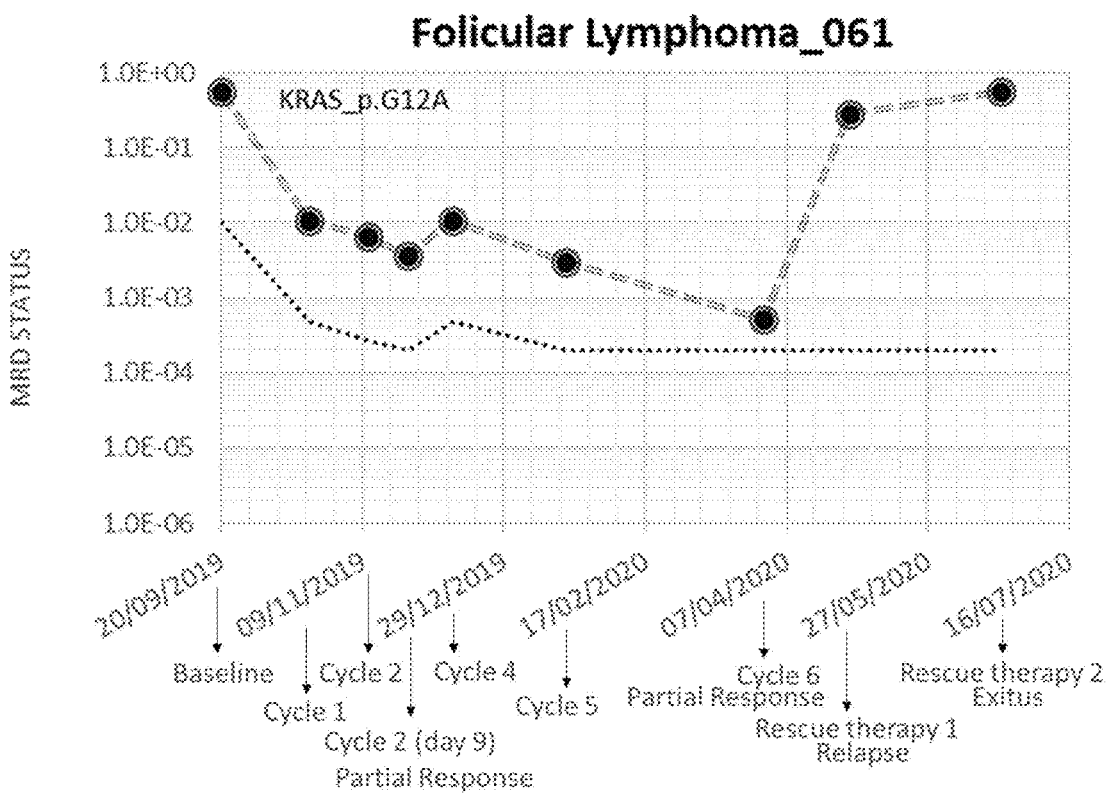

Subject FL_061 was diagnosed with FL in September 2019 (diagnosis sample at timepoint TP1, Sep. 20, 2019 as shown in FIG. 21D). Six different sequential samples were collected and analysed to define the level of response to standard-of-care treatment in FL: anthracycline-based regimen followed rituximab maintenance (TPs 2-7, cycles of treatment from 1 to 6). The patient presented a relapse detected in April 2020 (TP8) and was treated with lenalidomide as rescue treatment. The analysis of the last cycle before relapse, (TP7, cycle 6 of treatment, 30/3/2020) within the analysis of the diagnosis sample, as necessary to determine the genetic markers, is described in the present example.

ii) cfDNA Extraction and Quantification from Samples.

Peripheral Blood cfDNA extraction was performed in a Maxwell®16MDx instrument (Promega Biotech Iberica, SL) and quantified on a Qubit®2.0 Fluorometer (Invitrogen™, Thermo Fisher Scientific, Inc., WA, USA). The diagnosis sample presented 12 ng/µL in 30 µL elution volume. TP7 presented 3 ng/µL in 30 µL elution volume (total amount of cfDNA obtained in TP7=65 ng).

iii) Determination of Genetic Markers at Diagnosis.

Aiming to define genetic markers for further tracking of the presence of MRD, a mutational profile screening was performed at diagnosis with a custom next-generation sequencing (NGS) using a lymphoma specific panel of multiple genes that are frequently mutated in subjects with follicular lymphoma (FL), and other types of lymphoma [see Table 5, showing genes included in said lymphoma panel for NGS sequencing, including the chromosome where it is located, the number of amplicons that the panel includes for each gene, the region of the gene that encompasses all the amplicons expressed as a percentage, and the number of exons]. Library preparation and NGS sequencing of cfDNA diagnosis sample TP1 was performed using said lymphoma panel according to the standard protocols defined by Thermo Fisher Scientific Inc.

TABLE 5

Genes included in the NGS lymphoma cancer panel

| Gene | Chr. | No. of Amp. | Coverage (%) | No.of Exons |
|---|---|---|---|---|
| ARID1A | chr1 | 89 | 96 | 21 |
| CD58 | chr1 | 14 | 100 | 7 |
| CTSS | chr1 | 14 | 100 | 7 |
| ITPKB | chr1 | 37 | 99.7 | 7 |
| TNFRSF14 | chr1 | 16 | 100 | 9 |
| ID3 | chr1 | 5 | 100 | 2 |
| BCL10 | chr1 | 10 | 100 | 3 |
| RRAGC | chr1 | 17 | 93.9 | 8 |
| ETS1 | chr11 | 21 | 100 | 10 |
| BTG1 | chr12 | 7 | 100 | 2 |
| BCL7A | chr12 | 10 | 94.2 | 7 |
| KMT2D | chr12 | 217 | 99.1 | 54 |
| STAT6 | chr12 | 43 | 99.9 | 22 |
| FOXO1 | chr13 | 21 | 88.6 | 2 |
| B2M | chr15 | 6 | 100 | 3 |
| CIITA | chr16 | 55 | 100 | 21 |
| CREBBP | chr16 | 107 | 99 | 31 |
| IRF8 | chr16 | 19 | 100 | 8 |
| SOCS1 | chr16 | 9 | 100 | 1 |
| CD79B | chr17 | 11 | 100 | 7 |
| GNA13 | chr17 | 15 | 98.8 | 5 |
| IKZF3 | chr17 | 23 | 99.6 | 9 |
| TP53 | chr17 | 23 | 98.8 | 15 |
| STAT3 | chr17 | 38 | 100 | 25 |
| BCL2 | chr18 | 9 | 97.2 | 3 |
| CD79A | chr19 | 12 | 100 | 6 |
| MEF2B | chr19 | 18 | 100 | 8 |
| MUM1 | chr19 | 31 | 100 | 13 |
| SMARCA4 | chr19 | 79 | 100 | 37 |
| TCF3 | chr19 | 38 | 100 | 19 |
| S1PR2 | chr19 | 13 | 100 | 1 |
| CXCR4 | chr2 | 13 | 100 | 3 |
| XPO1 | chr2 | 53 | 99.4 | 24 |
| PCBP1 | chr2 | 11 | 100 | 1 |
| EP300 | chr22 | 99 | 100 | 31 |
| MYD88 | chr3 | 16 | 100 | 7 |
| ARID1B | chr6 | 86 | 94.5 | 20 |
| CCND3 | chr6 | 16 | 100 | 8 |
| IRF4 | chr6 | 19 | 97.4 | 9 |
| PIM1 | chr6 | 19 | 98.8 | 7 |
| PRDM1 | chr6 | 33 | 100 | 8 |
| TNFAIP3 | chr6 | 32 | 100 | 8 |
| HIST1H1E | chr6 | 7 | 96.1 | 1 |
| CARD11 | chr7 | 57 | 100 | 24 |

TABLE 5-continued

Genes included in the NGS lymphoma cancer panel

| Gene | Chr. | No. of Amp. | Coverage (%) | No.of Exons |
|---|---|---|---|---|
| EZH2 | chr7 | 37 | 100 | 21 |
| BRAF | chr7 | 44 | 100 | 18 |
| MYC | chr8 | 18 | 100 | 3 |
| MFHAS1 | chr8 | 34 | 97.5 | 3 |
| CDKN2A | chr9 | 13 | 99.3 | 7 |
| PAX5 | chr9 | 21 | 100 | 12 |
| NOTCH1 | chr9 | 113 | 98.4 | 34 |
| CDKN2B | chr9 | 6 | 100 | 3 |
| HNRNPK | chr9 | 29 | 99.7 | 16 |
| BTK | chrX | 29 | 100 | 21 |
| P2RY8 | chrX | 11 | 99.5 | 1 |
| PIM2 | chrX | 13 | 100 | 6 |
| KRAS | chr12 | 7 | 100 | 5 |

Chr. = chromosome
Amp. = amplicons iv) Quantification of the Level of MRD and Determination of Experimental Sensitivity (ES)

After mutational screening to select the genetic marker, one cancer-specific (somatic) mutations was detected, one frameshift insertion (indel) on KRAS G12A with a VRF of 57%, This cancer specific mutation detected at diagnosis was subsequently studied in follow-up diagnoses.

Previously, a protocol (FIG. 4) that included DNA amplification, library preparation and sequencing as experimental steps was established, as follows:

(a) Specific primer pairs that cover these two mutations were selected from Table X and used to amplify 65 ng of cfDNA from patient sample at timepoint TP7, collected after cycle 6 of treatment. The amount of cfDNA used in PCR amplification allowed the first parameter of the error corrected algorithm, min VRF, to be determined as follows:

$$\text{min}VRF = [6.49 \times 10^{-3} \text{ ng DNA per diploid cell}] /$$
$$[\text{amount of cfDNA used in PCR amplification } (ng) =$$
$$6.49 \times 10^{-3} / 65 \text{ ng gDNA} = 1.0 \times 10^{-4}$$

(b) The cfDNA was amplified by the first PCR using the selected primers and Platinum™ Taq DNA Polymerase High Fidelity (Invitrogen™, Thermo Fisher Scientific, Inc.) under the following conditions: 60 seconds at 94° C. for initial denaturation, followed by 35 cycles of 15 seconds at 94° C. for denaturation, 30 seconds at 58° C. for annealing and 30 seconds at 68° C. for extension. The final volume was 100 µL (79.6 µL DNA-H$_2$O, 10 µL 10× High Fidelity PCR Buffer, 4 µL 50 nM MgSO$_4$, 2 µL 10 mM dNTP Mix (NZYTech, Lda, Lisbon, Portugal), 0-4 µL DNA polymerase (5 U/µL), 2 µL of 10 µM forward primer and 2 µL of 10 µM reverse primer.

(c) Libraries were constructed using NEBNext® Fast DNA Library Prep Set for Ion Torrent™ (New England Biolabs, Inc., Ipswich, MA, USA). Specificity and quantification of the final product, both for amplified DNA and amplified libraries, was analysed with the Agilent Bioanalyser 2100 (Agilent Technologies, Palo Alto, CA, USA).

(d) Finally, the libraries were sequenced on the Ion Proton System platform (Life Technologies, Thermo Fisher Scientific Inc.) with an estimated depth of 1 million reads, generating fastq files. These files were analysed with the method of quantifying the level of MRD employed in the present invention that specifically detects target mutated sequences and wild-type sequences in absolute values. Using Ensembl perl API, the mutated sequence and the wt sequence are located in FASTA format bounded at 40 bp. Finally, a .csv file that contains the name identifier, run and barcode identifier, chromosomal position, the variant, the specific sequence in FASTA researched [mutated forward, mutated reverse, wt (wild-type) forward and wt reverse], the counts of each of them and the ratio (mutated/wt) in absolute values was obtained.

(e) The avPos parameter for indels like that in KRAS which was detected in this subject or for immunoglobulin rearrangements need not be calculated or considered in this method, as the probability of having exactly the alternative sequence of mutations in the same position and in the same order is approximately 0

(f) The avMut parameter for indels like that in KRAS which was detected in this subject or for immunoglobulin rearrangements need not be calculated or considered in this method, as the probability of having exactly the alternative sequence of mutations in the same position and in the same order is approximately 0.

(g) The same approach as described in steps (a) to (e) was repeated in 10-fold dilution curves performed from an initial commercial DNA with the mutation under study (KRAS G12A) presenting in 50% of the molecules. Thus, dilution libraries of up to seven successive 10-fold dilutions were prepared and sequenced as described above in order to calculate D-limit parameter by the method described herein v) Interpretation of NGS Results The ES for the KRAS G12A marker at timepoint TP7 is defined by the higher of the four parameters calculated as described above, namely min VRF, such that $ES_{(KRAS\ G12A)} = 1.0 \times 10^{-4}$. The MRD level calculated for this same marker at this same timepoint for this subject was $MRD_{(KRAS\ G12A)} = 5.5 \times 10^{-1}$. Since ES<MRD for this marker, the MRD status at this timepoint in this subject is therefore MRD-positive.

The invention claimed is:

1. A method of therapeutically treating a proliferative disease in a subject diagnosed with said disease, wherein said method comprises:
   (1) administering therapy to the subject, wherein said therapy is selected from chemotherapy, immunotherapy, radiotherapy, or combinations thereof:
   (2) determining the presence or absence of minimal residual disease (MRD) in the subject, wherein the determination comprises the following steps:
   (A)—amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
      sequencing each amplified nucleotide sequence, whereby a first list of characters reading from left to right is obtained from each nucleotide sequence thus sequenced;
   (B)—amplifying by polymerase chain reaction using the same locus-specific forward primer and the same locus-specific reverse primer as in step (A), at least one nucleotide sequence comprised in an amount, D, of genomic DNA from a biological sample obtained from said subject after treatment for said disease, wherein the genomic DNA has an average weight, k, per diploid cell of said biological sample; and
      sequencing each amplified nucleotide sequence, whereby a second list of characters reading from left to right is obtained from each nucleotide sequence thus sequenced;
   wherein each nucleotide sequence amplified in steps (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of a single nucleotide variant mutation, an indel mutation and somatic gene rearrangement mutation;
   (C) determining, for each second list of characters obtained in step (B), a degree of similarity with each first list of characters obtained in step (A), wherein the degree of similarity, DS, of a second list of characters obtained in step (B) with a first list of characters obtained in step (A) is determined by:
      (i) counting a total number of characters, $C_c$, in the second and first lists of characters which are the same as in the first and second lists of characters, respectively;
      (ii) counting a total number of characters, $C_t$, in the first and second lists of characters; and
      (iii) calculating DS according to the following formula:

$$DS = C_c/C_t$$

(D) selecting, for each second list of characters obtained in step (B), the DS of highest value, $DS_{HV}$;
   (E) adding up the number of second lists of characters which have a $DS_{HV}$ that is greater than a threshold value, T, to obtain the total number of second lists of characters, $L_c$, which are the same as a first list of characters;
   (F) adding up
      (i) $L_c$; and
      (ii) the number of second lists of characters which do not have a $DS_{HV}$ that is greater than T,
         to obtain the total number of second lists of characters, $L_t$; and
   (G) calculating the level of minimal residual disease, MRD, according to any of the following formulae:

$$MRD = (L_c \times k)/(L_t \times D)$$

or $$MRD = L_c/L_t$$

or $$MRD = g \times L_c \times (D/k)/L_t^2$$

wherein g is the number of gene copies per cell, D is in units of ng and k is in units of ng/cell;
   (H) determining:
      (i) a minimum variant read frequency, min VRF, of said genetic marker, wherein min VRF is calculated according to the following formula:

$$\min VRF = k/D$$

wherein D and k are as defined above; and
      (ii) a limit of detection, D-limit, of said genetic marker, by:
         (a) obtaining a first composition by diluting one part of a solution of genomic DNA comprising said genetic marker with 10 parts of a solution of genomic DNA which does not comprise said genetic marker;
         (b) determining the level of MRD of said genetic marker in said first composition;
         (c) obtaining a second composition by diluting one part of said first composition with 10 parts of a solution of genomic DNA which does not comprise said genetic marker;
         (d) determining the level of MRD of said genetic marker in said second composition;
         (e) obtaining a third composition by diluting one part of said second composition with 10 parts of a solution of genomic DNA which does not comprise said genetic marker;
         (f) determining the level of MRD of said genetic marker in said third composition;

(g) obtaining a fourth composition by diluting one part of said third composition with 10 parts of a solution of genomic DNA which does not comprise said genetic marker;
(h) determining the level of MRD of said genetic marker in said fourth composition;
(i) calculating:
  an average logarithm of the level of MRD, av log MRD1, of said genetic marker in the first, second and third compositions and an average logarithm of the concentration, av log C1, of said genetic marker in the first, second and third compositions; and
  an average logarithm of the level of MRD, av log MRD2, of said genetic marker in the second, third and fourth compositions and an average logarithm of the concentration, av log C2, of said genetic marker in the second, third and fourth compositions;
(j) calculating:
  a difference, D1A, between the logarithm of the level of MRD of said genetic marker in the first composition and the av log MRD1;
  a difference, D1B, between the logarithm of the level of MRD of said genetic marker in the second composition and the av log MRD1;
  a difference, D1C, between the logarithm of the level of MRD of said genetic marker in the third composition and the av log MRD1;
  a difference, D1D, between the logarithm of the concentration of said genetic marker in the first composition and the av log C1;
  a difference, D1E, between the logarithm of the concentration of said genetic marker in the second composition and the av log C1;
  a difference, D1F, between the logarithm of the concentration of said genetic marker in the third composition and the av log C1;
  a difference, D2A, between the logarithm of the level of MRD of said genetic marker in the second composition and the av log MRD2;
  a difference, D2B, between the logarithm of the level of MRD of said genetic marker in the third composition and the av log MRD2;
  a difference, D2C, between the logarithm of the level of MRD of said genetic marker in the fourth composition and the av log MRD2;
  a difference, D2D, between the logarithm of the concentration of said genetic marker in the second composition and the av log C2;
  a difference, D2E, between the logarithm of the concentration of said genetic marker in the third composition and the av log C2; and
  a difference, D2F, between the logarithm of the concentration of said genetic marker in the fourth composition and the av log C2;
(k) calculating:
  R1 by multiplying D1A and D1D;
  R2 by multiplying D1B and D1E;
  R3 by multiplying D1C and D1F;
  R4 by multiplying D1A by D1A;
  R5 by multiplying D1B by D1B;
  R6 by multiplying D1C by D1C;
  R7 by multiplying D2A and D2D;
  R8 by multiplying D2B and D2E;
  R9 by multiplying D2C and D2F;
  R10 by multiplying D2A by D2A;
  R11 by multiplying D2B by D2B;
  R12 by multiplying D2C by D2C;
(l) calculating:
  S1 using the following formula:

$$S1 = (R1+R2+R3)/(R4+R5+R6)$$

S2 using the following formula:

$$S2 = (R7+R8+R9)/(R0+R11+R12);$$

(m) comparing S1 and S2, whereby:
    when S2 is at least 30% lower than S1, the concentration of the third composition is the D-limit; and
    when S2 is equal to S1 or less than 30% lower than S1, steps (H)(ii)(a) to (H)(ii)(l) are repeated using said first composition in place of said solution of genomic DNA comprising said genetic marker; and
(iii) an average mutation noise, avMut, when said mutation is a single nucleotide variant mutation, by
  (a) amplifying by polymerase chain reaction using the same locus-specific forward primer and the same locus-specific reverse primer as in step (A), at least one nucleotide sequence of genomic DNA from a biological sample obtained from a subject without said disease and without said genetic marker;
  (b) sequencing each amplified nucleotide sequence, whereby a third list of characters reading from left to right is obtained from each nucleotide sequence thus sequenced;
  (c) repeating steps (H)(iii)(a) and (H)(iii)(b) in m subjects without said disease and without said genetic marker, wherein m is at least 9; and
  (d) calculating an average fraction of third lists of characters which are identical to that obtained from sequencing said genetic marker, wherein said average fraction is avMut; and
(iv) an average position noise, avPos, when said mutation is a single nucleotide variant mutation, by calculating a variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein the mean of said VRF values is avPos;
(I) determining an experimental sensitivity, ES, wherein ES is:
  (i) the greater of min VRF, D-limit, avMut and avPos, as calculated in step (H), when said mutation is a single nucleotide variant mutation; or
  (ii) the greater of min VRF and D-limit, as calculated in step (H), when said mutation is an indel mutation or somatic gene rearrangement mutation;
and
(J) determining the presence or absence of minimal residual disease in said subject by either:
  (i) comparing the value of the level of minimal residual disease, MRD, calculated in step (G) with the value of the experimental sensitivity, ES, determined in step (I), wherein
    (a) when said level of MRD value is equal to or greater than said ES value, minimal residual disease is present in said subject; and (b) when said level of MRD value is less than said ES value, minimal residual disease is absent from said subject;

or (ii) when said mutation is a single nucleotide variant mutation, comparing the value of the level of minimal residual disease, MRD, calculated in step (G) with the value of min VRF calculated in step (H), wherein
(a) when said level of MRD value is equal to or greater than said min VRF value, minimal residual disease is present in said subject; and
comparing the value of the level of minimal residual disease, MRD, calculated in step (G) with the value of avMut calculated in step (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in step (G) with the value of avPos calculated in step (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in step (G) with the value of D-limit calculated in step (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in step (G) with the value of min VRF calculated in step (I), wherein
(f) when said level of MRD value is equal to or greater than said min VRF value, minimal residual disease is present in said subject; and
comparing the value of the level of minimal residual disease, MRD, calculated in step (G) with the value of D-limit calculated in step (H) when said level of MRD value is less than said min VRF value, wherein
(g) when said level of MRD value is equal to or greater than said D-limit value, minimal residual disease is present in said subject; and
(h) when said level of MRD value is less than said min VRF and D-limit values, minimal residual disease is absent from said subject; and
(3) repeating steps (1) and (2) until minimal residual disease is determined to be absent in said subject.

2. The method according to claim 1, wherein said proliferative disease is selected from the group consisting of: acute myeloid leukaemia (AML), multiple myeloma (MM), chronic lymphocytic leukaemia (CLL), acute lymphoblastic leukaemia (ALL), a lymphoma, a myelodysplastic syndrome (MDS), myeloproliferative neoplasm (MPN), diffuse large B-cell lymphoma (DLBCL), follicular lymphoma (FL), Waldenström's lymphoma (WL), Hodgkin's lymphoma (HL) and a solid tumour.

3. The method according to claim 1, wherein said genetic marker causes said disease.

4. The method according to claim 1, wherein the variant read frequency, VRF, of said genetic marker in said genomic DNA from a tissue sample obtained from said subject prior to treatment for said disease is:
(i) at least 5% when said mutation is a single nucleotide variant mutation; or
(ii) at least 2% when said mutation is an indel mutation or a somatic gene rearrangement mutation.

5. The method according to claim 1, wherein the genetic marker is selected by the following steps:
(P) identifying at least one mutation comprised in a nucleotide sequence of a gene in said subject having said disease and determining the variant read frequency, VRF, of each mutation thus identified,
(Q) selecting a mutation identified in step (P) having a VRF of greater than 10%, by identifying the mutation having a VRF of greater than 10% which:
(a) is the somatic gene rearrangement mutation having the highest VRF; or
(b) is the indel mutation having the highest VRF, if no somatic gene rearrangement mutation identified in step (P) has a VRF of greater than 10%; or
(c) is the single nucleotide variant mutation having the highest VRF, if no somatic gene rearrangement mutation or an indel mutation identified in step (P) has a VRF of greater than 10%; and
(R) identifying a locus-specific forward primer and a locus-specific reverse primer which amplify by polymerase chain reaction the nucleotide sequence of the gene in said subject which comprises said mutation selected in step (Q),
wherein said nucleotide sequence which comprises said mutation selected in step (Q) is said genetic marker.

6. The method according to claim 5, wherein if no mutation identified in step (P) has a VRF of greater than 10%, the genetic marker is selected, together with a further n−1 genetic markers, by the following steps, wherein:
step (Q) is replaced by a step (Q') which comprises selecting:
(i) n mutations identified in step (P) having a VRF of between 2% and 10%, by identifying those mutations having a VRF of between 2% and 10% which:
(a) are the somatic gene rearrangement mutations having the highest VRF; or
(b) are the indel mutations having the highest VRF, if less than n somatic gene rearrangement mutations identified in step (P) have a VRF of between 2% and 10% were not;

or if less than n somatic gene rearrangement mutations identified in step (P) have a VRF of between 2% and 10% and if less than n indel mutations identified in step (P) have a VRF of between 2% and 10%, step (Q') comprises selecting:
(ii) n mutations identified in step (P) having a VRF of between 5% and 10%, by identifying those mutations having a VRF of between 5% and 10% which are single nucleotide variant mutations; and
step (R) is replaced by a step (R') which comprises:
(i) choosing one of the n mutations selected in step (Q') and identifying a locus-specific forward primer and a locus-specific reverse primer which amplify by polymerase chain reaction the nucleotide sequence of the gene in said subject which comprises said chosen mutation, wherein said nucleotide sequence which comprises said chosen mutation is the genetic marker; and (ii) repeating step (R')(i) n−1 times, each time for one of the remaining n−1 mutations selected in step (Q') not previously chosen in step (R')(i);

wherein said method additionally comprises repeating steps (A) to (I) a further n−1 times, each time using a different pair of primers identified in step (R'), and replacing step (J) with a step (J') of:

(i) comparing an average value of the level of minimal residual disease, avMRD, and an average value of the experimental sensitivity, avES, wherein (a) when said avMRD value is equal to or greater than said avES value, minimal residual disease is present in said subject; and (b) when said avMRD value is less than said avES value, minimal residual disease is absent from said subject or (ii) when said mutation is a single nucleotide variant mutation, comparing the average value of the level of minimal residual disease, avMRD, with an average value of min VRF, avmin VRF, wherein (a) when said avMRD value is equal to or greater than said avmin VRF value, minimal residual disease is present in said subject; and comparing the average value of the level of minimal residual disease, avMRD, with an average value of avMut, avavMut, when said avMRD value is less than said avmin VRF value, wherein (b) when said avMRD value is equal to or greater than said avavMut value, minimal residual disease is present in said subject; and comparing the average value of the level of minimal residual disease, avMRD, with an average value of avPos, avavPos, when said avMRD value is less than said avavMut value, wherein (c) when said avMRD value is equal to or greater than said avavPos value, minimal residual disease is present in said subject; and comparing the average value of the level of minimal residual disease, avMRD, with an average value of D-limit, avD-limit, when said avMRD value is less than said avavPos value, wherein (d) when said avMRD value is equal to or greater than said avD-limit value, minimal residual disease is present in said subject; and (e) when said avMRD value is less than said avmin VRF, avavMut, avavPos and avD-limit values, minimal residual disease is absent from said subject;

or (iii) when said mutation is an indel mutation or somatic gene rearrangement mutation, comparing the average value of the level of minimal residual disease, avMRD, with the average value of min VRF, avmin VRF, wherein (f) when said avMRD value is equal to or greater than said avmin VRF value, minimal residual disease is present in said subject; and comparing the average value of the level of minimal residual disease, avMRD, with the average value of D-limit, avD-limit, when said avMRD value is less than said avmin VRF value, wherein (g) when said avMRD value is equal to or greater than said avD-limit value, minimal residual disease is present in said subject; and (h) when said avMRD value is less than said avmin VRF and avD-limit values, minimal residual disease is absent from said subject wherein n is a natural number selected from 2 to 5.

7. The method according to claim 1, wherein when the disease is acute myeloid leukaemia (AML), myeloproliferative neoplasm (MPN) or a myelodysplastic syndrome (MDS), the nucleotide sequence is a nucleotide sequence of a gene selected from the group consisting of: ASXL1, BCOR, BCORL1, CALR, CBL, CEBPA, CSF3R, DNMT3A, EGLN1, EPAS1, EPOR, ETV6, EZH2, FLT3, IDH1, IDH2, JAK2, KDM6A, KIT, KMT2A, KRAS, MPL, NF1, NPM1, NRAS, PHF6, PRPF40B, RAD21, RUNX1, SETBP1, SF3A1, SF3B1, SH2B3, SMC1A, SRSF2, STAG2, TET2, THPO, TP53, U2AF1, VHL, WT1 and ZRSR2.

8. The method according to claim 1, wherein when the disease is chronic lymphocytic leukaemia (CLL) or acute lymphoblastic leukaemia (ALL), the nucleotide sequence is a nucleotide sequence of a gene selected from the group consisting of: IGH, IGK, EZH2, FLT3, JAK2, KRAS, NRAS, PHF6, SF3B1, TP53, IL7R, PTEN, STAT5B, CRLF2, EGR2, NFKBIE, PLCG2, JAK3, JAK1, IL7, WHSC1, TYK2, FBXW7, IKZF, BIRC3, POT1, RPS15, KLHL6, PTPN11, ATM, IRF4, BRA, XPO1, CXCR4, BCL2, CDKN2A, MYD88, KMT2D, CREBBP, PAX5, NOTCH1, STAT3 and BTK.

9. The method according to claim 1, wherein when the disease is diffuse large B-cell lymphoma (DLBCL), follicular lymphoma (FL), Waldenström's lymphoma (WL) or Hodgkin's lymphoma (HL), the nucleotide sequence is a nucleotide sequence of a gene selected from the group consisting of: ARID1A, ARID1B, B2M, BCL10, BCL2, BCL7A, BRAF, BTG1, BTK, CARD11, CCND3, CD58, CD79A, CD79B, CDKN2A, CDKN2B, CIITA, CREBBP, CTSS, CXCR4, EP300, ETS1, EZH2, FOXO1, GNA13, HIST1H1E, HNRNPK, ID3, IKZF3, IRF4, IRF8, ITPKB, KMT2D, KRAS, MEF2B, MFHAS1, MUM1, MYC, MYD88, NOTCH1, P2RY8, PAX5, PCBP1, PIM1, PIM2, PRDM1, RRAGC, SIPR2, SMARCA4, SOCS1, STAT3, STAT6, TCF3, TNFAIP3, TNFRSF4, TP53 and XPO1.

10. The method according to claim 1, wherein when the disease is multiple myeloma (MM), the nucleotide sequence is a nucleotide sequence of a gene selected from the group consisting of: IGH, IGK, CRBN, IRF4, TP53, NFKB2, KRAS, NRAS, BRAF, FAM46C, FGFR3, DIS3, TRAF3, ATM, MAX, RB1, CYLD, CCND1, NF1, KLHL6, PTPN11, ACTG1, MAF, ZNF292, ROBO1, EGR1, FAT3, PRKD2, HUWE1, TRAF2, CDKN1B, RASA2, UBRS, ZFHX4, DUSP2, SP140, BIRC2, CRBN and LTB.

11. The method of claim 1, wherein a repetition of step (1) comprises administering the same therapy as previously administered to said subject or therapy different to that previously administered to said subject.

12. The method of claim 1, wherein the therapy is chemotherapy and comprises administration of: (i) a protease inhibitor and an immunomodulator; or (ii) cytarabine and an anthracycline antibiotic or an anthracenedione, optionally followed by administration of cytarabine.

13. The method of claim 1, wherein the therapy is chemotherapy and comprises administration of: (i) bortezomib and prednisone (VMP); or (ii) cytarabine and an anthracycline antibiotic or an anthracenedione, optionally followed by administration of cytarabine.

14. The method of claim 13, wherein the anthracycline antibiotic or an anthracenedione is idarubicin.

15. The method of claim 1, wherein when said proliferative disease is:
(i) acute myeloid leukaemia (AML), and said therapy is chemotherapy comprising at least one cycle of administration of cytarabine over 7 days and subsequent administration of idarubicin over 3 days, followed by administration of cytarabine if a second round of treatment is required; or
(ii) multiple myeloma (MM), and said therapy is chemotherapy comprising at least one cycle of administration of a proteasome inhibitor and an immunomodulator.

16. A system for determining the presence or absence of minimal residual disease (MRD) in a subject who has been treated for a proliferative disease, wherein said system comprises the following:
(A)—a PCR instrument for amplifying by polymerase chain reaction using a pair of primers comprising a locus-specific forward primer and a locus-specific reverse primer, at least one nucleotide sequence comprised in genomic DNA from a biological sample obtained from said subject prior to treatment for said disease; and
  a massively parallel sequencing platform for sequencing each amplified nucleotide sequence, whereby a first list of characters reading from left to right is obtained from each nucleotide sequence thus sequenced;
(B)—a PCR instrument for amplifying by polymerase chain reaction using the same locus-specific forward primer and the same locus-specific reverse primer as in (A), at least one nucleotide sequence comprised in an amount, D, of genomic DNA from a biological sample obtained from said subject after treatment for said disease, wherein the genomic DNA has an average weight, k, per diploid cell of said biological sample; and
  a massively parallel sequencing platform for sequencing each amplified nucleotide sequence, whereby a second list of characters reading from left to right is obtained from each nucleotide sequence thus sequenced;
wherein each nucleotide sequence amplified in (A) and (B) is shorter than 400 nucleotides and is either a mutated nucleotide sequence or a non-mutated nucleotide sequence of a gene, wherein when a nucleotide sequence is mutated it is a genetic marker comprising a mutation selected from the group of: a single nucleotide variant mutation, an indel mutation and somatic gene rearrangement mutation;
(C) at least one first computer program product for determining, for each second list of characters obtained in (B), a degree of similarity with each first list of characters obtained in (A), wherein the degree of similarity, DS, of a second list of characters obtained in (B) with a first list of characters obtained in (A) is determined by:
  (i) counting a total number of characters, $C_c$, in the second and first lists of characters which are the same as in the first and second lists of characters, respectively;
  (ii) counting a total number of characters, $C_t$, in the first and second lists of characters; and
  (iii) calculating DS according to the following formula:

$$DS = C_c/C_t$$

(D) at least one second computer program product for selecting, for each second list of characters obtained in (B), a DS of highest value, $DS_{HV}$;
(E) at least one third computer program product for adding up the number of second lists of characters which have a $DS_{HV}$ that is greater than a threshold value, T, to obtain a total number of second lists of characters, $L_c$, which are the same as a first list of characters;
(F) at least one fourth computer program product for adding up
  (i) $L_c$; and
  (ii) the number of second lists of characters which do not have a $DS_{HV}$ that is greater than T,
  to obtain a total number of second lists of characters, $L_t$; and
(G) at least one fifth computer program product for calculating the level of minimal residual disease, MRD, according to any of the following formulae:

$$MRD = (L_c \times k)/(L_t \times D)$$

or $$MRD = L_c/L_t$$

or $$MRD = g \times L_c \times (D/k)/L_t^2$$

wherein g is the number of gene copies per cell, D is in units of ng and k is in units of ng/cell;
(H) at least one sixth computer program product for determining:
  (i) a minimum variant read frequency, min VRF, of said genetic marker, wherein min VRF is calculated according to the following formula:

$$\min VRF = k/D$$

wherein D and k are as defined above; and
  (ii) a limit of detection, D-limit, of said genetic marker by:
    (a) obtaining a first composition by diluting one part of a solution of genomic DNA comprising said genetic marker with 10 parts of a solution of genomic DNA which does not comprise said genetic marker;
    (b) determining the level of MRD of said genetic marker in said first composition;
    (c) obtaining a second composition by diluting one part of said first composition with 10 parts of a solution of genomic DNA which does not comprise said genetic marker;
    (d) determining the level of MRD of said genetic marker in said second composition;
    (e) obtaining a third composition by diluting one part of said second composition with 10 parts of a solution of genomic DNA which does not comprise said genetic marker;
    (f) determining the level of MRD of said genetic marker in said third composition;
    (g) obtaining a fourth composition by diluting one part of said third composition with 10 parts of a solution of genomic DNA which does not comprise said genetic marker;
    (h) determining the level of MRD of said genetic marker in said fourth composition;

(i) calculating:
an average logarithm of the level of MRD, av log MRD1, of said genetic marker in the first, second and third compositions and an average logarithm of the concentration, av log C1, of said genetic marker in the first, second and third compositions; and
an average logarithm of the level of MRD, av log MRD2, of said genetic marker in the second, third and fourth compositions and an average logarithm of the concentration, av log C2, of said genetic marker in the second, third and fourth compositions;

(j) calculating:
a difference, D1A, between the logarithm of the level of MRD of said genetic marker in the first composition and the av log MRD1;
a difference, D1B, between the logarithm of the level of MRD of said genetic marker in the second composition and the av log MRD1; and
a difference, D1C, between the logarithm of the level of MRD of said genetic marker in the third composition and the av log MRD1;
a difference, D1D, between the logarithm of the concentration of said genetic marker in the first composition and the av log C1;
a difference, D1E, between the logarithm of the concentration of said genetic marker in the second composition and the av log C1;
a difference, D1F, between the logarithm of the concentration of said genetic marker in the third composition and the av log C1;
a difference, D2A, between the logarithm of the level of MRD of said genetic marker in the second composition and the av log MRD2;
a difference, D2B, between the logarithm of the level of MRD of said genetic marker in the third composition and the av log MRD2;
a difference, D2C, between the logarithm of the level of MRD of said genetic marker in the fourth composition and the av log MRD2;
a difference, D2D, between the logarithm of the concentration of said genetic marker in the second composition and the av log C2;
a difference, D2E, between the logarithm of the concentration of said genetic marker in the third composition and the av log C2; and
a difference, D2F, between the logarithm of the concentration of said genetic marker in the fourth composition and the av log C2;

(k) calculating:
R1 by multiplying D1A and D1D;
R2 by multiplying D1B and D1E;
R3 by multiplying D1C and D1F;
R4 by multiplying D1A by D1A;
R5 by multiplying D1B by D1B;
R6 by multiplying D1C by D1C;
R7 by multiplying D2A and D2D;
R8 by multiplying D2B and D2E;
R9 by multiplying D2C and D2F;
R10 by multiplying D2A by D2A;
R11 by multiplying D2B by D2B;
R12 by multiplying D2C by D2C;

(l) calculating:
S1 using the following formula:

$S1=(R1+R2+R3)/(R4+R5+R6)$

S2 using the following formula:

$S2=(R7+R8+R9)/(R10+R1+R12)$;

(m) comparing S1 and S2, whereby:
when S2 is at least 30% lower than S1, the concentration of the third composition is the D-limit; and
when S2 is equal to S1 or less than 30% lower than S1, (H)(ii)(a) to (H)(ii)(l) are repeated using said first composition in place of said solution of genomic DNA comprising said genetic marker; and (iii) an average mutation noise, avMut, when said mutation is a single nucleotide variant mutation, using:
(a) a PCR instrument for amplifying by polymerase chain reaction using the same locus-specific forward primer and the same locus-specific reverse primer as in (A), at least one nucleotide sequence of genomic DNA from a biological sample obtained from a subject without said disease and without said genetic marker;
(b) a massively parallel sequencing platform for sequencing each amplified nucleotide sequence, whereby a third list of characters reading from left to right is obtained from each nucleotide sequence thus sequenced;
(c) a PCR instrument and a massively parallel sequencing platform for repeating (H)(iii)(a) and (H)(iii)(b) in m subjects without said disease and without said genetic marker, wherein m is at least 9; and
(d) at least one ninth computer program product for calculating an average fraction of third lists of characters which are identical to that obtained from sequencing said genetic marker, wherein said average fraction is avMut; and (iv) an average position noise, avPos, when said mutation is a single nucleotide variant mutation, using at least one tenth computer program product for calculating a variant read frequency, VRF, for each nucleotide sequence that is identical to said genetic marker and to said non-mutated sequence, but wherein the nucleotide responsible for said single nucleotide variant mutation in said genetic marker is different from that in said genetic marker and said non-mutated sequence, wherein a mean of said VRF values is avPos;

(I) at least one seventh computer program product for determining an experimental sensitivity, ES, wherein ES is:
(i) the greater of min VRF, D-limit, avMut and avPos, as calculated in (H), when said mutation is a single nucleotide variant mutation; and
(ii) the greater of min VRF and D-limit, as calculated in (H), when said mutation is an indel mutation or somatic gene rearrangement mutation;

and (J) at least one eighth computer program product for determining the presence or absence of minimal residual disease in said subject by either:
(i) comparing the value of the level of minimal residual disease, MRD, calculated in (G) with the value of the experimental sensitivity, ES, determined in (I), wherein (a) when said level of MRD value is equal to or greater than said ES value, minimal residual disease is present in said subject; and
(b) when said level of MRD value is less than said ES value, minimal residual disease is absent from said subject or (ii) when said mutation is a single nucleotide variant mutation, comparing the value of the level of minimal residual disease, MRD, calculated in (G) with the value of min VRF calculated in (H), wherein
(a) when said level of MRD value is equal to or greater than said min VRF value, minimal residual disease is present in said subject; and
comparing the value of the level of minimal residual disease, MRD, calculated in (G) with the value of avMut calculated in (H) when said level of MRD value is less than said min VRF value, wherein
(b) when said level of MRD value is equal to or greater than said avMut value, minimal residual disease is present in said subject; and
comparing the value of the level of minimal residual disease, MRD, calculated in (G) with the value of avPos calculated in (H) when said level of MRD value is less than said avMut value, wherein
(c) when said level of MRD value is equal to or greater than said avPos value, minimal residual disease is present in said subject; and
comparing the value of the level of minimal residual disease, MRD, calculated in (G) with the value of D-limit calculated in (H) when said level of MRD value is less than said avPos value, wherein
(d) when said level of MRD value is equal to or greater than said D-limit value, minimal residual disease is present in said subject; and
(e) when said level of MRD value is less than said min VRF, avMut, avPos and D-limit values, minimal residual disease is absent from said subject;

or (iii) when said mutation is an indel mutation or somatic gene rearrangement mutation, comparing the value of the level of minimal residual disease, MRD, calculated in (G) with the value of min VRF calculated in (I), wherein
(f) when said level of MRD value is equal to or greater than said min VRF value, minimal residual disease is present in said subject; and
comparing the value of the level of minimal residual disease, MRD, calculated in (G) with the value of D-limit calculated in (H) when said level of MRD value is less than said min VRF value, wherein
(g) when said level of MRD value is equal to or greater than said D-limit value, minimal residual disease is present in said subject; and
(h) when said level of MRD value is less than said min VRF and D-limit values, minimal residual disease is absent from said subject.

17. The system according to claim 16, wherein said proliferative disorder is selected from the group consisting of: acute myeloid leukaemia (AML), multiple myeloma (MM), chronic lymphocytic leukaemia (CLL), acute lymphoblastic leukaemia (ALL), a lymphoma, a myelodysplastic syndrome (MDS), myeloproliferative neoplasm (MPN), diffuse large B-cell lymphoma (DLBCL), follicular lymphoma (FL), Waldenström's lymphoma (WL), Hodgkin's lymphoma (HL) and a solid tumour.

18. The system according to claim 16, wherein said genetic marker causes said disease.

19. The system according to claim 16, wherein the genetic marker is selected by the following:
(P) at least one eleventh computer program product for identifying at least one mutation comprised in a nucleotide sequence of a gene in said subject having said disease and determining the variant read frequency, VRF, of each mutation thus identified,
(Q) at least one twelfth computer program product for selecting a mutation identified in (P) having a VRF of greater than 10%, by identifying the mutation having a VRF of greater than 10% which:
(a) is the somatic gene rearrangement mutation having the highest VRF; or
(b) is the indel mutation having the highest VRF, if no somatic gene rearrangement mutation identified in (P) has a VRF of greater than 10%; or
(c) is the single nucleotide variant mutation having the highest VRF, if no somatic gene rearrangement mutation or an indel mutation identified in (P) has a VRF of greater than 10%; and
(R) at least one thirteenth computer program product for identifying a locus-specific forward primer and a locus-specific reverse primer which amplify by polymerase chain reaction the nucleotide sequence of the gene in said subject which comprises said mutation selected in (Q),
wherein said nucleotide sequence which comprises said mutation selected in (Q) is said genetic marker.

20. The system according to claim 19, wherein if no mutation identified in (P) has a VRF of greater than 10%, the genetic marker is selected, together with a further n−1 genetic markers, by the following, wherein:
(Q) is replaced by (Q') which comprises:
(i) at least one fourteenth computer program product for selecting n mutations identified in (P) having a VRF of between 2% and 10%, by identifying those mutations having a VRF of between 2% and 10% which:
(a) are the somatic gene rearrangement mutations having the highest VRF; or
(b) are the indel mutations having the highest VRF, if less than n somatic gene rearrangement mutations identified in (P) have a VRF of between 2% and 10% were not;

or if less than n somatic gene rearrangement mutations identified in (P) have a VRF of between 2% and 10% and if less than n indel mutations identified in (P) have a VRF of between 2% and 10%, (Q') comprises at least one fifteenth computer program product for selecting:
(ii) n mutations identified in (P) having a VRF of between 5% and 10%, by identifying those mutations having a VRF of between 5% and 10% which are single nucleotide variant mutations; and
(R) is replaced by (R') which comprises:
(i) at least one sixteenth computer program product for choosing one of the n mutations selected in (Q') and identifying a locus-specific forward primer and a locus-specific reverse primer which amplify by polymerase chain reaction the nucleotide sequence of the gene in said subject which comprises said chosen mutation, wherein said nucleotide sequence which comprises said chosen mutation is the genetic marker; and (ii) at least one seventeenth computer program product for repeating (R')(i) n−1 times, each time for one of the remaining n−1 mutations selected in (Q') not previously chosen in (R')(i);

wherein said system additionally comprises repeating (A) to (I) a further n−1 times, each time using a different pair of primers identified in (R'), and replacing (J) with (J') of:

(i) at least one eighteenth computer program product for comparing an average value of the level of minimal residual disease, avMRD, and an average value of the experimental sensitivity, avES, wherein
  (a) when said avMRD value is equal to or greater than said avES value, minimal residual disease is present in said subject; and
  (b) when said avMRD value is less than said avES value, minimal residual disease is absent from said subject or (ii) when said mutation is a single nucleotide variant mutation, at least one ninteenth computer program product for comparing the average value of the level of minimal residual disease, avMRD, with an average value of min VRF, avmin VRF, wherein
  (a) when said avMRD value is equal to or greater than said avmin VRF value, minimal residual disease is present in said subject; and at least one twenthieth computer program product for comparing the average value of the level of minimal residual disease, avMRD, with an average value of avMut, avavMut, when said avMRD value is less than said avmin VRF value, wherein
  (b) when said avMRD value is equal to or greater than said avavMut value, minimal residual disease is present in said subject; and at least one 21st computer program product for comparing the average value of the level of minimal residual disease, avMRD, with an average value of avPos, avavPos, when said avMRD value is less than said avavMut value, wherein (c) when said avMRD value is equal to or greater than said avavPos value, minimal residual disease is present in said subject; and at least one 22nd computer program product for comparing the average value of the level of minimal residual disease, avMRD, with an average value of D-limit, avD-limit, when said avMRD value is less than said avavPos value, wherein
  (d) when said avMRD value is equal to or greater than said avD-limit value, minimal residual disease is present in said subject; and
  (e) when said avMRD value is less than said avmin VRF, avavMut, avavPos and avD-limit values, minimal residual disease is absent from said subject;

or (iii) when said mutation is an indel mutation or somatic gene rearrangement mutation, at least one 23rd computer program product for comparing the average value of the level of minimal residual disease, avMRD, with the average value of min VRF, avmin VRF, wherein
  (f) when said avMRD value is equal to or greater than said avmin VRF value, minimal residual disease is present in said subject; and at least one 24th computer program product for comparing the average value of the level of minimal residual disease, avMRD, with the average value of D-limit, avD-limit, when said avMRD value is less than said avmin VRF value, wherein
  (g) when said avMRD value is equal to or greater than said avD-limit value, minimal residual disease is present in said subject; and
  (h) when said avMRD value is less than said avmin VRF and avD-limit values, minimal residual disease is absent from said subject, wherein n is a natural number selected from 2 to 5.

* * * * *

SEQUENCE LISTING

```
<160> NUMBER OF SEQ ID NOS: 130

<210> SEQ ID NO 1
<211> LENGTH: 25
<212> TYPE: DNA
<213> ORGANISM: Artificial Sequence
<220> FEATURE:
<223> OTHER INFORMATION: Primer VH1-FR1

<400> SEQUENCE: 1
ggcctcagtg aaggtctcct gcaag                                          25

<210> SEQ ID NO 2
<211> LENGTH: 25
<212> TYPE: DNA
<213> ORGANISM: Artificial Sequence
<220> FEATURE:
<223> OTHER INFORMATION: Primer VH2-FR1

<400> SEQUENCE: 2
gtctggtcct acgctggtga aaccc                                          25

<210> SEQ ID NO 3
<211> LENGTH: 25
<212> TYPE: DNA
<213> ORGANISM: Artificial Sequence
<220> FEATURE:
<223> OTHER INFORMATION: Primer VH3-FR1

<400> SEQUENCE: 3 ctgggggtc cctgagactc tcctg                                           25

<210> SEQ ID NO 4
<211> LENGTH: 25
<212> TYPE: DNA
<213> ORGANISM: Artificial Sequence
<220> FEATURE:
<223> OTHER INFORMATION: Primer VH4-FR1

<400> SEQUENCE: 4
cttcggagac cctgtccctc acctg                                          25
```

```
<210> SEQ ID NO 5
<211> LENGTH: 25
<212> TYPE: DNA
<213> ORGANISM: Artificial Sequence
<220> FEATURE:
<223> OTHER INFORMATION: Primer VH5-FR1

<400> SEQUENCE: 5
cggggagtct ctgaagatct cctgt                                             25

<210> SEQ ID NO 6
<211> LENGTH: 25
<212> TYPE: DNA
<213> ORGANISM: Artificial Sequence
<220> FEATURE:
<223> OTHER INFORMATION: Primer VH6-FR1

<400> SEQUENCE: 6
tcgcagaccc tctcactcac ctgtg                                             25

<210> SEQ ID NO 7
<211> LENGTH: 25
<212> TYPE: DNA
<213> ORGANISM: Artificial Sequence
<220> FEATURE:
<223> OTHER INFORMATION: Primer VH1-FR2

<400> SEQUENCE: 7
ctgggtgcga caggcccctg gacaa                                             25

<210> SEQ ID NO 8
<211> LENGTH: 25
<212> TYPE: DNA
<213> ORGANISM: Artificial Sequence
<220> FEATURE:
<223> OTHER INFORMATION: Primer VH2-FR2

<400> SEQUENCE: 8
tggatccgtc agcccccagg gaagg                                             25

<210> SEQ ID NO 9
<211> LENGTH: 21
<212> TYPE: DNA
<213> ORGANISM: Artificial Sequence
<220> FEATURE:
<223> OTHER INFORMATION: Primer VH3-FR2

<400> SEQUENCE: 9
ggtccgccag gctccaggga a                                                 21

<210> SEQ ID NO 10
<211> LENGTH: 25
<212> TYPE: DNA
<213> ORGANISM: Artificial Sequence
<220> FEATURE:
<223> OTHER INFORMATION: Primer VH4-FR2

<400> SEQUENCE: 10
tggatccgcc agcccccagg gaagg                                             25

<210> SEQ ID NO 11
<211> LENGTH: 25
<212> TYPE: DNA
<213> ORGANISM: Artificial Sequence
<220> FEATURE:
<223> OTHER INFORMATION: Primer VH5-FR2
```

<400> SEQUENCE: 11
gggtgcgcca gatgcccggg aaagg                                              25

<210> SEQ ID NO 12
<211> LENGTH: 25
<212> TYPE: DNA
<213> ORGANISM: Artificial Sequence
<220> FEATURE:
<223> OTHER INFORMATION: Primer VH6-FR2

<400> SEQUENCE: 12
tggatcaggc agtccccatc gagag                                              25

<210> SEQ ID NO 13
<211> LENGTH: 25
<212> TYPE: DNA
<213> ORGANISM: Artificial Sequence
<220> FEATURE:
<223> OTHER INFORMATION: Primer VH7-FR2

<400> SEQUENCE: 13
ttgggtgcga caggcccctg gacaa                                              25

<210> SEQ ID NO 14
<211> LENGTH: 25
<212> TYPE: DNA
<213> ORGANISM: Artificial Sequence
<220> FEATURE:
<223> OTHER INFORMATION: Primer VH1-FR3

<400> SEQUENCE: 14
tggagctgag cagcctgaga tctga                                              25

<210> SEQ ID NO 15
<211> LENGTH: 25
<212> TYPE: DNA
<213> ORGANISM: Artificial Sequence
<220> FEATURE:
<223> OTHER INFORMATION: Primer VH2-FR3

<400> SEQUENCE: 15
caatgaccaa catggaccct gtgga                                              25

<210> SEQ ID NO 16
<211> LENGTH: 25
<212> TYPE: DNA
<213> ORGANISM: Artificial Sequence
<220> FEATURE:
<223> OTHER INFORMATION: Primer VH3-FR3

<400> SEQUENCE: 16
tctgcaaatg aacagcctga gagcc                                              25

<210> SEQ ID NO 17
<211> LENGTH: 25
<212> TYPE: DNA
<213> ORGANISM: Artificial Sequence
<220> FEATURE:
<223> OTHER INFORMATION: Primer VH4-FR3

<400> SEQUENCE: 17
gagctctgtg accgccgcgg acacg                                              25

<210> SEQ ID NO 18
<211> LENGTH: 25

-continued

<210> SEQ ID NO 18
<211> LENGTH: 25
<212> TYPE: DNA
<213> ORGANISM: Artificial Sequence
<220> FEATURE:
<223> OTHER INFORMATION: Primer VH5-FR3

<400> SEQUENCE: 18
cagcaccgcc tacctgcagt ggagc                                    25

<210> SEQ ID NO 19
<211> LENGTH: 25
<212> TYPE: DNA
<213> ORGANISM: Artificial Sequence
<220> FEATURE:
<223> OTHER INFORMATION: Primer VH6-FR3

<400> SEQUENCE: 19
gttctccctg cagctgaact ctgtg                                    25

<210> SEQ ID NO 20
<211> LENGTH: 24
<212> TYPE: DNA
<213> ORGANISM: Artificial Sequence
<220> FEATURE:
<223> OTHER INFORMATION: Primer VH7-FR3

<400> SEQUENCE: 20
cagcacggca tatctgcaga tcag                                     24

<210> SEQ ID NO 21
<211> LENGTH: 18
<212> TYPE: DNA
<213> ORGANISM: Artificial Sequence
<220> FEATURE:
<223> OTHER INFORMATION: Primer DH1

<400> SEQUENCE: 21
ggcggaatgt gtgcaggc                                            18

<210> SEQ ID NO 22
<211> LENGTH: 21
<212> TYPE: DNA
<213> ORGANISM: Artificial Sequence
<220> FEATURE:
<223> OTHER INFORMATION: Primer DH2

<400> SEQUENCE: 22
gcactgggct cagagtcctc t                                        21

<210> SEQ ID NO 23
<211> LENGTH: 20
<212> TYPE: DNA
<213> ORGANISM: Artificial Sequence
<220> FEATURE:
<223> OTHER INFORMATION: Primer DH3

<400> SEQUENCE: 23
gtggccctgg gaatataaaa                                          20

<210> SEQ ID NO 24
<211> LENGTH: 19
<212> TYPE: DNA
<213> ORGANISM: Artificial Sequence
<220> FEATURE:
<223> OTHER INFORMATION: Primer DH4

<400> SEQUENCE: 24
agatccccag gacgcagca                                                19

<210> SEQ ID NO 25
<211> LENGTH: 20
<212> TYPE: DNA
<213> ORGANISM: Artificial Sequence
<220> FEATURE:
<223> OTHER INFORMATION: Primer DH5

<400> SEQUENCE: 25
cagggggaca ctgtgcatgt                                               20

<210> SEQ ID NO 26
<211> LENGTH: 19
<212> TYPE: DNA
<213> ORGANISM: Artificial Sequence
<220> FEATURE:
<223> OTHER INFORMATION: Primer DH6

<400> SEQUENCE: 26
tgaccccagc aagggaagg                                                19

<210> SEQ ID NO 27
<211> LENGTH: 18
<212> TYPE: DNA
<213> ORGANISM: Artificial Sequence
<220> FEATURE:
<223> OTHER INFORMATION: Primer DH7

<400> SEQUENCE: 27
cacaggcccc ctaccagc                                                 18

<210> SEQ ID NO 28
<211> LENGTH: 22
<212> TYPE: DNA
<213> ORGANISM: Artificial Sequence
<220> FEATURE:
<223> OTHER INFORMATION: Primer JH57

<400> SEQUENCE: 28
cttacctgag gagacggtga cc                                            22

<210> SEQ ID NO 29
<211> LENGTH: 25
<212> TYPE: DNA
<213> ORGANISM: Artificial Sequence
<220> FEATURE:
<223> OTHER INFORMATION: Primer VK1f/6

<400> SEQUENCE: 29
tcaaggttca gcggcagtgg atctg                                         25

<210> SEQ ID NO 30
<211> LENGTH: 26
<212> TYPE: DNA
<213> ORGANISM: Artificial Sequence
<220> FEATURE:
<223> OTHER INFORMATION: Primer VK2f

<400> SEQUENCE: 30
ggcctccatc tcctgcaggt ctagtc                                        26

<210> SEQ ID NO 31
<211> LENGTH: 27
<212> TYPE: DNA
<213> ORGANISM: Artificial Sequence

```
<220> FEATURE:
<223> OTHER INFORMATION: Primer VK3f

<400> SEQUENCE: 31
cccaggctcc tcatctatga tgcatcc                                              27

<210> SEQ ID NO 32
<211> LENGTH: 27
<212> TYPE: DNA
<213> ORGANISM: Artificial Sequence
<220> FEATURE:
<223> OTHER INFORMATION: Primer VK4

<400> SEQUENCE: 32
caactgcaag tccagccaga gtgtttt                                              27

<210> SEQ ID NO 33
<211> LENGTH: 26
<212> TYPE: DNA
<213> ORGANISM: Artificial Sequence
<220> FEATURE:
<223> OTHER INFORMATION: Primer VK5

<400> SEQUENCE: 33
cctgcaaagc cagccaagac attgat                                               26

<210> SEQ ID NO 34
<211> LENGTH: 27
<212> TYPE: DNA
<213> ORGANISM: Artificial Sequence
<220> FEATURE:
<223> OTHER INFORMATION: Primer VK6

<400> SEQUENCE: 34
gaccgatttc accctcacaa ttaatcc                                              27

<210> SEQ ID NO 35
<211> LENGTH: 27
<212> TYPE: DNA
<213> ORGANISM: Artificial Sequence
<220> FEATURE:
<223> OTHER INFORMATION: Primer JK1-4

<400> SEQUENCE: 35
cttacgtttg atctccacct tggtccc                                              27

<210> SEQ ID NO 36
<211> LENGTH: 27
<212> TYPE: DNA
<213> ORGANISM: Artificial Sequence
<220> FEATURE:
<223> OTHER INFORMATION: Primer JK5

<400> SEQUENCE: 36
cttacgttta atctccagtc gtgtccc                                              27

<210> SEQ ID NO 37
<211> LENGTH: 27
<212> TYPE: DNA
<213> ORGANISM: Artificial Sequence
<220> FEATURE:
<223> OTHER INFORMATION: Primer Kde

<400> SEQUENCE: 37
cctcagaggt cagagcaggt tgtccta                                              27
```

```
<210> SEQ ID NO 38
<211> LENGTH: 22
<212> TYPE: DNA
<213> ORGANISM: Artificial Sequence
<220> FEATURE:
<223> OTHER INFORMATION: Primer INTR

<400> SEQUENCE: 38
cgtggcaccg cgagctgtag ac                                                 22

<210> SEQ ID NO 39
<211> LENGTH: 27
<212> TYPE: DNA
<213> ORGANISM: Artificial Sequence
<220> FEATURE:
<223> OTHER INFORMATION: Forward primer for TP53

<400> SEQUENCE: 39
aaggtgataa aagtgaatct gaggcat                                            27

<210> SEQ ID NO 40
<211> LENGTH: 22
<212> TYPE: DNA
<213> ORGANISM: Artificial Sequence
<220> FEATURE:
<223> OTHER INFORMATION: Reverse primer for TP53

<400> SEQUENCE: 40
aatgggacag gtaggacctg at                                                 22

<210> SEQ ID NO 41
<211> LENGTH: 22
<212> TYPE: DNA
<213> ORGANISM: Artificial Sequence
<220> FEATURE:
<223> OTHER INFORMATION: Forward primer for TP53

<400> SEQUENCE: 41
ctgctcacca tcgctatctg ag                                                 22

<210> SEQ ID NO 42
<211> LENGTH: 26
<212> TYPE: DNA
<213> ORGANISM: Artificial Sequence
<220> FEATURE:
<223> OTHER INFORMATION: Reverse primer for TP53

<400> SEQUENCE: 42
ctttcaactc tgtctccttc ctcttc                                             26

<210> SEQ ID NO 43
<211> LENGTH: 22
<212> TYPE: DNA
<213> ORGANISM: Artificial Sequence
<220> FEATURE:
<223> OTHER INFORMATION: Forward primer for TP53

<400> SEQUENCE: 43
tgtgatgaga ggtggatggg ta                                                 22

<210> SEQ ID NO 44
<211> LENGTH: 22
<212> TYPE: DNA
<213> ORGANISM: Artificial Sequence
<220> FEATURE:
<223> OTHER INFORMATION: Reverse primer for TP53
```

<400> SEQUENCE: 44
cctcatcttg ggcctgtgtt at                                                22

<210> SEQ ID NO 45
<211> LENGTH: 22
<212> TYPE: DNA
<213> ORGANISM: Artificial Sequence
<220> FEATURE:
<223> OTHER INFORMATION: Forward primer for TP53

<400> SEQUENCE: 45
tcatagggca ccaccacact at                                                22

<210> SEQ ID NO 46
<211> LENGTH: 22
<212> TYPE: DNA
<213> ORGANISM: Artificial Sequence
<220> FEATURE:
<223> OTHER INFORMATION: Reverse primer for TP53

<400> SEQUENCE: 46
tacaagcagt cacagcacat ga                                                22

<210> SEQ ID NO 47
<211> LENGTH: 22
<212> TYPE: DNA
<213> ORGANISM: Artificial Sequence
<220> FEATURE:
<223> OTHER INFORMATION: Forward primer for TP53

<400> SEQUENCE: 47
cttgcttacc tcgcttagtg ct                                                22

<210> SEQ ID NO 48
<211> LENGTH: 27
<212> TYPE: DNA
<213> ORGANISM: Artificial Sequence
<220> FEATURE:
<223> OTHER INFORMATION: Reverse primer for TP53

<400> SEQUENCE: 48
gcttctcttt tcctatcctg agtagtg                                           27

<210> SEQ ID NO 49
<211> LENGTH: 20
<212> TYPE: DNA
<213> ORGANISM: Artificial Sequence
<220> FEATURE:
<223> OTHER INFORMATION: Forward primer for TP53

<400> SEQUENCE: 49
ggctcctgac ctggagtctt                                                   20

<210> SEQ ID NO 50
<211> LENGTH: 19
<212> TYPE: DNA
<213> ORGANISM: Artificial Sequence
<220> FEATURE:
<223> OTHER INFORMATION: Reverse primer for TP53

<400> SEQUENCE: 50
aaggcgcact ggcctcatc                                                    19

<210> SEQ ID NO 51

```
<211> LENGTH: 22
<212> TYPE: DNA
<213> ORGANISM: Artificial Sequence
<220> FEATURE:
<223> OTHER INFORMATION: Forward primer for TP53

<400> SEQUENCE: 51
ggccagacct aagagcaatc ag                                              22

<210> SEQ ID NO 52
<211> LENGTH: 22
<212> TYPE: DNA
<213> ORGANISM: Artificial Sequence
<220> FEATURE:
<223> OTHER INFORMATION: Reverse primer for TP53

<400> SEQUENCE: 52
catggccatc tacaagcagt ca                                              22

<210> SEQ ID NO 53
<211> LENGTH: 19
<212> TYPE: DNA
<213> ORGANISM: Artificial Sequence
<220> FEATURE:
<223> OTHER INFORMATION: Forward primer for TP53

<400> SEQUENCE: 53
acaacctccg tcatgtgct                                                  19

<210> SEQ ID NO 54
<211> LENGTH: 26
<212> TYPE: DNA
<213> ORGANISM: Artificial Sequence
<220> FEATURE:
<223> OTHER INFORMATION: Reverse primer for TP53

<400> SEQUENCE: 54
gtctccttcc tcttcctaca gtactc                                          26

<210> SEQ ID NO 55
<211> LENGTH: 29
<212> TYPE: DNA
<213> ORGANISM: Artificial Sequence
<220> FEATURE:
<223> OTHER INFORMATION: Forward primer for NRAS

<400> SEQUENCE: 55
gctcctagta cctgtagagg ttaatatcc                                       29

<210> SEQ ID NO 56
<211> LENGTH: 28
<212> TYPE: DNA
<213> ORGANISM: Artificial Sequence
<220> FEATURE:
<223> OTHER INFORMATION: Reverse primer for NRAS

<400> SEQUENCE: 56
gttatagatg gtgaaacctg tttgttgg                                        28

<210> SEQ ID NO 57
<211> LENGTH: 22
<212> TYPE: DNA
<213> ORGANISM: Artificial Sequence
<220> FEATURE:
<223> OTHER INFORMATION: Forward primer for NRAS

<400> SEQUENCE: 57
```
cgacaagtga gagacaggat ca                                              22

<210> SEQ ID NO 58
<211> LENGTH: 24
<212> TYPE: DNA
<213> ORGANISM: Artificial Sequence
<220> FEATURE:
<223> OTHER INFORMATION: Reverse primer for NRAS

<400> SEQUENCE: 58
tcttgctggt gtgaaatgac tgag                                            24

<210> SEQ ID NO 59
<211> LENGTH: 23
<212> TYPE: DNA
<213> ORGANISM: Artificial Sequence
<220> FEATURE:
<223> OTHER INFORMATION: Forward primer for KRAS

<400> SEQUENCE: 59
caaagaatgg tcctgcacca gta                                             23

<210> SEQ ID NO 60
<211> LENGTH: 27
<212> TYPE: DNA
<213> ORGANISM: Artificial Sequence
<220> FEATURE:
<223> OTHER INFORMATION: Reverse primer for KRAS

<400> SEQUENCE: 60
aaggcctgct gaaaatgact gaatata                                         27

<210> SEQ ID NO 61
<211> LENGTH: 23
<212> TYPE: DNA
<213> ORGANISM: Artificial Sequence
<220> FEATURE:
<223> OTHER INFORMATION: Forward primer for KRAS

<400> SEQUENCE: 61
gctgtatcgt caaggcactc ttg                                             23

<210> SEQ ID NO 62
<211> LENGTH: 30
<212> TYPE: DNA
<213> ORGANISM: Artificial Sequence
<220> FEATURE:
<223> OTHER INFORMATION: Reverse primer for KRAS

<400> SEQUENCE: 62
aggtactggt ggagtatttg atagtgtatt                                      30

<210> SEQ ID NO 63
<211> LENGTH: 33
<212> TYPE: DNA
<213> ORGANISM: Artificial Sequence
<220> FEATURE:
<223> OTHER INFORMATION: Forward primer for KRAS

<400> SEQUENCE: 63
tgtcagctta ttatattcaa tttaaaccca cct                                  33

<210> SEQ ID NO 64
<211> LENGTH: 24
<212> TYPE: DNA

```
<213> ORGANISM: Artificial Sequence
<220> FEATURE:
<223> OTHER INFORMATION: Reverse primer for KRAS

<400> SEQUENCE: 64
tcttggatat tctcgacaca gcag                                          24

<210> SEQ ID NO 65
<211> LENGTH: 28
<212> TYPE: DNA
<213> ORGANISM: Artificial Sequence
<220> FEATURE:
<223> OTHER INFORMATION: Forward primer for BRAF

<400> SEQUENCE: 65
ccttcaatga ctttctagta actcagca                                      28

<210> SEQ ID NO 66
<211> LENGTH: 30
<212> TYPE: DNA
<213> ORGANISM: Artificial Sequence
<220> FEATURE:
<223> OTHER INFORMATION: Reverse primer for BRAF

<400> SEQUENCE: 66
cttacctaaa ctcttcataa tgcttgctct                                    30

<210> SEQ ID NO 67
<211> LENGTH: 25
<212> TYPE: DNA
<213> ORGANISM: Artificial Sequence
<220> FEATURE:
<223> OTHER INFORMATION: Forward primer for FLT3

<400> SEQUENCE: 67
ccctgacaac atagttggaa tcact                                         25

<210> SEQ ID NO 68
<211> LENGTH: 30
<212> TYPE: DNA
<213> ORGANISM: Artificial Sequence
<220> FEATURE:
<223> OTHER INFORMATION: Reverse primer for FLT3

<400> SEQUENCE: 68
cactccagga taatacacat cacagtaaat                                    30

<210> SEQ ID NO 69
<211> LENGTH: 25
<212> TYPE: DNA
<213> ORGANISM: Artificial Sequence
<220> FEATURE:
<223> OTHER INFORMATION: Forward primer for SF3B1

<400> SEQUENCE: 69
caagatggca cagcccataa gaata                                         25

<210> SEQ ID NO 70
<211> LENGTH: 22
<212> TYPE: DNA
<213> ORGANISM: Artificial Sequence
<220> FEATURE:
<223> OTHER INFORMATION: Reverse primer for SF3B1

<400> SEQUENCE: 70
agcttttgct gttgtagcct ct                                            22
```

<210> SEQ ID NO 71
<211> LENGTH: 22
<212> TYPE: DNA
<213> ORGANISM: Artificial Sequence
<220> FEATURE:
<223> OTHER INFORMATION: Forward primer for SF3B1

<400> SEQUENCE: 71
caagatggca cagcccataa ga                                    22

<210> SEQ ID NO 72
<211> LENGTH: 29
<212> TYPE: DNA
<213> ORGANISM: Artificial Sequence
<220> FEATURE:
<223> OTHER INFORMATION: Reverse primer for SF3B1

<400> SEQUENCE: 72
actcatgact gtcctttctt tgtttacat                             29

<210> SEQ ID NO 73
<211> LENGTH: 26
<212> TYPE: DNA
<213> ORGANISM: Artificial Sequence
<220> FEATURE:
<223> OTHER INFORMATION: Forward primer for SF3B1

<400> SEQUENCE: 73
aggtaattgg tggatttacc tttcct                                26

<210> SEQ ID NO 74
<211> LENGTH: 27
<212> TYPE: DNA
<213> ORGANISM: Artificial Sequence
<220> FEATURE:
<223> OTHER INFORMATION: Reverse primer for SF3B1

<400> SEQUENCE: 74
ggcatagtta aaacctgtgt ttggttt                               27

<210> SEQ ID NO 75
<211> LENGTH: 25
<212> TYPE: DNA
<213> ORGANISM: Artificial Sequence
<220> FEATURE:
<223> OTHER INFORMATION: Forward primer for SF3B1

<400> SEQUENCE: 75
tcatttcctc atcaggagac tggaa                                 25

<210> SEQ ID NO 76
<211> LENGTH: 28
<212> TYPE: DNA
<213> ORGANISM: Artificial Sequence
<220> FEATURE:
<223> OTHER INFORMATION: Reverse primer for SF3B1

<400> SEQUENCE: 76
tgtgttaaag cctttatgga agggtatc                              28

<210> SEQ ID NO 77
<211> LENGTH: 22
<212> TYPE: DNA
<213> ORGANISM: Artificial Sequence
<220> FEATURE:

<223> OTHER INFORMATION: Forward primer for SF3B1

<400> SEQUENCE: 77
gttggcggat acccttccat aa                                    22

<210> SEQ ID NO 78
<211> LENGTH: 28
<212> TYPE: DNA
<213> ORGANISM: Artificial Sequence
<220> FEATURE:
<223> OTHER INFORMATION: Reverse primer for SF3B1

<400> SEQUENCE: 78
ggcatagtta aaacctgtgt ttggtttt                              28

<210> SEQ ID NO 79
<211> LENGTH: 24
<212> TYPE: DNA
<213> ORGANISM: Artificial Sequence
<220> FEATURE:
<223> OTHER INFORMATION: Forward primer for EZH2

<400> SEQUENCE: 79
agttccaatt ctcacgtcaa aggt                                  24

<210> SEQ ID NO 80
<211> LENGTH: 25
<212> TYPE: DNA
<213> ORGANISM: Artificial Sequence
<220> FEATURE:
<223> OTHER INFORMATION: Reverse primer for EZH2

<400> SEQUENCE: 80
aattattcac tgggctgtgc ttact                                 25

<210> SEQ ID NO 81
<211> LENGTH: 22
<212> TYPE: DNA
<213> ORGANISM: Artificial Sequence
<220> FEATURE:
<223> OTHER INFORMATION: Forward primer for EZH2

<400> SEQUENCE: 81
agtgccttac ctctccacag ta                                    22

<210> SEQ ID NO 82
<211> LENGTH: 25
<212> TYPE: DNA
<213> ORGANISM: Artificial Sequence
<220> FEATURE:
<223> OTHER INFORMATION: Reverse primer for EZH2

<400> SEQUENCE: 82
ccagtccatt ttcaccctcc ttttt                                 25

<210> SEQ ID NO 83
<211> LENGTH: 19
<212> TYPE: DNA
<213> ORGANISM: Artificial Sequence
<220> FEATURE:
<223> OTHER INFORMATION: Forward primer for CREBBP

<400> SEQUENCE: 83
tcgccagaga caagcactg                                        19

-continued

<210> SEQ ID NO 84
<211> LENGTH: 18
<212> TYPE: DNA
<213> ORGANISM: Artificial Sequence
<220> FEATURE:
<223> OTHER INFORMATION: Reverse primer for CREBBP

<400> SEQUENCE: 84
gtgcagctcc accagcat                                                 18

<210> SEQ ID NO 85
<211> LENGTH: 18
<212> TYPE: DNA
<213> ORGANISM: Artificial Sequence
<220> FEATURE:
<223> OTHER INFORMATION: Forward primer for BCL2

<400> SEQUENCE: 85
gcacctgacg cccttcac                                                 18

<210> SEQ ID NO 86
<211> LENGTH: 20
<212> TYPE: DNA
<213> ORGANISM: Artificial Sequence
<220> FEATURE:
<223> OTHER INFORMATION: Reverse primer for BCL2

<400> SEQUENCE: 86
aagaaggcca caatcctccc                                               20

<210> SEQ ID NO 87
<211> LENGTH: 17
<212> TYPE: DNA
<213> ORGANISM: Artificial Sequence
<220> FEATURE:
<223> OTHER INFORMATION: Forward primer for MYD88

<400> SEQUENCE: 87
ttggcttgca ggtgccc                                                  17

<210> SEQ ID NO 88
<211> LENGTH: 20
<212> TYPE: DNA
<213> ORGANISM: Artificial Sequence
<220> FEATURE:
<223> OTHER INFORMATION: Reverse primer for MYD88

<400> SEQUENCE: 88
ggttggtgta gtcgcagaca                                               20

<210> SEQ ID NO 89
<211> LENGTH: 20
<212> TYPE: DNA
<213> ORGANISM: Artificial Sequence
<220> FEATURE:
<223> OTHER INFORMATION: Forward primer for BTK

<400> SEQUENCE: 89
tctttcccat gagaagctgg                                               20

<210> SEQ ID NO 90
<211> LENGTH: 20
<212> TYPE: DNA
<213> ORGANISM: Artificial Sequence
<220> FEATURE:
<223> OTHER INFORMATION: Reverse primer for BTK -continued

<400> SEQUENCE: 90
catccttgca catctctagc					20

<210> SEQ ID NO 91
<211> LENGTH: 20
<212> TYPE: DNA
<213> ORGANISM: Artificial Sequence
<220> FEATURE:
<223> OTHER INFORMATION: Forward primer for NOTCH1

<400> SEQUENCE: 91
gaactgaggc ctgagagctt					20

<210> SEQ ID NO 92
<211> LENGTH: 20
<212> TYPE: DNA
<213> ORGANISM: Artificial Sequence
<220> FEATURE:
<223> OTHER INFORMATION: Reverse primer for NOTCH1

<400> SEQUENCE: 92
cagacctgtg aggtcgacat					20

<210> SEQ ID NO 93
<211> LENGTH: 18
<212> TYPE: DNA
<213> ORGANISM: Artificial Sequence
<220> FEATURE:
<223> OTHER INFORMATION: Forward primer for NOTCH1

<400> SEQUENCE: 93
gtcccgcaga catcctga					18

<210> SEQ ID NO 94
<211> LENGTH: 20
<212> TYPE: DNA
<213> ORGANISM: Artificial Sequence
<220> FEATURE:
<223> OTHER INFORMATION: Reverse primer for NOTCH1

<400> SEQUENCE: 94
ggtggccgat ttgggagatc					20

<210> SEQ ID NO 95
<211> LENGTH: 19
<212> TYPE: DNA
<213> ORGANISM: Artificial Sequence
<220> FEATURE:
<223> OTHER INFORMATION: Forward primer for NOTCH1

<400> SEQUENCE: 95
ccgaaggctt gggaaagga					19

<210> SEQ ID NO 96
<211> LENGTH: 19
<212> TYPE: DNA
<213> ORGANISM: Artificial Sequence
<220> FEATURE:
<223> OTHER INFORMATION: Reverse primer for NOTCH1

<400> SEQUENCE: 96
cctcgcctgt ggacaacac					19

<210> SEQ ID NO 97
<211> LENGTH: 22

```
<212> TYPE: DNA
<213> ORGANISM: Artificial Sequence
<220> FEATURE:
<223> OTHER INFORMATION: Forward primer for XPO1

<400> SEQUENCE: 97
ctccaacctg aacctgaacg aa                                              22

<210> SEQ ID NO 98
<211> LENGTH: 29
<212> TYPE: DNA
<213> ORGANISM: Artificial Sequence
<220> FEATURE:
<223> OTHER INFORMATION: Reverse primer for XPO1

<400> SEQUENCE: 98
ctcactggaa atttctgaag actgtagtt                                       29

<210> SEQ ID NO 99
<211> LENGTH: 28
<212> TYPE: DNA
<213> ORGANISM: Artificial Sequence
<220> FEATURE:
<223> OTHER INFORMATION: Forward primer for BIRC3

<400> SEQUENCE: 99
ctttagtaga agcctggtaa aacagaca                                        28

<210> SEQ ID NO 100
<211> LENGTH: 30
<212> TYPE: DNA
<213> ORGANISM: Artificial Sequence
<220> FEATURE:
<223> OTHER INFORMATION: Reverse primer for BIRC3

<400> SEQUENCE: 100
aaaaacctga ctggattgag tatattttca                                      30

<210> SEQ ID NO 101
<211> LENGTH: 30
<212> TYPE: DNA
<213> ORGANISM: Artificial Sequence
<220> FEATURE:
<223> OTHER INFORMATION: Forward primer for BIRC3

<400> SEQUENCE: 101
ttcttagttt ttcactgaag aagcaaactg                                      30

<210> SEQ ID NO 102
<211> LENGTH: 29
<212> TYPE: DNA
<213> ORGANISM: Artificial Sequence
<220> FEATURE:
<223> OTHER INFORMATION: Reverse primer for BIRC3

<400> SEQUENCE: 102
tggttcttct tcatgaaaga aatgtacga                                       29

<210> SEQ ID NO 103
<211> LENGTH: 22
<212> TYPE: DNA
<213> ORGANISM: Artificial Sequence
<220> FEATURE:
<223> OTHER INFORMATION: Forward primer for EGR2

<400> SEQUENCE: 103
```
tctgtctcag gtggatcttg gt                                          22

<210> SEQ ID NO 104
<211> LENGTH: 21
<212> TYPE: DNA
<213> ORGANISM: Artificial Sequence
<220> FEATURE:
<223> OTHER INFORMATION: Reverse primer for EGR2

<400> SEQUENCE: 104
tgaccacctc accacccata t                                           21

<210> SEQ ID NO 105
<211> LENGTH: 24
<212> TYPE: DNA
<213> ORGANISM: Artificial Sequence
<220> FEATURE:
<223> OTHER INFORMATION: Forward primer for FBXW7

<400> SEQUENCE: 105
tttttggact gtactggatc agca                                        24

<210> SEQ ID NO 106
<211> LENGTH: 24
<212> TYPE: DNA
<213> ORGANISM: Artificial Sequence
<220> FEATURE:
<223> OTHER INFORMATION: Reverse primer for FBXW7

<400> SEQUENCE: 106
catgttttga tgggtcatgt tgca                                        24

<210> SEQ ID NO 107
<211> LENGTH: 24
<212> TYPE: DNA
<213> ORGANISM: Artificial Sequence
<220> FEATURE:
<223> OTHER INFORMATION: Forward primer for FBXW7

<400> SEQUENCE: 107
tagaggaaga agtcccaacc atga                                        24

<210> SEQ ID NO 108
<211> LENGTH: 30
<212> TYPE: DNA
<213> ORGANISM: Artificial Sequence
<220> FEATURE:
<223> OTHER INFORMATION: Reverse primer for FBXW7

<400> SEQUENCE: 108
tcacttttcc tttctaccca aaagtaatca                                  30

<210> SEQ ID NO 109
<211> LENGTH: 22
<212> TYPE: DNA
<213> ORGANISM: Artificial Sequence
<220> FEATURE:
<223> OTHER INFORMATION: Forward primer for FBXW7

<400> SEQUENCE: 109
caactgtcct tgctgggaat ca                                          22

<210> SEQ ID NO 110
<211> LENGTH: 22
<212> TYPE: DNA
<213> ORGANISM: Artificial Sequence

```
<220> FEATURE:
<223> OTHER INFORMATION: Reverse primer for FBXW7

<400> SEQUENCE: 110
caagaagtag caagctggct tt                                               22

<210> SEQ ID NO 111
<211> LENGTH: 21
<212> TYPE: DNA
<213> ORGANISM: Artificial Sequence
<220> FEATURE:
<223> OTHER INFORMATION: Forward primer for NFKBIE

<400> SEQUENCE: 111
gggacttgaa ggatcttcac g                                                21

<210> SEQ ID NO 112
<211> LENGTH: 21
<212> TYPE: DNA
<213> ORGANISM: Artificial Sequence
<220> FEATURE:
<223> OTHER INFORMATION: Reverse primer for NFKBIE

<400> SEQUENCE: 112
ggctgattcc acctatggct c                                                21

<210> SEQ ID NO 113
<211> LENGTH: 32
<212> TYPE: DNA
<213> ORGANISM: Artificial Sequence
<220> FEATURE:
<223> OTHER INFORMATION: Forward primer for IDH1

<400> SEQUENCE: 113
aagaataaaa cacatacaag ttggaaattt ct                                    32

<210> SEQ ID NO 114
<211> LENGTH: 28
<212> TYPE: DNA
<213> ORGANISM: Artificial Sequence
<220> FEATURE:
<223> OTHER INFORMATION: Reverse primer for IDH1

<400> SEQUENCE: 114
gagaagccat tatctgcaaa aatatccc                                         28

<210> SEQ ID NO 115
<211> LENGTH: 20
<212> TYPE: DNA
<213> ORGANISM: Artificial Sequence
<220> FEATURE:
<223> OTHER INFORMATION: Forward primer for IDH2

<400> SEQUENCE: 115
ggactaggcg tgggatgttt                                                  20

<210> SEQ ID NO 116
<211> LENGTH: 26
<212> TYPE: DNA
<213> ORGANISM: Artificial Sequence
<220> FEATURE:
<223> OTHER INFORMATION: Reverse primer for IDH2

<400> SEQUENCE: 116
gggttcaaat tctggttgaa agatgg                                           26
```

<210> SEQ ID NO 117
<211> LENGTH: 31
<212> TYPE: DNA
<213> ORGANISM: Artificial Sequence
<220> FEATURE:
<223> OTHER INFORMATION: Forward primer for U2AF1

<400> SEQUENCE: 117
attaactgtc tttgaaaaga acatgaagtt t                              31

<210> SEQ ID NO 118
<211> LENGTH: 28
<212> TYPE: DNA
<213> ORGANISM: Artificial Sequence
<220> FEATURE:
<223> OTHER INFORMATION: Reverse primer for U2AF1

<400> SEQUENCE: 118
tttcccttac agagtcaact gttcattt                                  28

<210> SEQ ID NO 119
<211> LENGTH: 24
<212> TYPE: DNA
<213> ORGANISM: Artificial Sequence
<220> FEATURE:
<223> OTHER INFORMATION: Forward primer for RUNX1

<400> SEQUENCE: 119
aatctgagac atggtccctg agta                                      24

<210> SEQ ID NO 120
<211> LENGTH: 23
<212> TYPE: DNA
<213> ORGANISM: Artificial Sequence
<220> FEATURE:
<223> OTHER INFORMATION: Reverse primer for RUNX1

<400> SEQUENCE: 120
ccatcactgt cttcacaaac cca                                       23

<210> SEQ ID NO 121
<211> LENGTH: 23
<212> TYPE: DNA
<213> ORGANISM: Artificial Sequence
<220> FEATURE:
<223> OTHER INFORMATION: Forward primer for RUNX1

<400> SEQUENCE: 121
agaccgagtt tctagggatt cca                                       23

<210> SEQ ID NO 122
<211> LENGTH: 23
<212> TYPE: DNA
<213> ORGANISM: Artificial Sequence
<220> FEATURE:
<223> OTHER INFORMATION: Reverse primer for RUNX1

<400> SEQUENCE: 122
ctaccgcagc catgaagaac cag                                       23

<210> SEQ ID NO 123
<211> LENGTH: 33
<212> TYPE: DNA
<213> ORGANISM: Artificial Sequence
<220> FEATURE:
<223> OTHER INFORMATION: Forward primer for KIT

<400> SEQUENCE: 123
aatgaaagtt aatatggaga agttaattgc tgc                                    33

<210> SEQ ID NO 124
<211> LENGTH: 29
<212> TYPE: DNA
<213> ORGANISM: Artificial Sequence
<220> FEATURE:
<223> OTHER INFORMATION: Reverse primer for KIT

<400> SEQUENCE: 124
gtgatgccag ctattatatt tctcctgta                                         29

<210> SEQ ID NO 125
<211> LENGTH: 32
<212> TYPE: DNA
<213> ORGANISM: Artificial Sequence
<220> FEATURE:
<223> OTHER INFORMATION: Forward primer for KIT

<400> SEQUENCE: 125
tgaatttaaa tggttttctt ttctcctcca ac                                     32

<210> SEQ ID NO 126
<211> LENGTH: 33
<212> TYPE: DNA
<213> ORGANISM: Artificial Sequence
<220> FEATURE:
<223> OTHER INFORMATION: Reverse primer for KIT

<400> SEQUENCE: 126
cacgtttcct ttaaccacat aattagaatc att                                    33

<210> SEQ ID NO 127
<211> LENGTH: 26
<212> TYPE: DNA
<213> ORGANISM: Artificial Sequence
<220> FEATURE:
<223> OTHER INFORMATION: Forward primer for KIT

<400> SEQUENCE: 127
attttggtct agccagagac atcaag                                            26

<210> SEQ ID NO 128
<211> LENGTH: 30
<212> TYPE: DNA
<213> ORGANISM: Artificial Sequence
<220> FEATURE:
<223> OTHER INFORMATION: Reverse primer for KIT

<400> SEQUENCE: 128
tgtgtgatat ccctagacag gatttacatt                                        30

<210> SEQ ID NO 129
<211> LENGTH: 22
<212> TYPE: DNA
<213> ORGANISM: Artificial Sequence
<220> FEATURE:
<223> OTHER INFORMATION: Forward primer for KIT

<400> SEQUENCE: 129
tggatggcac ctgaaagcat tt                                                22

<210> SEQ ID NO 130

```
<211> LENGTH: 29
<212> TYPE: DNA
<213> ORGANISM: Artificial Sequence
<220> FEATURE:
<223> OTHER INFORMATION: Reverse primer for KIT

<400> SEQUENCE: 130
gaaacttcaa gaagatgctc tgagtctaa                                              29
```